US007361475B2

(12) United States Patent
Sun et al.

(10) Patent No.: US 7,361,475 B2
(45) Date of Patent: Apr. 22, 2008

(54) COMPOSITIONS AND METHODS RELATING TO COLON SPECIFIC GENES AND PROTEINS

(75) Inventors: Yongming Sun, San Jose, CA (US); Herve E. Recipon, San Francisco, CA (US); Malavika G. Ghosh, San Jose, CA (US); Chenghua Liu, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 349 days.

(21) Appl. No.: 11/042,241

(22) Filed: Jan. 25, 2005

(65) Prior Publication Data

US 2005/0208546 A1 Sep. 22, 2005

Related U.S. Application Data

(62) Division of application No. 10/016,157, filed on Oct. 31, 2001, now abandoned.

(60) Provisional application No. 60/244,717, filed on Oct. 31, 2000.

(51) Int. Cl.
*G01N 33/53* (2006.01)
*C07K 16/00* (2006.01)
*A61K 39/395* (2006.01)

(52) U.S. Cl. .................. 435/7.1; 424/130.1; 530/387.1

(58) Field of Classification Search ..................... None
See application file for complete search history.

(56) References Cited

U.S. PATENT DOCUMENTS 5,695,980 A 12/1997 Wei et al. ................... 435/196

FOREIGN PATENT DOCUMENTS

| | | |
|---|---|---|
| WO | WO 96/39419 | 12/1996 |
| WO | WO 00/50588 | 8/2000 |
| WO | WO 01/75067 A3 | 10/2001 |
| WO | WO 02/14500 | 2/2002 |
| WO | WO 02/22638 A1 | 3/2002 |
| WO | WO 02/48370 A2 | 6/2002 |
| WO | WO 02/102993 A3 | 12/2002 |
| WO | WO 02/102994 A3 | 12/2002 |

OTHER PUBLICATIONS

Hunkapiller et al, Science 207: 523 (1980).*
Sigma. Biochemicals Organic Compounds. Sigma Catalog, 1990, pp. 776-778.
XP-002221239 *Homo sapiens* chromosome 15 clone RP11-745A24 Waterson R. H., Jan. 2, 2000, AC019146.
XP-002221240 Dias Neto et al., "Shotgun sequencing of the human transcriptome with ORF expressed sequence tags", Proc. Natl. Acad. Sci. USA 97(7) :3491-3496 2000.
XP-002221241 Escobedo et al., ABN62977.
NCBI Genbank Accession No. AC124067 [gi :21360160] Jun. 9, 2002 with Revision History—The Revision History for 27228921 which replaces 21360160 is provided.
NCBI Genbank Accession No. AC137579 [gi :25229246] Nov. 24, 2002 with Revision History—The Revision History for 27902325 which replaces 25229246 is provided.
NCBI Genbank Accession No. AK025743 {gi :10438355 Sep. 29, 2000 with Revision History.
NCBI Genbank Accession No. AP006302 [gi :29335770] Mar. 28, 2003 with Revision History.
NCBI Genbank Accession No. AP000067 [gi :4579988] Jan. 7, 2002-Nov. 20, 1999 with Revision History.
NCBI Genbank Accession No. AC084847 [gi :11276204] Nov. 22, 2000 with Revision History—The Revision History of 27597027 which replaces 11276204 is provided.

* cited by examiner

*Primary Examiner*—James Martinell
(74) *Attorney, Agent, or Firm*—Licata & Tyrrell PC; Keith R. McCollum

(57) ABSTRACT

The present invention relates to newly identified nucleic acids and polypeptides present in normal and neoplastic colon cells, including fragments, variants and derivatives of the nucleic acids and polypeptides. The present invention also relates to antibodies to the polypeptides of the invention, as well as agonists and antagonists of the polypeptides of the invention. The invention also relates to compositions comprising the nucleic acids, polypeptides, antibodies, variants, derivatives, agonists and antagonists of the invention and methods for the use of these compositions. These uses include identifying, diagnosing, monitoring, staging, imaging and treating colon cancer and non-cancerous disease states in colon tissue, identifying colon tissue, monitoring and identifying and/or designing agonists and antagonists of polypeptides of the invention. The uses also include gene therapy, production of transgenic animals and cells, and production of engineered colon tissue for treatment and research.

5 Claims, No Drawings

SEQUENCE LISTING

<160> NUMBER OF SEQ ID NOS: 250

<210> SEQ ID NO 1
<211> LENGTH: 421
<212> TYPE: DNA
<213> ORGANISM: Homo sapiens

<400> SEQUENCE: 1

```
cttaaaaata atttctagat tgttggcatt attaaaaccc taaatccttt taggaactat     60

tgcgaagaaa gaatatgata ttcgtaagag ctcagtgcta atattagcat tggttatggt    120

agtgaaagac cagataaatc ttttagttgg gaagtatgtc ttgaggtata cttccttata    180

atcattaagt aaataagtaa aactatatta catagataat gtgtaactct ctgtattaca    240

tagaatgtct gcagaatgta gataggaaaa ataaagtttg tcaataattt tcaacatctt    300

tattgagata cagttaatct gccatgacga tttgcctact ataaagtgta catttcagtg    360

tgtttagcta gtgtatttgc agagttgtgc agtcatcacc acagtaactt ccctaacact    420

c                                                                    421
```

<210> SEQ ID NO 2
<211> LENGTH: 426
<212> TYPE: DNA
<213> ORGANISM: Homo sapiens

<400> SEQUENCE: 2

```
agaaacccat tcctaagtga actgccactg ctctagtcta acttaggttg gcagagagcc     60

agcactttct tcagcattca gggcagggag cactgaggat attggcattg cttattacta    120

agcacacaga tacaagtatg tgcttgatat gtaaccaaag taagttaaac tccttattta    180

atcttagcac ctgtctaaag gctgggtgac tgtatttata gatgaggaaa actgaaaatt    240

gggggccaag gggcagtgaa gtgaagtgac ttgttctatg atacacagct agtaggaata    300

ttagcactgg aatttgaatt tcatgccatc ccattccaac ctgggtgttt actacttccc    360

actatctccc aagcatgggt attttaggaa atatagaaca ttttctcagc aatacagact    420

tatttc                                                               426
```

<210> SEQ ID NO 3
<211> LENGTH: 1016
<212> TYPE: DNA
<213> ORGANISM: Homo sapiens
<220> FEATURE:
<221> NAME/KEY: misc_feature
<222> LOCATION: (469)..(574)
<223> OTHER INFORMATION: n=a, c, g or t

<400> SEQUENCE: 3

```
agaaacccat tcctaagtga actgccactg ctctagtcta acttaggttg gcagagagcc     60

agcactttct tcagcattca gggcagggag cactgaggat attggcattg cttattacta    120

agcacacaga tacaagtatg tgcttgatat gtaaccaaag taagttaaac tccttattta    180

atcttagcac ctgtctaaag gctgggtgac tgtatttata gatgaggaaa actgaaaatt    240

gggggccaag gggcagtgaa gtgaagtgac ttgttctatg atacacagct agtaggaata    300

ttagcactgg aatttgaatt tcatgccatc ccattccaac cctgggtgtt tactacttcc    360

cactatctcc caagcatggg tattttagga aatatagaac attttctcag caatacagac    420

ttatttctct attctccttt ccacatactc tcttttccct taacaacann nnnnnnnnnn    480
```

nnnnnnnnnn nnnnnnnnnn nnnnnnnnnn nnnnnnnnnn nnnnnnnnnn nnnnnnnnnn 540
nnnnnnnnnn nnnnnnnnnn nnnnnnnnnn nnnntcacat catttattct taggccactt 600
tgatgctttt tcattgatgc tctttataga catagtgaag taaaagttta tctaggatat 660
atggtgggag gtgaggaaga cttaggtaga gaggttccaa accagttgtt actgcttagc 720
tcaatttcag acatacttcc tccagccctc tctaaactac ccaccagtct tcgcccctct 780
tttcttagtt ctgtggcact tgccctgggt gccctaactg tatggcatgc tgttctcatc 840
agtcgaggtg agactagcat cgaaaggcac atcaacaaga aggagagacg tcggctacag 900
gccaagggca gagtgagtag ggttgaaggc tcggggtggg taggtgggta actgaacttg 960
ctctccctgt aaacagaggc catgggcagg gctgactagg gcaagcatta taaaag 1016

<210> SEQ ID NO 4
<211> LENGTH: 1358
<212> TYPE: DNA
<213> ORGANISM: Homo sapiens

<400> SEQUENCE: 4
ctcctggggc tcgttttctc caggaggctg cattctgatc cataaacctt ctcctcgggg 60
tttagggtcg agctgttcct gatgtttatc ggagactggg atcaaagcta tccaggtcat 120
aaatctctct ctgtggctgt tggccccag ggcagctgaa gagggttgac agccctttgg 180
acctcaaagg aaaaaatgtg ctctactcca cccactccca gctctgccaa gaagctgtcc 240
tctgagaagc catggctggg ccgttccatt ctggggagct gctgaaaaga gctgggaggc 300
cgagaagaac ttgcgtgtgc tgggggagag gaagcctggc cttgagggag gggtgcaggt 360
gtggctcctg tgtgtgtggg ggctgggga ccttgtgtgc cttttccttg tggctgtgaa 420
atgctttatg agtacttcca taggaggatg gacagggagt cggggagata aactcagcca 480
caaggcccca gggcctcagg aaacttgcac ccaaccctct cattttacag aagaaaactg 540
tgcctggaag gttgaagggt ttgttcccag tcacacaacc agggatcctt aggacagcca 600
gaccaggaaa ccatttccaa actgccaagc catggcagag tatcaagacc tcaggaacca 660
tcgagacacc atggaagcat tgggaaaagc ctccttagct tttgaagctc ctcattgttc 720
ttgagtgtgc atggagccca tgactgcggg gttttgtaga cacctcaggg attacatgac 780
tggtacccct gacaaagtca aggctgctgg acaaaatgag tccgaggatt tcaggggcac 840
gctgggcgca ggagctggtg ggctgttggg agtgcccctt tactgggcag gcttccttcc 900
tcctggtgat ggggggttcc tcagcacaaa agtgaagggg tggaggggct ggaggagcag 960
gaatctctct tgttgatagg tatgaggcct tgaagtcctt ttctttgtcc caggattcat 1020
ggacgcttcg gggctgatct ttgagttttc aagcatgggg tgcagagacg tttaggtaaa 1080
ctcttaccgt cctctctctt cgtcagggct tcccaggaat caacaatgcc caagaaggaa 1140
gggattgtag aaatagctta accctttcat ttaccaacgt ggaaattgaa gcccagggaa 1200
gggaagggac cggtcgtgga agggagagcc atcagcagaa agagaccctg agatcttcgc 1260
ctgggattcc caggaagtcc agcccgagct gattcacaga acaaatgcat gcaaaccttg 1320
ctatcaataa attacacatg cacttacgta aaacacat 1358

<210> SEQ ID NO 5
<211> LENGTH: 2375
<212> TYPE: DNA
<213> ORGANISM: Homo sapiens

<400> SEQUENCE: 5

```
cttttctctt gttgagtgca aatggagaac agctgctcac gctcgtcgtc tgacatcagc     60
tatttctcag gatgaccctg cgagacaggc cagggtcatt agacccaatt tggttctcag    120
caaatatgtg tttattcctg catgcgtggg ccacaggctg gtttcttggg tgcaatgaat    180
agctgcaggt ttattagggt gtctttttag atggatgtat gtttcccgat gtctatagaa    240
cactccggac cccggagagt gaagactctg cctgtcggac ttgctttgag aagatccttc    300
tccacctccc catggcagaa gttgcttcac agaggggaac agttttatgg atgtggctga    360
gaccttaaac ttgaggcaac ccatctgagg tggcatccag aggagactgg ctggcccctc    420
cttcaccttg gatgtagtgc tgtttctagg atctcttttc aatcagcaaa acaggggatg    480
ttccaagagg gtgtggattc cctgccatcc cacatggtca agtggagggg acgggaaaaa    540
gctatgaagg gtttgtgacc acacagactc tcctggcccc ctgtcctttt ggaaagaaga    600
cagggatgaa atataatcaa gcaattaacc acccccatca tcaccaagaa caacagtatc    660
aacaagaaga acagggacaa caaaacccac ggatgaaaca ttcctttctc agctcagatc    720
ttatctggtg cgttctctct ctgctctgtc ttggtgtgtg gtttagagaa acatggacaa    780
cgctgtttgg aagaacaggt gagcgagggt ggggaatttc agaggcctgg gcccaccgcc    840
tccacccctt ccccagttta acctttgaca ggatcttcac ctctctctga tcagcattgc    900
ttcttgttca aaggcctcag ccacccagct gtgtcccttt ccccagaaag caagggcaga    960
tggcagtggg tctgttgatg agagaacttt aagggcccaa tcagtccctg ggcacccccct   1020
cctgggctcg ttttctccag gaggctgcat tctgatccat aaaccttctc ctcggggttt   1080
agggtcgagc tgttcctgat gtttatcgga gactgggatc aaagctatcc aggtcataaa   1140
tctctctctg tggctgttgg gccccagggc agctgaagag ggttgacagc cctttggacc   1200
tcaaaggaaa aaatgtgctc tactccaccc actcccagct ctgccaagaa gctgtcctct   1260
gagaagccat ggctgggccg ttccattctg gggagctgct gaaaagagct gggaggccga   1320
gaagaacttg cgtgtgctgg gggagaggaa gcctggcctt gagggagggg tgcaggtgtg   1380
gctcctgtgt gtgtgggggc tgggggacct tgtgtgcctt ttccttgtgg ctgtgaaatg   1440
ctttatgagt acttccatag gaggatggac agggagtcgg ggagataaac tcagccacaa   1500
ggccccaggg cctcaggaaa cttgcaccca accctctcat tttacagaag aaaactgtgc   1560
ctggaaggtt gaagggtttg ttcccagtca cacaaccagg gatccttagg acagccagac   1620
caggaaacca tttccaaact gccaagccat ggcagagtat caagacctca ggaaccatcg   1680
agacaccatg gaagcattgg gaaaagcctc cttagctttt gaagctcctc attgttcttg   1740
agtgtgcatg gagcccatga ctgcggggtt ttgtagacac ctcagggatt acatgactgg   1800
taccccctgac aaagtcaagg ctgctggaca aaatgagtcc gaggatttca ggggcacgct   1860
gggcgcagga gctggtgggc tgttgggagt gccccctttac tgggcaggct tccttcctcc   1920
tggtgatggg gggttcctca gcacaaaagt gaaggggtgg aggggctgga ggagcaggaa   1980
tctctcttgt tgataggtat gaggccttga agtccttttc tttgtcccag gattcatgga   2040
cgcttcgggg ctgatctttg agttttcaag catggggtgc agagacgttt aggtaaactc   2100
ttaccgtcct ctctcttcgt cagggcttcc caggaatcaa caatgcccaa gaaggaaggg   2160
attgtagaaa tagcttaacc ctttcattta ccaacgtgga aattgaagcc cagggaaggg   2220
aagggaccgg tcgtggaagg gagagccatc agcagaaaga gaccctgaga tcttcgcctg   2280
ggattcccag gaagtccagc ccgagctgat tcacagaaca aatgcatgca aaccttgcta   2340
```

```
tcaataaatt acacatgcac ttacgtaaaa cacat                          2375


<210> SEQ ID NO 6
<211> LENGTH: 410
<212> TYPE: DNA
<213> ORGANISM: Homo sapiens
<220> FEATURE:
<221> NAME/KEY: misc_feature
<222> LOCATION: (34)..(34)
<223> OTHER INFORMATION: n=a, c, g or t
<220> FEATURE:
<221> NAME/KEY: misc_feature
<222> LOCATION: (56)..(56)
<223> OTHER INFORMATION: n=a, c, g or t
<220> FEATURE:
<221> NAME/KEY: misc_feature
<222> LOCATION: (108)..(108)
<223> OTHER INFORMATION: n=a, c, g or t

<400> SEQUENCE: 6

cagagtcaag gccccaaggc cgtgggtctt tganggaggg gtttttgaga catgtncagg     60

gacaaaccta gcaacaagag aactcttaat cccatacgtg atattgcnaa ttagcttttc    120

ctttcacaaa tattgtccac cctaagtatg tttactataa tgttagctgt taaagacccc    180

tcctaccccc aaaccattta cccttcaata aaaatggtgc caagttgcaa gggttagaca    240

ggtatgtatt gaaatttaga aagtttgaat aatttcttta acacaaaagc atttttttct    300

tatttctcat acttttgaat ctatttaaat acaacttcag tgctgattaa tctactaaat    360

gtgaaagttt aagatttata gctgggtgca gtggctacac ctgtaatcct               410


<210> SEQ ID NO 7
<211> LENGTH: 416
<212> TYPE: DNA
<213> ORGANISM: Homo sapiens
<220> FEATURE:
<221> NAME/KEY: misc_feature
<222> LOCATION: (114)..(114)
<223> OTHER INFORMATION: n=a, c, g or t

<400> SEQUENCE: 7

ctcgagcaga gtcaaggccc caaggccgtg ggtctttgaa ggaggggttt ttgagacatg     60

tacagggaca aacctagcaa caagagaact cttaatccca tacgtgatat tgcnaattag    120

cttttccttt cacaaatatt gtccacccta agtatgttta ctataatgtt agctgttaaa    180

gacccctcct acccccaaac catttaccct tcaataaaaa tggtgccaag ttgcaagggt    240

tagacaggta tgtattgaaa tttagaaagt ttgaataatt tctttaacac aaaagcattt    300

ttttcttatt tctcatactt ttgaatctat ttaaatacaa cttcagtgct gattaatcta    360

ctaaatgtga aagtttaaga tttatagctg ggtgcagtgg ctacacctgt aatcct        416


<210> SEQ ID NO 8
<211> LENGTH: 786
<212> TYPE: DNA
<213> ORGANISM: Homo sapiens

<400> SEQUENCE: 8

atgttcctag tagaacacaa agtttgctca ggtaacacac aagtaagcat taaatgcctt     60

cctgttgtat ctgagaagtt tgttatgaaa tattttggta accgctgcat agtcagtgta    120

ggaggagcag atgaatttta gctgtggtta tgtgtgctgt aaaagactat acgtgcttgt    180

attagtcaga atgagtacac cactaatttt tgtatggtaa gagatttata ctaagctcat    240
```

```
catcagtttc tataattcag tgagataaaa ctgagtcaga ttgattttta ggtagcacat    300

gtagaaacag ctaattttat tcccctgatt tgatcctcat ctattgatta tataaactaa    360

agaagctaag aacaattaac ccttacgagg ttacacagtc aggagatgct gaactgagat    420

tcagtgtaga aagtctgtct tcagagccta tgcttttagt ctttatgcta agtttaactt    480

gtttaaatag caagattatg aagcactata cagtgacctc gtatagacaa aaatatagta    540

tattgattat tagagaaact acatattaga ctgttgtaca tacgtgggca agtatttgtt    600

aaatcatttc agttgcctaa atttaagcaa ctgtgctgtt taaaacatgc tcattcacat    660

tttttcttaa tctagaaagt cacttctgaa taattgcttg tttagatttt ctcatttggt    720

gtgggaaatt tatattaaaa ttttaactaa tattctaaca atacagagtc tgaacctaaa    780

gtccac                                                                786
```

<210> SEQ ID NO 9
<211> LENGTH: 1509
<212> TYPE: DNA
<213> ORGANISM: Homo sapiens

<400> SEQUENCE: 9

```
atcagaccta gtgcgtaggc ttctggatct cagaatcact tatacttaag tccaggctgt     60

tctcaaataa ggcaagaagc atctgctgtt aatagctgac agtaaattac acaaagtaaa    120

acatggaaaa ttaaagtcag aaaagctagg aagcttttct atcattttca attttctgca    180

aaaatacaga cataatcagg tttaggatct gcttgtgatg gataaattac atctgtaatt    240

ccttcttttc catattactg cattcagacg ataatttgct ttcagatatc ttgctcatct    300

aatcgttcat agactggaaa taagtagtaa catctcccaa tcctaggaag catttataac    360

tagtctttgc ctttttgggt gttgatagac tagtggtgat tataagcttt cgagcttctg    420

aaaagcacaa cgaagattaa aataatcata ggataataaa atactttaaa acccttctag    480

tctttaattt taaaatgttc cagtagaaca caaatttgct caggtaacac acaagtaagc    540

attaaatgcc ttcctgtgta tctgagaagt ttgttatgaa atattttgga aaccgctgca    600

tagtcagtgt aggaggagca gatgaatttt agctgtggtt atgtgtgctg taaaagacta    660

tacgtgcttg tattagtcag aatgagtaca ccactaattt ttgtatggta agagatttat    720

actaagctca tcatcagttt ctataattca gtgagataaa actgagtcag attgattttt    780

aggtagcaca tgtagaaaca gctaatttta ttcccctgat ttgatcctca tctattgatt    840

atataaacta aagaagctaa gaacaattaa cccttacgag gttacacagt caggagatgc    900

tgaactgaga ttcagtgtag aaagtctgtc ttcagagcct atgcttttag tctttatgct    960

aagtttaact tgtttaaata gcaagattat gaagcactat acagtgacct cgtatagaca   1020

aaaatatagt atattgatta ttagagaaac tacatattag actgttgtac atacgtgggc   1080

aagtatttgt taaatcattt cagttgccta aatttaagca actgtgctgt ttaaaacatg   1140

ctcattcaca ttttttctta atctagaaag tcacttctga ataattgctt gtttagattt   1200

tctcatttgg tgtgggaaat ttatattaaa attttaacta atattctaac aatacagagt   1260

ctgaacctaa agtccagaag aattttaagt catgccgcag acaggatgaa cagtatagca   1320

aatcagaata atagactgtg aggggggta gggggaacc catgagaatt tcaggatgtc   1380

aagataaagc ttggaattga ggtaaaggca tcagataagg aagtgatcat ttcataactt   1440

gtttttgctt gaaatatatt atattttaca tcacaaaagt agtataactg ttattttgct   1500

aatgcacag                                                            1509
```

<210> SEQ ID NO 10
<211> LENGTH: 283
<212> TYPE: DNA
<213> ORGANISM: Homo sapiens

<400> SEQUENCE: 10
ctaagtaatc cttgtcaggg gaggtggttc ccaattcgtg actcttggac cttggggcat 60
cttatgattt attgttatca ctaacaatag ctcgctatgt gtcatgtctt ctgctacata 120
ttttatgttt tatttcagct tttaaaaaga ttttcatgat tcatgattgt tgtaaagcag 180
gactaggctg tatgtacata tttgaaatga aagtttcaca aaacatcatt tacctttact 240
atgtgtgaca cactttgcta tttttcattt aatctatttt att 283

<210> SEQ ID NO 11
<211> LENGTH: 736
<212> TYPE: DNA
<213> ORGANISM: Homo sapiens

<400> SEQUENCE: 11
gtctttctga aaggaagcac tcggaatcct tccgaacttt ccaagtccat ccatgattca 60
gagatactgc cttctctctc tctgggattt tatgtgtttc tgatagtgaa ttgttgatgt 120
atttgctact ttgcttcttt tctctttcaa gacttgatca ttttatatgc tgtttggaga 180
aaaaaagaac ttttgttagc aaggaggttt cagaaatgat tttggatttt ctgtaagtgt 240
ttaatttagt tctaggggac agcatctctc atcccggagt aaatttctgc ctttgacctg 300
catggattat tttttcaggc tgcggaattt ctcggcacct acctgtagta tggggcactt 360
ggtttggttg cagagtaaga aggtggaaga atgagctgta cttggttaag cagttgaaac 420 ctttttttgag caggatctgt aaaagcataa ttgaatttgt ttcacccccg tggattccag 480
tgggcccgac agcgcaacag gtttgcagat ttcttttgaa attccttttt ccccccctccc 540 tctgcctcag caaaagaaaa gaatccatat aacaggttca tgttcaattg cttggctttt 600
cagcacttat tctgaagact ttataatatt tttaaacttg accttggaac acagagggct 660
ttgtgggtga ggtgtattta tatttactta agggtgcaca ttttaaaaat cttattctgt 720
gtttgtacaa agacgc 736

<210> SEQ ID NO 12
<211> LENGTH: 547
<212> TYPE: DNA
<213> ORGANISM: Homo sapiens

<400> SEQUENCE: 12
ccggttagaa tagagcttcc acaagctcct actttgatat ctgccctcct agcactgggg 60
ccactgtttc ctgctttccc tctatgtgaa ctctccgtgt ttctaatatc atctggatta 120
atcacatcct ctctggccta ctcaaagata gtaactctaa caacttttcc ctctctttca 180
tgcaattcct actttgcctc tctctgctgg actttttctc atcgacatat aaacatgctg 240
ttatgtctcc caaccaaaaa aaatgcaaaa accctttcag ccctatgctc acccatcatc 300
cagctgtagt cctcttcctt ccttttactc tcctttatta tagctaaatt tcttgaaagg 360
atggaatgtc cacttcctct cctcccatcc tttcctgaac ctaccccaat ctgccttttg 420
tccccactgt gccagtgaga gggctcttga taagctctcc cttcattgac ttccagttgc 480
tcaatgaaat gggcagttct cagtcctcat cttacttgac tttccagcag catttagtac 540
taccaga 547

<210> SEQ ID NO 13
<211> LENGTH: 1559
<212> TYPE: DNA
<213> ORGANISM: Homo sapiens
<220> FEATURE:
<221> NAME/KEY: misc_feature
<222> LOCATION: (1337)..(1337)
<223> OTHER INFORMATION: n=a, c, g or t

<400> SEQUENCE: 13
gttctacgct taaaacaacc tcttccccct aactttaaaa tcagatacag taaaagcctc 60
ttgttgagga tgtggttatc ttggtagatg agagtgtgtc agaaacaggt agaaacttac 120
ctagcaaaag aactagtact gtatcttgac ttgttacatg gcaacaatca attagatgat 180
aatttctatt taaaagcatt ctatatgggg aaagacatgt tcattttgat aagtaaagac 240
aaaatctagg tttttagttg atgtgtgttg tacatgtggt ctttggaaag caaacctaac 300
tatgtattat tgacattaaa aatgatgact taatgctggg taaatcctgt actcagaaga 360
tactcactga tgatccattc ctggctataa cctatgaact aaacgaattt tttaatcttg 420
gtgcttatta ttagcttcag cttgcctctc taataatccc aacaccttgt gctctcatcc 480
tgctctcagc ttattacttt gccccgtttt tcactgagaa gacagaagca gttagaatag 540
agcttccaca agctcctact ttgatatctg ccctcctagc actggggcca ctgtttcctg 600
ctttccctct atgtgaactc tccgtgtttc taatatcatc tggattaatc acatcctctc 660
tggcctactc aaagatagta actctaacaa cttttccctc tctttcatgc aattcctact 720
ttgcctctct ctgctggact ttttctcatc gacatataaa catgctgtta tgtctcccaa 780
ccaaaaaaaa tgcaaaaacc ctttcagccc tatgctcacc catcatccag ctgtagtcct 840
cttccttcct tttactctcc tttattatag ctaaatttct tgaaaggatg gaatgtccac 900
ttcctctcct cccatccttt cctgaaccta ccccaatctg ccttttgtcc ccactgtgcc 960
agtgagaggg ctcttgataa gctctccctt cattgacttc cagttgctca atgaaatggg 1020
cagttctcag tcctcatctt acttgacttt ccagcagcat ttagtactac cagccagtcc 1080
tcatccttga aatactttct tttcccatat ctctaactgc ttaagtcaaa agggttccat 1140
gatccagtcc ttacataact taccttcttt ggctacgctc attatctggg atctcatcca 1200
gtcttggggc tttaaatact atatggggac aactacagcc gagaaccttt ccctgaactt 1260
tagactcttt tgtccagaag attatacaaa ttctctgttt ggttatagaa tttagaatgc 1320
cccaaatcaa gataatnctc cctcaattct gttcctccta taagcttccc caatcggtaa 1380
atgaaaactg tgtccttcta gttaatcata ccaaaatcct aaaaatcatc cttaactcct 1440
ctcatctctg atatccatat ccaacccatg agcaaatact gtcaatctgc cagaatccaa 1500
acatctctcc agccccattg ccaccaccct ggtccaagcc accaccaggc cttgcctag 1559

<210> SEQ ID NO 14
<211> LENGTH: 1455
<212> TYPE: DNA
<213> ORGANISM: Homo sapiens

<400> SEQUENCE: 14
ggagtgtgaa ggtggtgagt catgggagtt ccaagggaat gggtgataaa gggaggtctc 60
aaatgaggca caagtggaga aggtagcttg ggaaaggaga aggatgcttc tccttataag 120
atgggaaagg cagaggaaga gggtcaagat acagtgatct aggggtgata tggaagtgag 180

```
ttgagagaac tcaactctgg gttctgaaac ccctaggttt ggggggcttt gagataggga    240

agaggtttaa agtcagttgt tctagcaaat atggtttgga atttatttgt gatgcttaaa    300

aatattgctg aagagaagtg aagtctatcc tagagttgga tggtgagatt atttagtgga    360

actaccagat ccatgttgtg attctttcca gtatcattca gcagcccttg ggcagttgcg    420

aggcaagtca tcagtggtgt atggagattt tcccaggtgg gtgtggttga aggcagggaa    480

gaacgagttc aggagcacat tacaagaaga aggtgactgt aaggtccagg ctgagcagga    540

aggtaaagca agaaggaaac atgaggttgt gaagagaagt ttagagggat gaggaggcag    600

gagagatgaa cagttgcagg atgtagctag agtggcgatg ttagatcttg gggccagaga    660

tctttacaat gattatgaag atcaaagggc attagaatca agctataaag agccactgtt    720

tgatgttggg atgtgaggat gctgcaggtg gatgtctgca cattgatggt gagaacatgg    780

tcatcctggc cctgctgggt ctttgctaaa gagactgtgc tctgttcttg gggccgtttt    840

catcatctga ttagagcagt ggtccccaca tggtgttctt tggaccatct gtataaaatg    900

ttcataggtc aaggataaaa tggaaaaaca gagaaaatgt cacagaaatg tgcccattgt    960

tgaaagacca ccagctgtcc tttttggagg attgttcttt attctaaaaa tgtatatatt   1020

ctattctatt aaaacatttt tgtattggca ttttttctc ttttatgaaa tgccatgggg   1080

tagaaatttg taatgtatcc aattctcctg tcttcatgta ttgccctgtg gtgggggagg   1140

ggatgtggct agtactggcc aagaggctgg gggcagaggt gcaatgttag acttctagcc   1200

tggagcattt aattcttagt acaagactct ctaacattct tctccctctg ttccctgctt   1260

ggtgatactc gaggtattgc aacccccatt aaccttagtc ttagggcaag tttgatggga   1320

aacagagcac cccacacctc cctgcagatg aagcatgagt gagaaaaaca acttctgatg   1380

tttgaagtta ccaagatttg ggagttgttt gttattgcag caaaacctca cctattctga   1440

ccaatcatgg tggaa                                                    1455
```

```
<210> SEQ ID NO 15
<211> LENGTH: 904
<212> TYPE: DNA
<213> ORGANISM: Homo sapiens
<220> FEATURE:
<221> NAME/KEY: misc_feature
<222> LOCATION: (281)..(281)
<223> OTHER INFORMATION: n=a, c, g or t
<220> FEATURE:
<221> NAME/KEY: misc_feature
<222> LOCATION: (329)..(329)
<223> OTHER INFORMATION: n=a, c, g or t
<220> FEATURE:
<221> NAME/KEY: misc_feature
<222> LOCATION: (469)..(469)
<223> OTHER INFORMATION: n=a, c, g or t
<220> FEATURE:
<221> NAME/KEY: misc_feature
<222> LOCATION: (471)..(471)
<223> OTHER INFORMATION: n=a, c, g or t
<220> FEATURE:
<221> NAME/KEY: misc_feature
<222> LOCATION: (539)..(540)
<223> OTHER INFORMATION: n=a, c, g or t
<220> FEATURE:
<221> NAME/KEY: misc_feature
<222> LOCATION: (662)..(662)
<223> OTHER INFORMATION: n=a, c, g or t
<220> FEATURE:
<221> NAME/KEY: misc_feature
<222> LOCATION: (692)..(693)
<223> OTHER INFORMATION: n=a, c, g or t
<220> FEATURE:
```

-continued

<221> NAME/KEY: misc_feature
<222> LOCATION: (701)..(703)
<223> OTHER INFORMATION: n=a, c, g or t
<220> FEATURE:
<221> NAME/KEY: misc_feature
<222> LOCATION: (776)..(776)
<223> OTHER INFORMATION: n=a, c, g or t
<220> FEATURE:
<221> NAME/KEY: misc_feature
<222> LOCATION: (785)..(785)
<223> OTHER INFORMATION: n=a, c, g or t

<400> SEQUENCE: 15

```
tggaaaacca aaaaattgat atgctaaagt atactcttaa aggtcttaat actttaaaag     60
tatatagatc tcatgaacat aattcatttg aggaaaaaaa tacaaatcat ttcttgtccc    120
aggaaaacag taaatcttta atggaacttt ttagcaatta tgacaaaaag aatggaaaaa    180
tgtttaaaca tatataaaag gctagacgtt tatcgccaaa tagtatctaa aggtcataga    240
atagttagga attctgtcat tttgttttgt gtaataaata ncccccttcct ttaccctttc    300
accctaataa tagatatcca ccattttgnt gtgattatcc aactatagag taccttttttc    360
aagaactcat tatataccaa agtaggagct tgctgacact gataatgctt tatttagttt    420
tgtagtgaca tacaattacc atttgcttag gaaaaaaaat aaagaacana nacaagtaaa    480
tttttttaaaa ctatggttgt gtatatataa gttgataaaa atcctttggg agaaaactnn    540
tgtcttgtgt gttaagagca ttaaatagtc ataccccctta gcctagtgtg tcttctatcc    600
tgaaaaaaaa ttaacaaagc aaatactaac ttaagaaaaa aaactacagc actgaaaaga    660
tntgttgtaa tattgtttat gctaacataa annatgtaaa nnnttatata ttgtttatac    720
tgacttataa tttattacta tacatagtgt aaattatgat acattggctt tggtangcag    780
ttttntaacc gctaataata taaataccat actattaaca atctagaaaa atgattctgg    840
tataggttat gtgaaaaggc acaaaataaa attgtatata gtacactagc aatgaacagt    900
ctga                                                                 904
```

<210> SEQ ID NO 16
<211> LENGTH: 984
<212> TYPE: DNA
<213> ORGANISM: Homo sapiens

<400> SEQUENCE: 16

```
acagatttac tctcctgaat tttccagaaa tgtagatact tttaaatcaa aggaaggctg     60
tattttgttt tgttcagaac ttttctattc cagaaaatca tgtcaattga cagcaaagcc    120
acttgtggtc attgagcctc ctgtgtaaag caccgacgtc attctgtagt tgtcatcact    180
gtattcaggg tgattctaca cgtaggagtg agcatttgac agcttccatg tcttctagtg    240
cggctgagaa tttacatatt aagatacaca ttatttatta tcaattactt tcctgtttca    300
atgtccattt agagcactaa aaatatcttt gtaggtagtt gatattactt atgaatttta    360
tttcaggaga gcaaaggaaa atacaagata gttgtatgaa aagggggcac cgggtgtgct    420
agagtggctc accaccgccc tacacagtgg gctaattggc tggagagtag agctgactct    480
gcacagttgc atgctgaccc tctgaagaat ttttttacaa aagcgtgacg tcgcgtgaag    540
accttgacag aattagcaaa gcggttgaga tgcatacttt ggagtcagac agactccagt    600
tcacatcttg gcttttatac ttacagctgt ataaccgtag acaatctatc taccctctgg    660
ccgactccat ttcctcaatt ataagatagg ataacttgtg aaatgctttc cacaagatta    720
ctattgcatt tattctcctc accactctta atgaagagag tcttgtaaca gataactcta    780
```

```
attgtcttca gagttcaggt ccccaagaaa gattatgcct tctaaaagct agtctgtttc    840

cttccagtgg gagccatttc attcatgctg ctctactctt tacttggact gctagcaaac    900

atggagctaa gtactcatgc ttaatttctg tggctttcct caaatagggt ttcaatacta    960

tagtttgccc tcactccatt ccct                                           984


<210> SEQ ID NO 17
<211> LENGTH: 429
<212> TYPE: DNA
<213> ORGANISM: Homo sapiens

<400> SEQUENCE: 17

cgtgataaaa atagtttgct ctgagttttt gcctttctgg aatttaatag caagaaaaat     60

atgttcccta ccctctcagc ccccactcta cctccctgtg gcttgttaag ccttccttct    120

gcctcctgca tcaacttcct gatggagagt gtatgaatgc aaaagctcct cccttagcac    180

ttacctagtg cttcactctc tgggctcctg ccactgggtc ccagctaaga gagtttgatt    240

ttaaaatcca gagtttatgg ctttttaaaa ataacctctc acctatttat caaaagctcc    300

ttctaaataa tatttacaac aacaacaatg ataatggcta ctatctagta tttcccattt    360

tccagacact gtgctgggct ctttccaaac actgttttaa tctttaccaa cacccagtcc    420

gccgctcta                                                            429


<210> SEQ ID NO 18
<211> LENGTH: 734
<212> TYPE: DNA
<213> ORGANISM: Homo sapiens

<400> SEQUENCE: 18

cttttggacc ataagcctca ggaagctata aggattattt gcattcttac acctgggcac     60

tcttcctttt tgctgaatac cagtttttca atcttttcta tttttgaaat aggtaagaaa    120

agaaaataat tttctagaat ttgaagaaaa atcttaaaac atttgaaatt ctttgttatg    180

atgactaata taacgaatag cactcaggtt tatcaaatat taacattttt ccatatttgt    240

tatagaattt ttttccatat ttgctacaga aataatttct ttatatatat aatacatatt    300

tgaacactga ttttacttga tacattaata taatgctgat gtgctgagat gaataaatca    360

aagaacctct tggagctctt ggtgtgcaat aagcatagtt aacgaatata aaataagtga    420

tattttctag aaaataaata ctggtctaca atgccttatc tgtcatttca aagtctctaa    480

aaagatctga aaatccaatg ccttttaaaa ataaaattac ggtaatctca tttggccaca    540

aaacctgttc agaattgatg tgaggctatt aagatattta tttctcttat ttattagtga    600

atattcatct ttcactacag aaatactaac gagtttgatt acagggtgct ttagacttcc    660

ctcaaggtgt acatatttgc tacttttctc taaaatccca aacatcctgg attctgaaac    720

acatctaaac cccc                                                      734


<210> SEQ ID NO 19
<211> LENGTH: 1184
<212> TYPE: DNA
<213> ORGANISM: Homo sapiens

<400> SEQUENCE: 19

attctaactc tgtgacatgc agtctgtgac actgagagtt acttgcacct tcctctggac     60

tggagatcct ttctagtgca gacattttat aattctattc tgtatcgtgt tcatttaagt    120
```

-continued

```
agtctgcttt atcattacat taacatttat gaaagacttg ctggtatcat tggcttagcg    180

attatttttc catctagatg ctttttttaa agaaatgaag agaatatgta atgttttaaa    240

tgtacatttt agtttgattt aaattttaat caaggatttt tattttatac attacatact    300

gatcactgtt ttatgttaac tctggtccta ataaacagaa aataacaatt tggaatatct    360

acaacaatga gagctcgagg taaaatatag cataaataag acatatatgt gtatgaactg    420

agatatatag aaataattaa atgtaacaat cttttggacc ataagcctca ggaagctata    480

aggattattt gcattcttac acctgggcac tcttcctttt tgctgaatac cagtttttca    540

atcttttcta tttttgaaat aggtaagaaa agaaaataat tttctagaat ttgaagaaaa    600

atcttaaaac atttgaaatt ctttgttatg atgactaata taacgaatag cactcaggtt    660

tatcaaatat taacattttt ccatatttgt tatagaattt ttttccatat ttgctacaga    720

aataatttct ttatatatat aatacatatt tgaacactga ttttacttga tacattaata    780

taatgctgat gtgctgagat gaataaatca aagaacctct tggagctctt ggtgtgcaat    840

aagcatagtt aacgaatata aaataagtga tattttctag aaaataaata ctggtctaca    900

atgccttatc tgtcatttca aagtctctaa aaagatctga aaatccaatg ccttttaaaa    960

ataaaattac ggtaatctca tttggccaca aaacctgttc agaattgatg tgaggctatt   1020

aagatattta tttctcttat ttattagtga atattcatct ttcactacag aaatactaac   1080

gagtttgatt acagggtgct ttagacttcc ctcaaggtgt acatatttgc tacttttctc   1140

taaaatccca aacatcctgg attctgaaac acatctaaac cccc                    1184


<210> SEQ ID NO 20
<211> LENGTH: 550
<212> TYPE: DNA
<213> ORGANISM: Homo sapiens

<400> SEQUENCE: 20

ctttcccgct cccggcccca gtgccttgca tgcagcaagg tcttggcatg tgcaagcttc     60

cttaaggagc ctgcagcttt gctccaaagc acacactggc agaccttggc cagatgcctg    120

gcacaggggc tggggaggga aaggctgccc aacccccgtt ttccctttgc agatgagcat    180

tctccaaatc catgtttacc cagtcctcct taatgctgcc ttccaaactg tcagcgggtg    240

ctaaaaagca cacattagga tgaattagaa catgccaggc tgcaagggcg ggtgtcatcc    300

cagaactcac agagcacgtt gagggctcag ccgctcagcc acatctttag gtcccaccag    360

catctccccc caggcatgga cctccccaat ttaccctgtg aaggctgcat ggagaagatg    420

caggtcttag gaacagccag catcaccaga ggtgccactt agtgagtacc cagtgggctc    480

ccaacaccgt gctgagctcc cagtgggaga accggaaccg tctgcctgtt ctctgttgta    540

ttccagcatc                                                           550


<210> SEQ ID NO 21
<211> LENGTH: 599
<212> TYPE: DNA
<213> ORGANISM: Homo sapiens

<400> SEQUENCE: 21

tactatgtgc cagacacagg agttttcagg atgagtcaat aagataataa acacaaagtc     60

ccggccccag tgccttgcat gcagcaaggt cttggcatgt gcaagcttcc ttaaggagcc    120

tgcagctttg ctccaaagca cacactggca gaccttggcc agatgcctgg cacaggggct    180

ggggagggaa aggctgccca acccccgttt tccctttgca gatgagcatt ctccaaatcc    240
```

atgtttaccc agtcctcctt aatgctgcct tccaaactgt cagcgggtgc taaaaagcac 300
acattaggat gaattagaac atgccaggct gcaagggcgg gtgtcatccc agaactcaca 360
gagcacgttg agggctcagc cgctcagcca catctttagg tcccaccagc atctcccccc 420
aggcatggac ctccccaatt taccctgtga aggctgcatg gagaagatgc aggtcttagg 480
aacagccagc atcaccagag gtgccactta gtgagtaccc agtgggctcc caacaccgtg 540
ctgagctccc agtgggagaa ccggaaccgt ctgcctgttc tctgttgtat tccagcatc 599

<210> SEQ ID NO 22
<211> LENGTH: 618
<212> TYPE: DNA
<213> ORGANISM: Homo sapiens

<400> SEQUENCE: 22
gaaaaactac tctttttggt gtaaagatat tttttatatt ttctttgctt gtaaagagtt 60
attatcaatt tgtaagtata aaaactgcaa gtatagttgg tagttgataa gaaaggtaga 120
taataaaact taaaagggat ggacacagat tgaaaaaggc cttgagtgcc aagacaagag 180
ctctgaactt taacaggcac tggaaaccgt cataggtctt aggtaggaat atgctgtgct 240
cccaccatct taattaggtc ttatggaggt ttgatagcaa gagggtagga atatcattta 300
gcaggctact gcaagtatcc aggtgaaatg tacagaggtt ttgaactagg ctgctgggga 360
gggtgcagag aagaaatatt ttggaaataa aatggacaga aagtgtataa atggataaag 420
agaggaatag aactgacacc aggcttcaag cctgatgcct gagaataaag gtgtaattat 480
gaagggaatc caggaagaca tggaaagagt ggttggagta aggttaaagt gatagtttta 540
gattgggtta ttttgacgtt gaagtgttga ccaacttctt aagtgaaaat gtgcaacagt 600
cattgaaaat atgagttt 618

<210> SEQ ID NO 23
<211> LENGTH: 711
<212> TYPE: DNA
<213> ORGANISM: Homo sapiens

<400> SEQUENCE: 23
gaaaaataag tttttgttaa tggttgggat tttcttactg gcctcgtggc aagttttgtt 60
atctcttatt atatatattc taccttttta tgggaaaaac tactcttttt ggtgtaaaga 120 tatttttat attttctttg cttgtaaaga gttattatca atttgtaagt ataaaaactg 180
caagtatagt tggtagttga taagaaaggt agataataaa acttaaaagg gatggacaca 240
gattgaaaaa ggccttgagt gccaagacaa gagctctgaa ctttaacagg cactggaaac 300
cgtcataggt cttaggtagg aatatgctgt gctcccacca tcttaattag gtcttatgga 360
ggtttgatag caagagggta ggaatatcat ttagcaggct actgcaagta tccaggtgaa 420
atgtacagag gttttgaact aggctgctgg ggagggtgca gagaagaaat attttggaaa 480
taaaatggac agaaagtgta taaatggata aagagaggaa tagaactgac accaggcttc 540
aagcctgatg cctgagaata aaggtgtaat tatgaaggga atccaggaag acatggaaag 600
agtggttgga gtaaggttaa agtgatagtt ttagattggg ttattttgac gttgaagtgt 660
tgaccaactt cttaagtgaa aatgtgcaac agtcattgaa aatatgagtt t 711

<210> SEQ ID NO 24
<211> LENGTH: 547
<212> TYPE: DNA

<213> ORGANISM: Homo sapiens

<400> SEQUENCE: 24

```
aacaaggtaa gcatagccgg ttttcatggg cttattttct catggaaatg attctgtgta     60
gaattgatta ttcatgaaga cacaatgtaa catcaagttt gggttaatgt tcctcagtgc    120
aacaacaaag acgtatttgt aatcactccc atgagtctac tttgcagcaa gaacatgcat    180
tttggaatta ttcccatcct gtgtgctgaa tactggatgt gactcttagt cagctctgtg    240
acccttgtca agtaacttaa gctctttgat catcagcttt gtcatctgta aaatgggcat    300
tctgcctact tcaaagagaa gttgaaggga ttaaacgaga taacctacaa agagcaccca    360
gcacaatggc ctaaaaaagg aaggcactga atcattctca ctcccctacc ttcagtctga    420
tcctgctctt attgtcaaaa ggataatttc aattttaata gatctgagat cctgtttttt    480
aataataatt ttatagaatt tttcatttta tggcaggcac agggctcatg cctgtaatcc    540
cagcact                                                              547
```

<210> SEQ ID NO 25
<211> LENGTH: 549
<212> TYPE: DNA
<213> ORGANISM: Homo sapiens

<400> SEQUENCE: 25

```
gcaaagacct catgaggggt caacgagggg aagccctcgt gggtcagagt acgccacggg     60
acagactatg ctggcagctt ctagatcgtt gaactctgtt cttgaagact gggcagaatc    120
taggaagaac ggaggcacct gagttcacca ggtgggacga acctggcctt agcacggaat    180
gtggcattta ggtgcttaag tttgttgttt tttttaaatt aaagtggttg acctggagag    240
ctggtgtgga aatgtagcag gaggtctatt tggaaagaag gatggagtag attatgaaag    300
ttcttaaata tcataatgag gcttgtggat tttattctgt ggtttggatg ctctcttctt    360
ccatcccttg gatgccaaca ggcatgcact gtttaatctt ggaattcaaa cggtggcctc    420
aaacagtgag gctgagtatg tggcctcatt agcttcagac ccagcagggc tgggctcaca    480
ggcgtgtcat ttatcaaggg cttgaatctc tgccagctaa tttatctaag acaactctat    540
gagatgggg                                                            549
```

<210> SEQ ID NO 26
<211> LENGTH: 350
<212> TYPE: DNA
<213> ORGANISM: Homo sapiens

<400> SEQUENCE: 26

```
ctttaagata gatgggtaca catattatga atatactttc cttttgccag accttgacat     60
tctgtagact tttaatggaa tattatttgc ctctttcatc ttaccttgac gtatgaggtg    120
gatggcttac gtgcagggta atgtatgaac cttcccaagc tctgtacaaa tataacttgt    180
cattcgtaga gacgtatgta tttatatgtg tgcatgcagt cttatttgta gattttcttc    240
ccatttgctt aatactgaac gctatggcct agatgtgaaa tttaccaggt actactcata    300
gcaggcagtg aaaccgtgga ctcagctgct ctttccttct ttcctcccca               350
```

<210> SEQ ID NO 27
<211> LENGTH: 627
<212> TYPE: DNA
<213> ORGANISM: Homo sapiens

<400> SEQUENCE: 27

```
ccacgcgtcc ggtttcaaaa aagaagagta agtcaaaggt taaacttttg gggcggagga      60

aaaaggataa gaaagaggat acagagttta atcagagttg gcatcagata gagtaaccat     120

ggacatttgg aagctgtaac ctctctcata tttcgccaag gataactgct tcctgtatta     180

tcatgtaatg agttttatgc gtgatggaaa atgtaaaagt aatcttaacc caaacctgca     240

ttttaatgcc acatggaccg gctgtaattt atggcatctt taagatagat gggtacacat     300

attatgaata tactttcctt ttgccagacc ttgacattct gtagactttt aatggaatat     360

tatttgcctc tttcatctta ccttgacgta tgaggtggat ggcttacgtg caggtaatg      420

tatgaacctt cccaagctct gtacaaatat aacttgtcat tcgtagagac gtatgtattt     480

atatgtgtgc atgcagtctt atttgtagat tttcttccca tttgcttaat actgaacgct     540

atggcctaga tgtgaaattt accaggtact actcatagca ggcagtgaaa ccgtggactc     600

agctgctctt tccttctttc ctcccca                                         627
```

<210> SEQ ID NO 28
<211> LENGTH: 548
<212> TYPE: DNA
<213> ORGANISM: Homo sapiens
<220> FEATURE:
<221> NAME/KEY: misc_feature
<222> LOCATION: (133)..(348)
<223> OTHER INFORMATION: n=a, c, g or t

<400> SEQUENCE: 28

```
gttgcatgtg ttggggatat ttctccatta gcaagaagtt tccaaacctt accagtgttt      60

tgatgaatct aggaacagat ctggcagtga gacctacatc cattttcccc acggacagca     120

tcttgctgga gtnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnnnnnnnnn nnnnnnnnnn nnnnnnnntc ctcctgttaa     360

atgttgatag aaaaatggtt tgatggcagc atatatccag attgtagatt tcataatatt     420

aaaggggagt gggcaaataa taaaatgcaa gaaatgaaag catttgaaaa tttagaggac     480

agaaatgact tttaagtaag tgattttagg tgtactggaa tgagtaatct agaatatttg     540

atatgaga                                                              548
```

<210> SEQ ID NO 29
<211> LENGTH: 988
<212> TYPE: DNA
<213> ORGANISM: Homo sapiens

<400> SEQUENCE: 29

```
aaatccacaa ataataattt acatttgaga aaatccccca gtacttctat gaataagatc      60

aagggcaaaa gtgtgctctt ttacatgcca gaaacctcaa gaatttttcg taaggtacag     120

ttcaaggaaa accaagcagc tcttgactca acaaataaaa atgtaagtct gtctgaagaa     180

ttagtgaacc agggcaccca gtcagctttc tcctaaaata aatttggaga gctgaaagat     240

atggatgagg tcagatttct aaaaaatcag tatacacaca gtgttttaag aataaaaaac     300

agattgatta aagggaaaaa taatttgtaa ataacagaag ccataactta gagataaaaa     360

taactgtcct ctgattaaca gaacttttag aatgatgaga aaaattaata acacagttaa     420

agatatcaca gtgattttta aaaatatttc aaggttgaag aaaaaatatt cctatgagaa     480
```

-continued tacaggctga aaaagatcaa agtaaaatga atcaggtcgg tatcagaaat ttcagtgata 540
tacaatgaag gaataaaatg gagcagcagc tatagttttg aaacaaaatg tattttccaa 600
ggttcttgta cccaaccaaa ttataactta tgtgttagga caatagagaa gtaattttag 660
ccaaagaaat aatctgaaat tatagcatct atgcacattt attgaaacaa gaaactcaga 720
aatcaaaata gccgagaaat taataaaata ttcaaaagga ggaaaataca ttttagaata 780
aagcataatg aggaataaaa tcactatgac tttttgaaag tataaaaatt gttatttttt 840
tctatgaata cttgctcaaa tttaaagtag tggatttaat gttgtagcgc taagtattca 900
gccaagaggt agaactaata aataaaaatg atagttcttt taaaaaaaca taaaaataat 960
tatctcatga gtagcctaag aaaaaagc 988

<210> SEQ ID NO 30
<211> LENGTH: 651
<212> TYPE: DNA
<213> ORGANISM: Homo sapiens

<400> SEQUENCE: 30
acaccaaata aggtaatgga gataaacttt agaaatcatg tttttaaact gatgtttaaa 60
agggatggaa ctcacactat ttaaaaggtg aagactgcca cgtcagtgtg aaattgttta 120
aaaaagtcca acacatttgg ggctggacac accagtcaaa tggttgaaat tagaagatgg 180
ggaaaaaata tgtcaggtaa atactttatt tcattggatt tatgacttcc cctgtaagaa 240
gcattattat tttatataaa tacccaaaaa aaaaaaacaa caaaggcagc taaattctga 300
aattaattgc atatgcatca tgatttcaga tatattaaac tgtgaaaaaa gtgcgttaaa 360
atggtaaagc acaataatca aaataaagtt tgtatagcaa tattaatatc acataaaata 420
taaattagaa caaaaaagca cttataggga taaagagaaa caccagagaa aaacaaagaa 480
aaaatcctaa gaaaatataa ccttcacata cttatatggt ttaacagcaa agcccgtgaa 540
ctgtttaata taggaagcac aaacgtgact gaagttacaa gagactgaga caactttcaa 600
aactcatggg ggagaaattt tatcacttca acagaaactt aacaatttaa c 651

<210> SEQ ID NO 31
<211> LENGTH: 553
<212> TYPE: DNA
<213> ORGANISM: Homo sapiens

<400> SEQUENCE: 31
actggacttc ctctttcttc catcaaagac taagatgcct tttttccttg atgtacttta 60
ttttgtggag catattatct actttcctga aaaaatggtt tatgggagat aaatcataaa 120
aaggttttat tagattctac atctcatgat tgatccaaaa gacgttttaa aaacaaaaca 180
aaaaaaggcc ttgtaggtct taactcttac ttagcctcac atttatttga tagtttgagt 240
gagtatctta aaaattgaag atgattataa aaattttaat gtagacatta ttttttctca 300
gaattttgaa ggcactgctc tgtcttttgc agttggagag tctgatgcca ttctgattct 360
taaatctttt atacaaaaca tgtttttgct tttggcagga agctttacct tttctttctt 420
tcaagtgtcc tgaaacttca ctgagatgta tcatggtata ggtccacttt gatccactgt 480
cctggacact tgctaggcct tttcagtctc gaagctcatg actttcaggt aagagaaatt 540
tacgtctaag acc 553

<210> SEQ ID NO 32
<211> LENGTH: 2159

<212> TYPE: DNA
<213> ORGANISM: Homo sapiens

<400> SEQUENCE: 32

```
ggccgcttaa ttaaagatct tttttttttt tttttttag tgctgaataa tagtccattg     60
tctttatgta ccacagttta tccactcacc tactgaagga catcttagtt gcttcaatgt    120
tttggaggtt acagataatg ctactataaa catccatgtg caggtttttg tgtgaatgta    180
aagtttccaa ttcatttgag taaataccaa agcatgcaat tgctacatca tataaaagta    240
tgtttggtac tataagaaac tgccaaactg tcctcttaag tggctatgca tattttcact    300
tccaccagca ataaatggag ttcctgttgc tccacatgct cactagcatt tggtgttgtc    360
agtgttctgg attttggtca ttctaataag tacatagtca tatctcgttg ttttaattta    420
caattcccta atgacatatg atgttgaaca tcttctcata tgcttatttg ccatctgtat    480
atctactttg gtgaggtatc tgttcagatc ttttgccttt tttttttctt tgagacagag    540
tctcactctt gtcacccagg ctggagtgca gtggcacgat ctcagctcac tgcaacctct    600
gcctgctggg ttcaagcaat tcttctgcct cagcctccca agtagctggg attacaggca    660
cccaccacca cgcccaggta atttttatat ttttcataga gatggggttt cgccatattg    720
gccaggctgg tctcaaactc ctgacctcag gtgatccacc tgcctcagcc tccgaaagtg    780
ctgggattac aggcgtgaga caccacaccc ggctcttgtg cacgtaattc tattttattt    840
gagatggagt cttgctctgt tgcccaggct ggagtgcagt ggcatgatct cggctcaccg    900
caacctccgc ctctcaggct caagagattc ttgtgcctca gccttccagg tagctgggac    960
tgtgcaccac catgctgggc taatgtttgt atttttagta gagttggggt ttcacttagc   1020
caggctggtc ccgaacttct ggccycaaaa gatctgcccg cctcggcttc tcaaagtgcc   1080
ttggattccc aaagtgctgg gattacaggt gtgaaccatc atgactggca aagcatatgc   1140
ttttgaggcc cattgtcttt cctaatttgt tgaatacata ctacatgagt atcttcaaac   1200
actgagcaac tacgaaattt tttgtgaaat gccagtagaa atactaataa gtattatatt   1260
tccaggtaaa atgagacacg ggttttttaa agtcactgaa tgtgcatgga agtatttttg   1320
agactcacta aggaaataga ggcaccagca ctctctgtaa tttttagtaa aagactccta   1380
tctgagggaa tctgggattc cccccaaaag gatctcagtt tgatcaccct acagtgaagg   1440
tcaacaagtc ctacccaaga attcaaaaca cctgtcagtc tttagttccc tagtcttgaa   1500
gtttgagcag agtcacatat taccagagaa ttcgaggata gtatctccga gaagccggga   1560
aaaaactcag ttaagagaga agggatgctt taaaaaaaaa aaaagaggtc ttagacgtaa   1620
atttctctta cctgaaagtc atgagcttcg agactgaaaa ggcctagcaa gtgtccagga   1680
cagtggatca aagtggacct ataccatgat acatctcagt gaagtttcag gacacttgaa   1740
agaaagaaaa ggtaaagctt cctgccaaaa gcaaaaacat gttttgtata aaagatttaa   1800
gaatcagaat ggcatcagac tctccaactg caaaagacag agcagtgcct tcaaaattct   1860
gagaaaaaat aatgtctaca ttaaaatttt tataatcatc ttcaattttt aagatactca   1920
ctcaaactat caaataaatg tgaggctaag taagagttaa gacctacaag gccttttttt   1980
gttttgtttt taaaacgtct tttggatcaa tcatgagatg tagaatctaa taaaaccttt   2040
ttatgattta tctcccataa accatttttt caggaaagta gataatatgc tccacaaaat   2100
aaagtacatc aaggaaaaaa ggcatcttag tctttgatgg aagaaagagg aagtccagt    2159
```

<210> SEQ ID NO 33

<211> LENGTH: 450
<212> TYPE: DNA
<213> ORGANISM: Homo sapiens

<400> SEQUENCE: 33

```
agaaaacaag atccagatac aaaaatcgat tgtattttaa ctatgctaat aattagcaga     60

tattgaaact ttttaaacat acaatttatt atagcatcag aaaaatggaa tgcttaagta    120

taaatctgac aaaaaatgtg agctacctgt acactggacc actaaacact agtgaaacaa    180

aattgaagag ctacttaatt ggaaatcagt ttcccccag atttatctat agagtcagtg    240

aaatcccaat caaaatctca gcaaggtctt taagaaattg acaatcttat tttaaaattt    300

aagtggagat gcgaaataac taaagcaatt ctctgacaaa aacaagaaaa aagctagaag    360

gctaacaacc acactgattg caagatttat cagaacaggt ataataatca ggccagtgtc    420

atatcggcat acacgataga ccaggagatc                                     450
```

<210> SEQ ID NO 34
<211> LENGTH: 584
<212> TYPE: DNA
<213> ORGANISM: Homo sapiens

<400> SEQUENCE: 34

```
ctagacttat ggatttgagg gagctgtgtg aaactcatca tggcaaatat gcttatgtgt     60

atatatcctt tgccatacat gtgctgcaaa ctgtaatgaa atgttattta taagactggt    120

aaggcatgtg ttattagact ggacacacaa aagcccttga ttatctagga agcaatcctc    180

tagggtccag atgtagtttg gaatgtgggt gtttagtatc actgtacttc attactgatt    240

tttatttcta tgctgtttga ctgtattagc tctttgttat tattggggag gtagccagag    300

gtctccagat tcccataatg aatttacagg tgtgatctta tggacaagga ggagtcagct    360

gtattagttg gggttcaat cttgcctgat aagcttttcc tagttggttt tacagatacg    420

agccctgatc tactccctgc tgccactgtc tgtttctatg atgcatgtca ccatgatatc    480

tgagtatgta tgaaaatata tttaggctaa ttttaactag aatatggaaa ggaaaaagtt    540

ctattgctct gcattgctct gttttcagca atcactgttt ttca                     584
```

<210> SEQ ID NO 35
<211> LENGTH: 642
<212> TYPE: DNA
<213> ORGANISM: Homo sapiens

<400> SEQUENCE: 35

```
gctagactta tggatttgag ggagctgtgt gaaactcatc atggcaaata tgcttatgtg     60

tatatatcct ttgccataca tgtgctgcaa actgtaatga aatgttattt ataagactgg    120

taaggcatgt gttattagac tggacacaca aaagcccttg attatctagg aagcaatcct    180

ctagggtcca gatgtagttt ggaatgtggg tgtttagtat cactgtactt cattactgat    240

ttttatttct atgctgtttg actgtattag ctctttgtta ttattgggga ggtagccaga    300

ggtctccaga ttcccataat gaatttacag gtgtgatctt atggacaagg aggagtcagc    360

tgtattagtt gggggttcaa tcttgcctga taagcttttc ctagttggtt ttacagatac    420

gagccctgat ctactccctg ctgccactgt ctgtttctat gatgcatgtc accatgatat    480

ctgagtatgt atgaaaatat atttaggcta attttaacta gaatatggaa aggaaaaagt    540

tctattgctc tgcatttgct ctgtttttca gcaatcactg tttttcaccc acatatagaa    600

agtttgaaag ctctctctga tgtctggcaa ccagatctcc ca                       642
```

<210> SEQ ID NO 36
<211> LENGTH: 669
<212> TYPE: DNA
<213> ORGANISM: Homo sapiens

<400> SEQUENCE: 36

```
ccaaaattta ctagaatgtc ctgaaccaca tctttcataa tgttgctgac tcaaagactc     60
ttgaaggctc ctgaccacat tattcgcaat tctaactctc ttgccacccc ttccccatga    120
cccatgtaca attacatgct ctagatcttc tcctcaaaga tgaacataag tctgaaatat    180
caacaccttg gcagccctat tatcaattgc tgatctgtag tccccatgta agtacgcctt    240
ttttagcaac cagtttttgt cccagccata ttaatacttg tggtcagtgg ttaacaatgt    300
tgaagcttaa attatatcca gatgaaattt taaaaaggaa tcacttgtgt tcctctgtgt    360
taacacagga atcccagcat gtgtttctct tccaggaaac cataattata tgtacaaata    420
tctacccgga caattagggg cataatcatg ctctaaatag aagtgttcaa acaagtcaac    480
accttctctc cagttattcc tctttcttct ttctcttaga tgtcatggtt tctgtgtctc    540
aagacattta tgatttgatt tttctaaccc tttctaggtt ctattagagt caattagaca    600
acatattcct tctttctaag aatctggaca aggaggtata cttttctaaa ttttaatcct    660
attaatgcc                                                            669
```

<210> SEQ ID NO 37
<211> LENGTH: 1006
<212> TYPE: DNA
<213> ORGANISM: Homo sapiens

<400> SEQUENCE: 37

```
tcttaaaatg agcaccctca ggactgttag gtaggagagg tgttagattt caagtagata     60
caaataggtc cagaaggtaa aatgaggacc caaggataga agagcgacag tgatttcagc    120
tgagcctcag ttccaagcac agaacttttc agaaacagaa tgggttgcat aatatgtccc    180
cttttaaaag acactttgca gacctggatg cctgtgtgtt ggcatggagc atagaggttt    240
cctgtcctgg gtaaacatgc tgtgctggac taggttctct ctgaaagtct ctccctgctt    300
caggagtcta gaattctaag tttcttctca ggagactcca aaatttacta gaatgtcctg    360
aaccacatct ttcataatgt tgctgactca aagactcttg aaggctcctg accacattat    420
tcgcaattct aactctcttg ccaccccttc cccatgaccc atgtacaatt acatgctcta    480
gatcttctcc tcaaagatga acataagtct gaaatatcaa caccttggca gccctattat    540
caattgctga tctgtagtcc ccatgtaagt acgccttttt tagcaaccag tttttgtccc    600
agccatatta atacttgtgg tcagtggtta acaatgttga agcttaaatt atatccagat    660
gaaattttaa aaaggaatca cttgtgttcc tctgtgttaa cacaggaatc ccagcatgtg    720
tttctcttcc aggaaaccat aattatatgt acaaatatct acccggacaa ttaggggcat    780
aatcatgctc taaatagaag tgttcaaaca agtcaacacc ttctctccag ttattcctct    840
ttcttctttc tcttagatgt catggtttct gtgtctcaag acatttatga tttgattttt    900
ctaacccttt ctaggttcta ttagagtcaa ttagacaaca tattccttct ttctaagaat    960
ctggacaagg aggtatactt ttctaaattt taatcctatt aatgcc                  1006
```

<210> SEQ ID NO 38
<211> LENGTH: 589
<212> TYPE: DNA

<213> ORGANISM: Homo sapiens

<400> SEQUENCE: 38

```
aggagctggg ttttgcttaa cagaaggagc actgacccat gttatagaca atcgcagaat     60
ttcatatccc catctataaa atgaaaacac aatacttctc accaacactt atacagcacc    120
tactatgtgc taggttagag atcataaact ggtgatatgt aagtggaata taaccctcag    180
acttggtctg tgtgttctac gcagttgatc tgcaccagcc tttgttaaaa ttggaaggaa    240
attgctaata tttaaaatca ggatatttcc cacgaaaatc tacatttcta gtatctcaga    300
aaaatcatta tttggcagca ctgggccaga atttctgcag ggcaattgtt gtcctgactt    360
gggtggctgg tggaaatggg cgtgtactcc taagtttgtc ccaattgcta ccgctctatt    420
acttcatcct ttaatgttca ctactcttgg ccctgtggga tttttgaggc tgagattcct    480
atattaggtt ctgaaggcaa aacacacaca gaaaagaatg atttcaggcc cttcctgagc    540
atactcatga tgtataactt ttatgacagt aatagtagta tctagcaat                589
```

<210> SEQ ID NO 39
<211> LENGTH: 528
<212> TYPE: DNA
<213> ORGANISM: Homo sapiens

<400> SEQUENCE: 39

```
aagacctgtc tttattttta gaagtaagaa taaaagagat tgtggtggag tatcacaggc     60
agcgtgggag cactgaggga gcccctgacc caccctagga gtggatcagg atgacttctg    120
aaaggccaaa ctgattaata agggataaat aaagtcatgc aaatgaaaag gttgtatatg    180
tgttggggga aagcattcca gacagaagga ccagtgtgtg caaaggccct ggggtgagag    240
gtgcctaatc agtactgaat atacaaagag gtagagctgg gactaaacca ctgtgctcac    300
tttgcctgct tgaattccga ttccaaggag tggaatagac ttcaaatgtc ttcaagtcca    360
cttgtttctg ccaagttctc atttttgttc catgaaggca gagcaccttc tttatttcat    420
ccactgatga cttctcagcc tctagaattc tgccttatga tggatttctc agaaatatgt    480
ttgtgtaatg aagacaagga cagtggttag agtttacatt ctactggg                 528
```

<210> SEQ ID NO 40
<211> LENGTH: 673
<212> TYPE: DNA
<213> ORGANISM: Homo sapiens

<400> SEQUENCE: 40

```
caaaaaataa aaaccaaaac attagttggg cgtggtagtg tgtcccaggt actcaggaag     60
ctgaggtggg aggattgctt gagtcccgga gttggatgct gcagtgagct atgattgtgc    120
cactgcagcc tgggtgacag aacaagaccc tgtctttaaa aacaagaagt aagaataaaa    180
gagattgtgg tggagtatca caggcagcgt gggagcactg agggagcccc tgacccaccc    240
taggagtgga tcaggatgac ttctgaaagg ccaaactgat taataaggga taaataaagt    300
catgcaaatg aaaaggttgt atatgtgttg ggggaaagca ttccagacag aaggaccagt    360
gtgtgcaaag gccctggggt gagaggtgcc taatcagtac tgaatataca aagaggtaga    420
gctgggacta aaccactgtg ctcactttgc ctgcttgaat tccgattcca aggagtggaa    480
tagacttcaa atgtcttcaa gtccacttgt ttctgccaag ttctcatttt tgttccatga    540
aggcagagca ccttctttat ttcatccact gatgacttct cagcctctag aattctgcct    600
tatgatggat ttctcagaaa tatgtttgtg taatgaagac aaggacagtg gttagagttt    660
```

-continued

```
acattctact ggg                                                       673

<210> SEQ ID NO 41
<211> LENGTH: 447
<212> TYPE: DNA
<213> ORGANISM: Homo sapiens

<400> SEQUENCE: 41

ctcaagcagg gctagcacct ccaatctaga gcaccctgca cttccggctc caccggtctt     60

cttgtccctt cactgccttg cctaggggtg ccttctcctc ctctcttaag ctgagtacaa    120

gtgataatat agtgattaac acaatgctgt agtgttttcc tgttaaacag ggaatggttg    180

attttccagg agaatagaaa atgaaattgt cattggagga cctcctcagt tgaaatcatt    240

ctgtggctga tttcctccta ttttgttttt tgttggttgg ttggtttttg ctttttcagt    300

agctacccag gtatacaaat agcttctttg cagttctgat catctttagg ggccgcattg    360

ggcataattg gaataataat actagctaac ctgcttgcag ggcttgctct gtgctgtgca    420

ctttgtgagc actttaaata taggagc                                        447

<210> SEQ ID NO 42
<211> LENGTH: 562
<212> TYPE: DNA
<213> ORGANISM: Homo sapiens

<400> SEQUENCE: 42

ctcaagcagg gctagcacct ccaatctaga gcaccctgca cttccggctc caccggtctt     60

cttgtccctt cactgccttg cctaggggtg ccttctcctc ctctcttaag ctgagtacaa    120

gtgataatat agtgattaac acaatgctgt agtgttttcc tgttaaacag ggaatggttg    180

attttccagg agaatagaaa atgaaattgt cattggagga cctcctcagt tgaaatcatt    240

ctgtggctga tttcctccta ttttgttttt tgttggttgg ttggtttttg ctttttcagt    300

agctacccag gtatacaaat agcttctttg cagttctgat catctttagg ggccgcattg    360

ggcataattg gaataataat actagctaac ctgcttgcag ggcttgctct gtgctgtgca    420

ctttgtgagc actttaaata taggagccaa acctctcttt ccaaaagcct gaagggcagg    480

tgtcctcgca gttcccattc catagatcac catccttcca tggaaagtac tctgtggact    540

gtaacttgcc atctagactt tt                                             562

<210> SEQ ID NO 43
<211> LENGTH: 848
<212> TYPE: DNA
<213> ORGANISM: Homo sapiens

<400> SEQUENCE: 43

gggtctttct agctttcttg tcctttgtga agctggactg gtgatgtgca gttgaagaca     60

gcatcatcgg gggccttctg ctccatgtgt accctccagt atttgcaaaa gattgaacct    120

acaagatacg ttattagggc aagtatttac atggaaaggc tctgagttct ccaagacttt    180

ggtcattttt tacaagatga tgtactaccc tgatgatttg tggaatcttc ttaggaaccg    240

tgactgtgtt gcttttctga tcatgggtac agggccatct ttgttgaggc ttcccatgtg    300

tgtgggcaca gagcttctgt ggcattccag cagtagatta atggagctgt catcctctga    360

agcctcatgg gttgtgcatg caaacctggt cctgtgaact gcatgggagt ctcttaaaag    420

ggcagaggga ttccttcctt tgtgaaaggt ttagaatggc acatatttgt aatttccaga    480
```

-continued

```
ctcatctttt cccactctca cattcactct gtatttggcc gtactaaatt gttgacagtt    540

ctccaaatac aacagcattg ctattctgct gccttcgtac atgccgttta cattactgtc    600

acattgtcca ggaattcatc cctgccatga ctgcagtgcc ccctctggga gctccccgtg    660

ccctgtgcct gccgctgtca gagcttccag catgctgggc tgtggaggtg ttggtctgtt    720

tgcccaccca gcaagcctct aagctcctca aagacaccaa ctgtcacgca tatctggagc    780

agcacctggt accttacggg tccttaaatg ccggctgaat gaatgatgtc ttctgtctct    840

ttaaaccc                                                             848
```

<210> SEQ ID NO 44
<211> LENGTH: 1111
<212> TYPE: DNA
<213> ORGANISM: Homo sapiens

<400> SEQUENCE: 44

```
gggtctttct agctttcttg tcctttgtga agctggactg gtgatgtgca gttgaagaca     60

gcatcatcgg gggccttctg ctccatgtgt accctccagt atttgcaaaa gattgaacct    120

acaagatacg ttattagggc aagtatttac atggaaaggc tctgagttct ccaagacttt    180

ggtcattttt tacaagatga tgtactaccc tgatgatttg tggaatcttc ttaggaaccg    240

tgactgtgtt gcttttctga tcatgggtac agggccatct ttgttgaggc ttcccatgtg    300

tgtgggcaca gagcttctgt ggcattccag cagtagatta atggagctgt catcctctga    360

agcctcatgg gttgtgcatg caaacctggt cctgtgaact gcatgggagt ctcttaaaag    420

ggcagaggga ttccttcctt tgtgaaaggt ttagaatggc acatatttgt aatttccaga    480

ctcatctttt cccactctca cattcactct gtatttggcc gtactaaatt gttgacagtt    540

ctccaaatac aacagcattg ctattctgct gccttcgtac atgccgttta cattactgtc    600

acattgtcca ggaattcatc cctgccatga ctgcagtgcc ccctctggga gctccccgtg    660

ccctgtgcct gccgctgtca gagcttccag catgctgggc tgtggaggtg ttggtctgtt    720

tgcccaccca gcaagcctct aagctcctca aagacaccaa ctgtcacgca tatctggagc    780

agcacctggt accttacggg tccttaaatg ccggctgaat gaatgatgtc ttctgtctct    840

ttaaacccac cttctactat gctaccataa tggatatttc ttctaactgg caattttaaa    900

gatcctgctg tggcctttgg tcaggctttt gagcagggtt tggcaaatcc gtggcctatg    960

gaccaggtct ggcccgcggc ctgatggtca tccttgcgct ggccgtttca ggatgaattt   1020

acagttactg acaccaattc ctgtggaaaa taataaaaga ctcgcggctt tcacatcacg   1080

tagcttaaaa agggaacacg gggacaaact g                                  1111
```

<210> SEQ ID NO 45
<211> LENGTH: 626
<212> TYPE: DNA
<213> ORGANISM: Homo sapiens

<400> SEQUENCE: 45

```
tgttctgaca tcaacaggaa aaatggtaca agaatatttt cagatcatgc caaaaagcag     60

cacttcgtta aaaggaagaa aaaatttcaa gtaaaacata aacaggtttt tagattgctc    120

gataattcaa ttagtgaatc aaacaatgat aaaagctata tatttcctgc tgatttgtca    180

ggaaatagtg acactgacaa agatagcatt acctaagaat ataaaagcaa agatagcgtt    240

gccacagact gcttaatgtg tgtcatctat caaaggggta tatgtgatga gaagaaaaac    300

ttgaaatgcc ctcaaatgtt tcagctatca gaaactgaaa aaactcttac tagtgtgttc    360
```

-continued cgcataattg tgagcaatat tctaaagatc gacgtttctt cagttatgat tttcttgagg 420
ctacatcaga gaacttcctt aaacctgtcg gtaatacaaa atcagtgagt catggcaaag 480
gggagacatt atctatctgt tcttgactat ggaaaataat gttgcagaat ctttgtcctg 540
tgtgtgaaga agcgatgagt acaggaccag aactgtccgg aagacgtatt tcaggagacg 600
cacatggcag tcgggcgccg ctctag 626

<210> SEQ ID NO 46
<211> LENGTH: 185
<212> TYPE: DNA
<213> ORGANISM: Homo sapiens

<400> SEQUENCE: 46
gaagaaactg tgaggtcaca atacttttga ttcattatgt gaatatacat acacactcac 60
atctctatta ctgtatccat ctctatatac ttgaactcca tatgctctat attaacttcg 120
ccaaatccaa cccaacaaac agggttcatc tctgattttt ccccccatat ttatgattct 180
cagac 185

<210> SEQ ID NO 47
<211> LENGTH: 268
<212> TYPE: DNA
<213> ORGANISM: Homo sapiens

<400> SEQUENCE: 47
atggatttgc cacaagctgg ctttgaaagc agtggtagag tgtgaaagaa gttaccttaa 60
gacttcttgc cagttgcact gtaggtacga tgtactgttt gttgtgattt gactttcctc 120
caccaccccc ctgccccagg aagatgtgat cttgtgcatc ttgtgttcac gcagagtagg 180
gtagttggat ctttgtcaag tctcagtgat ccacatgcgt gcatctattt tgtcagtctg 240
cttgtctttg tatccatgtc atactgtc 268

<210> SEQ ID NO 48
<211> LENGTH: 108
<212> TYPE: DNA
<213> ORGANISM: Homo sapiens

<400> SEQUENCE: 48
gtcgacgacg acagcaatgc cgatccgcgt cacgcccgca accggctgcg gctgcaggtg 60
atgcctgccc tgcgcgaggc cttcccgcag gcgccgctgg cgctggcc 108

<210> SEQ ID NO 49
<211> LENGTH: 83
<212> TYPE: DNA
<213> ORGANISM: Homo sapiens

<400> SEQUENCE: 49
gatcgagatc ggcggcgtgc cgctggtgca tctgcccgcc gaggcggtgc gcgcgccctg 60
gccgctcgac gagcgcgagg tgc 83

<210> SEQ ID NO 50
<211> LENGTH: 475
<212> TYPE: DNA
<213> ORGANISM: Homo sapiens

<400> SEQUENCE: 50
aaagaaacaa gcaacaaata ggaaaatcaa atttttagaa gtaggtgcat aataggggaa 60

```
tagcttaagg ggagaactat gatgttaatt ctttgaaagt gagtaatgta attagaacaa    120

taacactatg agtttttcta taaacaaaat atagcaagat taagttgata acatacattt    180

ctaaaatttt ggcttcctta gagaaagcca accaaatata aaattttaca gcagagtcaa    240

gtttttcag tttggcctat attttctttg gtaacactgt tctgaatgta tatgcagtgt     300

ttatttcaca acttccctct gaatgacctt tcaaaaatta atgattcttc acattcatga    360

ccagatgttt tctctgatgg aagcatctga tgtttgcagt catcaaataa gattcaaaat    420

gtctgtttca agcaaatcaa gtaaaacttc tccatcacat caaaagtaag gcttg         475
```

<210> SEQ ID NO 51
<211> LENGTH: 607
<212> TYPE: DNA
<213> ORGANISM: Homo sapiens

<400> SEQUENCE: 51

```
aaagaaacaa gcaacaaata ggaaaatcaa atttttagaa gtaggtgcat aatagggga      60

tagcttaagg ggagaactat gatgttaatt ctttgaaagt gagtaatgta attagaacaa    120

taacactatg agtttttcta taaacaaaat atagcaagat taagttgata acatacattt    180

ctaaaatttt ggcttcctta gagaaagcca accaaatata aaattttaca gcagagtcaa    240

gtttttcag tttggcctat attttctttg gtaacactgt tctgaatgta tatgcagtgt     300

ttatttcaca acttccctct gaatgacctt tcaaaaatta atgattcttc acattcatga    360

ccagatgttt tctctgatgg aagcatctga tgtttgcagt catcaaataa gattcaaaat    420

gtctgtttca agcaaatcaa gtaaaacttc tccatcacat caaaagtaag gctttatatg    480

gttcacaagt agctatatga aataaacaga atttaaacga tcttaataat ttttttcttt    540

aaacaaggtg acaaaataac aatgccaata tataaaaact cctcattaat gataagtgct    600

agatgga                                                              607
```

<210> SEQ ID NO 52
<211> LENGTH: 590
<212> TYPE: DNA
<213> ORGANISM: Homo sapiens

<400> SEQUENCE: 52

```
ctcctcatta atgataattg ctagatggac accatgtaaa gtatggaaaa tgcctgtctg     60

aacaaatgct tttgctaaat tctctgaatt tttttttgtt tttcctcacc agttagcttt    120

gatgttttga tcagagtttt tagaaaattt ctaggatctg ttgcctttgg actttagagc    180

ttcttggagc cacatgtcag tactaaaacg ttttcttaag ccctcgcttt ccatagcaaa    240

aacatgttat gtccattatc cacctaactc atacttaaaa acaacaccca agatgctcta    300

ttttgttttc aaagtcagag aagaaaatag aggggaagta tttttatgtt cttttccctg    360

aattggtcga agctagttag ttcaaaaaag atacaaaata tggaatacca cctattttat    420

ttcctggcaa ctgtttcatt caaatcatag agtaacatat gatttactac actcctttat    480

gaatattaat ctcgtatctt cacagaatga cttaatatca ttgatcagct agaacatcga    540

cctcacctgt ctgttgtttt taacgaaatg tttattccta gtcaaaccac               590
```

<210> SEQ ID NO 53
<211> LENGTH: 217
<212> TYPE: DNA
<213> ORGANISM: Homo sapiens

<400> SEQUENCE: 53

```
agtctgctaa ctcattccag tggtttttc caactgcatc tcagttatct tacatagact     60

gcaagaagtg agaaagacaa gaggttatct agtccagcct tgctatttta tagtttaaat    120

ccctcaacca catccctgat gaacttttgc cagtgccggt aattaacaat atcacaaggc    180

tgttctgatt gtctgtattt ctcagtgttt gttagag                             217
```

<210> SEQ ID NO 54
<211> LENGTH: 430
<212> TYPE: DNA
<213> ORGANISM: Homo sapiens

<400> SEQUENCE: 54

```
aataaagata agaatgacaa cagatttctt tttgggaaca atgagagtgg gaagacaatg     60

agcaacatct ttaaagtact gaaaggtatc agcagaccca tgctacaaaa aatgtaaaag    120

aacatcatca ggcagaagga aaaaaatagt atcagattga agtctgttct acacaaagta    180

atgaatacca gaaatgataa ctacctgggt aaatatataa gattattttc ttcttattta    240

aagtaagagt gagattctta tcaacaatag cataaaggct gaaggggaga aatggaagtc    300

tattagtgta atcttataca tgatgtggta tgatgtcact tgaatgtaga attataaaga    360

taaacagcat aaactcttaa agcaaccacc aaaataacaa agagttataa ctaataattc    420

agcaaaggag                                                           430
```

<210> SEQ ID NO 55
<211> LENGTH: 2956
<212> TYPE: DNA
<213> ORGANISM: Homo sapiens

<400> SEQUENCE: 55

```
gttgttgttg ttttttttga gacagagtct tgctctgtcg tctaggctag agtgcagtgg     60

cgccacctcg gctcactgca acctccacct cctgggttca agtgattttc ctgcctcagc    120

ctcccgagta gctgggttta caggtgctcg ccaccacgcc cggctaattt ttgtttcttt    180

agtagggttt caccgtgttg gccaggctgg tctcgaactg ctgacctcgt gatctgccca    240

ccttggcctc ccaaagtggt gagattacag gcgtgagcca ctgcacctgg ctttttattt    300

ttttaacttt gtatacggta ttttcttttt ctgtatagaa gtcaaactat tttccttcat    360

ggattctggt ttttgtctct tcattccaag accatttaaa aaaatgtgtt cacattttcc    420

tctgatactt ttaaggtgtc tttctgaaga taaaacctga tgtgtctgca atgctagagt    480

gaggcttgag tatgggcaag cttcctgagt gcacgtgtga gctgaggaca gcatggcgtg    540

tgaggaagga tcagtccaca cagctcatgt aagctcacga gagaggctac tggcttcact    600

gcacgtgtct actgggtgtt ttgacaacgt ggagtgaata cttcatgtcc tcacaaattc    660

aaatgctgtt tttatcatgt ataaatatta tattggaaaa aaataaaatc ataatgaagt    720

tatttgctca cttatcttga agaaaaacac atacatgttg cacttctgaa tttaccttaa    780

cctgtttaat acctactgag aaagtctact attcagaatg cagaaaaagg tggaaggagt    840

ggttagggcc ctaaaagtca aactgggtcc ccgcagccca gagatcaaca ttatttaaaa    900

actcaccatg caaagctaat agagaacgaa ccatgtaacc ctttttgaac tattacattt    960

tcaactcaaa gcttggccct atcttccagt tacacgtcta taaatgtcaa ctacgaagcc   1020

tttcagaggc cctacacttt gcaaatgaag tcagtggaac cctcctgcac acagacagag   1080

cccaaaggac aggagtgcag ctggcagtgc agcccttggt ggggccaagg ggcaggtcac   1140
```

-continued

```
atggaagggt gcgggttcct cccatgtcca tacgctgacc cctcactcat gctcccagac   1200
ccctctggac accgtgctgc tggcagatgc tgtgctcctg ggaggtggga tgcaagctga   1260
accttgctca ctccctttgg gctaaatgac aggtgagcac tgggcacagc aaatgtgact   1320
ggccacagcc tcatctgcag gggcaacaag tttcccacac aagatcccgt taccatccca   1380
cacaccccgt ctccatctct ctggatcctt gttcagacac agtgttttta tcaacaccca   1440
cagaggaaaa tgggtaaatg cgaaaactcg tttttgcagc tttaaattac ctatgtcctc   1500
agaatgtagc agaattcaca gctggctggg aaaagctata atacatgcac tgcacacact   1560
aacgcgtttg aatataaata agcgtatctt taagttctgt aaagttcctt accgccaagt   1620
agaataaaga caccaacctc ttttgtcatg aggctcaaag tctcctctgg ataccgttct   1680
ataatctgaa gtaatctagg aaacttcaat ctggcttcat tggaatttaa ttttaaagct   1740
ttcaacattt tctccaccac aagtgctgga tacgcctgca gttctgcaga atcaataact   1800
atcaaggaca ccaaagaaga aagcaatggt caatgtatcc caatatccat aaactatgat   1860
gttaaatgct aacactttcc ctttttggct tgtattttgt agtgtcattg ttctcttctt   1920
aactaccact ttacaccaac aaacaccagg tacagttttg tatctatcct ggagccaaat   1980
ccttccatta gagtgcccat tctgcatgaa gcacagtttg aatcctgggc tgggaacata   2040
aggggcaatt ggtggttatt gaatttattc caggagcatg aagcaggcca cacgagccag   2100
taatattgaa gctgcaagca aaatatcaaa gtagaaatta aacaaatgga aacagaggac   2160
cacttgactc catttaaatg taggtcatgt tgcttagaga ggccattgtc tctctctttt   2220
ttttttttta agatggagtc tcgctctgtc acccaggctg gtgtgcagta gtggatatcg   2280
gctcactgca acctctgcct cctgggttca agcaattctc ctgccccagc ctcctgagta   2340
gctgggacta caggcatggg ccaccacgcc cagctaattt ttttgtattc ttagtagaga   2400
tggggtttca ccacgttggc caggctggtc ccgaactcct gacctcaagt gatccacctg   2460
ccttagcttc ccaaagtgct gggattacag gcgtgagcca cctcacctgg cctaatttca   2520
ttttatctcc tttgctgaat tattagttat aactctttgt tattttggtg gttgctttaa   2580
gagtttatgc tgtttatctt tataattcta cattcaagtg acatcatacc acatcatgta   2640
taagattaca ctaatagact tccatttctc cccttcagcc tttatgctat tgttgataag   2700
aatctcactc ttactttaaa taagaagaaa ataatcttat atatttaccc aggtagttat   2760
catttctggt attcattact ttgtgtagaa cagacttcaa tctgatacta ttttttttcct   2820
tctgcctgat gatgttcttt tacatttttt gtagcatggg tctgctgata cctttcagta   2880
ctttaaagat gttgctcatt gtcttcccac tctcattgtt cccaaaaaga aatctgttgt   2940
cattcttatc tttatt                                                   2956
```

<210> SEQ ID NO 56
<211> LENGTH: 517
<212> TYPE: DNA
<213> ORGANISM: Homo sapiens

<400> SEQUENCE: 56

```
cctggctgga gcggacacgg tcaagaccgt cctccctacc ttctcccttc aacccaagct     60
caactcaacc aaaaatggcc cctctgtccc catgcctgat aggaaagtca ggggaaagtc    120
tgtccgatta ctgtcaaaga agacaggagg taagggtcag agtggaccac tgactgaata    180
tgagtcgcag aagtgttaga ggcagaagtc cagggccatt tccttaatat cgaagtgtct    240
```

-continued

```
ctgctggagg tctgggatgg atttttgccc tgcatttaga agttctgggg tcctgggaga    300

ggggagagaa gcccaatagc agaggagaca gagtgtgggc ggggcgagcc ggaggggtgc    360

atcctgggag agcaccaggg tgagggaggg gtgaagatga gccccgtcag ggaagcgctg    420

gcgagtgtgg gaagtcacct gcccctcggc ctgtgagctg ctctgcttgg agtgactaag    480

gctcgggagg tccaggctcg gccagaggca gctcata                              517
```

<210> SEQ ID NO 57
<211> LENGTH: 1490
<212> TYPE: DNA
<213> ORGANISM: Homo sapiens

<400> SEQUENCE: 57

```
ggggaaccag acgcccagtc acaggcgaga gccctgggat gcaccggcca gaggccatgc     60

tgctgctgct cacgcttgcc ctcctggggg gccccacctg ggcagggagt aagtcagtgg    120

ggtctgccct caatctcccc tgcctccctc caggagagcc agggactcac ccggcccttg    180

tcccagacta actctggtca cagaaccatc ctgtctgcct ggaggggcgg ggtcccctgt    240

tctggcagag gtcacccccca tatcaccgca tggggatttt cttccctttg ggtctctctt    300

ttcttcagag atgtatggcc ctggaggagg caagtatttc agcaccactg aagactacga    360

ccatgaaatc acagggctgc gggtgtctgt aggtcttctc ctggtgaaaa ggtgagtagg    420

gctatggtca tgggcccagc gccatgtccc ctcccatccc acagtttcag gaactcaggg    480

cagcgggtaa gcacccgtgg ccacttttgc cacacatgcc tggctactgt cgatgcttcc    540

tggctcccgc tgatgcttcc tggctggagc ggacacggtc agaccgtcct ccctaccttc    600

tcccttcaac ccaagctcaa ctcaaccaaa aatggcccct ctgtccccat gcctgatagg    660

aaagtcaggg gaaagtctgt ccgattactg tcaaagaaga caggaggtaa gggtcagagt    720

ggaccactga ctgaatatga gtcgcagaag tgttagaggc agaagtccag ggccatttcc    780

ttaatatcga agtgtctctg ctggaggtct gggatggatt tttgccctgc atttagaagt    840

tctggggtcc tgggagaggg gagagaagcc caatagcaga ggagacagag tgtgggcggg    900

gcgagccgga ggggtgcatc ctgggagagc accagggtga gggaggggtg aagatgagcc    960

ccgtcaggga agcgctggcg agtgtgggaa gtcacctgcc cctcggcctg tgagctgctc   1020

tgcttggagt gactaaggct cgggaggtcc aggctcggcc agaggcagct catatgtggg   1080

ccacagtgac ggcagctggt gccttctggg tcacggagac ctggcgctgc acgcagctct   1140

cctcaccagg atctcagtga ctcctcccaa aagtcacacc cactttgcag acggggaaac   1200

tgagtccgga gaggctgggt aacgagctca agatcacagg gcccaaaagt ggtagaatca   1260

gggttggtga ccagtgagtc tgtgtcagag acccaaagtc tgatggtgct ggactctctg   1320

catcccggga aggaggatgg gggcgctgag gacccgggat gtgctgggcc atcccagatc   1380

tggacgtcca aagctttgcc tctctcccag tgtccaggtg aaacttggag actcctggga   1440

cgtgaaactg ggagccttag gtgggaatac ccaggaagtc accctgcagc               1490
```

<210> SEQ ID NO 58
<211> LENGTH: 436
<212> TYPE: DNA
<213> ORGANISM: Homo sapiens
<220> FEATURE:
<221> NAME/KEY: misc_feature
<222> LOCATION: (197)..(197)
<223> OTHER INFORMATION: n=a, c, g or t
<220> FEATURE:
<221> NAME/KEY: misc_feature -continued

```
<222> LOCATION: (432)..(432)
<223> OTHER INFORMATION: n=a, c, g or t

<400> SEQUENCE: 58

ctctgtctcc tcataggaat ttcttagttt cttggctttc gaatgtgact caacccctcc     60

cttggcctgt ctgtctgctg tgtcgctttt aggttctgct gccacggcta actatgtttc    120

cctgtgtttc cagataaact tgtgagggtc agaagctgac agaccaagct catttttcaa    180

gccaatctgt gtcatanaga gaccacgggt tttccttggg ttgggtcctt ctacctggtt    240

cagtcagctg tgaacaaaac ttgtggaatt tggtcatttt ccttaaaatg gagatacgag    300

agatcaccat ggctggcgtg aaactagttc tggatctgat tgtcttttca attgtttgtc    360

catcaggtga acccactctg aagggacttt tggtaacatt ttccccaaaa taaagatcat    420

taattaatta tnaaaa                                                    436


<210> SEQ ID NO 59
<211> LENGTH: 458
<212> TYPE: DNA
<213> ORGANISM: Homo sapiens

<400> SEQUENCE: 59

ctctgtctcc tcataggaat ttcttagttt cttggctttc gaatgtgact caacccctcc     60

cttggcctgt ctgtctgctg tgtcgctttt aggttctgct gccacggcta actatgtttc    120

cctgtgtttc cagataaact tgtgagggtc agaagctgac agaccaagct catttttcaa    180

gccaatctgt gtcatacaga gaccacgggt tttccttggg ttgggtcctt ctacctggtt    240

cagtcagctg tgaacaaaac ttgtggaatt tggtcatttt ccttaaaatg gagatacgag    300

agatcaccat ggctggcgtg aaactagttc tggatctgat tgtcttttca attgtttgtc    360

catcaggtga acccactctg aagggacttt tggtaacatt ttccccaaaa taaagatcat    420

taattaatta taaaaaaaaa aaaaaaaaat gagcggcc                            458


<210> SEQ ID NO 60
<211> LENGTH: 359
<212> TYPE: DNA
<213> ORGANISM: Homo sapiens
<220> FEATURE:
<221> NAME/KEY: misc_feature
<222> LOCATION: (336)..(336)
<223> OTHER INFORMATION: n=a, c, g or t

<400> SEQUENCE: 60

cggacgcgtg ggaaacacaa actgcatcat ccaaaaatac acctttggtc cacggatgcc     60

actggaagac atctgaattt tagacctcca gagagaagat ctgggtggct agctccagag    120

tggaggcatg cttgcttttt ctttacactt gtgaagagga atggatccgg acatctgcaa    180

tctgggtaga ggacggcagg cagcaagctt agccactcgg ccaggcttct cagcccttac    240

tctagacatg tgatccttcc tccacgtgat atacttcaca actttcttac ggctactcaa    300

ggcatcccaa gttaaaagga aggtcagatg tgattnatca ctttattatg ataaaaaaa     359


<210> SEQ ID NO 61
<211> LENGTH: 932
<212> TYPE: DNA
<213> ORGANISM: Homo sapiens
<220> FEATURE:
<221> NAME/KEY: misc_feature
<222> LOCATION: (161)..(180)
<223> OTHER INFORMATION: n=a, c, g or t
```

<400> SEQUENCE: 61

```
tggccagaga catatgaaaa gatgccttag acatatagca tcttttctca tccacttact     60
aggagaaatg ctcactaaaa ttatcctgta atgccattta aaaaaatctc agattgttga    120
agtacaaaaa gttagataac atattatcaa ccaaaatgtg nnnnnnnnnn nnnnnnnnnn    180
ttgggccagc tgtgtttggg taaactagtt aaggtggtag ggttgtttgg tcaggaatta    240
aatcataaag aaaaacaaaa cctctgaaat gaaaactcat ggtgagggta aaacttcacc    300
ccttgtagtc acttatgttt aactggtcta ctggattttt ttaaaggtta agaaaacaca    360
aactgcatca tccaaaaata cacctttggt ccacggatgc cactggaaga catctgaatt    420
ttagacctcc agagagaaga tctgggtggc tagctccaga gtggaggcat gcttgctttt    480
tctttacact tgtgaagagg aatggatccg gacatctgca atctgggtag aggacggcag    540
gcagcaagct tagccactcg gccaggcttc tcagccctta ctctagacat gtgatccttc    600
ctccacgtga tatacttcac aactttctta cggctactca aggcatccca agttaaaagg    660
aaggtcagat gtgattctca ctttattatg ataaaaaaaa ttactattta aatactataa    720
ataaatatta taataaatac taagctagaa ccatcagaat acatcacttc tgtatccagt    780
tttcaaagta tctttggtgt ttgtcaggaa taaataaaag taatcatttt atttctatta    840
aattatatct ggcactagtg gctagtactt ttgtacttat tagtacaacc ttaaaaagtc    900
ttaaaaagat ttcttttggt ttcagaacat aa                                  932
```

<210> SEQ ID NO 62
<211> LENGTH: 554
<212> TYPE: DNA
<213> ORGANISM: Homo sapiens

<400> SEQUENCE: 62

```
ctggcagatc cggacgggca ggactgggtg tgtcccatga gagcacctcc ttcctggcct     60
ttcctgtgga ctttgtccca caccacctgc ctgggttcct tcctttagtc acttccagct    120
ccaggcacag cagttggtga ctccttggtg ggagccgtgt cccacccggt cctgatactg    180
ccgtcttctc tttcacagtc ctccaggctt gggccagcct tgggggcagc agagcttctg    240
gggtgagtgt cgagatcctg tgtcctgaga gcggtagtca gggagagggc tggtcggggc    300
agggctgccc gggcaggaca caggatgcgg ccggccaggc tggggccaag gtgttcagac    360
ctggactttg ggctcgtgct ttcttcatgg ttgcgccttg ctcgctgtcc cttggagtct    420
tcatttggtt ttgctttttt tgtttgtttg ttttcaccta atttttgcca gacttaagct    480
agttttgctg ccttttgaaa ctagtggaag aatcatttta tttcctgggg ataatttggg    540
ggcttttgaa tcca                                                      554
```

<210> SEQ ID NO 63
<211> LENGTH: 786
<212> TYPE: DNA
<213> ORGANISM: Homo sapiens

<400> SEQUENCE: 63

```
ccagtggcct gtgtcctagc aaatgagagc caccctgaaa aataaaatcc tgtctcccca     60
acgccagccc tggcaaggca cccagaactc tccggaatgc ttgaaggcag ggcctggcct    120
ttccatgggg tccagggctg tggggtccct ggcggtactg tgggcctgca gagcggggca    180
tgtgggctga agaccgtctc cccaccatgg tgggaaggga caaagggtgg ccctggcaga    240
tccggacggg caggactggg tgtgtcccat gagagcacct ccttcctggc ctttcctgtg    300
```

-continued

```
gactttgtcc cacaccacct gcctgggttc cttcctttag tcacttccag ctccaggcac    360

agcagttggt gactccttgg tgggagccgt gtcccacccg gtcctgatac tgccgtcttc    420

tctttcacag tcctccaggc ttgggccagc cttgggggca gcagagcttc tggggtgagt    480

gtcgagatcc tgtgtcctga gagcggtagt cagggagagg gctggtcggg gcagggctgc    540

ccgggcagga cacaggatgc ggccggccag gctggggcca aggtgttcag acctggactt    600

tgggctcgtg ctttcttcat ggttgcgcct tgctcgctgt cccttggagt cttcatttgg    660

ttttgctttt tttgtttgtt tgttttcacc taatttttgc cagacttaag ctagttttgc    720

tgccttttga aactagtgga agaatcattt tatttcctgg ggataatttg ggggcttttg    780

aatcca                                                               786
```

<210> SEQ ID NO 64
<211> LENGTH: 575
<212> TYPE: DNA
<213> ORGANISM: Homo sapiens
<220> FEATURE:
<221> NAME/KEY: misc_feature
<222> LOCATION: (411)..(411)
<223> OTHER INFORMATION: n=a, c, g or t

<400> SEQUENCE: 64

```
ggcacagcta gttggtgact ccttggtggg agccgtgtcc cacccggtcc tgatactgcc     60

gtcttctctt tcacagtcct ccaggcttgg gccagccttg gggcagcag agctttctgg    120

gctgacatgg ggctcattgc tcctttctcc aagccctctg agggacatca aaagcgtggg    180

acgcatccac ttttccacca tcttggcttg ccccactgtt ccctccatcc tggagggcct    240

tccttaagca catgtgtggg ggtgggcagg cacactggct gatagctgtg gatgcggccg    300

tgacatcctt cacccctgcc cccatggcat gcatgatcca ttagggagga ccgtctgcac    360

aaaggtctct tgccctgtgc aagcttcctg caagactgga cttgcaaaag ntccagcctg    420

tatggctgga gttccccatg cctgccaatc tcctgtcgac tgcgagtcag ctccgatact    480

tcaccagatt cagccacctg ggggagctgg aagtgaatct cctcgtagct gagccttctg    540

atgagactgc agccccggct gacacctgga ttgca                               575
```

<210> SEQ ID NO 65
<211> LENGTH: 834
<212> TYPE: DNA
<213> ORGANISM: Homo sapiens

<400> SEQUENCE: 65

```
cagcagttgg tgactccttg gtgggagccg tgtcccaccc ggtcctgata ctgccgtctt     60

ctctttcaca gtcctccagg cttgggccag ccttgggggc agcagagctt ctgggctgac    120

atgggctcat tgctccttct ccaagccctc tgaggacatc aaaagcgtgg acgcatcact    180

ttccaccatc ttgctgccca ctgtccctcc atcctgaggc ctccttaagca catgtgtggg    240

gtggcaggca cactgctgat agctgtggat gcggccgtga catccttcac ccctgccccc    300

atggcatgca tgatccatta gggaggaccg tctgcacaaa ggtctcttgc cctgtgcagc    360

ttcctgcaga ctggacttgc aaagtccagc ctgtatggct ggagttccca tgcctgccaa    420

tctcctgtcg actgcgagtc agctccgata cttcaccaga ttcagccacc tgggggagct    480

ggaagtgaat ctcctcgtag ctgagccttc tgatgagact gcagccccgg ctgacacctg    540

gattgcagca ctcatgaaag accctgagca gcaggaccag tttggcagag cccgaattcc    600
```

```
tgacccacag gaactgggag ataaaactct gtggttttaa tcttctcatt ttagagtgct    660

cagtgtccat gtggtgtgaa cacgcttcat tcaacctggg cccttgggag agatgctgag    720

tggttcccgg gctgtcccca ctccacacca tggcagtgaa gagctgctga agtacatgct    780

tcatagtccc ttgcgtctcc tctatgagta cagttcctgt ttgtggagta gcaa          834
```

<210> SEQ ID NO 66
<211> LENGTH: 437
<212> TYPE: DNA
<213> ORGANISM: Homo sapiens

<400> SEQUENCE: 66

```
cgagaaagaa aaggtatagc ttaaagtggc ttttgagcag gcatgagttt atggaaccaa     60

ggattcctgt gaagacattt tcttttgata aaagaatatt gataagaata ttataccaaa    120

ttgaacaaaa gtagccacag tatgaaggat tcagtacatg gccaaataac ttatttcaaa    180

atagtttaga gttatattcc ttgaagacgg aggttggatg gggattaaat tttgtaaaga    240

cgccaatggc tgttaaacaa aagagctgag atggatgtgc tcttgaatta aaaataaaaa    300

tattttaaat atactattac atcataaaca ttctatgtct ctacttttcc atctagaagc    360

aagaattctt tagtactttc cgagcatcta ctgtgtagac tatcttgtgt tatgaccaat    420

tgcttatatt tatttac                                                   437
```

<210> SEQ ID NO 67
<211> LENGTH: 80
<212> TYPE: DNA
<213> ORGANISM: Homo sapiens

<400> SEQUENCE: 67

```
acaaaaccat atgcttcaac acctcaggtt gaccatttgg ggggagtgtg tatgggtgtt     60

ttaagatggc ggggtatgcc                                                 80
```

<210> SEQ ID NO 68
<211> LENGTH: 663
<212> TYPE: DNA
<213> ORGANISM: Homo sapiens

<400> SEQUENCE: 68

```
gtgtagagca tggaagcagg gagaccagtt aggagtctat tgtaatagtc ctggtgagag     60

accacagcgg cttggactaa gatggcaact aagataatga tggttgcagg gcccctcttc    120

aatggaggca ttgccagcct tctggccatg aaggagaaag tgatttcaac taacccagga    180

aactcttacc tctaaatgga gatacttcct gataacagaa gaaactgggc atctaaccca    240

gaaataccag ctgagtagga gaagagaaaa ggcatcagcc agtcaaggtt tcagaaggct    300

gccaacagtc tttgtaagcc accttgggag tagatgagaa cggcaatcaa tcaacatggt    360

ttggtgaaca aaccatatat tacaaagtgc ttctgtgaag tctgcatcct cacaactaat    420

gagtgagaca tttctcattg tttctgctca cccaggaata ccatgctgtg ccagctcttg    480

ccatttatta accaactgat aatggtgcag tgctgtagtc atggaagcta tttcaaaagg    540

ttaaggaagt ctactggaat cctggttctt ctagttgcca ttcagactta tttttaaagt    600

ctcattgaaa tgtaatgcat gttatggaaa gtcaggatga aataaaattg agattttttt    660

ttt                                                                  663
```

<210> SEQ ID NO 69
<211> LENGTH: 695

<212> TYPE: DNA
<213> ORGANISM: Homo sapiens
<220> FEATURE:
<221> NAME/KEY: misc_feature
<222> LOCATION: (309)..(482)
<223> OTHER INFORMATION: n=a, c, g or t

<400> SEQUENCE: 69
gaaacacaga aagaggggag aaacaggaga ggggaaagag agaggagaga gaaaccaagg 60
aaatgtgaca tataataatt ttttaaagaa tattttttca tttttttatt gaggtataaa 120
atacatgtag taaggtatgt caataactca aatcttatgt gattttttta tgtacatgta 180
tacctgtgta cacctgtgta accactacct aagtcaagat agagaacatt ttaatcatct 240
taaaagattt cctgtgtctc ttcccaccaa tacctgctga tgagcccact ctccttacag 300
ctatcagcnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nnnnnnnnnn nnnnnnnnnn 480
nnccttcatg ttaatgaaca tttgaattgt tttcatgttc ttgttatgaa tcaacatggt 540
tatgaatagt ttggttatga agagttttac acatgttttt agtctatttt gtttctctta 600
aatatatact tagtcacggg attactggtc atatagtata ggcaggcaga tgttcagctt 660
taattgacac aaccaactgt ttttgaaagg ggttg 695

<210> SEQ ID NO 70
<211> LENGTH: 739
<212> TYPE: DNA
<213> ORGANISM: Homo sapiens

<400> SEQUENCE: 70
ggtttctctt catggacatt gtttgcatct acatgtgaca cttaggaatg atctgtttag 60
tctcaatcac tcactcctgg atctgcctgt ctctctctga gataacaaag gccttaatgt 120
ttagccacct gcatcagagt tggtgaggtg gtttgaaaca attcatccta atataaaaag 180
aacagctttt gtaaggggc actgagtgtc tcaaacagcc gcatgggcag gaagagtgct 240
cagtccagtt ttggttgaac ttgtcttgtt gccctaaggc ctcctatgaa agactgacag 300
gcttggactg aatcttgtga tctggacacc aagggtcacc tgtgggccca gagctagctc 360
tgaagaatgg ggtagtttct ttgagaacct ccacagcaaa agtttggtcc tctgttccca 420
atgcatgtcc cactttacca gctacatccc ccagtacctg cccatggctc atgactcatg 480
aaatataaaa ctcagtaggc aggcataact ggttcagacc tgccagggct atgtgggaac 540
tatcattggt acaaaaactc taagtgtgga gaagactgtg gtagacaaga ggggacatgt 600
ctgttctaaa cgcacatcag aaacttccaa tgactatggc caagtgagat aagggtgtac 660
agaacttctc aggacatgca gacctatgtg tcactcataa ctgaaattca aataaatatt 720
ttgtggattt cctgtggac 739

<210> SEQ ID NO 71
<211> LENGTH: 9883
<212> TYPE: DNA
<213> ORGANISM: Homo sapiens
<220> FEATURE:
<221> NAME/KEY: misc_feature
<222> LOCATION: (7153)..(7153)
<223> OTHER INFORMATION: n=a, c, g or t

<400> SEQUENCE: 71

-continued

```
ataagaataa aaattacccc aaatttccaa atcaagaagt aatcatggtt caggtttggg      60
cagatgttct ttctaggcat gaacacacgt tatctcattg tttacttaac accgggttat     120
aaacatttac ccatagcatt tgaaaggtag ctatagatag aaaagaatca gagaagttct     180
aaaacagctc ttgcgctttg tttcaaattc tctgcaggaa agatgaggtc ttcagccttt     240
tttttagctg gacggcaccg ttgcagcagt ggtgaacagg gcactggatt gagtcaggaa     300
acccagctgt gaccttgggc aagccacttg ccctctttga gcttcactcc tgctaaggca     360
aggggcgcta ttcgtaccct gtctgcccac ctcacaggct ctggtgaagt ccttgatttg     420
aacgccttta gctcccaagg ttgtggtttg gagatagggc aggtcacatg accatgaaga     480
ctgaaggaga aacgtggaag cacgtgtgcc tgttgcttct tttccaactt aaaatgcttg     540
gtgatctcct gaagactcca gcctcctctc tgggaagcca ggatccacag accctttacc     600
tgcgggtcat gggcagtccc agatggtccc cctccccaac agagggggtg cagtgagacc     660
tccggaagtt actgcctctg ttaccctcaa agggattttc agatcagaca gcccccctac     720
tccaagggac gtgtgtggag cttggtacct ttatttatct cctgctccaa cccctgtgga     780
ctgcctgcac ccagaatggg gcctctcctg ctggcaagtg gctgagaacc tccactccac     840
tcagcagggc tgttccccat ttaccgaaaa gctccgagag aaaataacta accccatggc     900
gccgctgtag ctactggcag agcctcctgg tccccacctc tagcgcctgt ggtttttgtt     960
tcatgcagag tgagcagtga atctgggatc ccatcagcag tcagtttggg tgcctgcgag    1020
gcacaatgat agatgttggt gaagggtatg tgtgaggata ttaattaata ttaacatgct    1080
agttatatta atattctcat tggaatttgt ggggctttgc aagttatatt tcaaatatat    1140
ggttttatgt aatcctttta actgccctga aaccttgaaa ttattgcacc tattttatag    1200
atggagagac tgaggctcag aggggtgaat tgcctaagat cctgggggag gaagcaccca    1260
ggttttctgg ttttgagtcc tgggcccttc ctgctgagta gctacccccca acacagacct    1320
gcccttggag agcttgcagc cacactggga aggccagtgt attggattgc tgcttagacc    1380
tggaaagcac gtgaataaag cttcaggtta aaaccatggg ggttccagga ggcagcagtc    1440
ggctctgcct gggggtgagc tgaggagccg gtgctctctg gaacaagggt agttgggctg    1500
aggctcagtg gacagtggag gttggcaggt gaagtgcagg aggtctttgc agggagtggg    1560
accaccttga gcacacacag aggaatgaga caggcaggtt actcaaggag cagaggtctc    1620
gtgaccactt cccagagcat gtggggtcct agcctcatct ccaggaggag aaagtgcatc    1680
tatacacaga tttgtcaatg gagtttaaat aggatgtggg aaaatctaga ttttccaaaa    1740
cagtacatat ttgctttgag aagaaaggta gatgcaggat gcataggtta gataatttta    1800
atagcagtaa cctcagagca tgtaagtatg atttgattta ctggagtgcc tggccgtctc    1860
agtcagtggg agcacggctt gggctgggag atgaggttga caagggttct ttctctcaaa    1920
tgcttccttt ggtttgctaa gaggtatctc ctactcggcc gggggcagaa gacttttcct    1980
tcttttccca gtttgcagta gttgggccag atttgtggaa gtgggagaaa ggcctgccct    2040
gcttctacat agagttggct gtcctgactt gatactcggt gtgccttcca gagacccgcc    2100
tccatctcct caactccctg gcttgatgct taggtggtga tggctgttgg gcacaggagt    2160
tacataacag atctgtgatg gacccaggag cagagccagc tgagtgaatg tcatggagtg    2220
ggagtggtct tgcatggctg tggtgtcccc tgcagcttgt gcagggtatg tggcaagagg    2280
tgctcaccac tcatctggaa tggctagact ggaagcactt ggccctcttg ggctctgcac    2340
ccccaccccc tcccacctgg cctgcctgct catcttcatg ggcgcctggg gagaccaatt    2400
```

-continued

```
atggctgctt gtcatagtgg ctcaggtcac cgttcacact tcctgggacc aggacatcag   2460
agccctgaga agggtcaagg ggccaagtgg gcctagcctt ttactgacag ctgggaaatg   2520
caagcgtgtg gaccagagca ccaagtgagt tggggccggt gtgggttcag caccgtgtcc   2580
ctacccagag ctccatttgt tgaaaacagc ctttctctac cgtttcttca cttggacaac   2640
tttaaactat gtattggctg gtcgcggtgg ctcacgcctg taatcccagc actttgggag   2700
gccgaggtgg gcaggtaact tgaggtcagg aggtcgagac cagcctggcc aacatggtga   2760
aacctcatct ctactaaaaa tacaaaaatt agcccagcgt ggtgacacgc acctgtaatc   2820
ccagctactc gggaggctga ggcagaagaa tcgcttgaac ttgggaggca aagattgcag   2880
tgagctgaga ttgcatcacc gcacttcagc ctgggagaca gagcgagact gcatctcaaa   2940
aaacaaacag aaacctacat attttctata tttcccccaa cattgaggct catttcttgg   3000
atgaacaatt taaatgtact gtgcctctct ggcaatattt tccaaaatta cagatgtttc   3060
tatactttca ccggcagctc tgcctcccag aatttattct acggatgggt taacacgtgt   3120
gcaaaatgat ttatttgcaa ggttcgtcat tgttgcctta tttttaatag caaaagattg   3180
gaggcagctt aaatgttcat tcgcaggggc caatgaacaa accatggccc gtctaaacat   3240
gggataccgc gtggccataa tacataagat ggacgctcaa cgcactgtgc cggattgagc   3300
agcaaggtgg attgccgagg gaagaagcag gtctgggcgg tgtgtctcgg agctgccatc   3360
agtgtaaaag ggaagagaat caaaagtgtc tttgcttgtc tatgcccagg gggtctctgg   3420
gcagacaccg caagtcggtg attgtgatgc ctctggaggg ggtgctggtc atgggagatt   3480
gcttgtttgc tggagatccc atgtaccttt tgattgctga agcaggtgaa tgtacgcctt   3540
tccaagaaat taaaatgggc caggtgcggt ggctcacgcc tgtaatccca gcagtttggg   3600
aggctgatgt tggaggatca cttgaggtga ggggttcgag accagcctgg ccaacatgat   3660
gaaaccccat ctccactaaa aatacacaaa ttagccagac atggtggtac atgcctgtaa   3720
tcccagctgc tctagaggct gaggcaggag aatcatgtga accctagagg ctgagtttac   3780
agtgagccaa gatcatgcca ttgtactcca gcctgagcta cagagcgaga ctctgtctca   3840
aataataaaa taaaataaat taaaaacata aggactgtaa ccttgcctcc tgcccagtgt   3900
aggaaggtca aggttctggc tacttctcaa gtacaggagc ctcactcagg ccccagacca   3960
ctaatcaaaa aatatgtgct tggttctcac aaaggggccg agtgtgaggg cttgggtgtt   4020
gcttggtaaa tacgaccccc ggtcccggcc ttggagagat ggagccctct ctgggcccct   4080
tggacacact gctgttggct gactttgtca ttttcaaccc ttgctccgat tggctcacgt   4140
catgatttct gaaacctttg gggcttcccc cactgacaga aagatacact ttaactcagc   4200
actgggcatc ccaggccctc tttactgggc ctcttcttga gccgcacttg gcctgtcacc   4260
ccttcctctg tctgccctct taactcccca cctccgtgcc tttgctcata tagttccctt   4320
tgcctgcctt tccgtccaga gcagtctcca cgtgcccagg tcctgtctga ctttcaaggg   4380
ccagcttagt ttccacttct gcactgcctt ctgacctccc tggcttctgt gtaaactgcc   4440
cagatcaagc cacacaatgg ttcctgcacc caaggaagct ccctggggcc ccctcctggc   4500
cactcgctct tcgccggtag tcaccactca caccttggca ctttcgcgtg gtgcctgccg   4560
ctgcctgttt gggcctccca cacacagagt gtacagaacg gactcctcgg tgtctggctg   4620
ccttcccgca gcactgtcag atcatccagg ttgcctgtag tggccctttg gttttttttct   4680
ctgctgcgta ggagttcacc aaatatacca ctatttattc attctcctgt ggacaggcat   4740
```

-continued

```
tgggttatgt ccagcctctt cggtgaattc attcttgtct ttgggggcgc gtgtgcgctc   4800
tttgctgggt atacacccag ggtgggttga tggcttacct gactcagaat gtgtttgcat   4860
gaatgaaatt caggttggta tgagaaatct agggtgtcct ggctggagcc aggcttcttg   4920
attacaggga cagagcaggt acagggatcc tggtttagac agcctgctcc catggggtgg   4980
tagcattgtt ggggtgcagg atgctgaatc tgcaggggac ctatccgctc agtgcccagt   5040
gggattttag ctggctggaa aggtggtcac atgtagaggg gctcaacaat ccagctaaag   5100
aggctgagcg ttggtccatt gttctcaatt tgagagaaaa ctgagatcat caaaattagg   5160
actggtatgt actaaaggaa agaacctaat tacaaggctg aattgagtaa gccctcgctg   5220
agggactttg gatttctttg ttgttcccct ttatttctgc acccccaccc aagtgacaga   5280
tatgtacatg attggatgat tttgctttcc tggttgagag attcctggga acttggccca   5340
ggagaagggg gagaaatgtg gagccgctag agtggcctcc gcttgtttgt gttgattgaa   5400
ggggagacgg aaggagagct gtggacccct gaccccttgt gagggcatgt gatccttttc   5460
aaaaggctca ccaggcagaa gtgcctggcc aggggccgct ctttccctct aatcccctct   5520
ggagaagggc caggctgtgg gttgctgacc tgctctgatg tggatcagcc tcccccaata   5580
atgcagctgc ccagaagctc agagagccca ggcaaccccc aaaggcagga gggccggctg   5640
tcattcccgt tgtcattccc aggcggctgg agtgggagca gagcggtcag ttcagatgaa   5700
cagtgctcga gtctgacccc aaccagcgag ttatggtaag atggaaggtt ctccatctat   5760
attaaataag agaacaaaag ccctcccagg ctgcatgaat attccaggga tatatatgtg   5820
aacgggttgc cagtttagct tggcctgtgg gtggcagccg cctgagtgag cacttcgtgg   5880
ctgcagctct aaagggtttg gatctgaaac taatgaatga aaatatgacc tcagaagatt   5940
taaagagagc aaatacccag caacagaacc tgggtcccag agactgttgg gagcatgaaa   6000
tcccaggctg gccgaaggag gaagtgggag agcaatggca gctgacatca catggtgcca   6060
gaccttctca gtgctttctg tgttcactca ttattccgtc cctctctctc agaggcaggt   6120
atggctgctt ccccatttta tagatgagga agctaaggca aggagaggtt gtgtaacttg   6180
ctcacagaca caaagctagc cagtggcaaa gctggaggtc aggtctaggt ggtcaggctc   6240
cagagttctg cggatttcac agcacggcag tggcagtcgg aagaaccatt tgtcaggtga   6300
ttgtgggcaa atgacgtcag cccttcaaac ctctgttttg catctgcaag ctgcttgctg   6360
ctgcaacaaa ttaccagaaa cttagtgact taaaacacaa attaggtcgg gtgcggtggc   6420
tcacatctgt aatcccagca ctttgggagg ctgaggtgag tggatcactt gaggtcagga   6480
gttcgagacc agcctggcca acatgatgaa accctgtctc taacaaaaat ataaaaaatt   6540
agccaggcat ttggccgggt gtggtggatc acgcctgtaa tcccagaact ttgggaggac   6600
aaggtgggcg gaacacaagg tcaggagttc aagaccagcc tgaccaatat ggtgaaagcc   6660
tgtctctact aagaatacaa aattagcagg acgtggtggc acgcgcctgt agtcccagtt   6720
actgggaggc ggaggttgca gtgagccaag atcacgccac tgcactccag cctgggtgac   6780
agagtgagac tccatctcaa aaaaaaaaaa aaaaagtaca aaagagcaaa acaaaacaaa   6840
agttatgaaa atgaaaacct gagccatcct ttatcttatt tccccaaatc cactaattat   6900
taacagaaag taaaagctat gaaaaatgaa tgaaagtgac tgcaatttcc ttgaagtgtg   6960
ttagaacctg cctttagtgt cagctatggg ttccctcatg aaggtcagct gagccatgac   7020
ccatgaacca tggaagcttg actctagatt gaccatcttg agatgccaaa gatgtccacg   7080
tcctaatccc atgtgggaga cagaataatg gccctgcaga ccttcccagc tggccatgac   7140
```

```
ccctcatttg acnagctctt cccttctctc tgaccagcac catgcttctc ctggtgacaa   7200
gccttctgct ctgtgagtta ccacacccag cattcctcct gatcccagag aaatcggatc   7260
tgcgaacagt ggcaccagcc tctagtctca atgtgaggtt tgactccagg acgatgaatt   7320
taagctggga ctgccaagaa aacacaacct tcagcaagtg tttcttaact gacaagaaga   7380
acagagtcgt ggaacccagg ctcagtaaca acgaatgttc gtgcacattt cgtgaaattt   7440
gtctgcatga aggagtcaca tttgaggttc acgtgaatac tagtcaaaga ggatttcaac   7500
agaaactgct ttatccaaat tcaggaaggg agggtaccgc tgctcagaat ttctcctgtt   7560
tcatctacaa tgcggattta atgaactgta cctgggcgag ggtccgacg gcccccgtg    7620
acgtccagta ttttttgtac atacgaaact caaagagaag gagggagatc cggtgtcctt   7680
attacataca agactcagga acccatgtgg gatgtcacct ggataacctg tcaggattaa   7740
cgtctcgcaa ttactttctg gttaacggaa ccagccgaga aattggcatc caattctttg   7800
attcactttt ggacacaaag aaaatagaac gattcaaccc tcccagcaat gtcaccgtac   7860
gttgcaacac gacgcactgc ctcgtacggt ggaaacagcc caggacctat cagaagctgt   7920
cgtacctgga ctttcagtac cagctggacg tccacagaaa gaatacccag cctggcacgg   7980
aaaacctact gattaatgtt tctggtgatt tggaaaatag atacaacttt ccaagctctg   8040
agcccagagc aaaacacagt gtgaagatca gagctgcaga cgtccgcatc ttgaattgga   8100
gctcctggag tgaagccatt gaatttggtt ctgacgacgg gaacctcggc tctgtgtaca   8160
tttatgtgct cctaatcgtg ggaacccttg tctgtggcat cgtcctcggc ttcctcttta   8220
aaaggttcct taggatacag cggctgttcc cgccagttcc acagatcaaa gacaaactga   8280
atgataacca tgaggtggaa gacgagatca tctgggagga attcacccca gaggaaggga   8340
aaggctaccg cgaagaggtc ttgaccgtga aggaaattac ctgagaccca gagggtgtag   8400
gaatggcatg gacatctccg cctccgcgac acgggggaac tgttttcttg atgatgctgt   8460
gaacctttat atcattttct atgtttttat ttaaaaacat gacatttggg gccaggcgcg   8520
gtggctcacg cctgtaatcc cagcactttg ggaggccaag gcaggcggat cacttgaggt   8580
caggagttcg agaccagcct gcccaacatg gtgaaacccc atctctacta aaaatacaaa   8640
aaaattagcc gggcgtggtg gtgggcgcct atagtcccag ctacttggga ggctgaggca   8700
ggagaattgc ttgaaccctg ggaagtggag gttgcagtca gccgagattt gtgccactgc   8760
actcccagcc tgggcgacag agccagactc catctggctc aaacaaacag acaaaacaaa   8820
acaaaataaa ataggcccag tatgatggct catgcctata atcccagcac tttgggaggc   8880
aaggcaggtg gatcacttga ggtccggagt tcgagacaag cctggtcaat acagtgaaac   8940
cctgtctcta ctaaaaatac aaaaattagc tgggcatggt ggtgcatgcc tgtaacccca   9000
gctactcggg aggctgaggc aggagactca cttgaacccg ggagatggag gttgcagtga   9060
gctgagattt gccactgcac tccagcctgg gcgacaccgt gagactccat ctaaaataga   9120
agaaaaggtt tctcttcatg gacattgttt gcatctacat gtgacactta ggaatgatct   9180
gtttagtctc aatcactcac tcctggatct gcctgtctct ctctgagata acaaaggcct   9240
taatgtttag ccacctgcat cagagttggt gaggtggttt gaaacaattc atcctaatat   9300
aaaaagaaca gcttttgtaa gggggcactg agtgtctcaa acagccgcat gggcaggaag   9360
agtgctcagt ccagttttgg ttgaatttgt cttgttgccc taaggcctcc tatgaaagac   9420
tgacaggctt ggactgaatc ttgtgatctg gacaccaagg gtcacctgtg ggcccagagc   9480
```

-continued

```
tagctctgaa gaatggggta gtttctttga gaacctccac agcaaaagtt tggtcctctg   9540
ttcccaatgc atgtcccact ttaccagcta catcccccag tacctgccca tggctcatga   9600
ctcatgaaat ataaaactca gtaggcaggc ataactggtt cagacctgcc agggctatgt   9660
gggaactatc attggtacaa aaactctaag tgtggagaag actgtggtag acaagagggg   9720
acatgtctgt tctaaacgca catcagaaac ttccaatgac tatggccaag tgagataagg   9780
gtgtacagaa cttctcagga catgcagacc tatgtgtcac tcataactga aattcaaata   9840
aatattttgt ggatttccaa aaaaaaaaaa aaaaaaggcg gcc                     9883
```

<210> SEQ ID NO 72
<211> LENGTH: 93
<212> TYPE: DNA
<213> ORGANISM: Homo sapiens

<400> SEQUENCE: 72

```
gttatattaa aacaatagaa acattaatct gtctgtcttt tctccattct atccattcgt     60
tctttaatgt ggtcactttt gaatgctgta tac                                  93
```

<210> SEQ ID NO 73
<211> LENGTH: 299
<212> TYPE: DNA
<213> ORGANISM: Homo sapiens

<400> SEQUENCE: 73

```
ctcgagcgct cacatattac cacctctgta aatccttttc taacttattc agggtgaccg     60
aattctgtgt ttctgtgccc ccttaatact tgttatataa gtctccttcc ccaaccaccc    120
ccacacttac cacatcacgt tagcaagaat gagagcaatt tgagggcagt ggctttgtat    180
cttatttata gccctggcac caaaacagtt tgtaaaaagt taatctggtg cagggtggca    240
taacacataa gagtctgttt cttttgagat atttggcaga ggttgtggtg tgcggagat     299
```

<210> SEQ ID NO 74
<211> LENGTH: 94
<212> TYPE: DNA
<213> ORGANISM: Homo sapiens
<220> FEATURE:
<221> NAME/KEY: misc_feature
<222> LOCATION: (85)..(85)
<223> OTHER INFORMATION: n=a, c, g or t

<400> SEQUENCE: 74

```
gctgtgttta tgctgctggc tgtactggga ggaatatggt cctttgtctc tgacccagga     60
gtttcatgtc ttctgccaag atacnttaca tgga                                 94
```

<210> SEQ ID NO 75
<211> LENGTH: 433
<212> TYPE: DNA
<213> ORGANISM: Homo sapiens

<400> SEQUENCE: 75

```
gctgtgttta tgctgctggc tgtactggga ggaatatggt cctttgtctc tgacccagga     60
gtttcatgtc ttctgccaag atacattaca tggatagata cattaggtag gtagatacat    120
tagatataga tagatacatt agatatagat agatacatta gatatagata gatacattag    180
atatagatac attagatata gatggataca cagatagata cacagataga tagatagata    240
gatagataga tagatagata gatagataga tagattcatt tatttattga gacagagtct    300
tgctctgtca ccgaagctgg agggtagtgg cttgttcttg gctcactgca acctccacct    360
```

-continued

```
cctgggttca ggtgattctc ctgcctcagc ctccacagca gctgggatta catgcccacc    420

tattttgtac ttc                                                       433
```

<210> SEQ ID NO 76
<211> LENGTH: 334
<212> TYPE: DNA
<213> ORGANISM: Homo sapiens

<400> SEQUENCE: 76

```
gctcgaggtt aatggaccat tcgggttata tggttcatat tttttgctca tttttatgtc     60

atggtgttta tcttttctgt gctgatttgt aaaagctatt ttaaaaccct tcatctgcca    120

tatatgttac atttctttcc tgctttctgc caccttccaa tttgttacca actttcttct    180

ccaaccttgg gccactggca tatacactca ttttaaatat cagaacttgt agtgctcttt    240

gaaatgcaga cagactatgg ttcattctgc aactgcatat tagttaacag gcaaaaatac    300

cttagtaaga gaaagtgtct tttccttcta atgt                                334
```

<210> SEQ ID NO 77
<211> LENGTH: 547
<212> TYPE: DNA
<213> ORGANISM: Homo sapiens

<400> SEQUENCE: 77

```
ggcttatatg tggagaactg acgtctgaac ccagatctga ttcccaagtg taatactttc     60

caataggcag ccttatatct ctgtacctca aaagagaagg ctatattatt taaaagatta    120

ggaattgtcc tatatggttt taaaatacac ttgctatagc acaataataa gtggtttagt    180

ggtgactgct actcctgtga gtttggttta aaaacagccc agtttgtacc ctgttggtca    240

tgataaaagc ataccaccct tactttgaga attttaacca tagagcacaa tatgtgtcaa    300

acaagctaaa aaagtattct tttcagttgc attttgatgg acattgaaat tgcttagact    360

ctttgaccaa aagtacaaac tgctgttaaa ctggtgacaa aatctgtttt catggacgct    420

aggctactta agctttattt tcctcctaag cattctctgc ctttgtaaag cactctagca    480

gcagtatttg cttagcttct aattttggtt ttgcttttgt gttttctctc tttctcttgg    540

ttgttcc                                                              547
```

<210> SEQ ID NO 78
<211> LENGTH: 263
<212> TYPE: DNA
<213> ORGANISM: Homo sapiens

<400> SEQUENCE: 78

```
tcgagggttg aaatgagtgt cattagccaa gtgacattta agtgccttgg tttgtctgct     60

tgcttttctg tggattgaaa aaaactgacc actgttaata tgattgtaca gtgacactgg    120

aaattatgag atgtgtgtct ggttagtcct gcttgtattt cagttgagat gcataccaag    180

tctgataatg cagagctttt ccatttcatg tgtctgttta ccattttcat gatcttaagc    240

aataaacatt tcttgacaac agc                                            263
```

<210> SEQ ID NO 79
<211> LENGTH: 765
<212> TYPE: DNA
<213> ORGANISM: Homo sapiens

<400> SEQUENCE: 79

-continued

```
gcgggaagag cacgcagccc tgcgagtact atttccgcgt gtaccactcg ctgtgcccca     60

tcagctgggt gagtcggcag agggggcgcc gggccaggcg tgtgcagggc tcggccgagg    120

ctgagccggc gtcccgctcc ctgcctttct gcttcccagg tggagagctg gaacgagcag    180

atcaagaacg ggattttcgc cggcaaaatc tgactgcccc agcgcggctt cctctgaaga    240

tgcagtgatc ctgcatcttt ttgtctcgcg gagccccggg tctcggttat ccacccctac    300

ctcccagtgt ctaagccacg aataatgcca ccagccttcg agttccttgt ttcccttgct    360

ctggtctcca cgtgtatgat ggggttctca ggcccaggct tcgaccagag gaccctctgc    420

caccaccgtt tcttcctgtc cttgagctac cttggtgaac tcatgacccc aggcccctgc    480

tccaccagga tgtcccccag gtcctgccag ctgggaagtg ccagcatgaa cgcctccaac    540

ttcgtggaag ccagggtccc ctgcagctga gggacgccaa gcagacacac ctgccctccc    600

cagccagctc ctgtctgtat gggcgagatg actgagagcg cccacgtccc taaggctgtc    660

ctgaccctcc atgctgcgac aaggacaggg aatggtcggt cactatgggc ctggtgtctc    720

ccctccccca ccacccggtg ctgcccagct caagccagaa gtgac                    765


<210> SEQ ID NO 80
<211> LENGTH: 162
<212> TYPE: DNA
<213> ORGANISM: Homo sapiens

<400> SEQUENCE: 80

cgctgcctca agaccaggac ccgccgcggg aagagcacgc agccctgcga gtactatttc     60

cgcgtgtacc actcgctgtg ccccatcagc tgggtggaga gctggaacga gcagatcgaa    120

gaacgggatt ttctgcctgt gcaaacatct tgacttgccc ca                       162


<210> SEQ ID NO 81
<211> LENGTH: 986
<212> TYPE: DNA
<213> ORGANISM: Homo sapiens

<400> SEQUENCE: 81

agcgggcggt gcacgacggc tcccattggc tggggctcgg gcgtcctagc caatccggcc     60

gcggggtgcg tttctcctga cccgggtggg accgcacccc gcggactcag aagcgagcgg    120

caccccggga ccatcccaca gcagatccag tggccgccaa cgtcaggctg gagttgcctc    180

cttcgtggat gttggatgtg gaagcccagg agccccccaa ggggaaatgg tcgacgccgc    240

ccttcgaccc gcgcttcccc agccagaacc agatccgtaa ctgctaccag aacttcctgg    300

actaccaccg ctgcctcaag accaggaccc gccgcgggaa gagcacgcag ccctgcgagt    360

actatttcct gcgtgtacca ctcgctgtgc cccatcagct gggtggagag ctggaacgag    420

cagatcaaga acgggatttt cgccggcaaa atctgactgc cccagcgcgg cttcctctga    480

agatgcagtg atcctgcatc tttttgtctc gcggagcccc gggtctcggt tatccacccc    540

tacctcccag tgtctaagcc acgaataatg ccaccagcct tcgagttcct tgtttgccct    600

tgctcgtggt ctccacgtgt atgatggggt tctcaggccc aggcttcgac cagaggagcc    660

ctctggccac caccgtttct tcctgtgcct tgagctacct tggtgaactc atgaccccag    720

gcccctgct ccaccaggat gtcccccagg gtcctgccag ctgggaagtg ccagcatgaa    780

cgcctccaac ttcgtggaag ccaggtcccc tgcagctgag ggacgccaag cagacacacc    840

tgccctcccc agacagctcc tgtctgtatg ggcgagatga ctgagagcgc ccacgtccct    900

aaggctgtcc tgacctccat gctgcgacaa ggacagggaa tggtcggtca ctatgggcct    960
```

```
ggtgtctccc ctcccccatc aaccgg                                          986


<210> SEQ ID NO 82
<211> LENGTH: 369
<212> TYPE: DNA
<213> ORGANISM: Homo sapiens

<400> SEQUENCE: 82

aacccaagat gactcgtctt ttggtgggag aattcactct gttcatgttt catttaacaa      60

ttgatctact gtacttaatt acctttggct tattttacat ttattggttt atcttgtgtt     120

tttcttccct ctgatctggt tatcgatttc ctttttcttc ccctgttgca ctttccattt     180

cattattggc agctgtccct tctctggggt tcctaatcaa acacatattc tttagcacat     240

gcctcgatgg ggattctttt cgcagcaccc tcatctggag ctcacagaac ctgtcactct     300

gtaggttctg gtctttttc agcttaggaa catctatttg ttgcttgatt tgattattgt      360

tagtttgtt                                                             369


<210> SEQ ID NO 83
<211> LENGTH: 923
<212> TYPE: DNA
<213> ORGANISM: Homo sapiens
<220> FEATURE:
<221> NAME/KEY: misc_feature
<222> LOCATION: (354)..(565)
<223> OTHER INFORMATION: n=a, c, g or t

<400> SEQUENCE: 83

aacccaagat gactcgtctt ttggtgggag aattcactct gttcatgttt catttaacaa      60

ttgatctact gtacttaatt acctttggct tattttacat ttattggttt atcttgtgtt     120

tttcttccct ctgatctggt tatcgatttc ctttttcttc ccctgttgca ctttccattt     180

cattattggc agctgtccct tctctggggt tcctaatcaa acacatattc tttagcacat     240

gcctcgatgg ggattctttt cgcagcaccc tcatctggag ctcacagaac ctgtcactct     300

gtaggttctg gtctttttc agcttaggaa catctatttg ttgcttgatt tgannnnnnn      360

nnnnnnnnnn nnnnnnnnnn nnnnnnnnnn nnnnnnnnnn nnnnnnnnnn nnnnnnnnnn     420

nnnnnnnnnn nnnnnnnnnn nnnnnnnnnn nnnnnnnnnn nnnnnnnnnn nnnnnnnnnn     480

nnnnnnnnnn nnnnnnnnnn nnnnnnnnnn nnnnnnnnnn nnnnnnnnnn nnnnnnnnnn     540

nnnnnnnnnn nnnnnnnnnn nnnnnccctg gataggaagg gataggaaga gactacttgg     600

tgccatgggg taggggtgag ggtataagta gatcagagtg ggaagacctc agccttgggt     660

ggcttgtctc tgcttcttgc caggtgggag ggcctgtcca cacctggatc cccgtaccac     720

agtgccagcc atgcccttcc ctgggctacc attgtccctt tcctcaccca gttggtagag     780

gagtcaggag gtgggaggcc gtgggctttg gttttataat gtaaccactg tgggggtggg     840

ggaggatggt gaaccatgta tttcagtgaa atatttaata tatttaaata tcaataaaat     900

caaactcttt gtaaaaaaag ccg                                             923


<210> SEQ ID NO 84
<211> LENGTH: 338
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n=a, c, g or t
```

<400> SEQUENCE: 84

```
ataatttttt tntttttaaa ggaaatgaac gtggaggact ggggtgaagg gccagcctgg     60

gtagtttaat ctttttggga agacatgact ttaaggagat tccctgcttt gtgacaggtt    120

gctccatgct gtcttgggga caagggcctg tactgccttc aaatctgggc tcaccccaca    180

ttttggtgag gggaagatag ggtgggggga taaggaggag aaaagactct agcttttttt    240

ttctatgcat gatatactgt gtgggtttat caagagtgta gacacagttg ctgttctcaa    300

ataataggcc aaataaaatg cgattctttt tttctttg                            338
```

<210> SEQ ID NO 85
<211> LENGTH: 436
<212> TYPE: DNA
<213> ORGANISM: Homo sapiens

<400> SEQUENCE: 85

```
ataatttttt tctttttaaa ggaaatgaac gtggaggact ggggtgaagg gccagcctgg     60

gtagtttaat ctttttggga agacatgact ttaaggagat tccctgcttt gtgacaggtt    120

gctccatgct gtcttgggga caagggcctg tactgccttc aaatctgggc tcaccccaca    180

ttttggtgag gggaagatag ggtgggggga taaggaggag aaaagactct agcttttttt    240

ttctatgcat gatatactgt gtgggtttat caagagtgta gacacagttg ctgttctcaa    300

ataataggcc aaataaaatg cgattctttt tttctttgaa acacacagaa cagcccagct    360

ataaaacagg caactgagga agaaccaaac cgcataccgg caagactcta gcatgtcaag    420

gtcaaagact ctccag                                                    436
```

<210> SEQ ID NO 86
<211> LENGTH: 462
<212> TYPE: DNA
<213> ORGANISM: Homo sapiens

<400> SEQUENCE: 86

```
agggaacgtt ggatgtagtc acactgctgt tggtgttact tagaccttca tttttccacc     60

agactgtagt gttcaaaatt ctttttagta agagaaccct ttttttctga actttttaca    120

accatctcca aattataaaa cataagactt ttttttagta aaaatatatt tttttacaag    180

cacagtggct tgcaccatgg aggggagagg aggtgttttg tccttggagc tgctggcctg    240

agagaacctt gtcatcgtgg gagctgggcc attcctacac agtggtctgg caatgacccg    300

gtggtggtgg aggcctgtga gtgggcactg gtaatgggaa cagctgtaaa accctggagg    360

ccagccccag gagagtgacc ttacccagga aagttctggg aaacaaacca cagggaggct    420

ttacaggaat ttttggttgt gcccacaggc aaggcacatg ag                       462
```

<210> SEQ ID NO 87
<211> LENGTH: 1435
<212> TYPE: DNA
<213> ORGANISM: Homo sapiens
<220> FEATURE:
<221> NAME/KEY: misc_feature
<222> LOCATION: (1012)..(1119)
<223> OTHER INFORMATION: n=a, c, g or t

<400> SEQUENCE: 87

```
ttagaggtag aagaactgac tataagcaga agtgtttgag gaggctgcat ggagaacaag     60

gggcatcatc ttggcccttg gcaggttggc aggatttgac ttggtgaaga gaacgagaaa    120

ggggacttta actgggagga ctactctggc tttgatttct ccatcatgcg gagattggtc    180
```

-continued

```
tttggaagtt gtagcttcca gagaccttcg atgtttgcta acatgtccaa gctctacatt    240
tattgattgt tggttctgtt catggctatg ttcaaattct tgtacctttt tgtcctccac    300
agtttcttgt ctcatccctg tcttccacct ctgctccccg ctcttgtctg gtctaattaa    360
cttcctctgt tggagcagct tcccctcttg ggtaaactca gacatgaccg cagcaaagca    420
gcgtggaatc ttctgtttgg tcagtgttcc ccccagcttc cccgcagata cagctgcatt    480
ggagcccctg aagacaaacc agagaagtgc tgcatcctgg ggggcaggag gctttgcttt    540
gcccagggct gggctcctga atgaattttg gtgcagcctt aacggccgag ttgtgctgtt    600
gaaggtgcac tgctctgtgt ccaggcactt catggagggg agaggaggtg ttttgtcctt    660
ggagctgctg gcctgagaga accttgtcat cgtgggagct gggccattcc tacacagtgg    720
tctggcaatg acccggtggt ggtggaggcc tgtgagtggg cactggtaat gggaacagct    780
gtaaaaccct ggaggccagc cccaggagag tgaccttacc aggaaagttc tgggaaacaa    840
accacaggga ggctttacag gaatttttgg ttgtgcccac aggcaaggca catgaggaaa    900
agaaatgtaa ttatagtttg taagtcgatg aaaagaggca atgagtgaca tgaaatagct    960
gctctaagtt tcttcttcct gtcggacagg aagaaatggg gttttatgca tnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnc ttctgaggga agactgagat   1140
taagcagata actgtataaa tgcataatta cacagcatgg tgagtgctct gaaggataag   1200
tgtggggagc ctcatttaga ttggaggatt gtgaaagtca agagacagga gagtcaaggt   1260
gaggcaaggt gagtaagagc tatccaggca aagactgctt ggtaggggag tgtcccagca   1320
acgggaaaca acctggaaaa aatatgacac ctcaggggaa ctaaaagcag ttgtatgtgg   1380
ctgatgcaca gacagggaag ggcaggaagt gtgctgaaag aaggcaggag gagaa        1435
```

<210> SEQ ID NO 88
<211> LENGTH: 459
<212> TYPE: DNA
<213> ORGANISM: Homo sapiens
<220> FEATURE:
<221> NAME/KEY: misc_feature
<222> LOCATION: (437)..(437)
<223> OTHER INFORMATION: n=a, c, g or t

<400> SEQUENCE: 88

```
gtctggtttg agtctaggat gaaggtacct tcctccagga aggccctggt gttccttctg     60
ccagactcct gagggtctcg ccagttcaag cccacttgaa gcccagctcg tttggggtta    120
cttgaaccat ctgggggatt ccaactagta tctttagctc ctgacatgag ctgttctact    180
gtgggctcag cccttgtctg agactgtatc cctatagggt cccggtcttc tgttgacccc    240
tcaccttctg tgggcctggg catggacctc tgatccttcc atctgaagaa gtgtcaaaat    300
aaaagtccat gcttccggga atcaggaagt cgcctcaagg caaaagtagc tgagtgtttc    360
tatatctgtt ttgttttcct ttctaacttc tctttttggt gggtaattct tcaccatctt    420
gttgattctt taagtcntag cataacacac attttaaaa                           459
```

<210> SEQ ID NO 89
<211> LENGTH: 1263
<212> TYPE: DNA
<213> ORGANISM: Homo sapiens

<400> SEQUENCE: 89

-continued

```
gtctggtttg agtctaggat gaaggtacct tcctccagga aggccctggt gttccttctg      60

ccagactcct gagggtctcg ccagttcaag cccacttgaa gcccagctcg tttggggtta     120

cttgaaccat ctgggggatt ccaactagta tctttagctc ctgacatgag ctgttctact     180

gtgggctcag cccttgtctg agactgtatc cctatagggt cccggtcttc tgttgacccc     240

tcaccttctg tgggcctggg gcatggacct ctgatccttc catctgaaga agctgtcaaa     300

ataaaagtcc atgcttccgg gaatcaggaa gtcgcctcaa ggcaaaagta gctgagtgtt     360

tctatatctg ttttgttttc ctttctatct tctctttttg gtgggtaatt cttcaccatc     420

ttgttgattc tttaagtctt agcataacac acattttaaa aatccagttg ttttagttgc     480

tttctgtctc catagaaggt caccatggtt ctcagccctg tcggacctgg agcctggtac     540

catgaccagg gacagggagt cctcatgccg ttttaagcag tggtgatcta agttttattt     600

cttaggtgag tcaaggtcgg aaaagcttga gacccctgct ctaggggctg tacctgtccc     660

tttctccctt ttctcctgtc tggactaggg ttcgaagggg ctggtgggcc atgtggagac     720

caagtagctg acaatcccca ggacctgtgg gctcagacac agggccctgc acctctcagc     780

ccttccggtc tcagctcagc acctcccttg cctggcccct ctttcctgca tgagctccct     840

gcctctgcca ggaggaacct ctgtcctgtt tctagatgcg ccatatcctc tcccacctcc     900

tgctctttcc tccagttgtg tgcctcgtaa cctcttcctc cctccaaggc taaatcaaac     960

cctacctcct tatacaggag gaagtaattt ctgggttgat gtatgcatcc ggcagattca    1020

tgctgagcca acaggttagg ggctggagaa acagtgatga gcttaaccag gccctgccag    1080

cctgcccacc ccgagtctgg tgagggtagc aaaaaacata aagtggaatt gataaataat    1140

ataatctatc catatccata tttttatttt ttattatttt gggacgaagt cttgctctgt    1200

cactccagcc tgagctacag agtgagaccg tgtctcaaaa aaaaataaga aaaaaaaaaa    1260

aaa                                                                  1263
```

<210> SEQ ID NO 90
<211> LENGTH: 554
<212> TYPE: DNA
<213> ORGANISM: Homo sapiens

<400> SEQUENCE: 90

```
gctcgagctg ttttcttcag gtgagtagaa caatggcatt ttaaatctaa gaggcaccta      60

gtaaatacat ttatttcaat tcctttccta catagggggaa gaaacagagg ctgcaaaaga     120

tttagttagt tcaagaaaaa acagtataat ttggagtttt tgactttgtg agttttgtta     180

cggcgctgac attcattctt ttgtgcgttc agtgtattca aatcttcaaa tctagagcac     240

attgtatgct gggcagaagg cacagtactt gaggattcag tggacagtga tacagaaaag     300

gctgctgtcc ttgggcactg atgagcctcg ggctactaca agtaagcagg cagtggcagt     360

aggtggaatg agggctgcag gtcctggcat catggatacc aatttgggct tagaatggaa     420

gcggaggctt ccttgaagaa cagcggtcta agctgagact tgtaggaata gtggtaatta     480

acaaacagac aggaagaaga gctttccagg aagacagcaa aacataggca aaggtctgga     540

gaggagagag agca                                                      554
```

<210> SEQ ID NO 91
<211> LENGTH: 435
<212> TYPE: DNA
<213> ORGANISM: Homo sapiens
<220> FEATURE:
<221> NAME/KEY: misc_feature
<222> LOCATION: (406)..(406)
<223> OTHER INFORMATION:
<220> FEATURE:
<221> NAME/KEY: misc_feature
<222> LOCATION: (406)..(406)
<223> OTHER INFORMATION: n=a, c, g or t
<220> FEATURE:
<221> NAME/KEY: misc_feature
<222> LOCATION: (411)..(412)
<223> OTHER INFORMATION: n=a, c, g or t
<220> FEATURE:
<221> NAME/KEY: misc_feature
<222> LOCATION: (421)..(421)
<223> OTHER INFORMATION: n=a, c, g or t

<400> SEQUENCE: 91

```
tattagtcca taaaggctat ttctagtatt aaacaatgct taagaatagc ttggatccat     60

gaaaactttt gagaaggagg acaaagcaga cggaacctaa tctctgaaca atttcaatta    120

catcttttac aagtggctgt tggctagtca ttaaaaatga gccattcaca cttgtggaca    180

ccttttttgc catgcagact tgacttgcaa agcctttatt atccctggtt aagaacagca    240

cagctaataa aaacgaatca tatggcttta aactacttgc atccaacagg gacatcctaa    300

aaatggtccg gatagtgact tcatgaccat ttaggctgca agtgccatag ttactaatga    360

gaacagatat ttccaaatgg cggcaataga ttatggaaaa tggagnaagg nnagagagta    420

ntttactttc agcta                                                     435
```

<210> SEQ ID NO 92
<211> LENGTH: 580
<212> TYPE: DNA
<213> ORGANISM: Homo sapiens
<220> FEATURE:
<221> NAME/KEY: misc_feature
<222> LOCATION: (556)..(557)
<223> OTHER INFORMATION: n=a, c, g or t
<220> FEATURE:
<221> NAME/KEY: misc_feature
<222> LOCATION: (566)..(566)
<223> OTHER INFORMATION: n=a, c, g or t
<220> FEATURE:
<221> NAME/KEY: misc_feature
<222> LOCATION: (551)..(551)
<223> OTHER INFORMATION: n=a, c, g or t

<400> SEQUENCE: 92

```
aaaaaaactg tttagaaaac cttcatattt actctcccgt tcaaactatt ggccctgatt     60

tttacagata atcaaaagtc aggctgccaa acttattttc tttgaatttg gaatatcttt    120

taaaatttgc ctttttcttt cttattatta gtccataaag gctatttcta gtattaaaca    180

atgcttaaga atagcttgga tccatgaaaa cttttgagaa ggaggacaaa gcagacggaa    240

cctaatctct gaacaatttc aattacatct tttacaagtg gctgttggct agtcattaaa    300

aatgagccat tcacacttgt ggacaccttt tttgccatgc agacttgact tgcaaagcct    360

ttattatccc tggttaagaa cagcacagct aataaaaacg aatcatatgg ctttaaacta    420

cttgcatcca acagggacat cctaaaaatg gtccggatag tgacttcatg accatttagg    480

ctgcaagtgc catagttact aatgagaaca gatatttcca aatggcggca atagattatg    540

gaaaatggag naaggnnaga gagtanttta ctttcagcta                         580
```

<210> SEQ ID NO 93
<211> LENGTH: 724
<212> TYPE: DNA
<213> ORGANISM: Homo sapiens
<220> FEATURE:

-continued

<221> NAME/KEY: misc_feature
<222> LOCATION: (297)..(602)
<223> OTHER INFORMATION: n=a, c, g or t

<400> SEQUENCE: 93
tactgatgtg cttttgattt gtctggaggg tgactactac ctctttgagg tgcctcctgg 60
gaccctcaaa atattaactt ttatactctg tgtagcctgt actttaagcc agaacattca 120
aagtacactg aagaaatgtg ttgaaaatct atgcaaccat tttcgcatta tgtactagca 180
aataaacaat ctttaatttc tggaattttc cattttcctc agtgatattg ttgattgatt 240
tgtagttttc tttctttgct aggtttcagt atcagggctg taccaatttt tttcttnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nnnnnnnnnn nnnnnnnnnn 480
nnnnnnnnnn nnnnnnnnnn nnnnnnnnnn nnnnnnnnnn nnnnnnnnnn nnnnnnnnnn 540
nnnnnnnnnn nnnnnnnnnn nnnnnnnnnn nnnnnnnnnn nnnnnnnnnn nnnnnnnnnn 600
nntgtgccat ctttatgaag tgaattatga agctttccaa tctttttat tttgtagaac 660 agtttaaata cacaacaata tactaagttc ttagattgaa gctgttttta aatcacaaag 720
acag 724

<210> SEQ ID NO 94
<211> LENGTH: 586
<212> TYPE: DNA
<213> ORGANISM: Homo sapiens

<400> SEQUENCE: 94
ctaagacagt ggccaatctg actgtgaaaa taagggcagg ctacactgga gagcagggat 60
agggacaccc ggggggcaga gatgtgggtc accttagggg aggacacact caggaggccg 120
gcccatgatg gcacatgaag gctgggagca cggtgctcaa ggatcagctc atcagggaac 180
ttgaccaaat ttagagcaag gccctttgat agtgtataga gatgtttgtt ctaagcagca 240
atagaaagct tctggaatct gttccattaa gaggtgatag aaacaaaata tgagtcgttt 300
tggagttgtt ttcagcagag tcacaatgat agcaccatta tagatatttt acagacataa 360
tcctgatctt ttgggtggat gaccagaatg tctagttggt tcactgagcc ctggttttga 420
cccaatatgg taattcgtga actcttagga ggccagaaat atcctaatcc tgtgcaaggc 480
agggaccctt ggactgtaac tgtcttgtct gcttttggtc gtgaaggaga ctcagaggcc 540
caaacaagaa tttaggaaaa agagcaatag gattgtgttt aaaaaa 586

<210> SEQ ID NO 95
<211> LENGTH: 491
<212> TYPE: DNA
<213> ORGANISM: Homo sapiens
<220> FEATURE:
<221> NAME/KEY: misc_feature
<222> LOCATION: (480)..(480)
<223> OTHER INFORMATION: n=a, c, g or t

<400> SEQUENCE: 95
aaataattta acctaggaaa agaaaaagaa aattgaaaat tggagctaaa ataatttgat 60
ttttccctca acagggttat tggctgtctt ttaagtgact aaaagagcgt atctttatgt 120
gaattttagg catggtcata tgattaatac aaggataaag caaccaaatg ctctcagtat 180
ttattcccgt gctatttgtc tgttttttag ttcatggagt attgtattgt acttggtaat 240

```
ttgatgcttt tgagatgtcc tttagacaga tttttaacta caggacttcc tctgtagaat    300

cgacaatgtg tttcactctc tgtggcattg acaatgtttt tgaatgccta attgttcagt    360

agaactccgt ggttattatt acaactttgt acattattat aaatatttta tattagttgt    420

atattccact gcagatagca accagaaaac taaaatacag aaatattaca tattagaggn    480

gattataatg g                                                         491
```

<210> SEQ ID NO 96
<211> LENGTH: 634
<212> TYPE: DNA
<213> ORGANISM: Homo sapiens

<400> SEQUENCE: 96

```
aaataattta acctaggaaa agaaaaagaa aattgaaaat tggagctaaa ataatttgat     60

ttttccctca acagggttat tggctgtctt ttaagtgact aaaagagcgt atctttatgt    120

gaattttagg catggtcata tgattaatac aaggataaag caaccaaatg ctctcagtat    180

ttattcccgt gctatttgtc tgttttttag ttcatggagt attgtattgt acttggtaat    240

ttgatgcttt tgagatgtcc tttagacaga tttttaacta caggacttcc tctgtagaat    300

cgacaatgtg tttcactctc tgtggcattg acaatgtttt tgaatgccta attgttcagt    360

agaactccgt ggttattatt acaactttgt acattattat aaatatttta tattagttgt    420

atattccact gcagatagca accagaaaac taaatacaga aatattacat atagagagaa    480

tataatgtac aaaaaaaatc ttgggagatg agtgctttgg gtttaattct atttttactg    540

aaaccagaga ataataggat tcaaatctac ctaatttttc tatttttctg attttccatt    600

ctgtatgctc ttctttgaat tttttccttg gtca                                634
```

<210> SEQ ID NO 97
<211> LENGTH: 397
<212> TYPE: DNA
<213> ORGANISM: Homo sapiens
<220> FEATURE:
<221> NAME/KEY: misc_feature
<222> LOCATION: (326)..(326)
<223> OTHER INFORMATION: n=a, c, g or t
<220> FEATURE:
<221> NAME/KEY: misc_feature
<222> LOCATION: (331)..(331)
<223> OTHER INFORMATION: n=a, c, g or t
<220> FEATURE:
<221> NAME/KEY: misc_feature
<222> LOCATION: (337)..(337)
<223> OTHER INFORMATION: n=a, c, g or t
<220> FEATURE:
<221> NAME/KEY: misc_feature
<222> LOCATION: (371)..(371)
<223> OTHER INFORMATION: n=a, c, g or t

<400> SEQUENCE: 97

```
aataattagc caagttgtgg tgctttgagt tttttgagtc tgtggtttaa tatctgtcaa     60

caattttgga aaattatcag ccattttatt tgaagtcttt cttctgtcac atatttcttt    120

tccttataca attagaattg catttatatt agggagtttg atattatccc acagatcctg    180

gatgatatat ttcattttct tccttttctt tttcctagtg tttcagtttg gacgagtttt    240

atcgacatat ctttaaggtc actaatgatt ttctcagctg tgtcaagtct cctgataagg    300

ccaataaaga gactatatct attatngtgt ntttaanttc tagcatttcc attttattct    360

tagagtttaa nctctctaat gaaattaccc atcttat                             397
```

<210> SEQ ID NO 98
<211> LENGTH: 342
<212> TYPE: DNA
<213> ORGANISM: Homo sapiens

<400> SEQUENCE: 98

```
ataaagatgg ggtgagggaa gaaaagatga caaaaggaga ggaccaggca tgagaagagg     60

aagaggagaa tgcggaggag gctgcttgcc tgctgtggga tggatggcag gggcacttcc    120

ccagactcac ttttctcaga tgtaaaactg accagccttg tgccacagat gtgaagatag    180

ccccatagaa cttaaagagc agaccataac ttcccatgaa tgagagctac taacatttac    240

atctgaaaaa caatttggat acttacccaa gtctccaaca aacaaagtca cactgaagct    300

ggagagcaca ctcataacac ccggaaaaac attttttttt aa                       342
```

<210> SEQ ID NO 99
<211> LENGTH: 873
<212> TYPE: DNA
<213> ORGANISM: Homo sapiens
<220> FEATURE:
<221> NAME/KEY: misc_feature
<222> LOCATION: (338)..(528)
<223> OTHER INFORMATION: n=a, c, g or t

<400> SEQUENCE: 99

```
ataaagatgg ggtgagggaa gaaaagatga caaaaggaga ggaccaggca tgagaagagg     60

aagaggagaa tgcggaggag gctgcttgcc tgctgtggga tggatggcag gggcacttcc    120

ccagactcac ttttctcaga tgtaaaactg accagccttg tgccacagat gtgaagatag    180

ccccatagaa cttaaagagc agaccataac ttcccatgaa tgagagctac taacatttac    240

atctgaaaaa caatttggat acttacccaa gtctccaaca aacaaagtca cactgaagct    300

ggagagcaca ctcataacac ccggaaaaac atttttttnnn nnnnnnnnnn nnnnnnnnnn    360

nnnnnnnnnn nnnnnnnnnn nnnnnnnnnn nnnnnnnnnn nnnnnnnnnn nnnnnnnnnn    420

nnnnnnnnnn nnnnnnnnnn nnnnnnnnnn nnnnnnnnnn nnnnnnnnnn nnnnnnnnnn    480

nnnnnnnnnn nnnnnnnnnn nnnnnnnnnn nnnnnnnnnn nnnnnnnntg aggagggcaa    540

aaatcacctg gtgaccattg gacaggcccc agagacaaat cttcttacct gggcaattca    600

gaagggagcc aagaccacct ggtgaccatc aaacaggcca tctggaggca aaactcctta    660

tctggggaat ttagaagtaa tcaaacttcc ctagtatctg aagacggcat ctgatcatga    720

tacaggaact agaaagaaat catttaggca gttagtgagg gtgagggaag agagaggccc    780

tctcatattg tttatttagg ccattagtga gggtgaggga agagagagac cctctcatat    840

tgtttcatat tgttttatac tcagtacctg att                                  873
```

<210> SEQ ID NO 100
<211> LENGTH: 297
<212> TYPE: DNA
<213> ORGANISM: Homo sapiens
<220> FEATURE:
<221> NAME/KEY: misc_feature
<222> LOCATION: (48)..(48)
<223> OTHER INFORMATION: n=a, c, g or t

<400> SEQUENCE: 100

```
ggaaaaggcc cccttaacct tcctcctcag gcccactcag caaatgtngc cactttgtgg     60

ccactttgtg taaggcattc cagagatctg gtgaggcacc tatctacaaa tatttataca    120

cacacattca tatatggttt cagtcacaaa atggggtcat tctctcccct gacctatcat    180
```

```
ttagggcatt ggaacatggc tgcatgtggc tctgtttgtg agggtccagg ggatggacag    240

ggaggctctg cattattttg cttttaccaa cattgcagca tgaacgtttt tttaact       297
```

<210> SEQ ID NO 101
<211> LENGTH: 258
<212> TYPE: DNA
<213> ORGANISM: Homo sapiens

<400> SEQUENCE: 101

```
aatataaata cgcctttaat agtaacacct aattacctaa caccatcaaa aatggggtgc     60

tccatgaaga agcacataat tcaaattatt gaagtttatc ccttctaatg accacataga    120

tttctcttgc cccattaaaa aattagataa tcagtatttc taggatagtt gttttcttcc    180

aaccaattaa ggcataatct atgtagcaga acattcagag gatgatgcct ggtcaacatt    240

tgaataaaca atcactgt                                                  258
```

<210> SEQ ID NO 102
<211> LENGTH: 712
<212> TYPE: DNA
<213> ORGANISM: Homo sapiens
<220> FEATURE:
<221> NAME/KEY: misc_feature
<222> LOCATION: (603)..(603)
<223> OTHER INFORMATION: n=a, c, g or t

<400> SEQUENCE: 102

```
aatataaata cgcctttaat agtaacacct aattacctaa caccatcaaa aatggggtgc     60

tccatgaaga agcacataat tcaaattatt gaagtttatc ccttctaatg accacataga    120

tttctcttgc cccattaaaa aattagataa tcagtatttc taggatagtt gttttcttcc    180

aaccaattaa ggcataatct atgtagcaga acattcagag gatgatgcct ggtcaacatt    240

tgaataaaca atcactgtga tgttacctct atttaagatg actccaataa aacttctatg    300

gtttgcatta ttagttgatc agactttaag cattatcttt tgatagggtc aaggaacctg    360

tcttaactcc ccatctctga ccaaaatata cttgttttct ataagctata aagccagata    420

gccaatttta tgagaattgt ccctatacta tatccatgtg agcgatgagt gcctggcatg    480

aagatgcata aaggaggcag taatatacaa caactgaagc ataacctctg gagccagtct    540

tcttcagaca aatcccaatt ccattactca ctggccacct aaacaagcta cttaattcat    600

ctncctcagt tttcttcaac tgtttaatgg gtatgatcaa caaaccaact tcagtgggtt    660

atcataaata ttaataaatg agagaatgca tgtgaaacaa agctataagc aa            712
```

<210> SEQ ID NO 103
<211> LENGTH: 173
<212> TYPE: DNA
<213> ORGANISM: Homo sapiens
<220> FEATURE:
<221> NAME/KEY: misc_feature
<222> LOCATION: (96)..(96)
<223> OTHER INFORMATION: n=a, c, g or t
<220> FEATURE:
<221> NAME/KEY: misc_feature
<222> LOCATION: (140)..(140)
<223> OTHER INFORMATION: n=a, c, g or t

<400> SEQUENCE: 103

```
gaatgtggct ggtgagtagg cacttggtgt ggcagtgtgg ctagtgggta agaacatggc     60

tggtgattag gcatgtggtg tggcagtgtg gctggngggg acgagcatgg ctggtgggta    120
```

-continued

```
agaacgtggc tgggagtagn agcatggccg gtggttggga atgtggctag tga          173


<210> SEQ ID NO 104
<211> LENGTH: 688
<212> TYPE: DNA
<213> ORGANISM: Homo sapiens

<400> SEQUENCE: 104

tctgaatgtt ttggtgaata aatctgttct tcagcaaccc tacctgcttc tccaaactgc     60

ctaaagagat ccagtactga tgacgctgtt cttccatctt tactccctgg aaactaacca    120

cgttgtcttc tttccttcac caccacccag gagctcagag atctaagctg ctttccatct    180

tttctcccag ccccaggaca ctgactctgt acaggatggg gccgtcctct tgcctccttc    240

tcatcctaat ccccctctc cagctgatca acctggggag tactcagtgt tccttagact    300

ccgttatgga taagaagatc aaggatgttc tcaacagtct agagtacagt ccctctccta    360

taagcaagaa gctctcgtgt gctagtgtca aaagccaagg cagaccgtcc tcctgccctg    420

ctgggatggc tgtcactggc tgtgcttgtg gctatggctg tggttcgtgg gatgttcagc    480

tggaaaccac ctgccactgc cagtgcagtg tggtggactg gaccactgcc cgctgctgcc    540

acctgacctg acagggagga ggctgagaac tcagttttgt gaccatgaca gtaatgaaac    600

cagggtccca accaagaaat ctaactcaaa cgtcccactt catttgttcc attcctgatt    660

cttgggtaat aaagacaaac tttgtaaa                                       688


<210> SEQ ID NO 105
<211> LENGTH: 977
<212> TYPE: DNA
<213> ORGANISM: Homo sapiens

<400> SEQUENCE: 105

ggcttggaga gggtcacaga ggctagtagc tgtgtggact tgcaggcagc cccaaatgct     60

cacctatgtg cagagtcagc atgtcctgcc tcccctggta atgtggtcgc ctgcatctct    120

gtggccagcg ctctcgttca tcattcagtc tgatggcttg agtgcctcta tgtttgctac    180

atgctgagac cgtattctag tgccgtattc tggaggtact gggtgtacct acagatttaa    240

gaatgcaaat ctggaggtac acccagtgga ttcaaagtag tctcatagaa caaagagact    300

tatatagtga cctttgctgc atccactagt atacaccatc tgaggtctct tgaactgaaa    360

atgaatgtgg aagcaaggga acagtgtgat gttcagctct cagatctcac atggcatctg    420

atttggcttg aggtgcctcc cctcctctct gtcccctggc tgtgggctca tggattggca    480

gagcccagtt atggcttccg ttttacttgc tataaatatcc agaggcaatg tactagtcta    540

cctagaaaat tgtgctcacg gcatcccttt gtcacattaa taagcattat ggacactacg    600

acattttatt aagtattttg ttctggtatc tacttgatta tagtaaatta tcaaaatcct    660

tatttagctc atggactctc attaaagcat gttctggaaa ccttggccat aggttaggag    720

cctgtaaagt ttgattcatt gcaagatata agtgattagc agttggtagt agtgacattg    780

atgggcccca ttaaaaggtc tattggatgt ggtggtggca tagcgatagg ttggagttgg    840

aggtcagcat ggatgtctct gatttagaac caagcttacc tttgcataac ctatagtgac    900

actctcttca tctccccacg ccttagccat gtctccctga ggttcatact gtttggaatt    960

tcacaggctc atttatc                                                   977


<210> SEQ ID NO 106
<211> LENGTH: 500
```

<212> TYPE: DNA
<213> ORGANISM: Homo sapiens
<220> FEATURE:
<221> NAME/KEY: misc_feature
<222> LOCATION: (357)..(357)
<223> OTHER INFORMATION: n=a, c, g or t
<220> FEATURE:
<221> NAME/KEY: misc_feature
<222> LOCATION: (367)..(367)
<223> OTHER INFORMATION: n=a, c, g or t
<220> FEATURE:
<221> NAME/KEY: misc_feature
<222> LOCATION: (391)..(391)
<223> OTHER INFORMATION: n=a, c, g or t
<220> FEATURE:
<221> NAME/KEY: misc_feature
<222> LOCATION: (407)..(407)
<223> OTHER INFORMATION: n=a, c, g or t
<220> FEATURE:
<221> NAME/KEY: misc_feature
<222> LOCATION: (410)..(410)
<223> OTHER INFORMATION: n=a, c, g or t
<220> FEATURE:
<221> NAME/KEY: misc_feature
<222> LOCATION: (430)..(430)
<223> OTHER INFORMATION: n=a, c, g or t

<400> SEQUENCE: 106
cagagcaggc attgacctag atgtcttccc ctgccttcat tgggagggtg ctgagccacg 60
ggttccacct ctgccaaagg cacacctagg agactcctca tgtccagctg agaagagggg 120
gacacctcct gtctgagact gcagctcaca ctgctgcatg cttcctggac accatctctc 180
tgaccttggt cgcatctgcc tagcctgcag ctacgttctc tgacctccag ctcttcctct 240
ttctcccctc ggtaatacca aagtctcaag aacacagccc tcacttctag acagaaaggc 300
ctcaccagga cccacctgtg tggcccaggt gtgacctcat gtacaaacac atctccnaaa 360
atcaccntct cgtcatcatg gaccctagta ntatccatga gttaacnctn atttctgtgt 420
taatcggggn tgcagcacat tttggtgcag attcattgtg gctttggggt gccatttggg 480
actctccccc atgcacaatg 500

<210> SEQ ID NO 107
<211> LENGTH: 476
<212> TYPE: DNA
<213> ORGANISM: Homo sapiens
<220> FEATURE:
<221> NAME/KEY: misc_feature
<222> LOCATION: (466)..(466)
<223> OTHER INFORMATION: n=a, c, g or t

<400> SEQUENCE: 107
gccatctttc cactcattcc ttctcaaaag gaatgtagta ccatatagta gttaagaata 60
tagacactgg agccgatctt cttgagttcc aatagtggct cttctacttt ttaaatctca 120
ttttccttca tctttaaatt gaagatagta acaatctcat ggggttgtga taactaaggg 180
ggtaatgcat gtaaagtgct tagaaaatgc ctggacatag gaagctctaa gtttgctgct 240
actactgtta ttatggttac tattattaat cattgcaagg aaaatgtatc aacagatgaa 300
tttggttcaa tactgccttc tagttttgtg accttagaat ttataggaac aaaaaagatt 360
tgaagggagg ttgggctgga tcatagagag ccttgattcc atgttttagg atgtatacac 420
agtgagaagt ccttcaggtt ttggtcctgg gaagagttgt gaatcngaaa gttaac 476

<210> SEQ ID NO 108
<211> LENGTH: 834
<212> TYPE: DNA

<213> ORGANISM: Homo sapiens
<220> FEATURE:
<221> NAME/KEY: misc_feature
<222> LOCATION: (824)..(824)
<223> OTHER INFORMATION: n=a, c, g or t

<400> SEQUENCE: 108
ataagtatgc atgcttcata tacttcattt attctttctt ccttgaagcc tctcctcttt 60
attaggcact attcatttgt ctacttggta cctgtatttt tttaatgtca ctattttgac 120
agtaccaata aaggtaaagc cactcaatta cgcagggctc tctctttatg ctttgggtag 180
gtgcacctgt gcaactgagg ggacggtcag tgttatcaag gttacctgtt attacaagta 240
gaagaaccca caaagatcag gagagagctc attttcctcc attagtagga ggtaggacta 300
tacattcaca aacacgaacc ttaaaatagc tcacaaaata gtgtcataca tgtacccagc 360
catctttcca ctcattcctt ctcaaaagga atgtagtacc atatagtagt taagaatata 420
gacactggag ccgatcttct tgagttccaa tagtggctct tctacttttt aaatctcatt 480
ttccttcatc tttaaattga agatagtaac aatctcatgg ggttgtgata actaaggggg 540
taatgcatgt aaagtgctta gaaaatgcct ggacatagga agctctaagt ttgctgctac 600
tactgttatt atggttacta ttattaatca ttgcaaggaa aatgtatcaa cagatgaatt 660
tggttcaata ctgccttcta gttttgtgac cttagaattt ataggaacaa aaaagatttg 720
aagggaggtt gggctggatc atagagagcc ttgattccat gttttaggat gtatacacag 780
tgagaagtcc ttcaggtttt ggtcctggga agagttgtga atcngaaagt taac 834

<210> SEQ ID NO 109
<211> LENGTH: 498
<212> TYPE: DNA
<213> ORGANISM: Homo sapiens

<400> SEQUENCE: 109
tttaaattgg gagttaagga tgagcacttt tactgtatta aaaaatactc accagttaaa 60
aaaaaatact cttttcccct tcctcggaca cctaaatcta agagaacaac tcctatataa 120
aaatgatata aaaatcatac attttggaag tatgtttcta actgttctga gaggctgcat 180
ggtaaagctg aagtgaaaga tgtattttaa atctgtatat atgagcaagt atatattgat 240
gattgaagct aggtgctgcc taaatacatg gcccagactt tgaggaatta tagtgtaatg 300
gctgggaata caggtttgga gtcacaccgt agagctgaaa gcttggcttt tatttagctg 360
tgggtccttg ggcaggatac gtaatctgtc tgtgcctgaa atacccacca cacccatcct 420
gtaatggggg gataataagc ctgcctatct catggggcta ttaagaattt tcagttaact 480
tttacttatg aagtgcta 498

<210> SEQ ID NO 110
<211> LENGTH: 259
<212> TYPE: DNA
<213> ORGANISM: Homo sapiens

<400> SEQUENCE: 110
tttaatgtgg tttagtttta gtcacttaga tttgcttttt atggagtgac tggagtttgg 60
ggaggggagc agggaggttt ttcttttttt ctttataaca ctggctaaat attttaatta 120
ctgctataga aggaagaagc taaaagtatt gcattcacaa atattgcata gattatacaa 180
acacagaaat atatgcatat gcatgtttaa aatatatgcc acatatcaac accatgtatc 240
caacttgaat aaggtcatt 259

<210> SEQ ID NO 111
<211> LENGTH: 414
<212> TYPE: DNA
<213> ORGANISM: Homo sapiens

<400> SEQUENCE: 111
atgaaaggga tgaggggaac tcaaagttac aatgtcctac ttggagcagt aagttcagta 60
gacatatcac ttgcctcatt aacatcaagc atcccaaaac ccagtctggg tcagttttgc 120
ccagagtggg gtttgtagaa cacgggttct cctgggatcc tatacctagc ccagaatcag 180
ttgcaaaagc caggccatag caaattgtcc tgccagccag atagcagaga atctgacggc 240
agcaggcaga aggagccgct ccattgcagt aagccaagat cgcgccactt gcctcattac 300
atcaagcatc ccaaaaccca gtctgggtca gttttgccca gagtgaggtt tgtagaacac 360
gggttctcct gggatctata cctagcccag aatcagttcc aaaagtccaa aaga 414

<210> SEQ ID NO 112
<211> LENGTH: 589
<212> TYPE: DNA
<213> ORGANISM: Homo sapiens

<400> SEQUENCE: 112
ctgggcaaca ttggggagac tctgtctcta aagaaaaaaa ggagagctgg tggtgaaagt 60
gtgaaggacc caggaagtac agacactggt ggtcaaagaa caagggtagg agtgtcatca 120
aatgatagtg ttggcagcat gggagctgtg ggtagagagt gagataccta aatttatgat 180
ttctgggtgg cagtaacttc tagggtgtgg ctgtgggagt gggcctctga atggggtgga 240
ggagaaaatc attaaagatt agaaaatctt gggatttaga ggataggttg tgggatgggt 300
gatacacgtt agtgttgcat ttgcccaggg taacgccaag agttggcaga gaaaataata 360
ctgacctaga ctttaataaa ggatttggga atgacagaga agcaacagta aaaataaggg 420
ataattagat gtttgggtgt ttcgcctggc tgtgtctgtc ctgtgtctgg ccaattatta 480
caatgtattt acactgtaaa tacatgtaat tcatataata gttttataag tagcaaaatg 540
tagtttaata aaaaaccatc ttagtcttct tacagaatat ttagttacc 589

<210> SEQ ID NO 113
<211> LENGTH: 471
<212> TYPE: DNA
<213> ORGANISM: Homo sapiens

<400> SEQUENCE: 113
cccaggctgg gggtcaggtg aggagggagc tgggatccag caagcctagt gaaacccagg 60
ggacagtgga ctcggtcaca tccaggatgg tgatcaacag ctgcatcatc ccgcttcctt 120
ctcaagcgac aattccagag ccttggccac acggtgcttg tatctttcgt attcagaccc 180
cctggggttc cagcccctta ctgccttcac tttcctctca ccccttgact catctttcct 240
gctacttgtc acttgagata cctaagatga tgtgtgttat ggagaggtta gagcaccagc 300
ttcagaacca ccctgtgact ttggcctagt cacctgacat ttctagactt tggtgtcttc 360
attcataaag gcagtgtgga ctgcttgctg atgttatcgt gaacctgaat tccttcttag 420
agtttctaag tgctttctgg ggattaacct tttaaatcct tgcagtagcc c 471

<210> SEQ ID NO 114
<211> LENGTH: 1032
<212> TYPE: DNA

<213> ORGANISM: Homo sapiens

<400> SEQUENCE: 114

```
aatgagggag ctcttgagct cccttgatga gcaccacaca gggccctctg ggaagcagta     60
agaacccatc ccagggctca ataagaacct aacccagcct gggatggccc ttccctttct    120
gccaaggtcc ttcccatgcc aaacctcagg cccttatctt ggtatctgtc accacccacc    180
acccccccga cacacacaca gtcatgcaag ttgtaagaca gtgacagaag atttgaagaa    240
gaccaccaga gcaggggata gcagaacatg cagacttagg gggaagccag gcgttcatac    300
caaagaatta gacctgttgg gtacccaggc tgggggtcag gtgaggaggg agctgggatc    360
cagcaagcct agtgaaaccc aggggacagt ggactcggtc acatccagga tggtgatcaa    420
cagctgcatc atcccgcttc cttctcaagc gacaattcca gagccttggc cacacggtgc    480
ttgtatcttt cgtattcaga ccccctgggg ttccagcccc ttactgcctt cactttcctc    540
tcaccccttg actcatcttt cctgctactt gtcacttgag atacctaaga tgatgtgtgt    600
tatggagagg ttagagcacc agcttcagaa ccaccctgtg actttggcct agtcacctga    660
catttctaga ctttggtgtc ttcattcata aaggcagtgt ggactgcttg ctgatgttat    720
cgtgaacctg aattccttct tagagtttct aagtgctttc tggggattaa ccttttaaat    780
ccttgcagta gcccaataag gtaggtattg ttgttatccc cattttacag gtaaggaaac    840
tgaggcacag agagtaattt gcacaaggct tatggctttt tagtggagga gccaagagtc    900
aaattaagag tggttgagtc aggcatggtg gcccctgcct atagtcccag ctacttgaaa    960
gagtgaggtg ggaggatcgc ttgagcccag gagttcaatg ctacagagca agacctcaac   1020
tctttaaaaa aa                                                       1032
```

<210> SEQ ID NO 115
<211> LENGTH: 440
<212> TYPE: DNA
<213> ORGANISM: Homo sapiens
<220> FEATURE:
<221> NAME/KEY: misc_feature
<222> LOCATION: (428)..(428)
<223> OTHER INFORMATION: n=a, c, g or t

<400> SEQUENCE: 115

```
ggactacatc catgttccac cacaccaggc tccaattaca ttttgacttc tccacttgga     60
tgtttaaaat gcttctcaaa tttaacatat cctaaagata attttgtgtc tccccacaaa    120
acttgctctt tttgcattca ttgctgtctt agttaatggc accaccatcc atactgttac    180
tttagccaga aacctttgaa acatcccaat tggtctttct gattttctct gtttcacaac    240
ttattctcca cagacaggat actccaaaca gtacccaaag ccattgtctc ttatactttt    300
caatctataa aatatacata cataagagta tataaaatat attataaagt aaatatccat    360
gtatccaaac acacaggttt agaactggga acacaatatg caaaagaata atattgggac    420
ccccctancc tcatgtcata                                                440
```

<210> SEQ ID NO 116
<211> LENGTH: 249
<212> TYPE: DNA
<213> ORGANISM: Homo sapiens

<400> SEQUENCE: 116

```
aaaaaaagtt ctgacaattt gtttgctttt acattttcaa atttgtgaaa tgtagagata     60
attttgtttt caaatctttg taattccctg aagcaaatac tttcaagcca gttgcaaaat    120
```

```
gctgctttag aaataattca tataaacatg cttctctatt taatcacaag gggagatgtg    180

gagaatggat gttttatttt ttcagtagtt tttgctctat aaaaatatta aattgctatt    240

atgattact                                                            249


<210> SEQ ID NO 117
<211> LENGTH: 1017
<212> TYPE: DNA
<213> ORGANISM: Homo sapiens

<400> SEQUENCE: 117

gcccttttt ggtgtgcccg ctgaatgagc actccaggct gtggagttcg ggacatgcct      60

tggtttgtgg ggaccatgct gcctgcctgt cgagaccaag catcgatact gtgtgtctac    120

ctgatgaaag tgtccagtat gtgtctgcat gacttgggga cactaagaaa accaaaggga    180

ttagcaacaa agagagcttg tcacctttgt gcggaaccag ctggcatctc acagggacaa    240

cctacaacct gagctgctgc gtcctcacta aatctgggcc cctagggacc ccgttttact    300

cctgctctcc tggagcttat tacgggcctg gctaccaaag ggaaagaggg gaaaatagac    360

caggagcctt atgctagaac catttatttt gtttcacgtg atgcagacag agataaaact    420

gcaaatttaa tgaaacttta acaatcagta caatgtttct ccttaagaac tttgtaaata    480

gcatttatct ttcaagagtt ctttctctct ttttgtgatt attttataaa cttaaaggaa    540

aaagagaaaa agtcagtggt tccagcattt gctttagtct gtgacttaaa tggattataa    600

ctcttgaccg ctgacattta ccaagataaa tcagtggtca tagatgtgga gcttgatgtc    660

tcttcggctc tgggaccaat ccccttggac aaaagttttc ctgtgttctt agtattctga    720

actggctaca gcaactttta ggaaaataaa ggttacaaaa aaagttctga caatttgttt    780

gcttttacat tttcaaattt gtgaaatgta gagataattt tgttttcaaa tctttgtaat    840

tccctgaagc aaatactttc aagccagttg caaaatgctg ctttagaaat aattcatata    900

aacatgcttc tctatttaat cacaagggga gatgtggaga atggatgttt tatttttca     960

gtagtttttg ctctataaaa atattaaatt gctattatga ttactaaaga taaaaaa      1017


<210> SEQ ID NO 118
<211> LENGTH: 332
<212> TYPE: DNA
<213> ORGANISM: Homo sapiens

<400> SEQUENCE: 118

ctgcctccac gtggattacc acatttctca cctcatccta caaggcagtt cctgtttcta     60

ttccccttc acacaaaata acttcgtatg ttgttagtaa gcaggagaac cagcctttga    120

actcaggact gtttaaagac caaggtcctg gccactgaaa taaaacatct gcaactggca    180

gattaatgaa aggctctaga aggaaacaaa aaacccaaga gactgctggc agtgatagct    240

gagttttagg gggaaaagtt gttttagttt tccctgtata ctttcttgtg tagttttaaa    300

aatctacagt atttacactt tcaaaacaaa at                                  332


<210> SEQ ID NO 119
<211> LENGTH: 344
<212> TYPE: DNA
<213> ORGANISM: Homo sapiens

<400> SEQUENCE: 119

gcgcagggga aattataggt ggctgtggtt gtaattacaa agttctgtca cgtcttcatt     60
```

-continued

```
gttaggagga aaagaattca ataatcctat cagttctgct gtaaaacaaa tgagctatga    120

aattctggtg aacactgatt ttatgtctcc attcttgagg acactgttag tttgttttca    180

tctgtatgcc ttgattagag caaataacct taaatatcct taaggaaact tagatataca    240

tcatttccag tttttatcaa atgtgaattt tttttgtcat actgcccacc taacatggga    300

tgttttctca gaatattgtt cacttatgtg tttgagtttc ttaa                      344


<210> SEQ ID NO 120
<211> LENGTH: 718
<212> TYPE: DNA
<213> ORGANISM: Homo sapiens

<400> SEQUENCE: 120

aaaaaatcat aatagtttat gatcttgaag ggtttaaaag tatttgatga agatgtcttt     60

tgaatttatt tgtaggtctt cttgtgtatt taaaagctaa gttatcttgt aatcattttt    120

ttctatacct ttgtcagtaa cctcttagtg atgaaataaa aagattaggg taatcatcca    180

gcaatgggga agaagttaag gaacaaagag ctcagattaa actagttttt agaatctaag    240

catttctgca tgaatttgaa tcatggaaaa caaaatgtag cactccaaca tttgatgcaa    300

aactaaaagt ggaatactgc tttgatattt gaatgaattg aaaaataatt aacatccttg    360

gaactgtatg taaagaagga cttcacaagt attatagata cccccaacct cagccctttt    420

cccatgtatc tctttgatca catccctacc tcatagatca cccatgtgct gaagactttc    480

agttctgtat cttcattcta gatctcctga actcaagatc agaatatctt tctgacttct    540

gactgtgtat ttctggatgt tatacaagaa cctcagctca aactcagtat tccctaaacc    600

attgtttttg aaactttatg ttggatgtga aatctgtatt gtagaataac attaaaaaaa    660

gaaagaatag tatgcaaaat atcagagtgc attgtatgta gcaagagtag gtattttc      718


<210> SEQ ID NO 121
<211> LENGTH: 2617
<212> TYPE: DNA
<213> ORGANISM: Homo sapiens

<400> SEQUENCE: 121

atgtggaatc aacctacctg tccaggaaca gatgaagaga taagaaaatg cagtgtgtat     60

acacagtgga atgctcttca cccataaaaaa ttcacggaat catgtcattg cagcaacatg    120

gtggacaatg taagaaaagc tccccggaga agctgtacag aagctgcctc ctcagcagtc    180

agggccaggt accggagctg tttttaccca aggacagggc cggccccaag tcatcccaga    240

gctgccatgg caccccctca gtcgggtcct gaggaatcct acacaagcta cttatatcag    300

tgatcactag gataatccat agaacttttg ggaaagaagt ttaagacctt tctcccacca    360

tttcagcagg ataaattcca actggattag aaaatgaaat gttaataatg caaataagta    420

catatttata tctgtatata aaatacagtt gatatttgcc tggtgtttag gtgtctaaag    480

gactttctaa gcataaaggc aaaaaaaagt cataaaaatg ctatagcagt ttgagactct    540

atgcaggaaa gggcatcatc acgtgcatgg atgaatctgt atctaatttt aaacaatttc    600

caatggtgcc tgtttccttt tctttgaaaa tctctggaga aatagttcct cttgctgtgt    660

ctttctttag gcaagaattt ttactaattg atgtgtagtc tgaatcctgg ctaagtataa    720

acctttttatt ttttatacct gttcttagtg aaaatgaaac tgtgactttt tttttaattc    780

cttttgttgg tcaaaaacta caattaactc ttctgagttt cttctctggc tgaacaaaca    840

atggtcccat tggcctttca gggaactcca ggccgtctca aaaaccttca tgtttcattt    900
```

```
cttttcagag ctcccaaaaa gaatagcttg ctcttgacgt tgtacatgtt agtggaatga    960

tcaggactac tttgcaaaga tgaaaaattt gtgtttctag tgatttgaaa atagaaatct   1020

gatgtaacta ttagatattg ggaaagaagg tgacgaaggt aggtatcacc gaaagcactt   1080

aacaattctg aataattctg tacttgattg catttatgtg tatcatagga acagttgggt   1140

ttccttgagt gttaaattat ttattcactt attccacttc aagccagcta aatgattgtt   1200

tccctgatgg caaaagtctc agattgattg cacagtttat ttggttggat tgtttatgct   1260

ctttttatta tttattctta tttcaccaat gaaaatatca ctaagttctt tggtttgttg   1320

acctgattgt acctactttg acaaatcact gcctttctgg acccagtttt ctcattaagt   1380

ggcagtgata acctgtcata cttacagata taaaaacatg aaagttaaag tattgggtaa   1440

tactttcctc ctatcttttt tttattttga aaaagataaa aaattggcat aatgtattag   1500

ttaagatgga ataatcatat gttgatatcc agccatttct tctctcaaat gataggaaga   1560

tttttatgtg aaactacttg tgagagatct taacaatttg tagttagaga aagcactatt   1620

atatcatttg gaaatgcaag aaacaagtta cctttggggc aacagaggcc cttgtcattt   1680

tctcaaaaga aggaagcatc agcattttga tgatgatgtt gagattgtag aaatgatgaa   1740

ggtgaaaaag ttattctagc ttatgtttag caaaatgaaa tgaacccaaa taataaaaca   1800

gttacaacat tgaatctctt tgggagaaaa aaaaaagata gaatgctaat gtccttcaga   1860

acttcttaaa ccagaacctt aaaaaaaaga gaagctttta aaaaatcata atagtttatg   1920

atcttgaagg gtttaaaagt atttgatgaa gatgtctttt gaatttattt gtaggtcttc   1980

ttgtgtattt aaaagctaag ttatcttgta atcatttttt tctatacctt tgtcagtaac   2040

ctcttagtga tgaaataaaa aagattaggt aatcatccag caatggggaa gaagttaagg   2100

aacaaagagc tcagattaaa ctagttttta gaatctaagc atttctgcat gaatttgaat   2160

catggaaaac aaaatgtagc actccaacat ttgatgcaaa actaaaagtg gaatactgct   2220

ttgatatttg aatgaattga aaaataatta acatccttgg aactgtatgt aaagaaggac   2280

ttcacaagta ttatagatac ccccaacctc agccctttc ccatgtatct ctttgatcac    2340

atccctacct catagatcac ccatgtgctg aagactttca gttctgtatc ttcattctag   2400

atctcctgaa ctcaagatca gaatatcttt ctgacttctg actgtgtatt tctggatgtt   2460

atacaagaac ctcagctcaa actcagtatt ccctaaacca ttgtttttga aactttatgt   2520

tggatgtgaa atctgtattg tagaataaca ttaaaaaaag aaagaatagt atgcaaaata   2580

tcagagtgca ttgtatgtag caagagtagg tattttc                            2617
```

```
<210> SEQ ID NO 122
<211> LENGTH: 373
<212> TYPE: DNA
<213> ORGANISM: Homo sapiens
<220> FEATURE:
<221> NAME/KEY: misc_feature
<222> LOCATION: (74)..(294)
<223> OTHER INFORMATION: n=a, c, g or t

<400> SEQUENCE: 122

gtattataat aatggcctta atgaataaca ttctctatat tcacacttat ttgcaatata     60

atactgccat tctnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240
```

-continued

```
nnnnnnnnnn nnnnnnnnnn nnnnnnnnnn nnnnnnnnnn nnnnnnnnnn nnnncactaa    300

tctcaaagag ggcatgatct tcaagaatta ataaccctct caagtctcta caatctaatg    360

caattacctt ggg                                                       373


<210> SEQ ID NO 123
<211> LENGTH: 308
<212> TYPE: DNA
<213> ORGANISM: Homo sapiens

<400> SEQUENCE: 123

gctgaaagcc cagagcagag ctgttctcat ggggaaggac cctgtcttcc ccatcatcct     60

aggcgttcat tgaggatgag gactgtcttc ctccatcaga ccgagagttc ccaagggcaa    120

gggctgtctc tccctggtca gacagggagc tccccgaggg cagaggtcct gtctcctcca    180

tcagactggt agcccccaca accacaaagc tatgtctact ttcatcagaa ggagctccct    240

aagtggggaa gggttctccc tattttcccc ttccaggtgg gaaattcctg gccagggtcc    300

cctgtctc                                                             308


<210> SEQ ID NO 124
<211> LENGTH: 774
<212> TYPE: DNA
<213> ORGANISM: Homo sapiens

<400> SEQUENCE: 124

gccaacacca aagggggcac gggagaagga caggaggggt ggtttccctc agcaagctct     60

cagtcccact gacactggcc caagagggct gagtgtactg ggcactcacg cagggagatt    120

gttcccgaag gccctcggga aagttggtga atgcaaacag caggcagcca gagagcctgc    180

tgcagaggag accagagacg atgccccagg agggcacaga agtgtgcaaa agactcagca    240

gtgggaagga gcctggtccg tgagtgtgag gagataaccc gggccctagg cccttcctgc    300

cccaactttc caccacctgg cccagcccct tgcagcggtg aggcttagca tctctctgct    360

gggtttgtga gagcccagac tgccccagtg agggtacagg agtactctcc ccaggcagga    420

agggtgggcg gcctccctcc aggtacccaa gaggaaatgt tagcagctga aagccccaga    480

gcagagctgt tctcatgggg aaggaccctg tcttccccat catcctaggc gttcattgag    540

gatgaggact gtcttcctcc atcagaccga gagttcccaa gggcaagggc tgtctctccc    600

tggtcagaca gggagctccc cgagggcaga ggtcctgtct cctccatcag actggtagcc    660

cccacaacca caaagctatg tctactttca tcagaaggag ctccctaagt ggggaagggt    720

tctccctatt ttccccttcc aggtgggaaa ttcctggcca gggtcccctg tctc          774


<210> SEQ ID NO 125
<211> LENGTH: 271
<212> TYPE: DNA
<213> ORGANISM: Homo sapiens

<400> SEQUENCE: 125

aagtcgtacg catggttaaa aaaaaaagaa aagaaaatcc aaaatagtac tgaaggtatg     60

cagtacacag gaagcctccg cccacctcca cctcccagct tccccctttg gaggtatctg    120

ctgtagtggg ctcctcaaga tacttctagc catgctctgt ttgtgcatgc ttatccctgc    180

acagacagca gaagctgtct tggccaacaa gaccaggaag cattggtatt tgcaggttaa    240

ttgaaaaatt catttaaggt ggagaaccat a                                   271
```

-continued

<210> SEQ ID NO 126
<211> LENGTH: 1950
<212> TYPE: DNA
<213> ORGANISM: Homo sapiens

<400> SEQUENCE: 126

```
atgatgccac aggatgagcg cacttcaaag ctggaaggaa gcctggtgag ggagcagggc     60
agaatcttct cctggactgt gagggtacat acggtggatg tgtatggctt cattgaagat    120
gccagtcctt gcattggcat ctgcagattt gaagaagtag gcccctcttc tagtcttcat    180
ggactggatt tggcaagaaa agtccttcat cagtcagcca ttcagaaact ctgggaagcc    240
tatctggtaa cgtccatggg caggcaaaat ttgccattca gctacaagaa gtgcagttgg    300
cagacagcct tcaacttcag catcttcaga gtctgccttg actttcaagc tgaggccatg    360
gacttctcag gagctcctag ccaatggctg agaacaacgt gtctaacaca tgttctcttt    420
ctctttgatg gccaaggcat ggctggccaa tgggatgctt ctctctccaa aggagcaggg    480
agagctggag ataccctcct tgcaaacagc agcttgagga tccagcgcct ggtgcacagc    540
ccacagcgac cccaagaagc tgctccaacc cctgggacta tggagctcta cagctgtaga    600
gaccaccagg aagtggactg caggcccctg gcctctccat tcagattctg caaagagatc    660
ctgatgggtt gggccaatgg gtcaggcatc cagtcagctc tggctaaggg agctgcctgg    720
tgccaggacg agcgtaacac ggacccacag tgtccccaga agggggcagg cgttctgaga    780
gccacaaagt cctggctgcc agtgctccct ggtctgatcc taaacccgtc ctcctggggt    840
gacagcttcg ccgtgagcgc tgcctgggct cggaagggca tcgaggagtg gatcgggaga    900
cagcgctgcc cgggcggtgt ctcgggaccc cgacagctgc ggttggcggg caccataggc    960
cgaagcaccc gggaaagaga ccctgagacg ctgctgaatg agcaaagcaa ctgcaaaaca   1020
ttcataggcc atggtcctgt ttcttacagt gtgaaaaagt ctattcaggc ctgtgtcact   1080
gtgtatctgc agatggttgg atcagagcac cttcttgtga tgtcacaaat cggggccttt   1140
ctagccttct taaccttgga ggttctgctc agcagctgct actggcgtct cgtcctcttg   1200
gctctgggtc tggggcactg gaaggtaaac tccctgctga gttggaggca gcagcattga   1260
gtgggtggct gttttccagc caggatttac ccagggcttt atggcttgca aagccttcct   1320
cacagggctt tgtcaggcat ttaatattca caaaaatgtg gccaggatca aaattattat   1380
tatggggaaa ctgaggccag actgtaaagt ccacaggtca ggttctttgt ggctcactct   1440
tgtatccctg ggccttttgc actgattggc acatggcaga tcctcaagaa cattttccag   1500
gtggatgagg ttcagagggg ccatgcagct tggccagagg gcacacagcc agagaggcag   1560
ggattctgtt ctgttctgtc caagtcccca cctcttttat ggagccaggc tgttctgtgt   1620
ctttgaagag agcctctgcc cttcagaaag ggtcctcacc tttttccttt ctgtaaatta   1680
agtcgtacgc atggttaaaa aaaaaagaaa agaaaatcca aaatagtact gaaggtatgc   1740
agtacacagg aagcctccgc ccacctccac ctcccagctt ccccctttgg aggtatctgc   1800
tgtagtgggc tcctcaagat acttctagcc atgctctgtt tgtgcatgct tatccctgca   1860
cagacagcag aagctgtctt ggccaacaag accaggaagc attggtattt gcaggttaat   1920
tgaaaaattc atttaaggtg gagaaccata                                    1950
```

<210> SEQ ID NO 127
<211> LENGTH: 209
<212> TYPE: DNA
<213> ORGANISM: Homo sapiens

<400> SEQUENCE: 127

```
gttgggtgtg gtggggtgtt ttgttgttaa tgttgttttt gccagtctgt gttgataaga     60

tttattattg agaatagtgc ttgttctctg agtactcctg acttagaaaa ggagcatagc    120

cctactaaag gggacttcaa agtagaaatc gtcaataacc ttttacttgc tacagttagt    180

ggcctcaaca tgatgttttt aaagatctt                                      209
```

<210> SEQ ID NO 128
<211> LENGTH: 496
<212> TYPE: DNA
<213> ORGANISM: Homo sapiens
<220> FEATURE:
<221> NAME/KEY: misc_feature
<222> LOCATION: (101)..(403)
<223> OTHER INFORMATION: n=a, c, g or t

<400> SEQUENCE: 128

```
gcctccggtg gatggaatga agcaaggatg ggggctgcct gcagagctgt gtcactcact     60

tgtattcagc tttcctgcct ctggctctct gtcttttacc nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnnnnnnn    360

nnnnnnnnnn nnnnnnnnnn nnnnnnnnnn nnnnnnnnnn nnnttttatc acttttaaaa    420

ctaagaaaac aatgatcacc atacatgctc tgcttccaaa ctatactttc acatccaaag    480

taaccccaga ttcata                                                    496
```

<210> SEQ ID NO 129
<211> LENGTH: 252
<212> TYPE: DNA
<213> ORGANISM: Homo sapiens

<400> SEQUENCE: 129

```
catttctaac atttattgtc ctccagtaca aagaagtaac ccattgtcat gtctactcta     60

tgataggcta gaactatagg gttgctctat attgatcagg tttttaaaga taaaaatgaa    120

aaaaaaatcc tatccagaca aaataaatca gtgttttata tttttggagc atcagaactt    180

actttaagac ctcactggta attctttagc ctctcacatg tgataaagac attgtgctta    240

catttttta aa                                                         252
```

<210> SEQ ID NO 130
<211> LENGTH: 149
<212> TYPE: DNA
<213> ORGANISM: Homo sapiens

<400> SEQUENCE: 130

```
atcagaatcc tgggaagggt ttgttaaaac actactaggc agggtgaggt aacctaagag     60

cttttggagg cccaggtgag agggatcact tgcggccagc agagttcaag agcagcccag    120

gcaacacagg gagacctctt ctctacaaa                                      149
```

<210> SEQ ID NO 131
<211> LENGTH: 390
<212> TYPE: DNA
<213> ORGANISM: Homo sapiens
<220> FEATURE:
<221> NAME/KEY: misc_feature

```
<222> LOCATION: (217)..(273)
<223> OTHER INFORMATION: n=a, c, g or t

<400> SEQUENCE: 131

agcaagtacg cagcattggg aatgaaccaa actcgtagga ggcacagccc actcagtgtg     60

cgggcccggg cgagctgcag gcctgaaacc cacccaccct cttagatgtg tctgtgggcc    120

atagaaatta ctagggttgt cttgggtgtg gcctcaacct gttcaacaac aggtgtgctg    180

tttccattct ggaaaccagt cctctgtctt ccagaannnn nnnnnnnnnn nnnnnnnnnn    240

nnnnnnnnnn nnnnnnnnnn nnnnnnnnnn nnntactagg cagggtgagg taacctaaga    300

gcttttggag gcccaggtga gagggatcac ttgaggccag cagagttcaa gagcagccca    360

ggcaacacag ggagacctct tctctacaaa                                     390


<210> SEQ ID NO 132
<211> LENGTH: 1079
<212> TYPE: DNA
<213> ORGANISM: Homo sapiens
<220> FEATURE:
<221> NAME/KEY: misc_feature
<222> LOCATION: (874)..(874)
<223> OTHER INFORMATION: n=a, c, g or t
<220> FEATURE:
<221> NAME/KEY: misc_feature
<222> LOCATION: (879)..(879)
<223> OTHER INFORMATION: n=a, c, g or t
<220> FEATURE:
<221> NAME/KEY: misc_feature
<222> LOCATION: (885)..(885)
<223> OTHER INFORMATION: n=a, c, g or t
<220> FEATURE:
<221> NAME/KEY: misc_feature
<222> LOCATION: (887)..(887)
<223> OTHER INFORMATION: n=a, c, g or t
<220> FEATURE:
<221> NAME/KEY: misc_feature
<222> LOCATION: (890)..(890)
<223> OTHER INFORMATION: n=a, c, g or t
<220> FEATURE:
<221> NAME/KEY: misc_feature
<222> LOCATION: (894)..(894)
<223> OTHER INFORMATION: n=a, c, g or t
<220> FEATURE:
<221> NAME/KEY: misc_feature
<222> LOCATION: (896)..(896)
<223> OTHER INFORMATION: n=a, c, g or t
<220> FEATURE:
<221> NAME/KEY: misc_feature
<222> LOCATION: (899)..(899)
<223> OTHER INFORMATION: n=a, c, g or t
<220> FEATURE:
<221> NAME/KEY: misc_feature
<222> LOCATION: (921)..(921)
<223> OTHER INFORMATION: n=a, c, g or t
<220> FEATURE:
<221> NAME/KEY: misc_feature
<222> LOCATION: (924)..(924)
<223> OTHER INFORMATION: n=a, c, g or t
<220> FEATURE:
<221> NAME/KEY: misc_feature
<222> LOCATION: (926)..(926)
<223> OTHER INFORMATION: n=a, c, g or t
<220> FEATURE:
<221> NAME/KEY: misc_feature
<222> LOCATION: (931)..(931)
<223> OTHER INFORMATION: n=a, c, g or t
<220> FEATURE:
<221> NAME/KEY: misc_feature
<222> LOCATION: (933)..(933)
<223> OTHER INFORMATION: n=a, c, g or t
<220> FEATURE:
<221> NAME/KEY: misc_feature
<222> LOCATION: (944)..(944)
```

<223> OTHER INFORMATION: n=a, c, g or t
<220> FEATURE:
<221> NAME/KEY: misc_feature
<222> LOCATION: (950)..(950)
<223> OTHER INFORMATION: n=a, c, g or t
<220> FEATURE:
<221> NAME/KEY: misc_feature
<222> LOCATION: (975)..(975)
<223> OTHER INFORMATION: n=a, c, g or t
<220> FEATURE:
<221> NAME/KEY: misc_feature
<222> LOCATION: (977)..(977)
<223> OTHER INFORMATION: n=a, c, g or t
<220> FEATURE:
<221> NAME/KEY: misc_feature
<222> LOCATION: (988)..(988)
<223> OTHER INFORMATION: n=a, c, g or t
<220> FEATURE:
<221> NAME/KEY: misc_feature
<222> LOCATION: (993)..(993)
<223> OTHER INFORMATION: n=a, c, g or t
<220> FEATURE:
<221> NAME/KEY: misc_feature
<222> LOCATION: (995)..(995)
<223> OTHER INFORMATION: n=a, c, g or t
<220> FEATURE:
<221> NAME/KEY: misc_feature
<222> LOCATION: (1007)..(1007)
<223> OTHER INFORMATION: n=a, c, g or t
<220> FEATURE:
<221> NAME/KEY: misc_feature
<222> LOCATION: (1013)..(1013)
<223> OTHER INFORMATION: n=a, c, g or t
<220> FEATURE:
<221> NAME/KEY: misc_feature
<222> LOCATION: (1030)..(1030)
<223> OTHER INFORMATION: n=a, c, g or t
<220> FEATURE:
<221> NAME/KEY: misc_feature
<222> LOCATION: (1037)..(1037)
<223> OTHER INFORMATION: n=a, c, g or t
<220> FEATURE:
<221> NAME/KEY: misc_feature
<222> LOCATION: (1050)..(1050)
<223> OTHER INFORMATION: n=a, c, g or t
<220> FEATURE:
<221> NAME/KEY: misc_feature
<222> LOCATION: (1061)..(1061)
<223> OTHER INFORMATION: n=a, c, g or t

<400> SEQUENCE: 132
gggatgaaaa cttcctttaa aagaatcctg ttgtatttta atattgttcc ggggttcttt 60
gcatatgtat atgctctata tgaacaatac tgaaatgaac atccatatct atgacctctc 120
tctgcactcc aggctcagat atgcaactcc ctatttgaca ggtctgcttg aaaacttgct 180
gggcatccca gaggtaacat ggatctaatg gaaggtttga ttttgtcctc caagccagtt 240
cttcccttga ctttctacat ttcaccaaat gataccccaa ccactcactt attctagccc 300
aagatctagg agttattctt aggttttcct ttaccccctc cacatggatc catcagcagg 360
tcttgttctt ttttcttccc aaatatatct caagtccatg ctcttctgtc tgtccctact 420
gccactatcc aagctctgag gccatccatt acatggacaa ctataaacta catgtcctaa 480
tgacatatta gcagtagagt tgctaggtca aaagatttgt gtgttttatt ttgatagact 540
ttgctacatt attctcaaag aggctttctc agtgttatct gcttattata tgagaatttc 600
tgtttctgta ctctgtcacc accactgaat atcagggtca ctcttagccc atagcctcgt 660
gagaattaga agtcacttcc tctgggtgag gcagctagct ccacagcaca gacttaacaa 720
gtggaacttt agcatgtatt taattcccac tcattctctt acctatgtgt ccttctgcag 780
tcaacactct acacaactgt acatgaccac aatgctgtgc ataaataatt ttttagactc 840
tttgtaaatc tatatgtaaa aaatggcatc ttantttgna taagnanggn ggangncant 900
taaaattcct tttccttgga ntgncnaatt nanagacttt cctnattttn agggttccta 960
acaaattgga aaatncnggg gttaaccnaa ggncnatcat atatttnacc atnaaaaatt 1020
ttttcctggn accttangtt tgttaaaagn actttttat ngaaaccttt aaattttta 1079

<210> SEQ ID NO 133
<211> LENGTH: 303
<212> TYPE: DNA
<213> ORGANISM: Homo sapiens
<220> FEATURE:
<221> NAME/KEY: misc_feature
<222> LOCATION: (295)..(295)
<223> OTHER INFORMATION: n=a, c, g or t

<400> SEQUENCE: 133
ttaagtattc aatttctgtt ttaaatgcca agaggtagaa attaaaggta ggcatggtgg 60
tcacagtcca ctaaaaaact agtattccaa cttctattcc ctggcacact actaaatagg 120
caaccaggga tttaaaaaat ggtttctggt gtccaggtaa gtttgcataa aaccaaaata 180
aaactgttta atactgggcc cactacatta atctatggtg ctaacacgtg ctgtgaaccg 240
tggggtcagg ggctggggga taaagttgca accatttttt ggggggttgg gggangagga 300
ggg 303

<210> SEQ ID NO 134
<211> LENGTH: 546
<212> TYPE: DNA
<213> ORGANISM: Homo sapiens

<400> SEQUENCE: 134
ccggcaaatt taaccaaaaa aaaaaagtaa tatgaccata attaatatca gtcaaaatat 60
tctttaaagg aaaaaaatac taataagaga actctataaa aataaagaat ataataaaaa 120
gagatcacat ttgcaaattt acattgttta atatcatagc ctcaaaataa attgcatata 180
aattttaaaa cctatggaga aattgacaaa tccaccaaca ctgtgggaaa tttttaatac 240
atatctctta gctattaatg cataaagtag gtaaggaaaa ccaataggat gcaaataatt 300
tgaacaataa aatcaacaac tttgatttag ttgatataca tatacagaca cttgcattta 360
gtaattggaa aatatacatt attttccaac acacacaaaa aaacacttgc aaaaatgggc 420
tgtgtcttaa atttttcaaa gaactgatat catacagaac acatgttatg accataatgt 480
agttacatta gaaaatgtgg cagggattct gattctcctt tctgtgctag ggcatacagt 540
taaatc 546

<210> SEQ ID NO 135
<211> LENGTH: 590
<212> TYPE: DNA
<213> ORGANISM: Homo sapiens

<400> SEQUENCE: 135
aaaaaagtaa tatgaccata attaatatca gtcaaaatat tctttaaagg aaaaaaatac 60
taataagaga actctataaa aataaagaat ataataaaaa gagatcacat ttgcaaattt 120
acattgttta atatcatagc ctcaaaataa attgcatata aattttaaaa cctatggaga 180
aattgacaaa tccaccaaca ctgtgggaaa tttttaatac atatctctta gctattaatg 240
cataaagtag gtaaggaaaa ccaataggat gcaaataatt tgaacaataa aatcaacaac 300

-continued

```
tttgatttag ttgatataca tatacagaca cttgcattta gtaattggaa aatatacatt    360

attttccaac acacacaaaa aaacacttgc aaaaatgggc tgtgtcttaa atttttcaaa    420

gaactgatat catacagaac acatgttatg accataatgt agttacatta gaaaatgtgg    480

cagggattct gattctcctt tctgtgctag ggcatacagt taaatcacat tttcaccttc    540

cttgtattta tgagacttag ctctgtcctt atgaatgtgg gcagaagtga               590
```

<210> SEQ ID NO 136
<211> LENGTH: 165
<212> TYPE: DNA
<213> ORGANISM: Homo sapiens

<400> SEQUENCE: 136

```
gctcgaggcc tggcatctga gttcttctgt tcaggagaaa cactttcagc aggccattga     60

gagggtcatc ggaggtgagc ctgggagccc ttagggaggg aggggtgttt gcagctctgg    120

gcctggcagg ctcacccccct ggccccagtt tcaattctgc atgca                   165
```

<210> SEQ ID NO 137
<211> LENGTH: 172
<212> TYPE: DNA
<213> ORGANISM: Homo sapiens

<400> SEQUENCE: 137

```
tagttacagt ccttaaatat atgtcttggg tgccctgtgg ctgtgatttt ttaagggaaa     60

ttaacttatt ttaaataaaa taaacttaat ttaaaataaa attttgttat ctaaagccaa    120

atagaaaaaa ttccacattt tttcttacag tgctcattca tcagaacctt tt            172
```

<210> SEQ ID NO 138
<211> LENGTH: 809
<212> TYPE: DNA
<213> ORGANISM: Homo sapiens

<400> SEQUENCE: 138

```
agtacgtaca gtatcaaaca gtctccctcc ttttctctgt gatttggtct ttctccttag     60

agaatgtcct ccctccaact ccaaaagaca tgcctctgtg gtatagttac agtccttaaa    120

tatatgtctt gggtgccctg tggctgtgat tttttaaggg aaattaactt attttaaata    180

aaataaactt aatttaaaat aaaattttgt tatctaaagc caaatagaaa aaattccaca    240

ttttttctta cagtgctcat tcatcagaac cttttttttt tcttcttatt ttttcttttt    300

ttggggagaa tgggtcctcc ctttggtgcg catcaggggg aataagaggt acaaacaggc    360

ggtgattata cgctcacttg ggagtttgga aactccgggg gcatcattgg gattcccatt    420

ttgtcctcaa gcctccggag tagctaggac atacgggttt tgcaccacaa ggccgggata    480

aatttcaaaa tttttctcac gagacaaagt ttgggattct tggccccagg attgggacgg    540

ggtatatcac aaaagaaact atttcagggg cgcttagaga ggctcaagtg acacctactt    600

atcaggggtt tccagtggag agaactgtac cctaccctta ctacctttta agtggtgcct    660

ctccctccac ctttaacctt tacacattac ggaactggcg ctatcatttt aaagtcaact    720

aacctggact ttggacttct ttaacacttc agctccggga tccaaactaa aatcttaggc    780

aaggcctaat ggacggtaga agtctacgc                                      809
```

<210> SEQ ID NO 139
<211> LENGTH: 294
<212> TYPE: DNA
<213> ORGANISM: Homo sapiens -continued

<400> SEQUENCE: 139
gtctttttca ttcatagtaa ccctgcaaaa caaacatata gaacagagac attatggaga 60
cttgaggatt gattttatgt attgattatg tatgtaagtc ccgataacat ctctggttca 120
ggaaattgca agaaaaagat tgggaatcag aacagcagaa aggtattttt ggaagggtaa 180
tttactgatt tttcgtttta aattgttgac attgccttcg ccggtggaaa tgaattactt 240
atgtgaatct ggcaggaaca caatttttaa aattagaaaa ttagtcctcc ttat 294

<210> SEQ ID NO 140
<211> LENGTH: 1056
<212> TYPE: DNA
<213> ORGANISM: Homo sapiens

<400> SEQUENCE: 140
acctaaacac attttaatta tattttgctc atttttggag aacccattcc ctttgacatc 60
tattatgaac attctaaaac ttaaatttgt gaaaacaaaa ctctgggaga tagattgtaa 120
ttttattcca tgaggaaggt gttaaaccag ctttgcagtt tgaattttat tcttaaaggc 180
tctgcagttc ttacctggat gtcgaaatga tttttaattt caactgctgt agacctcatc 240
ctgtgggaac tagaaataat gtccaactgc cgtccagtct ggcgacattc cagccgttcc 300
cccaccccac gataacggcc tgactcttcc tcaattcatg acagcccatt ctacacataa 360
cctttctcct ctggcaccgg tcctcccagc agagagggat cctgcccttc ccttcccact 420
ctccagcata cagaccagca ggaagccaca agagggaaaa acaaaagcct tctgtataag 480
gcctatgaaa ggaccatggg ccagcctcag aatctgctgc ccctacaaac cagtattcct 540
caaatgatag ttccacattt acttaataag gaggactaat tttctaattt taaaaattgt 600
gttcctgcca gattcacata agtaattcat ttccaccggc gaaggcaatg tcaacaattt 660
aaaacgaaaa atcagtaaat tacccttcca aaaatacctt tctgctgttc tgattcccaa 720
tctttttctt gcaatttcct gaaccagaga tgttatcggg acttacatac ataatcaata 780
cataaaatca atcctcaagt ctccataatg tctctgttct atatgtttgt tttgcagggt 840
tactatgaat gaaaaagaca atttcatgaa tgcagaaaat ctggggatcg tgtttgggcc 900
cactctgatg aggccccctg aggacagcac cctgaccacc ctgcatgata tgcggtacca 960
aaagctgatt gtgcagattt taatagaaaa cgaagacgtt ttattctaat ccatcaggga 1020
aatgagctga atggccccag caccatccaa gttgac 1056

<210> SEQ ID NO 141
<211> LENGTH: 968
<212> TYPE: DNA
<213> ORGANISM: Homo sapiens
<220> FEATURE:
<221> NAME/KEY: misc_feature
<222> LOCATION: (319)..(319)
<223> OTHER INFORMATION: n=a, c, g or t
<220> FEATURE:
<221> NAME/KEY: misc_feature
<222> LOCATION: (497)..(497)
<223> OTHER INFORMATION: n=a, c, g or t

<400> SEQUENCE: 141
acgagatgtc ccagtaacct aaaattatcc agtcggtctt cttactttac aactaagaaa 60
aataaggctt agaaagaggg attgccagaa actttggcag ctggattgcc tgtgcttgtt 120
cctctaagcc atacctaaat tctgcagtaa atacttaact ttttaatagg gaaattgctt 180

-continued

```
caagataact tgaccagtga tacggtaaaa taattagact attggactaa tggtttaaca    240
caagtggctt taaaaagtct gcttaaaaaa caatttttat ttagaaaaaa tagaaaaata    300
aaaacatctt caaaatttng gagcctgaag ggctgtttg tttcatatat ggataatctt    360
tgaaaaggca agtcctgtat gtatttttca tttgttgaaa gaagattggt tatcagtagg    420
cttgcaaaca taatttgctt ttaagttctt tcaaggtttt atgcaataaa acctattgat    480
ttggaacttt aaaaaanaaa acaacaaaaa aatactttca gggttttgta atttcaagtg    540
gtttttaag gggagcaata gtttgccatt taccaaaggc ttctccagat aatttcttaa    600
atgtttctac ttaaaaataa aagctattaa taataagctg tcatgggatc catttgaaga    660
cagggaaaat agaaaatttt tattgtaaag ggaagaactt atccttttaa ttttatggac    720
taacagagtc tgcaggtctt aactcatttc agcctgtcaa atgtgcaatt aaaaatgaat    780
tttctaattg tattcaaatg aggctctata gtgaatacag aatcactctt ctaagttttt    840
tcccagttaa tttgtttaaa agtgttgtac tctcttgcaa gaacgtttaa aagttaagtc    900
ttgtaactgt taacatctaa tgtattaata taagccattt gttttttacc atttttttaa    960
ggccgtat                                                              968
```

<210> SEQ ID NO 142
<211> LENGTH: 1466
<212> TYPE: DNA
<213> ORGANISM: Homo sapiens

<400> SEQUENCE: 142

```
gaaaatttga gtatcttttt gaaattttaa attgaaattt ggatagagat ggttatggag     60
agaaatcaaa caactggaat agctgtttga tatcacttaa aagtgataaa attttaagtt    120
gaatctggtc agtttgcaat ggcctatttg taagaaatat caagacttct tgagaaaaat    180
gaaaagtgaa tacataaatg cttaaaatct ggtacttctg agttaaggtt ttgctctttg    240
agcttaatcc aatttgggat gatttttcat cctagggctt tttgttttcc tttttttattt    300
ttatttttc tttttttagg ggaaggggac ttgctttctt ttccaaaaag gtgaatcctt    360
cttgtaggac ataggtaaaa aaaacaaagc tgaaatatat gttttgaata tagatagcta    420
attccctggg atataatatc ctttcaattt tttttttttt ttgggcccag tctgcctttg    480
gatgtttcaa aagtctgaac gagatgtccc agtaacctaa aattatccag tcggtcttct    540
tactttacaa ctaagaaaaa taaggcttag aaagagggat tgccagaaac tttggcagct    600
ggattgcctg tgcttgttcc tctaagccat acctaaattc tgcagtaaat acttaacttt    660
ttaataggga aattgcttca agataacttg accagtgata cggtaaaata attagactat    720
tggactaatg gtttaacaca agtggcttta aaaagtctgc ttaaaaaaca atttttattt    780
agaaaaaata gaaaaataaa aacatcttca aaatttagga gcctgaaggg gctgtttgtt    840
tcatatatgg ataatctttg aaaaggcaag tcctgtatgt atttttcatt tgttgaaaga    900
agattggtta tcagtaggct tgcaaacata atttgctttt aagttctttc aaggttttat    960
gcaataaaac ctattgattt ggaactttaa aaaaaaaaac aacaaaaaaa tactttcagg   1020
gttttgtaat ttcaagtggt tttttaaggg gagcaatagt ttgccattta ccaaaggctt   1080
ctccagataa tttcttaaat gtttctactt aaaaataaaa gctattaata ataagctgtc   1140
atgggatcca tttgaagaca gggaaaatag aaaattttta ttgtaaaggg aagaacttat   1200
ccttttaatt ttatggacta acagagtctg caggtcttaa ctcatttcag cctgtcaaat   1260
gtgcaattaa aaatgaattt tctaattgta ttcaaatgag gctctatagt gaatacagaa   1320
```

-continued

```
tcactcttct aagtttttc ccagttaatt tgtttaaaag tgttgtactc tcttgcaaga   1380

acgtttaaaa gttaagtctt gtaactgtta acatctaatg tattaatata agccatttgt   1440

tttttaccat ttttttaagg ccgtat                                        1466
```

<210> SEQ ID NO 143
<211> LENGTH: 306
<212> TYPE: DNA
<213> ORGANISM: Homo sapiens
<220> FEATURE:
<221> NAME/KEY: misc_feature
<222> LOCATION: (289)..(289)
<223> OTHER INFORMATION: n=a, c, g or t

<400> SEQUENCE: 143

```
gacacagcct atctcaaaga gagatgagaa gagccaggcc ccctctcttc ttcctccatg     60

ctgttagctc accagggcag atcttgacct caaagaatgc cgtcttccct tctggagctg    120

gtcctgtgat gtgaacctgg ctatcttcaa ttcacaggat agggagtaag acatttcatt    180

ttggccttag gtccaagcca tcttcttcaa tgtagctact actagagagc ccacaatgaa    240

gccaataatt ggctccccat ttggcaattt gtgtcctttt cagaaagang aagggttagt    300

aatcac                                                              306
```

<210> SEQ ID NO 144
<211> LENGTH: 494
<212> TYPE: DNA
<213> ORGANISM: Homo sapiens

<400> SEQUENCE: 144

```
gacacagcct atctcaaaga gagatgagaa gagccaggcc ccctctcttc ttcctccatg     60

ctgttagctc accagggcag atcttgacct caaagaatgc cgtcttccct tctggagctg    120

gtcctgtgat gtgaacctgg ctatcttcaa ttcacaggat agggagtaag acatttcatt    180

ttggccttag gtccaagcca tcttcttcaa tgtagctact actagagagc ccacaatgaa    240

gccaataatt ggctccccat ttggcaattt gtgtcccttt tcagaaagag gaagggttag    300

taatcagcac ttttaagtac cagcatgcag cattaacaag ttctcaaggc ctgcaagcca    360

tagggtttct gtcttccctg tattggcctt gtaatctctg accatgatta gggtaagagt    420

taagagactc ccaggacagg aaacggaaaa catcagattg tgtatggaat gaaccctctt    480

ggctggatgt ggtg                                                     494
```

<210> SEQ ID NO 145
<211> LENGTH: 174
<212> TYPE: DNA
<213> ORGANISM: Homo sapiens

<400> SEQUENCE: 145

```
gtggaacaac tctatgccat aaaatttctt atttcacagt taaatgaaca tatttgtgtt     60

atgtcacttt cttttagctt gcattccttt tataggaagg ccattttagg agtcctgggg    120

cattttgact caacttctta aatcatttat tctattcaca aaaggtttat tgaa          174
```

<210> SEQ ID NO 146
<211> LENGTH: 445
<212> TYPE: DNA
<213> ORGANISM: Homo sapiens
<220> FEATURE:
<221> NAME/KEY: misc_feature
<222> LOCATION: (371)..(371)

<223> OTHER INFORMATION: n=a, c, g or t
<220> FEATURE:
<221> NAME/KEY: misc_feature
<222> LOCATION: (391)..(391)
<223> OTHER INFORMATION: n=a, c, g or t
<220> FEATURE:
<221> NAME/KEY: misc_feature
<222> LOCATION: (406)..(406)
<223> OTHER INFORMATION: n=a, c, g or t
<220> FEATURE:
<221> NAME/KEY: misc_feature
<222> LOCATION: (427)..(427)
<223> OTHER INFORMATION: n=a, c, g or t

<400> SEQUENCE: 146
tgatttttaa caattgtgtg tgtgcaccca gctaaccatc tctacaatcg atctagaaca 60
ttttcatcac ttcagtgctt ctcgtatatt ccttcccagc taacccatga tccccaaccc 120
tggccatagg aacccgctga tccatcttct atcactttag attgaatttg tctttcctac 180
tgttttatat aaagaaatta cctcctttaa gtcctatcaa attcctgatc acccttaaaa 240
aacaattttt aggtattacc ataaaacctt ccatgacatt ctctgcttta tcttctctgt 300
gctactttgt ccattcattg ttgcattgta atgtatttct gtacatgtta tatcactaaa 360
ctgtctcctc nttgaaggga gggacatgtg ntcatcatct atttcnaagg cttatacaga 420
aactganaca tagtagatgc ttact 445

<210> SEQ ID NO 147
<211> LENGTH: 734
<212> TYPE: DNA
<213> ORGANISM: Homo sapiens

<400> SEQUENCE: 147
tgatttttaa caattgtgtg tgtgcaccca gctaaccatc tctacaatcg atctagaaca 60
ttttcatcac ttcagtgctt ctcgtatatt ccttcccagc taacccatga tccccaaccc 120
tggccatagg aacccgctga tccatcttct atcactttag attgaatttg tctttcctac 180
tgttttatat aaagaaatta cctcctttaa gtcctatcaa attcctgatc acccttaaaa 240
aacaattttt aggtattacc ataaaacctt ccatgacatt ctctgcttta tcttctctgt 300
gctactttgt ccattcattg ttgcattgta atgtatttct gtacatgtta tatcactaaa 360
ctgtctcctc cttgaaggga gggacatgtg ttcactcatc tattttcaag gcttattaca 420
gaaactgaaa catagtagat gcttacttgg gaatattata tctcaaaata gaaaaacacc 480
cagcaaatcg catcttatat tagtctttag aattagtatc aaagcctaat tattatgaca 540
cttgaaacat taaataactt agaaaacaaa gacttaaaag ttttatgata aagccagaaa 600
ctttttatac tgaccatttt taaatactga catttcagat taattggggg cagatgatat 660
atgaaattat agtttatact gtgacttctt aatacttcag ttgtgttaga taaactgata 720
gttcgtcaca tttt 734

<210> SEQ ID NO 148
<211> LENGTH: 29
<212> TYPE: PRT
<213> ORGANISM: Homo sapiens

<400> SEQUENCE: 148

Met Leu Lys Ile Ile Asp Lys Leu Tyr Phe Ser Tyr Leu His Ser Ala
1 5 10 15

Asp Ile Leu Cys Asn Thr Glu Ser Tyr Thr Leu Ser Met
20 25

<210> SEQ ID NO 149
<211> LENGTH: 87
<212> TYPE: PRT
<213> ORGANISM: Homo sapiens

<400> SEQUENCE: 149

```
Met Gly Trp His Glu Ile Gln Ile Pro Val Leu Ile Phe Leu Leu Ala
1               5                   10                  15

Val Tyr His Arg Thr Ser His Phe Thr Ser Leu Pro Leu Gly Pro Gln
            20                  25                  30

Phe Ser Val Phe Leu Ile Tyr Lys Tyr Ser His Pro Ala Phe Arg Gln
        35                  40                  45

Val Leu Arg Leu Asn Lys Glu Phe Asn Leu Leu Trp Leu His Ile Lys
    50                  55                  60

His Ile Leu Val Ser Val Cys Leu Val Ile Ser Asn Ala Asn Ile Leu
65                  70                  75                  80

Ser Ala Pro Cys Pro Glu Cys
                85
```

<210> SEQ ID NO 150
<211> LENGTH: 45
<212> TYPE: PRT
<213> ORGANISM: Homo sapiens

<400> SEQUENCE: 150

```
Ser Ser Val Ala Leu Ala Leu Gly Ala Leu Thr Val Trp His Ala Val
1               5                   10                  15

Leu Ile Ser Arg Gly Glu Thr Ser Ile Glu Arg His Ile Asn Lys Lys
            20                  25                  30

Glu Arg Arg Arg Leu Gln Ala Lys Gly Arg Val Ser Arg
        35                  40                  45
```

<210> SEQ ID NO 151
<211> LENGTH: 152
<212> TYPE: PRT
<213> ORGANISM: Homo sapiens

<400> SEQUENCE: 151

```
Met Val Pro Glu Val Leu Ile Leu Cys His Gly Leu Ala Val Trp Lys
1               5                   10                  15

Trp Phe Pro Gly Leu Ala Val Leu Arg Ile Pro Gly Cys Val Thr Gly
            20                  25                  30

Asn Lys Pro Phe Asn Leu Pro Gly Thr Val Phe Phe Cys Lys Met Arg
        35                  40                  45

Gly Leu Gly Ala Ser Phe Leu Arg Pro Trp Gly Leu Val Ala Glu Phe
    50                  55                  60

Ile Ser Pro Thr Pro Cys Pro Ser Ser Tyr Gly Ser Thr His Lys Ala
65                  70                  75                  80

Phe His Ser His Lys Glu Lys Ala His Lys Val Pro Gln Pro Pro His
                85                  90                  95

Thr Gln Glu Pro His Leu His Pro Ser Leu Lys Ala Arg Leu Pro Leu
            100                 105                 110

Pro Gln His Thr Gln Val Leu Leu Gly Leu Pro Ala Leu Phe Ser Ser
        115                 120                 125

Ser Pro Glu Trp Asn Gly Pro Ala Met Ala Ser Gln Arg Thr Ala Ser
    130                 135                 140
```

```
Trp Gln Ser Trp Glu Trp Val Glu
145                 150


<210> SEQ ID NO 152
<211> LENGTH: 29
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: X=any amino acid
<220> FEATURE:
<221> NAME/KEY: MISC_FEATURE
<222> LOCATION: (21)..(21)
<223> OTHER INFORMATION: X=any amino acid

<400> SEQUENCE: 152

Met Gly Leu Arg Val Leu Leu Leu Leu Gly Leu Ser Leu Xaa Met Ser
1               5                   10                  15

Gln Lys Pro Leu Xaa Gln Arg Pro Thr Ala Leu Gly Pro
            20                  25


<210> SEQ ID NO 153
<211> LENGTH: 46
<212> TYPE: PRT
<213> ORGANISM: Homo sapiens

<400> SEQUENCE: 153

Met Phe Leu Val Glu His Lys Val Cys Ser Gly Asn Thr Gln Val Ser
1               5                   10                  15

Ile Lys Cys Leu Pro Val Val Ser Glu Lys Phe Val Met Lys Tyr Phe
            20                  25                  30

Gly Asn Arg Cys Ile Val Ser Val Gly Gly Ala Asp Glu Phe
        35                  40                  45


<210> SEQ ID NO 154
<211> LENGTH: 34
<212> TYPE: PRT
<213> ORGANISM: Homo sapiens

<400> SEQUENCE: 154

Met Thr His Ser Glu Leu Leu Leu Val Ile Thr Ile Asn His Lys Met
1               5                   10                  15

Pro Gln Gly Pro Arg Val Thr Asn Trp Glu Pro Pro Pro Leu Thr Arg
            20                  25                  30

Ile Thr


<210> SEQ ID NO 155
<211> LENGTH: 99
<212> TYPE: PRT
<213> ORGANISM: Homo sapiens

<400> SEQUENCE: 155

Met Asp Ser Phe Leu Leu Leu Arg Gln Arg Glu Gly Gly Lys Arg Asn
1               5                   10                  15

Phe Lys Arg Asn Leu Gln Thr Cys Cys Ala Val Gly Pro Thr Gly Ile
            20                  25                  30

His Gly Gly Glu Thr Asn Ser Ile Met Leu Leu Gln Ile Leu Leu Lys
        35                  40                  45

Lys Gly Phe Asn Cys Leu Thr Lys Tyr Ser Ser Phe Phe His Leu Leu
    50                  55                  60

Thr Leu Gln Pro Asn Gln Val Pro His Thr Thr Gly Arg Cys Arg Glu
```

```
65                  70                  75                  80

Ile Pro Gln Pro Glu Lys Ile Ile His Ala Gly Gln Arg Gln Lys Phe
                85                  90                  95

Thr Pro Gly


<210> SEQ ID NO 156
<211> LENGTH: 55
<212> TYPE: PRT
<213> ORGANISM: Homo sapiens

<400> SEQUENCE: 156

Met Gln Phe Leu Leu Cys Leu Ser Leu Leu Asp Phe Phe Ser Ser Thr
1               5                   10                  15

Tyr Lys His Ala Val Met Ser Pro Asn Gln Lys Lys Cys Lys Asn Pro
            20                  25                  30

Phe Ser Pro Met Leu Thr His His Pro Ala Val Val Leu Phe Leu Pro
        35                  40                  45

Phe Thr Leu Leu Tyr Tyr Ser
    50                  55


<210> SEQ ID NO 157
<211> LENGTH: 59
<212> TYPE: PRT
<213> ORGANISM: Homo sapiens

<400> SEQUENCE: 157

Met Leu Gln Val Asp Val Cys Thr Leu Met Val Arg Thr Trp Ser Ser
1               5                   10                  15

Trp Pro Cys Trp Val Phe Ala Lys Glu Thr Val Leu Cys Ser Trp Gly
            20                  25                  30

Arg Phe His His Leu Ile Arg Ala Val Val Pro Thr Trp Cys Ser Leu
        35                  40                  45

Asp His Leu Tyr Lys Met Phe Ile Gly Gln Gly
    50                  55


<210> SEQ ID NO 158
<211> LENGTH: 62
<212> TYPE: PRT
<213> ORGANISM: Homo sapiens
<220> FEATURE:
<221> NAME/KEY: MISC_FEATURE
<222> LOCATION: (41)..(41)
<223> OTHER INFORMATION: X=any amino acid
<220> FEATURE:
<221> NAME/KEY: MISC_FEATURE
<222> LOCATION: (57)..(57)
<223> OTHER INFORMATION: X=any amino acid

<400> SEQUENCE: 158

Met Thr Lys Arg Met Glu Lys Cys Leu Asn Ile Tyr Lys Arg Leu Asp
1               5                  10                  15

Val Tyr Arg Gln Ile Val Ser Lys Gly His Arg Ile Val Arg Asn Ser
            20                  25                  30

Val Ile Leu Phe Cys Val Ile Asn Xaa Pro Phe Leu Tyr Pro Phe Thr
        35                  40                  45

Leu Ile Ile Asp Ile His His Phe Xaa Val Ile Ile Gln Leu
    50                  55                  60


<210> SEQ ID NO 159
<211> LENGTH: 47
<212> TYPE: PRT
```

-continued

<213> ORGANISM: Homo sapiens

<400> SEQUENCE: 159

```
His Leu Asn Arg Phe Ala Asn Ser Val Lys Val Phe Thr Arg Arg His
1               5                   10                  15

Ala Phe Val Lys Lys Phe Phe Arg Gly Ser Ala Cys Asn Cys Ala Glu
            20                  25                  30

Ser Ala Leu Leu Ser Ser Gln Leu Ala His Cys Val Gly Arg Trp
        35                  40                  45
```

<210> SEQ ID NO 160
<211> LENGTH: 43
<212> TYPE: PRT
<213> ORGANISM: Homo sapiens

<400> SEQUENCE: 160

```
Met Gln Glu Ala Glu Gly Arg Leu Asn Lys Pro Gln Gly Gly Arg Val
1               5                   10                  15

Gly Ala Glu Arg Val Gly Asn Ile Phe Phe Leu Leu Leu Asn Ser Arg
            20                  25                  30

Lys Ala Lys Thr Gln Ser Lys Leu Phe Leu Ser
        35                  40
```

<210> SEQ ID NO 161
<211> LENGTH: 62
<212> TYPE: PRT
<213> ORGANISM: Homo sapiens

<400> SEQUENCE: 161

```
Met Phe Gly Ile Leu Glu Lys Ser Ser Lys Tyr Val His Leu Glu Gly
1               5                   10                  15

Ser Leu Lys His Pro Val Ile Lys Leu Val Ser Ile Ser Val Val Lys
            20                  25                  30

Asp Glu Tyr Ser Leu Ile Asn Lys Arg Asn Lys Tyr Leu Asn Ser Leu
        35                  40                  45

Thr Ser Ile Leu Asn Arg Phe Cys Gly Gln Met Arg Leu Pro
    50                  55                  60
```

<210> SEQ ID NO 162
<211> LENGTH: 78
<212> TYPE: PRT
<213> ORGANISM: Homo sapiens

<400> SEQUENCE: 162

```
Met Thr Pro Ala Leu Ala Ala Trp His Val Leu Ile His Pro Asn Val
1               5                   10                  15

Cys Phe Leu Ala Pro Ala Asp Ser Leu Glu Gly Ser Ile Lys Glu Asp
            20                  25                  30

Trp Val Asn Met Asp Leu Glu Asn Ala His Leu Gln Arg Glu Asn Gly
        35                  40                  45

Gly Trp Ala Ala Phe Pro Ser Pro Ala Pro Val Pro Gly Ile Trp Pro
    50                  55                  60

Arg Ser Ala Ser Val Cys Phe Gly Ala Lys Leu Gln Ala Pro
65                  70                  75
```

<210> SEQ ID NO 163
<211> LENGTH: 51
<212> TYPE: PRT
<213> ORGANISM: Homo sapiens

<400> SEQUENCE: 163

Met Ser Ser Trp Ile Pro Phe Ile Ile Thr Pro Leu Phe Ser Gly Ile
1               5                   10                  15

Arg Leu Glu Ala Trp Cys Gln Phe Tyr Ser Ser Leu Tyr Pro Phe Ile
            20                  25                  30

His Phe Leu Ser Ile Leu Phe Pro Lys Tyr Phe Phe Ser Ala Pro Ser
        35                  40                  45

Pro Ala Ala
    50

<210> SEQ ID NO 164
<211> LENGTH: 27
<212> TYPE: PRT
<213> ORGANISM: Homo sapiens

<400> SEQUENCE: 164

Met Gly Ile Ile Pro Lys Cys Met Phe Leu Leu Gln Ser Arg Leu Met
1               5                   10                  15

Gly Val Ile Thr Asn Thr Ser Leu Leu Leu His
            20                  25

<210> SEQ ID NO 165
<211> LENGTH: 52
<212> TYPE: PRT
<213> ORGANISM: Homo sapiens

<400> SEQUENCE: 165

Met Lys Val Leu Lys Tyr His Asn Glu Ala Cys Gly Phe Tyr Ser Val
1               5                   10                  15

Val Trp Met Leu Ser Ser Ser Ile Pro Trp Met Pro Thr Gly Met His
            20                  25                  30

Cys Leu Ile Leu Glu Phe Lys Arg Trp Pro Gln Thr Val Arg Leu Ser
        35                  40                  45

Met Trp Pro His
    50

<210> SEQ ID NO 166
<211> LENGTH: 47
<212> TYPE: PRT
<213> ORGANISM: Homo sapiens

<400> SEQUENCE: 166

Met Gly Arg Lys Ser Thr Asn Lys Thr Ala Cys Thr His Ile Asn Thr
1               5                   10                  15

Tyr Val Ser Thr Asn Asp Lys Leu Tyr Leu Tyr Arg Ala Trp Glu Gly
            20                  25                  30

Ser Tyr Ile Thr Leu His Val Ser His Pro Pro His Thr Ser Arg
        35                  40                  45

<210> SEQ ID NO 167
<211> LENGTH: 42
<212> TYPE: PRT
<213> ORGANISM: Homo sapiens

<400> SEQUENCE: 167

Met Cys Trp Gly Tyr Phe Ser Ile Ser Lys Lys Phe Pro Asn Leu Thr
1               5                   10                  15

Ser Val Leu Met Asn Leu Gly Thr Asp Leu Ala Val Arg Pro Thr Ser
            20                  25                  30

-continued

```
Ile Phe Pro Thr Asp Ser Ile Leu Leu Glu
        35                  40


<210> SEQ ID NO 168
<211> LENGTH: 55
<212> TYPE: PRT
<213> ORGANISM: Homo sapiens

<400> SEQUENCE: 168

Met Asn Lys Ile Lys Gly Lys Ser Val Leu Phe Tyr Met Pro Glu Thr
1               5                   10                  15

Ser Arg Ile Phe Arg Lys Val Gln Phe Lys Glu Asn Gln Ala Ala Leu
            20                  25                  30

Asp Ser Thr Asn Lys Asn Val Ser Leu Ser Glu Glu Leu Val Asn Gln
        35                  40                  45

Gly Thr Gln Ser Ala Phe Ser
    50                  55


<210> SEQ ID NO 169
<211> LENGTH: 24
<212> TYPE: PRT
<213> ORGANISM: Homo sapiens

<400> SEQUENCE: 169

Met Met His Met Gln Leu Ile Ser Glu Phe Ser Cys Leu Cys Cys Phe
1               5                   10                  15

Phe Phe Leu Gly Ile Tyr Ile Lys
            20


<210> SEQ ID NO 170
<211> LENGTH: 68
<212> TYPE: PRT
<213> ORGANISM: Homo sapiens

<400> SEQUENCE: 170

Met Ile His Leu Ser Glu Val Ser Gly His Leu Lys Glu Arg Lys Gly
1               5                   10                  15

Lys Ala Ser Cys Gln Lys Gln Lys His Val Leu Tyr Lys Arg Phe Lys
            20                  25                  30

Asn Gln Asn Gly Ile Arg Leu Ser Asn Cys Lys Arg Gln Ser Ser Ala
        35                  40                  45

Phe Lys Ile Leu Arg Lys Asn Asn Val Tyr Ile Lys Ile Phe Ile Ile
    50                  55                  60

Ile Phe Asn Phe
65


<210> SEQ ID NO 171
<211> LENGTH: 100
<212> TYPE: PRT
<213> ORGANISM: Homo sapiens

<400> SEQUENCE: 171

Ser Phe Ala Phe Phe Phe Ser Leu Arg Gln Ser Leu Thr Leu Ser Pro
1               5                   10                  15

Arg Leu Glu Cys Ser Gly Thr Ile Ser Ala His Cys Asn Leu Cys Leu
            20                  25                  30

Leu Gly Ser Ser Asn Ser Ser Ala Ser Ala Ser Gln Val Ala Gly Ile
        35                  40                  45

Thr Gly Thr His His His Ala Gln Val Ile Phe Ile Phe Phe Ile Glu
    50                  55                  60
```

```
Met Gly Phe Arg His Ile Gly Gln Ala Gly Leu Lys Leu Leu Thr Ser
65                  70                  75                  80

Gly Asp Pro Pro Ala Ser Ala Ser Glu Ser Ala Gly Ile Thr Gly Val
                85                  90                  95

Arg His His Thr
            100


<210> SEQ ID NO 172
<211> LENGTH: 58
<212> TYPE: PRT
<213> ORGANISM: Homo sapiens

<400> SEQUENCE: 172

Met Glu Cys Leu Ser Ile Asn Leu Thr Lys Asn Val Ser Tyr Leu Tyr
1               5                   10                  15

Thr Gly Pro Leu Asn Thr Ser Glu Thr Lys Leu Lys Ser Tyr Leu Ile
            20                  25                  30

Gly Asn Gln Phe Pro Pro Arg Phe Ile Tyr Arg Val Ser Glu Ile Pro
        35                  40                  45

Ile Lys Ile Ser Ala Arg Ser Leu Arg Asn
    50                  55


<210> SEQ ID NO 173
<211> LENGTH: 47
<212> TYPE: PRT
<213> ORGANISM: Homo sapiens

<400> SEQUENCE: 173

Met Asp Lys Glu Glu Ser Ala Val Leu Val Gly Gly Ser Ile Leu Pro
1               5                   10                  15

Asp Lys Leu Phe Leu Val Gly Phe Thr Asp Thr Ser Pro Asp Leu Leu
            20                  25                  30

Pro Ala Ala Thr Val Cys Phe Tyr Asp Ala Cys His His Asp Ile
        35                  40                  45


<210> SEQ ID NO 174
<211> LENGTH: 106
<212> TYPE: PRT
<213> ORGANISM: Homo sapiens

<400> SEQUENCE: 174

Met Thr His Val Gln Leu His Ala Leu Asp Leu Leu Leu Lys Asp Glu
1               5                   10                  15

His Lys Ser Glu Ile Ser Thr Pro Trp Gln Pro Tyr Tyr Gln Leu Leu
            20                  25                  30

Ile Cys Ser Pro His Val Ser Thr Pro Phe Leu Ala Thr Ser Phe Cys
        35                  40                  45

Pro Ser His Ile Asn Thr Cys Gly Gln Trp Leu Thr Met Leu Lys Leu
    50                  55                  60

Lys Leu Tyr Pro Asp Glu Ile Leu Lys Arg Asn His Leu Cys Ser Ser
65                  70                  75                  80

Val Leu Thr Gln Glu Ser Gln His Val Phe Leu Phe Gln Glu Thr Ile
                85                  90                  95

Ile Ile Cys Thr Asn Ile Tyr Pro Asp Asn
            100                 105


<210> SEQ ID NO 175
<211> LENGTH: 35
```

<212> TYPE: PRT
<213> ORGANISM: Homo sapiens

<400> SEQUENCE: 175

```
Met Ser Met Leu Arg Lys Gly Leu Lys Ser Phe Phe Ser Val Cys Val
1               5                   10                  15

Leu Pro Ser Glu Pro Asn Ile Gly Ile Ser Ala Ser Lys Ile Pro Gln
            20                  25                  30

Gly Gln Glu
        35
```

<210> SEQ ID NO 176
<211> LENGTH: 54
<212> TYPE: PRT
<213> ORGANISM: Homo sapiens

<400> SEQUENCE: 176

```
Met Ser Ser Ser Pro Leu Val Ser Ala Lys Phe Ser Phe Leu Phe His
1               5                   10                  15

Glu Gly Arg Ala Pro Ser Leu Phe His Pro Leu Met Thr Ser Gln Pro
            20                  25                  30

Leu Glu Phe Cys Leu Met Met Asp Phe Ser Glu Ile Cys Leu Cys Asn
        35                  40                  45

Glu Asp Lys Asp Ser Gly
    50
```

<210> SEQ ID NO 177
<211> LENGTH: 20
<212> TYPE: PRT
<213> ORGANISM: Homo sapiens

<400> SEQUENCE: 177

```
Met Arg Pro Leu Lys Met Ile Arg Thr Ala Lys Lys Leu Phe Val Tyr
1               5                   10                  15

Leu Gly Ser Tyr
            20
```

<210> SEQ ID NO 178
<211> LENGTH: 66
<212> TYPE: PRT
<213> ORGANISM: Homo sapiens

<400> SEQUENCE: 178

```
Met Met Tyr Tyr Pro Asp Asp Leu Trp Asn Leu Leu Arg Asn Arg Asp
1               5                   10                  15

Cys Val Ala Phe Leu Ile Met Gly Thr Gly Pro Ser Leu Leu Arg Leu
            20                  25                  30

Pro Met Cys Val Gly Thr Glu Leu Leu Trp His Ser Ser Ser Arg Leu
        35                  40                  45

Met Glu Leu Ser Ser Ser Glu Ala Ser Trp Val Val His Ala Asn Leu
    50                  55                  60

Val Leu
65
```

<210> SEQ ID NO 179
<211> LENGTH: 70
<212> TYPE: PRT
<213> ORGANISM: Homo sapiens

<400> SEQUENCE: 179

-continued

```
Met Cys Val Ile Tyr Gln Arg Gly Ile Cys Asp Glu Lys Lys Asn Leu
1               5                   10                  15

Lys Cys Pro Gln Met Phe Gln Leu Ser Glu Thr Glu Lys Thr Leu Thr
            20                  25                  30

Ser Val Phe Arg Ile Ile Val Ser Asn Ile Leu Lys Ile Asp Val Ser
        35                  40                  45

Ser Val Met Ile Phe Leu Arg Leu His Gln Arg Thr Ser Leu Asn Leu
    50                  55                  60

Ser Val Ile Gln Asn Gln
65                  70


<210> SEQ ID NO 180
<211> LENGTH: 30
<212> TYPE: PRT
<213> ORGANISM: Homo sapiens

<400> SEQUENCE: 180

Met Asn Pro Val Cys Trp Val Gly Phe Gly Glu Val Asn Ile Glu His
1               5                   10                  15

Met Glu Phe Lys Tyr Ile Glu Met Asp Thr Val Ile Glu Met
            20                  25                  30


<210> SEQ ID NO 181
<211> LENGTH: 55
<212> TYPE: PRT
<213> ORGANISM: Homo sapiens

<400> SEQUENCE: 181

Met His Ala Cys Gly Ser Leu Arg Leu Asp Lys Asp Pro Thr Thr Leu
1               5                   10                  15

Leu Cys Val Asn Thr Arg Cys Thr Arg Ser His Leu Pro Gly Ala Gly
            20                  25                  30

Gly Trp Trp Arg Lys Val Lys Ser Gln Gln Thr Val His Arg Thr Tyr
        35                  40                  45

Ser Ala Thr Gly Lys Lys Ser
    50                  55


<210> SEQ ID NO 182
<211> LENGTH: 16
<212> TYPE: PRT
<213> ORGANISM: Homo sapiens

<400> SEQUENCE: 182

Met Pro Ala Leu Arg Glu Ala Phe Pro Gln Ala Pro Leu Ala Leu Ala
1               5                   10                  15


<210> SEQ ID NO 183
<211> LENGTH: 48
<212> TYPE: PRT
<213> ORGANISM: Homo sapiens

<400> SEQUENCE: 183

Met Thr Phe Gln Lys Leu Met Ile Leu His Ile His Asp Gln Met Phe
1               5                   10                  15

Ser Leu Met Glu Ala Ser Asp Val Cys Ser His Gln Ile Arg Phe Lys
            20                  25                  30

Met Ser Val Ser Ser Lys Ser Ser Lys Thr Ser Pro Ser His Gln Lys
        35                  40                  45


<210> SEQ ID NO 184
```

```
<211> LENGTH: 55
<212> TYPE: PRT
<213> ORGANISM: Homo sapiens

<400> SEQUENCE: 184

Met Ser Val Leu Lys Arg Phe Leu Lys Pro Ser Leu Ser Ile Ala Lys
1               5                   10                  15

Thr Cys Tyr Val His Tyr Pro Pro Asn Ser Tyr Leu Lys Thr Thr Pro
            20                  25                  30

Lys Met Leu Tyr Phe Val Phe Lys Val Arg Glu Glu Asn Arg Gly Glu
        35                  40                  45

Val Phe Leu Cys Ser Phe Pro
    50                  55


<210> SEQ ID NO 185
<211> LENGTH: 14
<212> TYPE: PRT
<213> ORGANISM: Homo sapiens

<400> SEQUENCE: 185

Met Trp Leu Arg Asp Leu Asn Tyr Lys Ile Ala Arg Leu Asp
1               5                   10


<210> SEQ ID NO 186
<211> LENGTH: 42
<212> TYPE: PRT
<213> ORGANISM: Homo sapiens

<400> SEQUENCE: 186

Met Met Phe Phe Tyr Ile Phe Cys Ser Met Gly Leu Leu Ile Pro Phe
1               5                   10                  15

Ser Thr Leu Lys Met Leu Leu Ile Val Phe Pro Leu Ser Leu Phe Pro
            20                  25                  30

Lys Arg Asn Leu Leu Ser Phe Leu Ser Leu
        35                  40


<210> SEQ ID NO 187
<211> LENGTH: 100
<212> TYPE: PRT
<213> ORGANISM: Homo sapiens

<400> SEQUENCE: 187

Leu Phe Phe Phe Leu Arg Trp Ser Leu Ala Leu Val Thr Gln Ala Gly
1               5                   10                  15

Val Gln Val Val Asp Ile Gly Ser Leu Gln Pro Leu Pro Pro Gly Phe
            20                  25                  30

Lys Gln Phe Ser Cys Pro Ser Leu Leu Ser Ser Trp Asp Tyr Arg His
        35                  40                  45

Gly Pro Pro Arg Pro Ala Asn Phe Phe Val Phe Leu Val Glu Met Gly
    50                  55                  60

Phe His His Val Gly Gln Ala Gly Pro Glu Leu Leu Thr Ser Ser Asp
65                  70                  75                  80

Pro Pro Ala Leu Ala Ser Gln Ser Ala Gly Ile Thr Gly Val Ser His
                85                  90                  95

Leu Thr Trp Pro
            100


<210> SEQ ID NO 188
<211> LENGTH: 106
<212> TYPE: PRT
```

<213> ORGANISM: Homo sapiens

<400> SEQUENCE: 188

```
Met Ser Cys Leu Trp Pro Ser Leu Asp Leu Pro Ser Leu Ser His Ser
1               5                   10                  15

Lys Gln Ser Ser Ser Gln Ala Glu Gly Gln Val Thr Ser His Thr Arg
            20                  25                  30

Gln Arg Phe Pro Asp Gly Ala His Leu His Pro Ser Leu Thr Leu Val
        35                  40                  45

Leu Ser Gln Asp Ala Pro Leu Arg Leu Ala Pro Pro Thr Leu Cys Leu
    50                  55                  60

Leu Cys Tyr Trp Ala Ser Leu Pro Ser Pro Arg Thr Pro Glu Leu Leu
65                  70                  75                  80

Asn Ala Gly Gln Lys Ser Ile Pro Asp Leu Gln Gln Arg His Phe Asp
                85                  90                  95

Ile Lys Glu Met Ala Leu Asp Phe Cys Leu
            100                 105
```

<210> SEQ ID NO 189
<211> LENGTH: 46
<212> TYPE: PRT
<213> ORGANISM: Homo sapiens

<400> SEQUENCE: 189

```
Met Val Ile Ser Arg Ile Ser Ile Leu Arg Lys Met Thr Lys Phe His
1               5                   10                  15

Lys Phe Cys Ser Gln Leu Thr Glu Pro Gly Arg Arg Thr Gln Pro Lys
            20                  25                  30

Glu Asn Pro Trp Ser Leu Tyr Asp Thr Asp Trp Leu Glu Lys
        35                  40                  45
```

<210> SEQ ID NO 190
<211> LENGTH: 46
<212> TYPE: PRT
<213> ORGANISM: Homo sapiens

<400> SEQUENCE: 190

```
Met Ser Arg Val Arg Ala Glu Lys Pro Gly Arg Val Ala Lys Leu Ala
1               5                   10                  15

Ala Cys Arg Pro Leu Pro Arg Leu Gln Met Ser Gly Ser Ile Pro Leu
            20                  25                  30

His Lys Cys Lys Glu Lys Ala Ser Met Pro Pro Leu Trp Ser
        35                  40                  45
```

<210> SEQ ID NO 191
<211> LENGTH: 50
<212> TYPE: PRT
<213> ORGANISM: Homo sapiens

<400> SEQUENCE: 191

```
Met Arg Pro Ala Arg Leu Gly Pro Arg Cys Ser Asp Leu Asp Phe Gly
1               5                   10                  15

Leu Val Leu Ser Ser Trp Leu Arg Leu Ala Arg Cys Pro Leu Glu Ser
            20                  25                  30

Ser Phe Gly Phe Ala Phe Phe Val Cys Leu Phe Ser Pro Asn Phe Cys
        35                  40                  45

Gln Thr
    50
```

-continued

<210> SEQ ID NO 192
<211> LENGTH: 76
<212> TYPE: PRT
<213> ORGANISM: Homo sapiens

<400> SEQUENCE: 192

```
Met Glu Gly Thr Val Gly Gln Ala Lys Met Val Glu Lys Trp Met Arg
1               5                   10                  15

Pro Thr Leu Leu Met Ser Leu Arg Gly Leu Gly Glu Arg Ser Asn Glu
            20                  25                  30

Pro His Val Ser Pro Glu Ser Ser Ala Ala Pro Lys Ala Gly Pro Ser
        35                  40                  45

Leu Glu Asp Cys Glu Arg Glu Asp Gly Ser Ile Arg Thr Gly Trp Asp
    50                  55                  60

Thr Ala Pro Thr Lys Glu Ser Pro Thr Ser Cys Ala
65                  70                  75
```

<210> SEQ ID NO 193
<211> LENGTH: 54
<212> TYPE: PRT
<213> ORGANISM: Homo sapiens

<400> SEQUENCE: 193

```
Arg Thr Val Cys Thr Lys Val Ser Cys Pro Val Gln Leu Pro Ala Asp
1               5                   10                  15

Trp Thr Cys Lys Val Gln Pro Val Trp Leu Glu Phe Pro Cys Leu Pro
            20                  25                  30

Ile Ser Cys Arg Leu Arg Val Ser Ser Asp Thr Ser Pro Asp Ser Ala
        35                  40                  45

Thr Trp Gly Ser Trp Lys
    50
```

<210> SEQ ID NO 194
<211> LENGTH: 27
<212> TYPE: PRT
<213> ORGANISM: Homo sapiens

<400> SEQUENCE: 194

```
Met Glu Pro Arg Ile Pro Val Lys Thr Phe Ser Phe Asp Lys Arg Ile
1               5                   10                  15

Leu Ile Arg Ile Leu Tyr Gln Ile Glu Gln Lys
            20                  25
```

<210> SEQ ID NO 195
<211> LENGTH: 17
<212> TYPE: PRT
<213> ORGANISM: Homo sapiens

<400> SEQUENCE: 195

```
Met Leu Gln His Leu Arg Leu Thr Ile Trp Gly Glu Cys Val Trp Val
1               5                   10                  15

Phe
```

<210> SEQ ID NO 196
<211> LENGTH: 51
<212> TYPE: PRT
<213> ORGANISM: Homo sapiens

<400> SEQUENCE: 196

```
Met Arg Asn Val Ser Leu Ile Ser Cys Glu Asp Ala Asp Phe Thr Glu
```

-continued

```
1               5                   10                  15

Ala Leu Cys Asn Ile Trp Phe Val His Gln Thr Met Leu Ile Asp Cys
            20                  25                  30

Arg Ser His Leu Leu Pro Arg Trp Leu Thr Lys Thr Val Gly Ser Leu
        35                  40                  45

Leu Lys Pro
    50


<210> SEQ ID NO 197
<211> LENGTH: 62
<212> TYPE: PRT
<213> ORGANISM: Homo sapiens

<400> SEQUENCE: 197

Met Ser His Gly Gln Val Leu Gly Asp Val Ala Gly Lys Val Gly His
1               5                   10                  15

Ala Leu Gly Thr Glu Asp Gln Thr Phe Ala Val Glu Val Leu Lys Glu
            20                  25                  30

Thr Thr Pro Phe Phe Arg Ala Ser Ser Gly Pro Thr Gly Asp Pro Trp
        35                  40                  45

Cys Pro Asp His Lys Ile Gln Ser Lys Pro Val Ser Leu Ser
    50                  55                  60


<210> SEQ ID NO 198
<211> LENGTH: 400
<212> TYPE: PRT
<213> ORGANISM: Homo sapiens

<400> SEQUENCE: 198

Met Leu Leu Leu Val Thr Ser Leu Leu Leu Cys Glu Leu Pro His Pro
1               5                   10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
        35                  40                  45

Trp Asp Cys Gln Glu Asn Thr Thr Phe Ser Lys Cys Phe Leu Thr Asp
    50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
    130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
        195                 200                 205

Leu Leu Asp Thr Lys Lys Ile Glu Arg Phe Asn Pro Pro Ser Asn Val
```

```
    210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
        275                 280                 285

Arg Ala Lys His Ser Val Lys Ile Arg Ala Ala Asp Val Arg Ile Leu
    290                 295                 300

Asn Trp Ser Ser Trp Ser Glu Ala Ile Glu Phe Gly Ser Asp Asp Gly
305                 310                 315                 320

Asn Leu Gly Ser Val Tyr Ile Tyr Val Leu Leu Ile Val Gly Thr Leu
                325                 330                 335

Val Cys Gly Ile Val Leu Gly Phe Leu Phe Lys Arg Phe Leu Arg Ile
            340                 345                 350

Gln Arg Leu Phe Pro Pro Val Pro Gln Ile Lys Asp Lys Leu Asn Asp
        355                 360                 365

Asn His Glu Val Glu Asp Glu Ile Ile Trp Glu Glu Phe Thr Pro Glu
    370                 375                 380

Glu Gly Lys Gly Tyr Arg Glu Glu Val Leu Thr Val Lys Glu Ile Thr
385                 390                 395                 400


<210> SEQ ID NO 199
<211> LENGTH: 10
<212> TYPE: PRT
<213> ORGANISM: Homo sapiens

<400> SEQUENCE: 199

Met Asp Arg Met Glu Lys Arg Gln Thr Asp
1               5                   10


<210> SEQ ID NO 200
<211> LENGTH: 20
<212> TYPE: PRT
<213> ORGANISM: Homo sapiens

<400> SEQUENCE: 200

Met Cys Tyr Ala Thr Leu His Gln Ile Asn Phe Leu Gln Thr Val Leu
1               5                   10                  15

Val Pro Gly Leu
            20


<210> SEQ ID NO 201
<211> LENGTH: 31
<212> TYPE: PRT
<213> ORGANISM: Homo sapiens

<400> SEQUENCE: 201

Met Cys Leu Cys Cys Trp Leu Tyr Trp Glu Glu Tyr Gly Pro Leu Ser
1               5                   10                  15

Leu Thr Gln Glu Phe His Val Phe Cys Gln Asp Thr Leu His Gly
            20                  25                  30


<210> SEQ ID NO 202
<211> LENGTH: 54
<212> TYPE: PRT
<213> ORGANISM: Homo sapiens
```

<400> SEQUENCE: 202

```
Met Asn His Ser Leu Ser Ala Phe Gln Arg Ala Leu Gln Val Leu Ile
1               5                   10                  15

Phe Lys Met Ser Val Tyr Ala Ser Gly Pro Arg Leu Glu Lys Lys Val
            20                  25                  30

Gly Asn Lys Leu Glu Gly Gly Arg Lys Gln Glu Arg Asn Val Thr Tyr
        35                  40                  45

Met Ala Asp Glu Gly Phe
    50
```

<210> SEQ ID NO 203
<211> LENGTH: 35
<212> TYPE: PRT
<213> ORGANISM: Homo sapiens

<400> SEQUENCE: 203

```
Met Ile Lys Ala Tyr His Pro Tyr Phe Glu Asn Phe Asn His Arg Ala
1               5                   10                  15

Gln Tyr Val Ser Asn Lys Leu Lys Lys Tyr Ser Phe Gln Leu His Phe
            20                  25                  30

Asp Gly His
        35
```

<210> SEQ ID NO 204
<211> LENGTH: 76
<212> TYPE: PRT
<213> ORGANISM: Homo sapiens

<400> SEQUENCE: 204

```
Met Lys Met Val Asn Arg His Met Lys Trp Lys Ser Ser Ala Leu Ser
1               5                   10                  15

Asp Leu Val Cys Ile Ser Thr Glu Ile Gln Ala Gly Leu Thr Arg His
            20                  25                  30

Thr Ser His Asn Phe Gln Cys His Cys Thr Ile Ile Leu Thr Val Val
        35                  40                  45

Ser Phe Phe Gln Ser Thr Glu Lys Gln Ala Asp Lys Pro Arg His Leu
    50                  55                  60

Asn Val Thr Trp Leu Met Thr Leu Ile Ser Thr Leu
65                  70                  75
```

<210> SEQ ID NO 205
<211> LENGTH: 94
<212> TYPE: PRT
<213> ORGANISM: Homo sapiens

<400> SEQUENCE: 205

```
Met Glu Gly Gln Asp Ser Leu Arg Asp Val Gly Ala Leu Ser His Leu
1               5                   10                  15

Ala His Thr Asp Arg Ser Trp Leu Gly Arg Ala Gly Val Ser Ala Trp
            20                  25                  30

Arg Pro Ser Ala Ala Gly Asp Pro Gly Phe His Glu Val Gly Gly Val
        35                  40                  45

His Ala Gly Thr Ser Gln Leu Ala Gly Pro Gly Gly His Pro Gly Gly
    50                  55                  60

Ala Gly Ala Trp Gly His Glu Phe Thr Lys Val Ala Gln Gly Gln Glu
65                  70                  75                  80

Glu Thr Val Val Ala Glu Gly Pro Leu Val Glu Ala Trp Ala
```

```
                85                  90


<210> SEQ ID NO 206
<211> LENGTH: 53
<212> TYPE: PRT
<213> ORGANISM: Homo sapiens

<400> SEQUENCE: 206

Met Pro Gln Asp Gln Asp Pro Pro Arg Glu Glu His Ala Ala Leu Arg
1               5                   10                  15

Val Leu Phe Pro Arg Val Pro Leu Ala Val Pro His Gln Leu Gly Gly
            20                  25                  30

Glu Leu Glu Arg Ala Asp Arg Arg Thr Gly Phe Ser Ala Cys Ala Asn
        35                  40                  45

Ile Leu Thr Cys Pro
    50


<210> SEQ ID NO 207
<211> LENGTH: 75
<212> TYPE: PRT
<213> ORGANISM: Homo sapiens

<400> SEQUENCE: 207

Trp Ser Thr Pro Pro Phe Asp Pro Arg Phe Pro Ser Gln Asn Gln Ile
1               5                   10                  15

Arg Asn Cys Tyr Gln Asn Phe Leu Asp Tyr His Arg Cys Leu Lys Thr
            20                  25                  30

Arg Thr Arg Arg Gly Lys Ser Thr Gln Pro Cys Glu Tyr Tyr Ser Cys
        35                  40                  45

Val Tyr His Ser Leu Cys Pro Ile Ser Trp Val Glu Ser Trp Asn Glu
    50                  55                  60

Gln Ile Lys Asn Gly Ile Phe Ala Gly Lys Ile
65                  70                  75


<210> SEQ ID NO 208
<211> LENGTH: 44
<212> TYPE: PRT
<213> ORGANISM: Homo sapiens

<400> SEQUENCE: 208

Met Arg Val Leu Arg Lys Glu Ser Pro Ser Arg His Val Leu Lys Asn
1               5                   10                  15

Met Cys Leu Ile Arg Asn Pro Arg Glu Gly Thr Ala Ala Asn Asn Glu
            20                  25                  30

Met Glu Ser Ala Thr Gly Glu Glu Lys Gly Asn Arg
        35                  40


<210> SEQ ID NO 209
<211> LENGTH: 83
<212> TYPE: PRT
<213> ORGANISM: Homo sapiens
<220> FEATURE:
<221> NAME/KEY: MISC_FEATURE
<222> LOCATION: (80)..(80)
<223> OTHER INFORMATION: X=any amino acid

<400> SEQUENCE: 209

Met His Arg Lys Lys Lys Leu Glu Ser Phe Leu Leu Leu Ile Pro Pro
1               5                   10                  15

Pro Tyr Leu Pro Leu Thr Lys Met Trp Gly Glu Pro Arg Phe Glu Gly
            20                  25                  30
```

-continued

Ser Thr Gly Pro Cys Pro Gln Asp Ser Met Glu Gln Pro Val Thr Lys
        35                  40                  45

Gln Gly Ile Ser Leu Lys Ser Cys Leu Pro Lys Lys Ile Lys Leu Pro
    50                  55                  60

Arg Leu Ala Leu His Pro Ser Pro Pro Arg Ser Phe Pro Leu Lys Xaa
65                  70                  75                  80

Lys Lys Leu

<210> SEQ ID NO 210
<211> LENGTH: 40
<212> TYPE: PRT
<213> ORGANISM: Homo sapiens

<400> SEQUENCE: 210

Met Thr Arg Phe Ser Gln Ala Ser Ser Ser Lys Asp Lys Thr Pro Pro
1               5                   10                  15

Leu Pro Ser Met Val Gln Ala Thr Val Leu Val Lys Lys Tyr Ile Phe
            20                  25                  30

Thr Lys Lys Lys Ser Tyr Val Leu
        35                  40

<210> SEQ ID NO 211
<211> LENGTH: 87
<212> TYPE: PRT
<213> ORGANISM: Homo sapiens

<400> SEQUENCE: 211

Met Pro Arg Pro Thr Glu Gly Glu Gly Ser Thr Glu Asp Arg Asp Pro
1               5                   10                  15

Ile Gly Ile Gln Ser Gln Thr Arg Ala Glu Pro Thr Val Glu Gln Leu
            20                  25                  30

Met Ser Gly Ala Lys Asp Thr Ser Trp Asn Pro Pro Asp Gly Ser Ser
        35                  40                  45

Asn Pro Lys Arg Ala Gly Leu Gln Val Gly Leu Asn Trp Arg Asp Pro
    50                  55                  60

Gln Glu Ser Gly Arg Arg Asn Thr Arg Ala Phe Leu Glu Glu Gly Thr
65                  70                  75                  80

Phe Ile Leu Asp Ser Asn Gln
                85

<210> SEQ ID NO 212
<211> LENGTH: 38
<212> TYPE: PRT
<213> ORGANISM: Homo sapiens

<400> SEQUENCE: 212

Met Met Pro Gly Pro Ala Ala Leu Ile Pro Pro Thr Ala Thr Ala Cys
1               5                   10                  15

Leu Leu Val Val Ala Arg Gly Ser Ser Val Pro Lys Asp Ser Ser Leu
            20                  25                  30

Phe Cys Ile Thr Val His
        35

<210> SEQ ID NO 213
<211> LENGTH: 88
<212> TYPE: PRT
<213> ORGANISM: Homo sapiens

<400> SEQUENCE: 213

```
Met Ser Leu Leu Asp Ala Ser Ser Leu Lys Pro Tyr Asp Ser Phe Leu
1               5                   10                  15

Leu Ala Val Leu Phe Leu Thr Arg Asp Asn Lys Gly Phe Ala Ser Gln
            20                  25                  30

Val Cys Met Ala Lys Lys Val Ser Thr Ser Val Asn Gly Ser Phe Leu
        35                  40                  45

Met Thr Ser Gln Gln Pro Leu Val Lys Asp Val Ile Glu Ile Val Gln
    50                  55                  60

Arg Leu Gly Ser Val Cys Phe Val Leu Leu Leu Lys Ser Phe His Gly
65                  70                  75                  80

Ser Lys Leu Phe Leu Ser Ile Val
                85


<210> SEQ ID NO 214
<211> LENGTH: 42
<212> TYPE: PRT
<213> ORGANISM: Homo sapiens

<400> SEQUENCE: 214

Met Val Ile Arg Glu Leu Leu Gly Gly Gln Lys Tyr Pro Asn Pro Val
1               5                   10                  15

Gln Gly Arg Asp Pro Trp Thr Val Thr Val Leu Ser Ala Phe Gly Arg
            20                  25                  30

Glu Gly Asp Ser Glu Ala Gln Thr Arg Ile
        35                  40


<210> SEQ ID NO 215
<211> LENGTH: 49
<212> TYPE: PRT
<213> ORGANISM: Homo sapiens
<220> FEATURE:
<221> NAME/KEY: MISC_FEATURE
<222> LOCATION: (46)..(46)
<223> OTHER INFORMATION: X=any amino acid

<400> SEQUENCE: 215

Met Pro Asn Cys Ser Val Glu Leu Arg Gly Tyr Tyr Tyr Asn Phe Val
1               5                   10                  15

His Tyr Tyr Lys Tyr Phe Ile Leu Val Val Tyr Ser Thr Ala Asp Ser
            20                  25                  30

Asn Gln Lys Thr Lys Ile Gln Lys Tyr Tyr Ile Leu Glu Xaa Ile Ile
        35                  40                  45
Met


<210> SEQ ID NO 216
<211> LENGTH: 37
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: X=any amino acid
<220> FEATURE:
<221> NAME/KEY: MISC_FEATURE
<222> LOCATION: (8)..(8)
<223> OTHER INFORMATION: X=any amino acid

<400> SEQUENCE: 216

Met Glu Met Leu Glu Xaa Lys Xaa Thr Ile Ile Asp Ile Val Ser Leu
1               5                   10                  15

Leu Ala Leu Ser Gly Asp Leu Thr Gln Leu Arg Lys Ser Leu Val Thr
            20                  25                  30
```

```
Leu Lys Ile Cys Arg
        35


<210> SEQ ID NO 217
<211> LENGTH: 72
<212> TYPE: PRT
<213> ORGANISM: Homo sapiens

<400> SEQUENCE: 217

Met Gly Ser Tyr Gly Leu Leu Phe Lys Phe Tyr Gly Ala Ile Phe Thr
1               5                   10                  15

Ser Val Ala Gln Gly Trp Ser Val Leu His Leu Arg Lys Val Ser Leu
            20                  25                  30

Gly Lys Cys Pro Cys His Pro Ser His Ser Arg Gln Ala Ala Ser Ser
        35                  40                  45

Ala Phe Ser Ser Ser Ser Ser His Ala Trp Ser Ser Pro Phe Val Ile
    50                  55                  60

Phe Ser Ser Leu Thr Pro Ser Leu
65                  70


<210> SEQ ID NO 218
<211> LENGTH: 49
<212> TYPE: PRT
<213> ORGANISM: Homo sapiens

<400> SEQUENCE: 218

Met Gly Ser Phe Ser Pro Leu Thr Tyr His Leu Gly His Trp Asn Met
1               5                   10                  15

Ala Ala Cys Gly Ser Val Cys Glu Gly Pro Gly Asp Gly Gln Gly Gly
            20                  25                  30

Ser Ala Leu Phe Cys Phe Tyr Gln His Cys Ser Met Asn Val Phe Leu
        35                  40                  45

Thr


<210> SEQ ID NO 219
<211> LENGTH: 34
<212> TYPE: PRT
<213> ORGANISM: Homo sapiens

<400> SEQUENCE: 219

Met Leu Thr Arg His His Pro Leu Asn Val Leu Leu His Arg Leu Cys
1               5                   10                  15

Leu Asn Trp Leu Glu Glu Asn Asn Tyr Pro Arg Asn Thr Asp Tyr Leu
            20                  25                  30

Ile Phe


<210> SEQ ID NO 220
<211> LENGTH: 34
<212> TYPE: PRT
<213> ORGANISM: Homo sapiens
<220> FEATURE:
<221> NAME/KEY: MISC_FEATURE
<222> LOCATION: (17)..(17)
<223> OTHER INFORMATION: X=any amino acid

<400> SEQUENCE: 220

Met Leu Leu Leu Pro Ala Thr Phe Leu Pro Thr Ser His Ala Arg Pro
1               5                   10                  15

Xaa Gln Pro His Cys His Thr Thr Cys Leu Ile Thr Ser His Val Leu
            20                  25                  30
```

-continued

Thr His

<210> SEQ ID NO 221
<211> LENGTH: 111
<212> TYPE: PRT
<213> ORGANISM: Homo sapiens

<400> SEQUENCE: 221

```
Met Gly Pro Ser Ser Cys Leu Leu Leu Ile Leu Ile Pro Leu Leu Gln
1               5                   10                  15

Leu Ile Asn Leu Gly Ser Thr Gln Cys Ser Leu Asp Ser Val Met Asp
            20                  25                  30

Lys Lys Ile Lys Asp Val Leu Asn Ser Leu Glu Tyr Ser Pro Ser Pro
        35                  40                  45

Ile Ser Lys Lys Leu Ser Cys Ala Ser Val Lys Ser Gln Gly Arg Pro
    50                  55                  60

Ser Ser Cys Pro Ala Gly Met Ala Val Thr Gly Cys Ala Cys Gly Tyr
65                  70                  75                  80

Gly Cys Gly Ser Trp Asp Val Gln Leu Glu Thr Thr Cys His Cys Gln
                85                  90                  95

Cys Ser Val Val Asp Trp Thr Thr Ala Arg Cys Cys His Leu Thr
            100                 105                 110
```

<210> SEQ ID NO 222
<211> LENGTH: 111
<212> TYPE: PRT
<213> ORGANISM: Homo sapiens

<400> SEQUENCE: 222

```
Met Gly Pro Ser Ser Cys Leu Leu Leu Ile Leu Ile Pro Leu Leu Gln
1               5                   10                  15

Leu Ile Asn Leu Gly Ser Thr Gln Cys Ser Leu Asp Ser Val Met Asp
            20                  25                  30

Lys Lys Ile Lys Asp Val Leu Asn Ser Leu Glu Tyr Ser Pro Ser Pro
        35                  40                  45

Ile Ser Lys Lys Leu Ser Cys Ala Ser Val Lys Ser Gln Gly Arg Pro
    50                  55                  60

Ser Ser Cys Pro Ala Gly Met Ala Val Thr Gly Cys Ala Cys Gly Tyr
65                  70                  75                  80

Gly Cys Gly Ser Trp Asp Val Gln Leu Glu Thr Thr Cys His Cys Gln
                85                  90                  95

Cys Ser Val Val Asp Trp Thr Thr Ala Arg Cys Cys His Leu Thr
            100                 105                 110
```

<210> SEQ ID NO 223
<211> LENGTH: 83
<212> TYPE: PRT
<213> ORGANISM: Homo sapiens

<400> SEQUENCE: 223

```
Met Asn Val Glu Ala Arg Glu Gln Cys Asp Val Gln Leu Ser Asp Leu
1               5                   10                  15

Thr Trp His Leu Ile Trp Leu Glu Val Pro Pro Leu Leu Ser Val Pro
            20                  25                  30

Trp Leu Trp Ala His Gly Leu Ala Glu Pro Ser Tyr Gly Phe Arg Phe
        35                  40                  45

Thr Cys Tyr Asn Ile Gln Arg Gln Cys Thr Ser Leu Pro Arg Lys Leu
```

```
    50                  55                  60

Cys Ser Arg His Pro Phe Val Thr Leu Ile Ser Ile Met Asp Thr Thr
65                  70                  75                  80

Thr Phe Tyr


<210> SEQ ID NO 224
<211> LENGTH: 132
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X=any amino acid
<220> FEATURE:
<221> NAME/KEY: MISC_FEATURE
<222> LOCATION: (11)..(11)
<223> OTHER INFORMATION: X=any amino acid
<220> FEATURE:
<221> NAME/KEY: MISC_FEATURE
<222> LOCATION: (14)..(14)
<223> OTHER INFORMATION: X=any amino acid

<400> SEQUENCE: 224

Met Asp Xaa Thr Arg Val His Asp Asp Glu Xaa Val Ile Xaa Gly Asp
1               5                   10                  15

Val Phe Val His Glu Val Thr Pro Gly Pro His Arg Trp Val Leu Val
            20                  25                  30

Arg Pro Phe Cys Leu Glu Val Arg Ala Val Phe Leu Arg Leu Trp Tyr
        35                  40                  45

Tyr Arg Gly Glu Lys Glu Glu Glu Leu Glu Val Arg Glu Arg Ser Cys
    50                  55                  60

Arg Leu Gly Arg Cys Asp Gln Gly Gln Arg Asp Gly Val Gln Glu Ala
65                  70                  75                  80

Cys Ser Ser Val Ser Cys Ser Leu Arg Gln Glu Val Ser Pro Ser Ser
                85                  90                  95

Gln Leu Asp Met Arg Ser Leu Leu Gly Val Pro Leu Ala Glu Val Glu
            100                 105                 110

Pro Val Ala Gln His Pro Pro Asn Glu Gly Arg Gly Arg His Leu Gly
        115                 120                 125

Gln Cys Leu Leu
    130


<210> SEQ ID NO 225
<211> LENGTH: 38
<212> TYPE: PRT
<213> ORGANISM: Homo sapiens

<400> SEQUENCE: 225

Met Ile Asn Asn Ser Asn His Asn Asn Ser Ser Ser Ser Lys Leu Arg
1               5                   10                  15

Ala Ser Tyr Val Gln Ala Phe Ser Lys His Phe Thr Cys Ile Thr Pro
            20                  25                  30

Leu Val Ile Thr Thr Pro
        35


<210> SEQ ID NO 226
<211> LENGTH: 58
<212> TYPE: PRT
<213> ORGANISM: Homo sapiens

<400> SEQUENCE: 226
```

-continued

```
Met Ser Thr Phe Thr Val Leu Lys Asn Thr His Gln Leu Lys Lys Asn
1               5                   10                  15

Thr Leu Phe Pro Phe Leu Gly His Leu Asn Leu Arg Glu Gln Leu Leu
            20                  25                  30

Tyr Lys Asn Asp Ile Lys Ile Ile His Phe Gly Ser Met Phe Leu Thr
        35                  40                  45

Val Leu Arg Gly Cys Met Val Lys Leu Lys
    50                  55


<210> SEQ ID NO 227
<211> LENGTH: 26
<212> TYPE: PRT
<213> ORGANISM: Homo sapiens

<400> SEQUENCE: 227

Met His Met His Ile Phe Leu Cys Leu Tyr Asn Leu Cys Asn Ile Cys
1               5                   10                  15

Glu Cys Asn Thr Phe Ser Phe Phe Leu Leu
            20                  25


<210> SEQ ID NO 228
<211> LENGTH: 47
<212> TYPE: PRT
<213> ORGANISM: Homo sapiens

<400> SEQUENCE: 228

Met Leu Asp Val Met Arg Gln Val Ala Arg Ser Trp Leu Thr Ala Met
1               5                   10                  15

Glu Arg Leu Leu Leu Pro Ala Ala Val Arg Phe Ser Ala Ile Trp Leu
            20                  25                  30

Ala Gly Gln Phe Ala Met Ala Trp Leu Leu Gln Leu Ile Leu Gly
        35                  40                  45


<210> SEQ ID NO 229
<211> LENGTH: 53
<212> TYPE: PRT
<213> ORGANISM: Homo sapiens

<400> SEQUENCE: 229

Met Gly Asn Ile Gly Glu Thr Leu Ser Leu Lys Lys Lys Arg Arg Ala
1               5                   10                  15

Gly Gly Glu Ser Val Lys Asp Pro Gly Ser Thr Asp Thr Gly Gly Gln
            20                  25                  30

Arg Thr Arg Val Gly Val Ser Ser Asn Asp Ser Val Gly Ser Met Gly
        35                  40                  45

Ala Val Gly Arg Glu
    50


<210> SEQ ID NO 230
<211> LENGTH: 80
<212> TYPE: PRT
<213> ORGANISM: Homo sapiens

<400> SEQUENCE: 230

Met Val Ile Asn Ser Cys Ile Ile Pro Leu Pro Ser Gln Ala Thr Ile
1               5                   10                  15

Pro Glu Pro Trp Pro His Gly Ala Cys Ile Phe Arg Ile Gln Thr Pro
            20                  25                  30

Trp Gly Ser Ser Pro Leu Leu Pro Ser Leu Ser Ser His Pro Leu Thr
        35                  40                  45
```

```
His Leu Ser Cys Tyr Leu Ser Leu Glu Ile Pro Lys Met Met Cys Val
    50                  55                  60

Met Glu Arg Leu Glu His Gln Leu Gln Asn His Pro Val Thr Leu Ala
65                  70                  75                  80


<210> SEQ ID NO 231
<211> LENGTH: 40
<212> TYPE: PRT
<213> ORGANISM: Homo sapiens

<400> SEQUENCE: 231

Met Phe Gln Arg Phe Leu Ala Lys Val Thr Val Trp Met Val Val Pro
1               5                   10                  15

Leu Thr Lys Thr Ala Met Asn Ala Lys Arg Ala Ser Phe Val Gly Arg
            20                  25                  30

His Lys Ile Ile Phe Arg Ile Cys
        35                  40


<210> SEQ ID NO 232
<211> LENGTH: 24
<212> TYPE: PRT
<213> ORGANISM: Homo sapiens

<400> SEQUENCE: 232

Met Leu Leu Tyr Leu Ile Thr Arg Gly Asp Val Glu Asn Gly Cys Phe
1               5                   10                  15

Ile Phe Ser Val Val Phe Ala Leu
            20


<210> SEQ ID NO 233
<211> LENGTH: 26
<212> TYPE: PRT
<213> ORGANISM: Homo sapiens

<400> SEQUENCE: 233

Met Pro Pro Arg Gly Leu Pro His Phe Ser Pro His Pro Thr Arg Gln
1               5                   10                  15

Phe Leu Phe Leu Phe Pro Leu His Thr Lys
            20                  25


<210> SEQ ID NO 234
<211> LENGTH: 37
<212> TYPE: PRT
<213> ORGANISM: Homo sapiens

<400> SEQUENCE: 234

Met Ser Tyr Glu Ile Leu Val Asn Thr Asp Phe Met Ser Pro Phe Leu
1               5                   10                  15

Arg Thr Leu Leu Val Cys Phe His Leu Tyr Ala Leu Ile Arg Ala Asn
            20                  25                  30

Asn Leu Lys Tyr Pro
        35


<210> SEQ ID NO 235
<211> LENGTH: 40
<212> TYPE: PRT
<213> ORGANISM: Homo sapiens

<400> SEQUENCE: 235

Met Gly Lys Gly Leu Arg Leu Gly Val Ser Ile Ile Leu Val Lys Ser
1               5                   10                  15
```

```
Phe Phe Thr Tyr Ser Ser Lys Asp Val Asn Tyr Phe Ser Ile His Ser
            20                  25                  30

Asn Ile Lys Ala Val Phe His Phe
        35                  40


<210> SEQ ID NO 236
<211> LENGTH: 40
<212> TYPE: PRT
<213> ORGANISM: Homo sapiens

<400> SEQUENCE: 236

Met Glu Glu Thr Gly Pro Leu Pro Ser Gly Ser Ser Leu Ser Asp Gln
1               5                   10                  15

Gly Glu Thr Ala Leu Ala Leu Gly Asn Ser Arg Ser Asp Gly Gly Arg
            20                  25                  30

Gln Ser Ser Ser Ser Met Asn Ala
        35                  40


<210> SEQ ID NO 237
<211> LENGTH: 50
<212> TYPE: PRT
<213> ORGANISM: Homo sapiens

<400> SEQUENCE: 237

Met His Lys Gln Ser Met Ala Arg Ser Ile Leu Arg Ser Pro Leu Gln
1               5                   10                  15

Gln Ile Pro Pro Lys Gly Glu Ala Gly Arg Trp Arg Trp Ala Glu Ala
            20                  25                  30

Ser Cys Val Leu His Thr Phe Ser Thr Ile Leu Asp Phe Leu Phe Phe
        35                  40                  45

Phe Phe
    50


<210> SEQ ID NO 238
<211> LENGTH: 49
<212> TYPE: PRT
<213> ORGANISM: Homo sapiens

<400> SEQUENCE: 238

Ser Ser Trp Gly Asp Ser Phe Ala Val Ser Ala Ala Trp Ala Arg Lys
1               5                   10                  15

Gly Ile Glu Glu Trp Ile Gly Arg Gln Arg Cys Pro Gly Gly Val Ser
            20                  25                  30

Gly Pro Arg Gln Leu Arg Leu Ala Gly Thr Ile Gly Arg Ser Thr Arg
        35                  40                  45

Glu


<210> SEQ ID NO 239
<211> LENGTH: 54
<212> TYPE: PRT
<213> ORGANISM: Homo sapiens

<400> SEQUENCE: 239

Met Leu Arg Pro Leu Thr Val Ala Ser Lys Arg Leu Leu Thr Ile Ser
1               5                   10                  15

Thr Leu Lys Ser Pro Leu Val Gly Leu Cys Ser Phe Ser Lys Ser Gly
            20                  25                  30

Val Leu Arg Glu Gln Ala Leu Phe Ser Ile Ile Asn Leu Ile Asn Thr
        35                  40                  45
```

```
Asp Trp Gln Lys Gln His
    50


<210> SEQ ID NO 240
<211> LENGTH: 23
<212> TYPE: PRT
<213> ORGANISM: Homo sapiens

<400> SEQUENCE: 240

Met Lys Lys Lys Ser Tyr Pro Asp Lys Ile Asn Gln Cys Phe Ile Phe
1               5                   10                  15

Leu Glu His Gln Asn Leu Leu
            20


<210> SEQ ID NO 241
<211> LENGTH: 59
<212> TYPE: PRT
<213> ORGANISM: Homo sapiens
<220> FEATURE:
<221> NAME/KEY: MISC_FEATURE
<222> LOCATION: (6)..(7)
<223> OTHER INFORMATION: X=any amino acid
<220> FEATURE:
<221> NAME/KEY: MISC_FEATURE
<222> LOCATION: (9)..(9)
<223> OTHER INFORMATION: X=any amino acid
<220> FEATURE:
<221> NAME/KEY: MISC_FEATURE
<222> LOCATION: (13)..(13)
<223> OTHER INFORMATION: X=any amino acid
<220> FEATURE:
<221> NAME/KEY: MISC_FEATURE
<222> LOCATION: (23)..(23)
<223> OTHER INFORMATION: X=any amino acid
<220> FEATURE:
<221> NAME/KEY: MISC_FEATURE
<222> LOCATION: (27)..(31)
<223> OTHER INFORMATION: X=any amino acid
<220> FEATURE:
<221> NAME/KEY: MISC_FEATURE
<222> LOCATION: (38)..(40)
<223> OTHER INFORMATION: X=any amino acid
<220> FEATURE:
<221> NAME/KEY: MISC_FEATURE
<222> LOCATION: (43)..(43)
<223> OTHER INFORMATION: X=any amino acid
<220> FEATURE:
<221> NAME/KEY: MISC_FEATURE
<222> LOCATION: (45)..(45)
<223> OTHER INFORMATION: X=any amino acid
<220> FEATURE:
<221> NAME/KEY: MISC_FEATURE
<222> LOCATION: (47)..(47)
<223> OTHER INFORMATION: X=any amino acid

<400> SEQUENCE: 241

Met Val Lys Tyr Met Xaa Xaa Leu Xaa Leu Thr Pro Xaa Phe Ser Asn
1               5                   10                  15

Leu Leu Gly Thr Leu Lys Xaa Arg Lys Val Xaa Xaa Xaa Xaa Xaa Pro
            20                  25                  30

Arg Lys Arg Asn Phe Xaa Xaa Xaa Pro Pro Xaa Leu Xaa Lys Xaa Arg
        35                  40                  45

Cys His Phe Leu His Ile Asp Leu Gln Arg Val
    50                  55


<210> SEQ ID NO 242
<211> LENGTH: 55
<212> TYPE: PRT
<213> ORGANISM: Homo sapiens
```

<220> FEATURE:
<221> NAME/KEY: MISC_FEATURE
<222> LOCATION: (53)..(53)
<223> OTHER INFORMATION: X=any amino acid

<400> SEQUENCE: 242

```
Met Val Ser Gly Val Gln Val Ser Leu His Lys Thr Lys Ile Lys Leu
1               5                   10                  15

Phe Asn Thr Gly Pro Thr Thr Leu Ile Tyr Gly Ala Asn Thr Cys Cys
            20                  25                  30

Glu Pro Trp Gly Gln Gly Leu Gly Asp Lys Val Ala Thr Ile Phe Trp
        35                  40                  45

Gly Val Gly Gly Xaa Gly Gly
    50                  55
```

<210> SEQ ID NO 243
<211> LENGTH: 75
<212> TYPE: PRT
<213> ORGANISM: Homo sapiens

<400> SEQUENCE: 243

```
Met Val Ile Thr Cys Val Leu Tyr Asp Ile Ser Ser Leu Lys Asn Leu
1               5                   10                  15

Arg His Ser Pro Phe Leu Gln Val Phe Phe Cys Val Cys Trp Lys Ile
            20                  25                  30

Met Tyr Ile Phe Gln Leu Leu Asn Ala Ser Val Cys Ile Cys Ile Ser
        35                  40                  45

Thr Lys Ser Lys Leu Leu Ile Leu Leu Phe Lys Leu Phe Ala Ser Tyr
    50                  55                  60

Trp Phe Ser Leu Pro Thr Leu Cys Ile Asn Ser
65                  70                  75
```

<210> SEQ ID NO 244
<211> LENGTH: 17
<212> TYPE: PRT
<213> ORGANISM: Homo sapiens

<400> SEQUENCE: 244

```
Met Ser Trp Val Pro Cys Gly Cys Asp Phe Leu Arg Glu Ile Asn Leu
1               5                   10                  15

Phe
```

<210> SEQ ID NO 245
<211> LENGTH: 30
<212> TYPE: PRT
<213> ORGANISM: Homo sapiens

<400> SEQUENCE: 245

```
Met Tyr Val Ser Pro Asp Asn Ile Ser Gly Ser Gly Asn Cys Lys Lys
1               5                   10                  15

Lys Ile Gly Asn Gln Asn Ser Arg Lys Val Phe Leu Glu Gly
            20                  25                  30
```

<210> SEQ ID NO 246
<211> LENGTH: 57
<212> TYPE: PRT
<213> ORGANISM: Homo sapiens

<400> SEQUENCE: 246

```
Arg Val Thr Met Asn Glu Lys Asp Asn Phe Met Asn Ala Glu Asn Leu
1               5                   10                  15
```

```
Gly Ile Val Phe Gly Pro Thr Leu Met Arg Pro Pro Glu Asp Ser Thr
            20                  25                  30

Leu Thr Thr Leu His Asp Met Arg Tyr Gln Lys Leu Ile Val Gln Ile
        35                  40                  45

Leu Ile Glu Asn Glu Asp Val Leu Phe
    50                  55
```

<210> SEQ ID NO 247
<211> LENGTH: 70
<212> TYPE: PRT
<213> ORGANISM: Homo sapiens
<220> FEATURE:
<221> NAME/KEY: MISC_FEATURE
<222> LOCATION: (38)..(38)
<223> OTHER INFORMATION: X=any amino acid

<400> SEQUENCE: 247

```
Met Phe Ala Ser Leu Leu Ile Thr Asn Leu Leu Ser Thr Asn Glu Lys
1               5                   10                  15

Tyr Ile Gln Asp Leu Pro Phe Gln Arg Leu Ser Ile Tyr Glu Thr Asn
            20                  25                  30

Ser Pro Phe Arg Leu Xaa Asn Phe Glu Asp Val Phe Ile Phe Leu Phe
        35                  40                  45

Phe Leu Asn Lys Asn Cys Phe Leu Ser Arg Leu Phe Lys Ala Thr Cys
    50                  55                  60

Val Lys Pro Leu Val Gln
65                  70
```

<210> SEQ ID NO 248
<211> LENGTH: 36
<212> TYPE: PRT
<213> ORGANISM: Homo sapiens

<400> SEQUENCE: 248

```
Met Arg Arg Ala Arg Pro Pro Leu Phe Phe Leu His Ala Val Ser Ser
1               5                   10                  15

Pro Gly Gln Ile Leu Thr Ser Lys Asn Ala Val Phe Pro Ser Gly Ala
            20                  25                  30

Gly Pro Val Met
        35
```

<210> SEQ ID NO 249
<211> LENGTH: 26
<212> TYPE: PRT
<213> ORGANISM: Homo sapiens

<400> SEQUENCE: 249

```
Met Ser Leu Ser Phe Ser Leu His Ser Phe Tyr Arg Lys Ala Ile Leu
1               5                   10                  15

Gly Val Leu Gly His Phe Asp Ser Thr Ser
            20                  25
```

<210> SEQ ID NO 250
<211> LENGTH: 43
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: X=any amino acid

<400> SEQUENCE: 250

-continued

```
Met Ser Leu Pro Ser Xaa Arg Arg Gln Phe Ser Asp Ile Thr Cys Thr
1               5                   10                  15

Glu Ile His Tyr Asn Ala Thr Met Asn Gly Gln Ser Ser Thr Glu Lys
            20                  25                  30

Ile Lys Gln Arg Met Ser Trp Lys Val Leu Trp
        35                  40
```

COMPOSITIONS AND METHODS RELATING TO COLON SPECIFIC GENES AND PROTEINS

This application is a Divisional Application of U.S. patent application Ser. No. 10/016,157 filed Oct. 31, 2001, now abandoned, which claims the benefit of priority to U.S. Provisional Application Ser. No. 60/244,717, filed Oct. 31, 2000, each of which are herein incorporated by reference in their entirety.

FIELD OF THE INVENTION

The present invention relates to newly identified nucleic acid molecules and polypeptides present in normal and neoplastic colon cells, including fragments, variants and derivatives of the nucleic acids and polypeptides. The present invention also relates to antibodies to the polypeptides of the invention, as well as agonists and antagonists of the polypeptides of the invention. The invention also relates to compositions comprising the nucleic acids, polypeptides, antibodies, variants, derivatives, agonists and antagonists of the invention and methods for the use of these compositions. These uses include identifying, diagnosing, monitoring, staging, imaging and treating colon cancer and non-cancerous disease states in colon tissue, identifying colon tissue and monitoring and identifying and/or designing agonists and antagonists of polypeptides of the invention. The uses also include gene therapy, production of transgenic animals and cells, and production of engineered colon tissue for treatment and research.

BACKGROUND OF THE INVENTION

Colorectal cancer is the second most common cause of cancer death in the United States and the third most prevalent cancer in both men and women. M. L. Davila & A. D. Davila, *Screening for Colon and Rectal Cancer*, in *Colon and Rectal Cancer* 47 (Peter S. Edelstein ed., 2000). Approximately 100,000 patients every year suffer from colon cancer and approximately half that number die of the disease. Hannah-Ngoc Ha & Bard C. Cosman, *Treatment of Colon Cancer*, in *Colon and Rectal Cancer* 157 (Peter S. Edelstein ed., 2000). Nearly all cases of colorectal cancer arise from adenomatous polyps, some of which mature into large polyps, undergo abnormal growth and development, and ultimately progress into cancer. Davila & Davila, supra at 55-56. This progression would appear to take at least 10 years in most patients, rendering it a readily treatable form of cancer if diagnosed early, when the cancer is localized. Id. at 56; Walter J. Burdette, *Cancer: Etiology, Diagnosis, and Treatment* 125 (1998).

Although our understanding of the etiology of colon cancer is undergoing continual refinement, extensive research in this area points to a combination of factors, including age, hereditary and nonheriditary conditions, and environmental/dietary factors. Age is a key risk factor in the development of colorectal cancer, Davila & Davila, supra at 48, with men and women over 40 years of age become increasingly susceptible to that cancer, Burdette, supra at 126. Incidence rates increase considerably in each subsequent decade of life. Davila et al., supra at 48. A number of hereditary and nonhereditary conditions have also been linked to a heightened risk of developing colorectal cancer, including familial adenomatous polyposis (FAP), hereditary nonpolyposis colorectal cancer (Lynch syndrome or KNPCC), a personal and/or family history of colorectal cancer or adenomatous polyps, inflammatory bowel disease, diabetes mellitus, and obesity. Id. at 47; Henry T. Lynch & Jane F. Lynch, *Hereditary Nonpolyposis Colorectal Cancer* (*Lynch Syndromes*), in *Colon and Rectal Cancer* 67-68 (Peter S. Edelstein ed., 2000).

In the case of FAP, the tumor suppressor gene APC (adenomatous polyposis coli), located at 5q21, has been either mutationally inactivated or deleted. Alberts et al., *Molecular Biology of the Cell* 1288 (3d ed. 1994). The APC protein plays a role in a number of functions, including cell adhesion, apoptosis, and repression of the c-myc oncogene. N. R. Hall & R. D. Madoff, *Genetics and the Polyp-Cancer Sequence, Colon and Rectal Cancer* 8 (Peter S. Edelstein, ed., 2000). Of those patients with colorectal cancer who have normal APC genes, over 65% have such mutations in the cancer cells but not in other tissues. Alberts et al., supra at 1288. In the case of HPNCC, patients manifest abnormalities in the tumor suppressor gene HNPCC, but only about 15% of tumors contain the mutated gene. Id. A host of other genes have also been implicated in colorectal cancer, including the K-ras, N-ras, H-ras and c-myc oncogenes, and the tumor suppressor genes DCC (deleted in colon carcinoma) and p53. Hall & Madoff, supra at 8-9; Alberts et al., supra at 1288.

Environmental/dietary factors associated with an increased risk of colorectal cancer include a high fat diet, intake of high dietary red meat, and sedentary lifestyle. Davila & Davila, supra at 47; Reddy, B. S., *Prev. Med.* 16(4): 460-7 (1987). Conversely, environmental/dietary factors associated with a reduced risk of colorectal cancer include a diet high in fiber, folic acid, calcium, and hormone-replacement therapy in post-menopausal women. Davila & Davila, supra at 50-55. The effect of antioxidants in reducing the risk of colon cancer is unclear. Id. at 53.

Because colon cancer is highly treatable when detected at an early, localized stage, screening should be a part of routine care for all adults starting at age 50, especially those with first-degree relatives with colorectal cancer. One major advantage of colorectal cancer screening over its counterparts in other types of cancer is its ability to not only detect precancerous lesions, but to remove them as well. Davila & Davila, supra at 56. The key colorectal cancer screening tests in use today are fecal occult blood test, sigmoidoscopy, colonoscopy, double-contrast barium enema, and the carcinoembryonic antigen (CEA) test. Id,; Burdette, supra at 125.

The fecal occult blood test (FOBT) screens for colorectal cancer by detecting the amount of blood in the stool, the premise being that neoplastic tissue, particularly malignant tissue, bleeds more than typical mucosa, with the amount of bleeding increasing with polyp size and cancer stage. Davila & Davila, supra at 56-57. While effective at detecting early stage tumors, FOBT is unable to detect adenomatous polyps (premalignant lesions), and, depending on the contents of the fecal sample, is subject to rendering false positives. Id. at 56-59. Sigmoidoscopy and colonoscopy, by contrast, allow direct visualization of the bowel, and enable one to detect, biopsy, and remove adenomatous polyps. Id. at 59-60, 61. Despite the advantages of these procedures, there are accompanying downsides: sigmoidoscopy, by definition, is limited to the sigmoid colon and below, colonoscopy is a relatively expensive procedure, and both share the risk of possible bowel perforation and hemorrhaging. Id. at 59-60. Double-contrast barium enema (DCBE) enables detection of lesions better than FOBT, and almost as well a colonoscopy, but it may be limited in evaluating the winding rectosigmoid region. Id. at 60. The CEA blood test, which involves screening the blood for carcinoembryonic antigen, shares the downside of FOBT, in that it is of limited utility in detecting colorectal cancer at an early stage. Burdette, supra at 125.

Once colon cancer has been diagnosed, treatment decisions are typically made in reference to the stage of cancer progression. A number of techniques are employed to stage the cancer (some of which are also used to screen for colon cancer), including pathologic examination of resected colon, sigmoidoscopy, colonoscopy, and various imaging techniques. *AJCC Cancer Staging Handbook* 84 (Irvin D. Fleming et al. eds., $5^{th}$ ed. 1998); Montgomery, R. C. and Ridge, J. A., *Semin. Surg. Oncol.* 15(3): 143-150 (1998). Moreover, chest films, liver functionality tests, and liver scans are employed to determine the extent of metastasis. Fleming et al. eds., supra at 84. While computerized tomography and magnetic resonance imaging are useful in staging colorectal cancer in its later stages, both have unacceptably low staging accuracy for identifying early stages of the disease, due to the difficulty that both methods have in (1) revealing the depth of bowel wall tumor infiltration and (2) diagnosing malignant adenopathy. Thoeni, R. F., *Radiol. Clin. N. Am.* 35(2): 457-85 (1997). Rather, techniques such as transrectal ultrasound (TRUS) are preferred in this context, although this technique is inaccurate with respect to detecting small lymph nodes that may contain metastases. David Blumberg & Frank G. Opelka, *Neoadjuvant and Adjuvant Therapy for Adenocarcinoma of the Rectum*, in *Colon and Rectal Cancer* 316 (Peter S. Edelstein ed., 2000).

Several classification systems have been devised to stage the extent of colorectal cancer, including the Dukes' system and the more detailed International Union against Cancer-American Joint Committee on Cancer TNM staging system, which is considered by many in the field to be a more useful staging system. Burdette, supra at 126-27. The TNM system, which is used for either clinical or pathological staging, is divided into four stages, each of which evaluates the extent of cancer growth with respect to primary tumor (T), regional lymph nodes (N), and distant metastasis (M). Fleming et al., eds., supra at 84-85. The system focuses on the extent of tumor invasion into the intestinal wall, invasion of adjacent structures, the number of regional lymph nodes that have been affected, and whether distant metastasis has occurred. Id. at 81.

Stage 0 is characterized by in situ carcinoma (Tis), in which the cancer cells are located inside the glandular basement membrane (intraepithelial) or lamina propria (intramucosal). Id. at 84-85; Burdette, supra at 127. In this stage, the cancer has not spread to the regional lymph nodes (N0), and there is no distant metastasis (M0). Fleming et al. eds., supra at 85; Burdette, supra at 127. In stage I, there is still no spread of the cancer to the regional lymph nodes and no distant metastasis, but the tumor has invaded the submucosa (T1) or has progressed further to invade the muscularis propria (T2). Fleming et al. eds., supra at 84-85; Burdette, supra at 127. Stage II also involves no spread of the cancer to the regional lymph nodes and no distant metastasis, but the tumor has invaded the subserosa, or the nonperitonealized pericolic or perirectal tissues (T3), or has progressed to invade other organs or structures, and/or has perforated the visceral peritoneum (T4). Id. Stage 3 is characterized by any of the T substages, no distant metastasis, and either metastasis in 1 to 3 regional lymph nodes (N1) or metastasis in four or more regional lymph nodes (N2). Fleming et al. eds., supra at 85; Burdette, supra at 127. Lastly, stage 4 involves any of the T or N substages, as well as distant metastasis. Id.

Currently, pathological staging of colon cancer is preferable over clinical staging as pathological staging provides a more accurate prognosis. Pathological staging typically involves examination of the resected colon section, along with surgical examination of the abdominal cavity. Fleming et al. eds., supra at 84. Clinical staging would be a preferred method of staging were it at least as accurate as pathological staging, as it does not depend on the invasive procedures of its counterpart.

Turning to the treatment of colorectal cancer, surgical resection results in a cure for roughly 50% of patients. Burdette, supra at 125. Irradiation is used both preoperatively and postoperatively in treating colorectal cancer. Id. at 125, 132-33. Chemotherapeutic agents, particularly 5-fluorouracil, are also powerful weapons in treating colorectal cancer. Id. at 125, 133. Other agents include irinotecan and floxuridine, cisplatin, levamisole, methotrexate, interferon-alpha, and leucovorin. Id. at 133. Nonetheless, thirty to forty percent of patients will develop a recurrence of colon cancer following surgical resection. Wayne De Vos, *Follow-up After Treatment of Colon Cancer, Colon and Rectal Cancer* 225 (Peter S. Edelstein ed., 2000), which in many patients is the ultimate cause of death. Accordingly, colon cancer patients must be closely monitored to determine response to therapy and to detect persistent or recurrent disease and metastasis.

From the foregoing, it is clear that procedures used for detecting, diagnosing, monitoring, staging, prognosticating, and preventing the recurrence of colorectal cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Accordingly, there is a great need for more sensitive and accurate methods for predicting whether a person is likely to develop colorectal cancer, for diagnosing colorectal cancer, for monitoring the progression of the disease, for staging the colorectal cancer, for determining whether the colorectal cancer has metastasized, and for imaging the colorectal cancer. There is also a need for better treatment of colorectal cancer.

SUMMARY OF THE INVENTION

The present invention solves these and other needs in the art by providing nucleic acid molecules and polypeptides as well as antibodies, agonists and antagonists, thereto that may be used to identify, diagnose, monitor, stage, image and treat colon cancer and non-cancerous disease states in colon; identify and monitor colon tissue; and identify and design agonists and antagonists of polypeptides of the invention. The invention also provides gene therapy, methods for producing transgenic animals and cells, and methods for producing engineered colon tissue for treatment and research.

Accordingly, one object of the invention is to provide nucleic acid molecules that are specific to colon cells and/or colon tissue. These colon specific nucleic acids (CSNAs) may be a naturally-occurring cDNA, genomic DNA, RNA, or a fragment of one of these nucleic acids, or may be a non-naturally-occurring nucleic acid molecule. If the CSNA is genomic DNA, then the CSNA is a colon specific gene (CSG). In a preferred embodiment, the nucleic acid molecule encodes a polypeptide that is specific to colon. In a more preferred embodiment, the nucleic acid molecule encodes a polypeptide that comprises an amino acid sequence of SEQ ID NO: 148 through 250. In another highly preferred embodiment, the nucleic acid molecule comprises a nucleic acid sequence of SEQ ID NO: 1 through 147. By nucleic acid molecule, it is also meant to be inclusive of sequences that selectively hybridize or exhibit substantial sequence similarity to a nucleic acid molecule encoding a CSP, or that selectively hybridize or exhibit substantial sequence similarity to a CSNA, as well as allelic variants of a nucleic acid molecule encoding a CSP, and allelic variants of a CSNA. Nucleic acid molecules comprising a part of a nucleic acid sequence that encodes a CSP or that comprises a part of a nucleic acid sequence of a CSNA are also provided.

A related object of the present invention is to provide a nucleic acid molecule comprising one or more expression control sequences controlling the transcription and/or translation of all or a part of a CSNA. In a preferred embodiment, the nucleic acid molecule comprises one or more expression control sequences controlling the transcription and/or translation of a nucleic acid molecule that encodes all or a fragment of a CSP.

Another object of the invention is to provide vectors and/or host cells comprising a nucleic acid molecule of the instant invention. In a preferred embodiment, the nucleic acid molecule encodes all or a fragment of a CSP. In another preferred embodiment, the nucleic acid molecule comprises all or a part of a CSNA.

Another object of the invention is to provided methods for using the vectors and host cells comprising a nucleic acid molecule of the instant invention to recombinantly produce polypeptides of the invention.

Another object of the invention is to provide a polypeptide encoded by a nucleic acid molecule of the invention. In a preferred embodiment, the polypeptide is a CSP. The polypeptide may comprise either a fragment or a full-length protein as well as a mutant protein (mutein), fusion protein, homologous protein or a polypeptide encoded by an allelic variant of a CSP.

Another object of the invention is to provide an antibody that specifically binds to a polypeptide of the instant invention.

Another object of the invention is to provide agonists and antagonists of the nucleic acid molecules and polypeptides of the instant invention.

Another object of the invention is to provide methods for using the nucleic acid molecules to detect or amplify nucleic acid molecules that have similar or identical nucleic acid sequences compared to the nucleic acid molecules described herein. In a preferred embodiment, the invention provides methods of using the nucleic acid molecules of the invention for identifying, diagnosing, monitoring, staging, imaging and treating colon cancer and non-cancerous disease states in colon. In another preferred embodiment, the invention provides methods of using the nucleic acid molecules of the invention for identifying and/or monitoring colon tissue. The nucleic acid molecules of the instant invention may also be used in gene therapy, for producing transgenic animals and cells, and for producing engineered colon tissue for treatment and research.

The polypeptides and/or antibodies of the instant invention may also be used to identify, diagnose, monitor, stage, image and treat colon cancer and non-cancerous disease states in colon. The invention provides methods of using the polypeptides of the invention to identify and/or monitor colon tissue, and to produce engineered colon tissue.

The agonists and antagonists of the instant invention may be used to treat colon cancer and non-cancerous disease states in colon and to produce engineered colon tissue.

Yet another object of the invention is to provide a computer readable means of storing the nucleic acid and amino acid sequences of the invention. The records of the computer readable means can be accessed for reading and displaying of sequences for comparison, alignment and ordering of the sequences of the invention to other sequences.

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology genetics and protein and nucleic acid chemistry and hybridization described herein are those well-known and commonly used in the art. The methods and techniques of the present invention are generally performed according to conventional methods well-known in the art and as described in various general and more specific references that are cited and discussed throughout the present specification unless otherwise indicated. See, e.g., Sambrook et al., *Molecular Cloning: A Laboratory Manual,* 2d ed., Cold Spring Harbor Laboratory Press (1989) and Sambrook et al., *Molecular Cloning: A Laboratory Manual,* 3d ed., Cold Spring Harbor Press (2001); Ausubel et al., *Current Protocols in Molecular Biology*, Greene Publishing Associates (1992, and Supplements to 2000); Ausubel et al., *Short Protocols in Molecular Biology: A Compendium of Methods from Current Protocols in Molecular Biology—4th Ed.*, Wiley & Sons (1999); Harlow and Lane, *Antibodies: A Laboratory Manual*, Cold Spring Harbor Laboratory Press (1990); and Harlow and Lane, *Using Antibodies: A Laboratory Manual*, Cold Spring Harbor Laboratory Press (1999); each of which is incorporated herein by reference in its entirety.

Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

A "nucleic acid molecule" of this invention refers to a polymeric form of nucleotides and includes both sense and antisense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." The term "nucleic acid molecule" usually refers to a molecule of at least 10 bases in length, unless otherwise specified. The term includes single- and double-stranded forms of DNA. In addition, a polynucleotide may include either or both naturally-occurring and modified nucleotides linked together by naturally-occurring and/or non-naturally occurring nucleotide linkages.

The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term "nucleic acid molecule" also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

A "gene" is defined as a nucleic acid molecule that comprises a nucleic acid sequence that encodes a polypeptide and the expression control sequences that surround the nucleic acid sequence that encodes the polypeptide. For instance, a gene may comprise a promoter, one or more enhancers, a nucleic acid sequence that encodes a polypeptide, downstream regulatory sequences and, possibly, other nucleic acid sequences involved in regulation of the expression of an RNA. As is well-known in the art, eukaryotic genes usually contain both exons and introns. The term "exon" refers to a nucleic acid sequence found in genomic DNA that is bioinformatically predicted and/or experimentally confirmed to contribute a contiguous sequence to a mature mRNA transcript. The term "intron" refers to a nucleic acid sequence found in genomic DNA that is predicted and/or confirmed to not contribute to a mature mRNA transcript, but rather to be "spliced out" during processing of the transcript.

A nucleic acid molecule or polypeptide is "derived" from a particular species if the nucleic acid molecule or polypeptide has been isolated from the particular species, or if the nucleic acid molecule or polypeptide is homologous to a nucleic acid molecule or polypeptide isolated from a particular species.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, or genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, (4) does not occur in nature as part of a larger sequence or (5) includes nucleotides or internucleoside bonds that are not found in nature. The term "isolated" or "substantially pure" also can be used in reference to recombinant or cloned DNA isolates, chemically synthesized polynucleotide analogs, or polynucleotide analogs that are biologically synthesized by heterologous systems. The term "isolated nucleic acid molecule" includes nucleic acid molecules that are integrated into a host cell chromosome at a heterologous site, recombinant fusions of a native fragment to a heterologous sequence, recombinant vectors present as episomes or as integrated into a host cell chromosome.

A "part" of a nucleic acid molecule refers to a nucleic acid molecule that comprises a partial contiguous sequence of at least 10 bases of the reference nucleic acid molecule. Preferably, a part comprises at least 15 to 20 bases of a reference nucleic acid molecule. In theory, a nucleic acid sequence of 17 nucleotides is of sufficient length to occur at random less frequently than once in the three gigabase human genome, and thus to provide a nucleic acid probe that can uniquely identify the reference sequence in a nucleic acid mixture of genomic complexity. A preferred part is one that comprises a nucleic acid sequence that can encode at least 6 contiguous amino acid sequences (fragments of at least 18 nucleotides) because they are useful in directing the expression or synthesis of peptides that are useful in mapping the epitopes of the polypeptide encoded by the reference nucleic acid. See, e.g., Geysen et al., *Proc. Natl. Acad. Sci. USA* 81:3998-4002 (1984); and U.S. Pat. Nos. 4,708,871 and 5,595,915, the disclosures of which are incorporated herein by reference in their entireties. A part may also comprise at least 25, 30, 35 or 40 nucleotides of a reference nucleic acid molecule, or at least 50, 60, 70, 80, 90, 100, 150, 200, 250, 300, 350, 400 or 500 nucleotides of a reference nucleic acid molecule. A part of a nucleic acid molecule may comprise no other nucleic acid sequences. Alternatively, a part of a nucleic acid may comprise other nucleic acid sequences from other nucleic acid molecules.

The term "oligonucleotide" refers to a nucleic acid molecule generally comprising a length of 200 bases or fewer. The term often refers to single-stranded deoxyribonucleotides, but it can refer as well to single- or double-stranded ribonucleotides, RNA:DNA hybrids and double-stranded DNAs, among others. Preferably, oligonucleotides are 10 to 60 bases in length and most preferably 12, 13, 14, 15, 16, 17, 18, 19 or 20 bases in length. Other preferred oligonucleotides are 25, 30, 35, 40, 45, 50, 55 or 60 bases in length. Oligonucleotides may be single-stranded, e.g. for use as probes or primers, or may be double-stranded, e.g. for use in the construction of a mutant gene. Oligonucleotides of the invention can be either sense or antisense oligonucleotides. An oligonucleotide can be derivatized or modified as discussed above for nucleic acid molecules.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP. The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well-known, this reaction can be prevented selectively, where desired, by removing the 5' phosphates of the other polynucleotide(s) prior to ligation.

The term "naturally-occurring nucleotide" referred to herein includes naturally-occurring deoxyribonucleotides and ribonucleotides. The term "modified nucleotides" referred to herein includes nucleotides with modified or substituted sugar groups and the like. The term "nucleotide linkages" referred to herein includes nucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081-9093 (1986); Stein et al. *Nucl. Acids Res.* 16:3209-3221 (1988); Zon et al *Anti-Cancer Drug Design* 6:539-568 (1991); Zon et al., in Eckstein (ed.) *Oligonucleotides and Analogues: A Practical Approach*, pp. 87-108, Oxford University Press (1991); U.S. Pat. No. 5,151,510; Uhlmann and Peyman *Chemical Reviews* 90:543 (1990), the disclosures of which are hereby incorporated by reference.

Unless specified otherwise, the left hand end of a polynucleotide sequence in sense orientation is the 5' end and the right hand end of the sequence is the 3' end. In addition, the left hand direction of a polynucleotide sequence in sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

The term "allelic variant" refers to one of two or more alternative naturally-occurring forms of a gene, wherein each gene possesses a unique nucleotide sequence. In a preferred embodiment, different alleles of a given gene have similar or identical biological properties.

The term "percent sequence identity" in the context of nucleic acid sequences refers to the residues in two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183: 63-98 (1990); Pearson, *Methods Mol. Biol.* 132: 185-219 (2000); Pearson, *Methods Enzymol.* 266: 227-258 (1996); Pearson, *J. Mol. Biol.* 276: 71-84 (1998); herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleic acid sequence encompasses its complement unless otherwise specified. Thus, a reference to a nucleic acid molecule having a particular sequence should-be understood to encompass its complementary strand, with its complementary sequence. The complementary strand is also useful, e.g., for antisense therapy, hybridization probes and PCR primers.

In the molecular biology art, researchers use the terms "percent sequence identity", "percent sequence similarity" and "percent sequence homology" interchangeably. In this application, these terms shall have the same meaning with respect to nucleic acid sequences only.

The term "substantial similarity" or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95-98% of the nucleotide bases, as measured by any well-known algorithm of sequence identity, such as FASTA, BLAST or Gap, as discussed above.

Alternatively, substantial similarity exists when a nucleic acid or fragment thereof hybridizes to another nucleic acid, to a strand of another nucleic acid, or to the complementary strand thereof, under selective hybridization conditions. Typically, selective hybridization will occur when there is at least about 55% sequence identity, preferably at least about 65%, more preferably at least about 75%, and most preferably at least about 90% sequence identity, over a stretch of at least about 14 nucleotides, more preferably at least 17 nucleotides, even more preferably at least 20, 25, 30, 35, 40, 50, 60, 70, 80, 90 or 100 nucleotides.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook (1989), supra, p. 9.51, hereby incorporated by reference.

The $T_m$ for a particular DNA-DNA hybrid can be estimated by the formula:

$$T_m=81.5° \text{ C.}+16.6 (\log_{10}[Na^+])+0.41 (\text{fraction } G+C)-0.63 (\% \text{ formamide})-(600/1)$$

where 1 is the length of the hybrid in base pairs.

The $T_m$ for a particular RNA-RNA hybrid can be estimated by the formula:

$$T_m=79.8° \text{ C.}+18.5 (\log_{10}[Na^+])+0.58 \text{ (fraction } G+C)+11.8 \text{ (fraction } G+C)^2-0.35 \text{ (\% formamide)}-(820/1).$$

The $T_m$ for a particular RNA-DNA hybrid can be estimated by the formula:

$$T_m=79.8° \text{ C.}+18.5(\log_{10}[Na^+])+0.58 \text{ (fraction } G+C)+11.8 \text{ (fraction } G+C)^2-0.50 \text{ (\% formamide)}-(820/1).$$

In general, the $T_m$ decreases by 1-1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10-15° C. would be subtracted from the calculated $T_m$ of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well-known in the art.

An example of stringent hybridization conditions for hybridization of complementary nucleic acid sequences having more than 100 complementary residues on a filter in a Southern or Northern blot or for screening a library is 50% formamide/6×SSC at 42° C. for at least ten hours and preferably overnight (approximately 16 hours). Another example of stringent hybridization conditions is 6×SSC at 68° C. without formamide for at least ten hours and preferably overnight. An example of moderate stringency hybridization conditions is 6×SSC at 55° C. without formamide for at least ten hours and preferably overnight. An example of low stringency hybridization conditions for hybridization of complementary nucleic acid sequences having more than 100 complementary residues on a filter in a Southern or Northern blot or for screening a library is 6×SSC at 42° C. for at least ten hours. Hybridization conditions to identify nucleic acid sequences that are similar but not identical can be identified by experimentally changing the hybridization temperature from 68° C. to 42° C. while keeping the salt concentration constant (6×SSC), or keeping the hybridization temperature and salt concentration constant (e.g. 42° C. and 6×SSC) and varying the formamide concentration from 50% to 0%. Hybridization buffers may also include blocking agents to lower background. These agents are well-known in the art. See Sambrook et al. (1989), supra, pages 8.46 and 9.46-9.58, herein incorporated by reference. See also Ausubel (1992), supra, Ausubel (1999), supra, and Sambrook (2001), supra.

Wash conditions also can be altered to change stringency conditions. An example of stringent wash conditions is a 0.2×SSC wash at 65° C. for 15 minutes (see Sambrook (1989), supra, for SSC buffer). Often the high stringency wash is preceded by a low stringency wash to remove excess probe. An exemplary medium stringency wash for duplex DNA of more than 100 base pairs is 1×SSC at 45° C. for 15 minutes. An exemplary low stringency wash for such a duplex is 4×SSC at 40° C. for 15 minutes. In general, signal-to-noise ratio of 2× or higher than that observed for an unrelated probe in the particular hybridization assay indicates detection of a specific hybridization.

As defined herein, nucleic acid molecules that do not hybridize to each other under stringent conditions are still substantially similar to one another if they encode polypeptides that are substantially identical to each other. This occurs, for example, when a nucleic acid molecule is created synthetically or recombinantly using high codon degeneracy as permitted by the redundancy of the genetic code.

Hybridization conditions for nucleic acid molecules that are shorter than 100 nucleotides in length (e.g., for oligonucleotide probes) may be calculated by the formula:

$$T_m=81.5° \text{ C.}+16.6(\log_{10}[Na^+])+0.41(\text{fraction } G+C)-(600/N),$$

wherein N is change length and the $[Na^+]$ is 1 M or less. See Sambrook (1989), supra, p. 11.46. For hybridization of probes shorter than 100 nucleotides, hybridization is usually performed under stringent conditions (5-10° C. below the $T_m$) using high concentrations (0.1-1.0 pmol/ml) of probe. Id. at p. 11.45. Determination of hybridization using mismatched probes, pools of degenerate probes or "guessmers," as well as hybridization solutions and methods for empirically determining hybridization conditions are well-known in the art. See, e.g., Ausubel (1999), supra; Sambrook (1989), supra, pp. 11.45-11.57.

The term "digestion" or "digestion of DNA" refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan. For analytical purposes, typically, 1 μg of plasmid or DNA fragment is digested with about 2 units of enzyme in about 20 μl of reaction buffer. For the purpose of isolating DNA fragments for plasmid construction, typically 5 to 50 μg of DNA are digested with 20 to 250 units of enzyme in proportionately larger volumes. Appropriate buffers and substrate amounts for particular restriction enzymes are described in standard laboratory manuals, such as those referenced below, and they are specified by commercial suppliers. Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well-known methods that are routine for those skilled in the art.

The term "ligation" refers to the process of forming phosphodiester bonds between two or more polynucleotides, which most often are double-stranded DNAS. Techniques for ligation are well-known to the art and protocols for ligation are described in standard laboratory manuals and references, such as, e.g., Sambrook (1989), supra.

Genome-derived "single exon probes," are probes that comprise at least part of an exon ("reference exon") and can hybridize detectably under high stringency conditions to transcript-derived nucleic acids that include the reference exon but do not hybridize detectably under high stringency conditions to nucleic acids that lack the reference exon. Single exon probes typically further comprise, contiguous to a first end of the exon portion, a first intronic and/or intergenic sequence that is identically contiguous to the exon in the genome, and may contain a second intronic and/or intergenic sequence that is identically contiguous to the exon in the genome. The minimum length of genome-derived single exon probes is defined by the requirement that the exonic portion be of sufficient length to hybridize under high stringency conditions to transcript-derived nucleic acids, as discussed above. The maximum length of genome-derived single exon probes is defined by the requirement that the probes contain portions of no more than one exon. The single exon probes may contain priming sequences not found in contiguity with the rest of the probe sequence in the genome, which priming sequences are useful for PCR and other amplification-based technologies.

The term "microarray" or "nucleic acid microarray" refers to a substrate-bound collection of plural nucleic acids, hybridization to each of the plurality of bound nucleic acids being separately detectable. The substrate can be solid or porous, planar or non-planar, unitary or distributed. Microarrays or nucleic acid microarrays include all the devices so called in Schena (ed.), *DNA Microarrays: A Practical Approach* (*Practical Approach Series*), Oxford University Press (1999); *Nature Genet.* 21(1)(suppl.):1-60 (1999); Schena (ed.), *Microarray Biochip: Tools and Technology*, Eaton Publishing Company/BioTechniques Books Division (2000). These microarrays include substrate-bound collections of plural nucleic acids in which the plurality of nucleic acids are disposed on a plurality of beads, rather than on a unitary planar substrate, as is described, inter alia, in Brenner et al., *Proc. Natl. Acad. Sci. USA* 97(4):1665-1670 (2000).

The term "mutated" when applied to nucleic acid molecules means that nucleotides in the nucleic acid sequence of the nucleic acid molecule may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. In a preferred embodiment, the nucleic acid molecule comprises the wild type nucleic acid sequence encoding a CSP or is a CSNA. The nucleic acid molecule may be mutated by any method known in the art including those mutagenesis techniques described infra.

The term "error-prone PCR" refers to a process for performing PCR under conditions where the copying fidelity of the DNA polymerase is low, such that a high rate of point mutations is obtained along the entire length of the PCR product. See, e.g., Leung et al., *Technique* 1: 11-15 (1989) and Caldwell et al., *PCR Methods Applic.* 2: 28-33 (1992).

The term "oligonucleotide-directed mutagenesis" refers to a process which enables the generation of site-specific mutations in any cloned DNA segment of interest. See, e.g., Reidhaar-Olson et al, *Science* 241: 53-57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" or "DNA shuffling" refers to a method of error-prone PCR coupled with forced homologous recombination between DNA molecules of different but highly related DNA sequence in vitro, caused by random fragmentation of the DNA molecule based on sequence similarity, followed by fixation of the crossover by primer extension in an error-prone PCR reaction. See, e.g., Stemmer, *Proc. Natl. Acad. Sci. U.S.A.* 91: 10747-10751 (1994). DNA shuffling can be carried out between several related genes ("Family shuffling").

The term "in vivo mutagenesis" refers to a process of generating random mutations in any cloned DNA of interest which involves the propagation of the DNA in a strain of bacteria such as *E. coli* that carries mutations in one or more of the DNA repair pathways. These "mutator" strains have a higher random mutation rate than that of a wild-type parent. Propagating the DNA in a mutator strain will eventually generate random mutations within the DNA.

The term "cassette mutagenesis" refers to any process for replacing a small region of a double-stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. See, e.g., Arkin et al., *Proc. Natl. Acad. Sci. U.S.A.* 89: 7811-7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins. See, e.g., Delegrave et al., *Biotechnology Research* 11: 1548-1552 (1993); Arnold, *Current Opinion in Biotechnology* 4: 450-455 (1993). Each of the references mentioned above are. hereby incorporated by reference in its entirety.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include the promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "vector," as used herein, is intended to refer to a nucleic acid molecule capable of transporting another nucleic acid to which it has been linked. One type of vector is a "plasmid", which refers to a circular double-stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome. Viral vectors that infect bacterial cells are referred to as bacteriophages. Certain vectors are capable of autonomous replication in a host cell into which they are introduced (e.g., bacterial vectors having a bacterial origin of replication). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include other forms of expression vectors that serve equivalent functions.

The term "recombinant host cell" (or simply "host cell"), as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the phrase "open reading frame" and the equivalent acronym "ORF" refer to that portion of a transcript-derived nucleic acid that can be translated in its entirety into a sequence of contiguous amino acids. As so defined, an ORF has length, measured in nucleotides, exactly divisible by 3. As so defined, an ORF need not encode the entirety of a natural protein.

As used herein, the phrase "ORF-encoded peptide" refers to the predicted or actual translation of an ORF.

As used herein, the phrase "degenerate variant" of a reference nucleic acid sequence intends all nucleic acid sequences that can be directly translated, using the standard genetic code, to provide an amino acid sequence identical to that translated from the reference nucleic acid sequence.

The term "polypeptide" encompasses both naturally-occurring and non-naturally-occurring proteins and polypeptides, polypeptide fragments and polypeptide mutants, derivatives and analogs. A polypeptide may be monomeric or polymeric. Further, a polypeptide may comprise a number of different modules within a single polypeptide each of which has one or more distinct activities. A preferred polypeptide in accordance with the invention comprises a CSP encoded by a nucleic acid molecule of the instant invention, as well as a fragment, mutant, analog and derivative thereof.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well-known in the art.

A protein or polypeptide is "substantially pure," "substantially homogeneous" or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well-known in the art, such as polyacrylamide gel electrophoresis of a protein sample, followed by visualizing a single polypeptide band upon staining the gel with a stain well-known in the art. For certain purposes, higher resolution may be provided by using HPLC or other means well-known in the art for purification.

The term "polypeptide fragment" as used herein refers to a polypeptide of the instant invention that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "derivative" refers to polypeptides or fragments thereof that are substantially similar in primary structural sequence but which include, e.g., in vivo or in vitro chemical and biochemical modifications that are not found in the native polypeptide. Such modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Other modification include, e.g., labeling with radionuclides, and various enzymatic modifications, as will be readily appreciated by those skilled in the art. A variety of methods for labeling polypeptides and of substituents or labels useful for such purposes are well-known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well-known in the art. See Ausubel (1992), supra; Ausubel (1999), supra, herein incorporated by reference.

The term "fusion protein" refers to polypeptides of the instant invention comprising polypeptides or fragments coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "analog" refers to both polypeptide analogs and non-peptide analogs. The term "polypeptide analog" as used herein refers to a polypeptide of the instant invention that is comprised of a segment of at least 25 amino acids that has substantial identity to a portion of an amino acid sequence but which contains non-natural amino acids or non-natural inter-residue bonds. In a preferred embodiment, the analog has the same or similar biological activity as the native polypeptide. Typically, polypeptide analogs comprise a conservative amino acid substitution (or insertion or deletion) with respect to the naturally-occurring sequence. Analogs typically are at least 20 amino acids long, preferably at least 50 amino acids long or longer, and can often be as long as a full-length naturally-occurring polypeptide.

The term "non-peptide analog" refers to a compound with properties that are analogous to those of a reference polypeptide of the instant invention. A non-peptide compound may also be termed a "peptide mimetic" or a "peptidomimetic." Such compounds are often developed with the aid of computerized molecular modeling. Peptide mimetics that are structurally similar to useful peptides may be used to produce an equivalent effect. Generally, peptidomimetics are structurally similar to a paradigm polypeptide (i.e., a polypeptide that has a desired biochemical property or pharmacological activity), but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —CH(OH)$CH_2$—, and —$CH_2SO$—, by methods well-known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo et al., *Ann. Rev. Biochem.* 61:387-418 (1992), incorporated herein by reference). For example, one may add internal cysteine residues capable of forming intramolecular disulfide bridges which cyclize the peptide.

A "polypeptide mutant" or "mutein" refers to a polypeptide of the instant invention whose sequence contains substitutions, insertions or deletions of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. Further, a mutein may have the same or different biological activity as the naturally-occurring protein. For instance, a mutein may have an increased or decreased biological activity. A mutein has at least 50% sequence similarity to the wild type protein, preferred is 60% sequence similarity, more preferred is 70% sequence similarity. Even more preferred are muteins having 80%, 85% or 90% sequence similarity to the wild type protein. In an even more preferred embodiment, a mutein exhibits 95% sequence identity, even more preferably 97%, even more preferably 98% and even more preferably 99%. Sequence similarity may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs. For example, single or multiple amino acid substitutions (preferably conservative amino acid substitutions) may be made in the naturally-occurring sequence (preferably in the portion of the polypeptide outside the domain(s) forming intermolecular contacts. In a preferred embodiment, the amino acid substitutions are moderately conservative substitutions or conservative substitutions. In a more preferred embodiment, the amino acid substitutions are conservative substitutions. A conservative amino acid substitution should not substantially change the structural characteristics of the parent sequence (e.g., a replacement amino acid should not tend to disrupt a helix that occurs in the parent sequence, or disrupt other types of secondary structure that characterizes the parent sequence). Examples of art-recognized polypeptide secondary and tertiary structures are described in Creighton (ed.), *Proteins, Structures and Molecular Principles*, W. H. Freeman and Company (1984); Branden et al. (ed.), *Introduction to Protein Structure*, Garland Publishing (1991); Thornton et al, *Nature* 354:105-106 (1991), each of which are incorporated herein by reference.

As used herein, the twenty conventional amino acids and their abbreviations follow conventional usage. See Golub et al. (eds.), *Immunology—A Synthesis* $2^{nd}$ Ed., Sinauer Associates (1991), which is incorporated herein by reference. Stereoisomers (e.g., D-amino acids) of the twenty conventional amino acids, unnatural amino acids such as -, -disubstituted amino acids, N-alkyl amino acids, and other unconventional amino acids may also be suitable components for polypeptides of the present invention. Examples of unconventional amino acids include: 4-hydroxyproline, γ-carboxyglutamate, —N,N,N-trimethyllysine, —N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the right hand direction is the carboxy-terminal direction, in accordance with standard usage and convention.

A protein has "homology" or is "homologous" to a protein from another organism if the encoded amino acid sequence of the protein has a similar sequence to the encoded amino acid sequence of a protein of a different organism and has a similar biological activity or function. Alternatively, a protein may have homology or be homologous to another protein if the two proteins have similar amino acid sequences and have similar biological activities or functions. Although two proteins are said to be "homologous," this does not imply that there is necessarily an evolutionary relationship between the proteins. Instead, the term "homologous" is defined to mean that the two proteins have similar amino acid sequences and similar biological activities or functions. In a preferred embodiment, a homologous protein is one that exhibits 50% sequence similarity to the wild type protein, preferred is 60% sequence similarity, more preferred is 70% sequence similarity. Even more preferred are homologous proteins that exhibit 80%, 85% or 90% sequence similarity to the wild type protein. In a yet more preferred embodiment, a homologous protein exhibits 95%, 97%, 98% or 99% sequence similarity.

When "sequence similarity" is used in reference to proteins or peptides, it is recognized that residue positions that are not identical often differ by conservative amino acid substitutions. In a preferred embodiment, a polypeptide that has "sequence similarity" comprises conservative or moderately conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 24: 307-31 (1994), herein incorporated by reference.

For instance, the following six groups each contain amino acids that are conservative substitutions for one another:

1) Serine (S), Threonine (T);

2) Aspartic Acid (D), Glutamic Acid (E);

3) Asparagine (N), Glutamine (Q);

4) Arginine (R), Lysine (K);

5) Isoleucine (I), Leucine (L), Methionine (M), Alanine (A), Valine (V), and

6) Phenylalanine (F), Tyrosine (Y), Tryptophan (W).

Alternatively, a conservative replacement is any change having a positive value in the PAM250 log-likelihood matrix disclosed in Gonnet et al., *Science* 256: 1443-45 (1992), herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Other programs include FASTA, discussed supra.

A preferred algorithm when comparing a sequence of the invention to a database containing a large number of sequences from different organisms is the computer program BLAST, especially blastp or tblastn. See, e.g., Altschul et al., *J. Mol. Biol.* 215: 403-410 (1990); Altschul et al., *Nucleic Acids Res.* 25:3389-402 (1997); herein incorporated by reference. Preferred parameters for blastp are:

| | |
|---|---|
| Expectation value: | 10 (default) |
| Filter: | seg (default) |
| Cost to open a gap: | 11 (default) |
| Cost to extend a gap: | 1 (default |
| Max. alignments: | 100 (default) |
| Word size: | 11 (default) |
| No. of descriptions: | 100 (default) |
| Penalty Matrix: | BLOSUM62 |

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

Database searching using amino acid sequences can be measured by algorithms other than blastp are known in the art. For instance, polypeptide sequences can be compared using FASTA, a program in GCG Version 6.1. FASTA (e.g., FASTA2 and FASTA3) provides alignments and percent sequence identity of the regions of the best overlap between the query and search sequences (Pearson (1990), supra; Pearson (2000), supra. For example, percent sequence identity between amino acid sequences can be determined using FASTA with its default or recommended parameters (a word size of 2 and the PAM250 scoring matrix), as provided in GCG Version 6.1, herein incorporated by reference.

An "antibody" refers to an intact immunoglobulin, or to an antigen-binding portion thereof that competes with the intact antibody for specific binding to a molecular species, e.g., a polypeptide of the instant invention. Antigen-binding portions may be produced by recombinant DNA techniques or by enzymatic or chemical cleavage of intact antibodies. Antigen-binding portions include, inter alia, Fab, Fab', $F(ab')_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. An Fab fragment is a monovalent fragment consisting of the VL, VH, CL and CH1 domains; an $F(ab')_2$ fragment is a bivalent fragment comprising two Fab fragments linked by a disulfide bridge at the hinge region; an Fd fragment consists of the VH and CH1 domains; an Fv fragment consists of the VL and VH domains of a single arm of an antibody; and a dAb fragment consists of a VH domain. See, e.g., Ward et al., *Nature* 341: 544-546 (1989).

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

A single-chain antibody (scFv) is an antibody in which a VL and VH region are paired to form a monovalent molecule via a synthetic linker that enables them to be made as a single protein chain. See, e.g., Bird et al., *Science* 242: 423-426 (1988); Huston et al., *Proc. Natl. Acad. Sci. USA* 85: 5879-5883 (1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. See e.g., Holliger et al., *Proc. Natl. Acad. Sci. USA* 90: 6444-6448 (1993); Poljak et al., *Structure* 2:1121-1123 (1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. It is known that purified proteins, including purified antibodies, may be stabilized with non-naturally-associated components. The non-naturally-associated component may be a protein, such as albumin (e.g., BSA) or a chemical such as polyethylene glycol (PEG).

A "neutralizing antibody" or "an inhibitory antibody" is an antibody that inhibits the activity of a polypeptide or blocks the binding of a polypeptide to a ligand that normally binds to it. An "activating antibody" is an antibody that increases the activity of a polypeptide.

The term "epitope" includes any protein determinant capable of specifically binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the dissociation constant is less than 1 μM, preferably less than 100 nM and most preferably less than 10 nM.

The term "patient" as used herein includes human and veterinary subjects.

Throughout this specification and claims, the word "comprise," or variations such as "comprises" or "comprising," will be understood to imply the inclusion of a stated integer or group of integers but not the exclusion of any other integer or group of integers.

The term "colon specific" refers to a nucleic acid molecule or polypeptide that is expressed predominantly in the colon as compared to other tissues in the body. In a preferred embodiment, a "colon specific" nucleic acid molecule or polypeptide is expressed at a level that is 5-fold higher than any other tissue in the body. In a more preferred embodiment, the "colon specific" nucleic acid molecule or polypeptide is expressed at a level that is 10-fold higher than any other tissue in the body, more preferably at least 15-fold, 20-fold, 25-fold, 50-fold or 100-fold higher than any other tissue in the body. Nucleic acid molecule levels may be measured by nucleic acid hybridization, such as Northern blot hybridization, or quantitative PCR. Polypeptide levels may be measured by any method known to accurately quantitate protein levels, such as Western blot analysis.

Nucleic Acid Molecules, Regulatory Sequences, Vectors, Host Cells and Recombinant Methods of Making Polypeptides

Nucleic Acid Molecules

One aspect of the invention provides isolated nucleic acid molecules that are specific to the colon or to colon cells or tissue or that are derived from such nucleic acid molecules. These isolated colon specific nucleic acids (CSNAs) may comprise a cDNA, a genomic DNA, RNA, or a fragment of one of these nucleic acids, or may be a non-naturally-occurring nucleic acid molecule. In a preferred embodiment, the nucleic acid molecule encodes a polypeptide that is specific to colon, a colon-specific polypeptide (CSP). In a more preferred embodiment, the nucleic acid molecule encodes a polypeptide that comprises an ammo acid sequence of SEQ ID NO: 148 through 250. In another highly preferred embodiment, the nucleic acid molecule comprises a nucleic acid sequence of SEQ ID NO: 1 through 147.

A CSNA may be derived from a human or from another animal. In a preferred embodiment, the CSNA is derived from a human or other mammal. In a more preferred embodiment, the CSNA is derived from a human or other primate. In an even more preferred embodiment, the CSNA is derived from a human.

By "nucleic acid molecule" for purposes of the present invention, it is also meant to be inclusive of nucleic acid sequences that selectively hybridize to a nucleic acid molecule encoding a CSNA or a complement thereof. The hybridizing nucleic acid molecule may or may not encode a polypeptide or may not encode a CSP. However, in a preferred embodiment, the hybridizing nucleic acid molecule encodes a CSP. In a more preferred embodiment, the invention provides a nucleic acid molecule that selectively hybridizes to a nucleic acid molecule that encodes a polypeptide comprising an amino acid sequence of SEQ ID NO: 148 through 250. In an even more preferred embodiment, the invention provides a nucleic acid molecule that selectively hybridizes to a nucleic acid molecule comprising the nucleic acid sequence of SEQ ID NO: 1 through 147.

In a preferred embodiment, the nucleic acid molecule selectively hybridizes to a nucleic acid molecule encoding a CSP under low stringency conditions. In a more preferred embodiment, the nucleic acid molecule selectively hybridizes to a nucleic acid molecule encoding a CSP under moderate stringency conditions. In a more preferred embodiment, the nucleic acid molecule selectively hybridizes to a nucleic acid molecule encoding a CSP under high stringency conditions. In an even more preferred embodiment, the nucleic acid molecule hybridizes under low, moderate or high stringency conditions to a nucleic acid molecule encoding a polypeptide comprising an amino acid sequence of SEQ ID NO: 148 through 250. In a yet more preferred embodiment, the nucleic acid molecule hybridizes under low, moderate or high stringency conditions to a nucleic acid molecule comprising a nucleic acid sequence selected from SEQ ID NO: 1 through 147. In a preferred embodiment of the invention, the hybridizing nucleic acid molecule may be used to express recombinantly a polypeptide of the invention.

By "nucleic acid molecule" as used herein it is also meant to be inclusive of sequences that exhibits substantial sequence similarity to a nucleic acid encoding a CSP or a complement of the encoding nucleic acid molecule. In a preferred embodiment, the nucleic acid molecule exhibits substantial sequence similarity to a nucleic acid molecule encoding human CSP. In a more preferred embodiment, the nucleic acid molecule exhibits substantial sequence similarity to a nucleic acid molecule encoding a polypeptide having an amino acid sequence of SEQ ID NO: 148 through 250. In a preferred embodiment, the similar nucleic acid molecule is one that has at least 60% sequence identity with a nucleic acid molecule encoding a CSP, such as a polypeptide having an amino acid sequence of SEQ ID NO: 148 through 250, more preferably at least 70%, even more preferably at least 80% and even more preferably at least 85%. In a more preferred embodiment, the similar nucleic acid molecule is one that has at least 90% sequence identity with a nucleic acid molecule encoding a CSP, more preferably at least 95%, more preferably at least 97%, even more preferably at least 98%, and still more preferably at least 99%. In another highly preferred embodiment, the nucleic acid molecule is one that has at least 99.5%, 99.6%, 99.7%, 99.8% or 99.9% sequence identity with a nucleic acid molecule encoding a CSP.

In another preferred embodiment, the nucleic acid molecule exhibits substantial sequence similarity to a CSNA or its complement. In a more preferred embodiment, the nucleic acid molecule exhibits substantial sequence similarity to a nucleic acid molecule comprising a nucleic acid sequence of SEQ ID NO: 1 through 147. In a preferred embodiment, the nucleic acid molecule is one that has at least 60% sequence identity with a CSNA, such as one having a nucleic acid sequence of SEQ ID NO: 1 through 147, more preferably at least 70%, even more preferably at least 80% and even more preferably at least 85%. In a more preferred embodiment, the nucleic acid molecule is one that has at least 90% sequence identity with a CSNA, more preferably at least 95%, more preferably at least 97%, even more preferably at least 98%, and still more preferably at least 99%. In another highly preferred embodiment, the nucleic acid molecule is one that has at least 99.5%, 99.6%, 99.7%, 99.8% or 99.9% sequence identity with a CSNA.

A nucleic acid molecule that exhibits substantial sequence similarity may be one that exhibits sequence identity over its entire length to a CSNA or to a nucleic acid molecule encoding a CSP, or may be one that is similar over only a part of its length. In this case, the part is at least 50 nucleotides of the CSNA or the nucleic acid molecule encoding a CSP, preferably at least 100 nucleotides, more preferably at least 150 or 200 nucleotides, even more preferably at least 250 or 300 nucleotides, still more preferably at least 400 or 500 nucleotides.

The substantially similar nucleic acid molecule may be a naturally-occurring one that is derived from another species, especially one derived from another primate, wherein the similar nucleic acid molecule encodes an amino acid sequence that exhibits significant sequence identity to that of SEQ ID NO: 148 through 250 or demonstrates significant sequence identity to the nucleotide sequence of SEQ ID NO: 1 through 147. The similar nucleic acid molecule may also be a naturally-occurring nucleic acid molecule from a human, when the CSNA is a member of a gene family. The similar nucleic acid molecule may also be a naturally-occurring nucleic acid molecule derived from a non-primate, mammalian species, including without limitation, domesticated species, e.g., dog, cat, mouse, rat, rabbit, hamster, cow, horse and pig; and wild animals, e.g., monkey, fox, lions, tigers, bears, giraffes, zebras, etc. The substantially similar nucleic acid molecule may also be a naturally-occurring nucleic acid molecule derived from a non-mammalian species, such as birds or reptiles. The naturally-occurring substantially similar nucleic acid molecule may be isolated directly from humans or other species. In another embodiment, the substantially similar nucleic acid molecule may be one that is experimentally produced by random mutation of a nucleic acid molecule. In another embodiment, the substantially similar nucleic acid molecule may be one that is experimentally produced by directed mutation of a CSNA. Further, the substantially similar nucleic acid molecule may or may not be a CSNA. However, in a preferred embodiment, the substantially similar nucleic acid molecule is a CSNA.

By "nucleic acid molecule" it is also meant to be inclusive of allelic variants of a CSNA or a nucleic acid encoding a CSP. For instance, single nucleotide polymorphisms (SNPs) occur frequently in eukaryotic genomes. In fact, more than 1.4 million SNPs have already identified in the human genome, International Human Genome Sequencing Consortium, *Nature* 409: 860-921 (2001). Thus, the sequence determined from one individual of a species may differ from other allelic forms present within the population. Additionally, small deletions and insertions, rather than single nucleotide polymorphisms, are not uncommon in the general population, and often do not alter the function of the protein. Further, amino acid substitutions occur frequently among natural allelic variants, and often do not substantially change protein function.

In a preferred embodiment, the nucleic acid molecule comprising an allelic variant is a variant of a gene, wherein the gene is transcribed into an mRNA that encodes a CSP. In a more preferred embodiment, the gene is transcribed into an mRNA that encodes a CSP comprising an amino acid sequence of SEQ ID NO: 148 through 250. In another preferred embodiment, the allelic variant is a variant of a gene, wherein the gene is transcribed into an mRNA that is a CSNA. In a more preferred embodiment, the gene is transcribed into an mRNA that comprises the nucleic acid sequence of SEQ ID NO: 1 through 147. In a preferred embodiment, the allelic variant is a naturally-occurring allelic variant in the species of interest. In a more preferred embodiment, the species of interest is human.

By "nucleic acid molecule" it is also meant to be inclusive of a part of a nucleic acid sequence of the instant invention. The part may or may not encode a polypeptide, and may or may not encode a polypeptide that is a CSP. However, in a preferred embodiment, the part encodes a CSP. In one aspect, the invention comprises a part of a CSNA. In a second aspect, the invention comprises a part of a nucleic acid molecule that hybridizes or exhibits substantial sequence similarity to a CSNA. In a third aspect, the invention comprises a part of a nucleic acid molecule that is an allelic variant of a CSNA. In a fourth aspect, the invention comprises a part of a nucleic acid molecule that encodes a CSP. A part comprises at least 10 nucleotides, more preferably at least 15, 17, 18, 20, 25, 30, 35, 40, 50, 60, 70, 80, 90, 100, 150, 200, 250, 300, 350, 400 or 500 nucleotides. The maximum size of a nucleic acid part is one nucleotide shorter than the sequence of the nucleic acid molecule encoding the full-length protein.

By "nucleic acid molecule" it is also meant to be inclusive of sequence that encoding a fusion protein, a homologous protein, a polypeptide fragment, a mutein or a polypeptide analog, as described below.

Nucleotide sequences of the instantly-described nucleic acids were determined by sequencing a DNA molecule that had resulted, directly or indirectly, from at least one enzymatic polymerization reaction (e.g., reverse transcription and/or polymerase chain reaction) using an automated sequencer (such as the MegaBACE™ 1000, Molecular Dynamics, Sunnyvale, Calif., USA). Further, all amino acid sequences of the polypeptides of the present invention were predicted by translation from the nucleic acid sequences so determined, unless otherwise specified.

In a preferred embodiment of the invention, the nucleic acid molecule contains modifications of the native nucleic acid molecule. These modifications include normative internucleoside bonds, post-synthetic modifications or altered nucleotide analogues. One having ordinary skill in the art would recognize that the type of modification that can be made will depend upon the intended use of the nucleic acid molecule. For instance, when the nucleic acid molecule is used as a hybridization probe, the range of such modifications will be limited to those that permit sequence-discriminating base pairing of the resulting nucleic acid. When used to direct expression of RNA or protein in vitro or in vivo, the range of such modifications will be limited to those that permit the nucleic acid to function properly as a polymerization substrate. When the isolated nucleic acid is used as a therapeutic agent, the modifications will be limited to those that do not confer toxicity upon the isolated nucleic acid.

In a preferred embodiment, isolated nucleic acid molecules can include nucleotide analogues that incorporate labels that are directly detectable, such as radiolabels or fluorophores, or nucleotide analogues that incorporate labels that can be visualized in a subsequent reaction, such as biotin or various haptens. In a more preferred embodiment, the labeled nucleic acid molecule may be used as a hybridization probe.

Common radiolabeled analogues include those labeled with $^{33}$P, $^{32}$P, and $^{35}$S, such as -$^{32}$P-dATP, -$^{32}$P-dCTP, -$^{32}$P-dGTP, -$^{32}$P-dTTP, -$^{32}$P-3'-dATP, -$^{32}$P-ATP, -$^{32}$P-CTP, -$^{32}$P-GTP, -$^{32}$P-UTP, -$^{35}$S-dATP, $\alpha$-$^{35}$S-GTP, $\alpha$-$^{33}$P-dATP, and the like.

Commercially available fluorescent nucleotide analogues readily incorporated into the nucleic acids of the present invention include Cy3-dCTP, Cy3-dUTP, Cy5-dCTP, Cy3-dUTP (Amersham Pharmacia Biotech, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY® TMR-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). One may also custom synthesize nucleotides having other fluorophores. See Henegariu et al, *Nature Biotechnol.* 18: 345-348 (2000), the disclosure of which is incorporated herein by reference in its entirety.

Haptens that are commonly conjugated to nucleotides for subsequent labeling include biotin (biotin-11-dUTP, Molecular Probes, Inc., Eugene, Oreg., USA; biotin-21-UTP, biotin-21-dUTP, Clontech Laboratories, Inc., Palo Alto, Calif., USA), digoxigenin (DIG-11-dUTP, alkali labile, DIG-11-UTP, Roche Diagnostics Corp.,. Indianapolis, Ind., USA), and dinitrophenyl (dinitrophenyl-11-dUTP, Molecular Probes, Inc., Eugene, Oreg., USA).

Nucleic acid molecules can be labeled by incorporation of labeled nucleotide analogues into the nucleic acid. Such analogues can be incorporated by enzymatic polymerization, such as by nick translation, random priming, polymerase chain reaction (PCR), terminal transferase tailing, and end-filling of overhangs, for DNA molecules, and in vitro transcription driven, e.g., from phage promoters, such as T7, T3, and SP6, for RNA molecules. Commercial kits are readily available for each such labeling approach. Analogues can also be incorporated during automated solid phase chemical synthesis. Labels can also be incorporated after nucleic acid synthesis, with the 5' phosphate and 3' hydroxyl providing convenient sites for post-synthetic covalent attachment of detectable labels.

Other post-synthetic approaches also permit internal labeling of nucleic acids. For example, fluorophores can be attached using a cisplatin reagent that reacts with the N7 of guanine residues (and, to a lesser extent, adenine bases) in DNA, RNA, and PNA to provide a stable coordination complex between the nucleic acid and fluorophore label (Universal Linkage System) (available from Molecular Probes, Inc., Eugene, Oreg., USA and Amersham Pharmacia Biotech, Piscataway, N.J., USA); see Alers et al., *Genes, Chromosomes & Cancer* 25: 301-305 (1999); Jelsma et al., *J. NIH Res.* 5: 82 (1994); Van Belkum et al, *BioTechniques* 16: 148-153 (1994), incorporated herein by reference. As another example, nucleic acids can be labeled using a disulfide-containing linker (FastTag™ Reagent, Vector Laboratories, Inc., Burlingame, Calif., USA) that is photo- or thermally-coupled to the target nucleic acid using aryl azide chemistry; after reduction, a free thiol is available for coupling to a hapten, fluorophore, sugar, affinity ligand, or other marker.

One or more independent or interacting labels can be incorporated into the nucleic acid molecules of the present invention. For example, both a fluorophore and a moiety that in proximity thereto acts to quench fluorescence can be included to report specific hybridization through release of fluorescence quenching or to report exonucleotidic excision. See, e.g., Tyagi et al., *Nature Biotechnol.* 14: 303-308 (1996); Tyagi et al., *Nature Biotechnol.* 16: 49-53 (1998); Sokol et al., *Proc. Natl. Acad. Sci. USA* 95: 11538-11543 (1998); Kostrikis et al., *Science* 279: 1228-1229 (1998); Marras et al., *Genet. Anal.* 14: 151-156 (1999); U.S. Pat. Nos. 5,846,726; 5,925,517; 5,925,517; 5,723,591 and 5,538,848; Holland et al., *Proc. Natl. Acad. Sci. USA* 88: 7276-7280 (1991); Heid et al., *Genome Res.* 6(10): 986-94 (1996); Kuimelis et al., *Nucleic Acids Symp. Ser.* (37): 255-6 (1997); the disclosures of which are incorporated herein by reference in their entireties.

Nucleic acid molecules of the invention may be modified by altering one or more native phosphodiester internucleoside bonds to more nuclease-resistant, internucleoside bonds. See Hartmann et al. (eds.), *Manual of Antisense Methodology: Perspectives in Antisense Science*, Kluwer Law International (1999); Stein et al. (eds.), *Applied Antisense Oligonucleotide Technology*, Wiley-Liss (1998); Chadwick et al. (eds.), *Oligonucleotides as Therapeutic Agents—Symposium No.* 209, John Wiley & Son Ltd (1997); the disclosures of which are incorporated herein by reference in their entireties. Such altered internucleoside bonds are often desired for antisense techniques or for targeted gene correction. See Gamper et al., *Nucl. Acids Res.* 28(21): 4332-4339 (2000), the disclosure of which is incorporated herein by reference in its entirety.

Modified oligonucleotide backbones include, without limitation, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925;

5,519,126; 5,536,821; 5,541,306; 5,550,111; 5,563,253; 5,571,799; 5,587,361; and 5,625,050, the disclosures of which are incorporated herein by reference in their entireties. In a preferred embodiment, the modified internucleoside linkages may be used for antisense techniques.

Other modified oligonucleotide backbones do not include a phosphorus atom, but have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above backbones include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437 and 5,677,439; the disclosures of which are incorporated herein by reference in their entireties.

In other preferred oligonucleotide mimetics, both the sugar and the internucleoside linkage are replaced with novel groups, such as peptide nucleic acids (PNA). In PNA compounds, the phosphodiester backbone of the nucleic acid is replaced with an amide-containing backbone, in particular by repeating N-(2-aminoethyl) glycine units linked by amide bonds. Nucleobases are bound directly or indirectly to aza nitrogen atoms of the amide portion of the backbone, typically by methylene carbonyl linkages. PNA can be synthesized using a modified peptide synthesis protocol. PNA oligomers can be synthesized by both Fmoc and tBoc methods. Representative U.S. patents that teach the preparation of PNA compounds include, but are not limited to, U.S. Pat. Nos. 5,539,082; 5,714,331; and 5,719,262, each of which is herein incorporated by reference. Automated PNA synthesis is readily achievable on commercial synthesizers (see, e.g., "PNA User's Guide," Rev. 2, February 1998, Perseptive Biosystems Part No. 60138, Applied Biosystems, Inc., Foster City, Calif.).

PNA molecules are advantageous for a number of reasons. First, because the PNA backbone is uncharged, PNA/DNA and PNA/RNA duplexes have a higher thermal stability than is found in DNA/DNA and DNA/RNA duplexes. The Tm of a PNA/DNA or PNA/RNA duplex is generally 1° C. higher per base pair than the Tm of the corresponding DNA/DNA or DNA/RNA duplex (in 100 mM NaCl). Second, PNA molecules can also form stable PNA/DNA complexes at low ionic strength, under conditions in which DNA/DNA duplex formation does not occur. Third, PNA also demonstrates greater specificity in binding to complementary DNA because a PNA/DNA mismatch is more destabilizing than DNA/DNA mismatch. A single mismatch in mixed a PNA/DNA 15-mer lowers the Tm by 8-20° C. (15° C. on average). In the corresponding DNA/DNA duplexes, a single mismatch lowers the Tm by 4-16° C. (11° C. on average). Because PNA probes can be significantly shorter than DNA probes, their specificity is greater. Fourth, PNA oligomers are resistant to degradation by enzymes, and the lifetime of these compounds is extended both in vivo and in vitro because nucleases and proteases do not recognize the PNA polyamide backbone with nucleobase sidechains. See, e.g., Ray et al, *FASEB J.* 14(9): 1041-60 (2000); Nielsen et al., *Pharmacol Toxicol.* 86(1): 3-7 (2000); Larsen et al., *Biochim Biophys Acta.* 1489(1): 159-66 (1999); Nielsen, *Curr. Opin. Struct. Biol.* 9(3): 353-7 (1999), and Nielsen, *Curr. Opin. Biotechnol.* 10(1): 71-5 (1999), the disclosures of which are incorporated herein by reference in their entireties.

Nucleic acid molecules may be modified compared to their native structure throughout the length of the nucleic acid molecule or can be localized to discrete portions thereof. As an example of the latter, chimeric nucleic acids can be synthesized that have discrete DNA and RNA domains and that can be used for targeted gene repair and modified PCR reactions, as further described in U.S. Pat. Nos. 5,760,012 and 5,731,181, Misra et al., *Biochem.* 37: 1917-1925 (1998); and Finn et al, *Nucl. Acids Res.* 24: 3357-3363 (1996), the disclosures of which are incorporated herein by reference in their entireties.

Unless otherwise specified, nucleic acids of the present invention can include any topological conformation appropriate to the desired use; the term thus explicitly comprehends, among others, single-stranded, double-stranded, triplexed, quadruplexed, partially double-stranded, partially-triplexed, partially-quadruplexed, branched, hairpinned, circular, and padlocked conformations. Padlock conformations and their utilities are further described in Banér et al., *Curr. Opin. Biotechnol.* 12: 11-15 (2001); Escude et al., *Proc. Natl. Acad. Sci. USA* 14: 96(19):10603-7 (1999); Nilsson et al., *Science* 265(5181): 2085-8 (1994), the disclosures of which are incorporated herein by reference in their entireties. Triplex and quadruplex conformations, and their utilities, are reviewed in Praseuth et al., *Biochim. Biophys. Acta.* 1489(1): 181-206 (1999); Fox, *Curr. Med. Chem.* 7(1): 17-37 (2000); Kochetkova et al, *Methods Mol. Biol.* 130: 189-201 (2000); Chan et al., *J. Mol. Med.* 75(4): 267-82 (1997), the disclosures of which are incorporated herein by reference in their entireties.

Methods for Using Nucleic Acid Molecules as Probes and Primers

The isolated nucleic acid molecules of the present invention can be used as hybridization probes to detect, characterize, and quantify hybridizing nucleic acids in, and isolate hybridizing nucleic acids from, both genomic and transcript-derived nucleic acid samples. When free in solution, such probes are typically, but not invariably, detectably labeled; bound to a substrate, as in a microarray, such probes are typically, but not invariably unlabeled.

In one embodiment, the isolated nucleic acids of the present invention can be used as probes to detect and characterize gross alterations in the gene of a CSNA, such as deletions, insertions, translocations, and duplications of the CSNA genomic locus through fluorescence in situ hybridization (FISH) to chromosome spreads. See, e.g., Andreeff et al. (eds.), *Introduction to Fluorescence In Situ Hybridization: Principles and Clinical Applications*, John Wiley & Sons (1999), the disclosure of which is incorporated herein by reference in its entirety. The isolated nucleic acids of the present invention can be used as probes to assess smaller genomic alterations using, e.g., Southern blot detection of restriction fragment length polymorphisms. The isolated nucleic acid molecules of the present invention can be used as probes to isolate genomic clones that include the nucleic acid molecules of the present invention, which thereafter can be restriction mapped and sequenced to identify deletions, insertions, translocations, and substitutions (single nucleotide polymorphisms, SNPs) at the sequence level.

In another embodiment, the isolated nucleic acid molecules of the present invention can be used as probes to detect, characterize, and quantify CSNA in, and isolate CSNA from, transcript-derived nucleic acid samples. In one aspect, the isolated nucleic acid molecules of the present invention can be used as hybridization probes to detect, characterize by length, and quantify mRNA by Northern blot of total or poly-$A^+$-selected RNA samples. In another aspect, the isolated nucleic acid molecules of the present invention can be used as hybridization probes to detect, characterize by location, and quantify mRNA by in situ hybridization to tissue sections. See, e.g., Schwarchzacher et al., *In Situ Hybridization*, Springer-Verlag New York (2000), the disclosure of which is incorporated herein by reference in its entirety. In another preferred embodiment, the isolated nucleic acid molecules of the present invention can be used as hybridization probes to measure the representation of clones in a cDNA library or to isolate hybridizing nucleic acid molecules acids from cDNA libraries, permitting sequence level characterization of mRNAs that hybridize to CSNAs, including, without limitations, identification of deletions, insertions, substitutions, truncations, alternatively spliced forms and single nucleotide polymorphisms. In yet another preferred embodiment, the nucleic acid molecules of the instant invention may be used in microarrays.

All of the aforementioned probe techniques are well within the skill in the art, and are described at greater length in standard texts such as Sambrook (2001), supra; Ausubel (1999), supra; and Walker et al. (eds.), *The Nucleic Acids Protocols Handbook*, Humana Press (2000), the disclosures of which are incorporated herein by reference in their entirety.

Thus, in one embodiment, a nucleic acid molecule of the invention may be used as a probe or primer to identify or amplify a second nucleic acid molecule that selectively hybridizes to the nucleic acid molecule of the invention. In a preferred embodiment, the probe or primer is derived from a nucleic acid molecule encoding a CSP. In a more preferred embodiment, the probe or primer is derived from a nucleic acid molecule encoding a polypeptide having an amino acid sequence of SEQ ID NO: 148 through 250. In another preferred embodiment, the probe or primer is derived from a CSNA. In a more preferred embodiment, the probe or primer is derived from a nucleic acid molecule having a nucleotide sequence of SEQ ID NO: 1 through 147.

In general, a probe or primer is at least 10 nucleotides in length, more preferably at least 12, more preferably at least 14 and even more preferably at least 16 or 17 nucleotides in length. In an even more preferred embodiment, the probe or primer is at least 18 nucleotides in length, even more preferably at least 20 nucleotides and even more preferably at least 22 nucleotides in length. Primers and probes may also be longer in length. For instance, a probe or primer may be 25 nucleotides in length, or may be 30, 40 or 50 nucleotides in length. Methods of performing nucleic acid hybridization using oligonucleotide probes are well-known in the art. See, e.g., Sambrook et al, 1989, supra, Chapter 11 and pp. 11.31-11.32 and 11.40-11.44, which describes radiolabeling of short probes, and pp. 11.45-11.53, which describe hybridization conditions for oligonucleotide probes, including specific conditions for probe hybridization (pp. 11.50-11.51).

Methods of performing primer-directed amplification are also well-known in the art. Methods for performing the polymerase chain reaction (PCR) are compiled, inter alia, in McPherson, *PCR Basics: From Background to Bench*, Springer Verlag (2000); Innis et al. (eds.), *PCR Applications: Protocols for Functional Genomics*, Academic Press (1999); Gelfand et al. (eds.), *PCR Strategies*, Academic Press (1998); Newton et al., *PCR*, Springer-Verlag New York (1997); Burke (ed.), *PCR: Essential Techniques*, John Wiley & Son Ltd (1996); White (ed.), *PCR Cloning Protocols: From Molecular Cloning to Genetic Engineering*, Vol. 67, Humana Press (1996); McPherson et al. (eds.), *PCR* 2: *A Practical Approach*, Oxford University Press, Inc. (1995); the disclosures of which are incorporated herein by reference in their entireties. Methods for performing RT-PCR are collected, e.g., in Siebert et al. (eds.), *Gene Cloning and Analysis by RT-PCR*, Eaton Publishing Company/Bio Techniques Books Division, 1998; Siebert (ed.), *PCR Technique: RT-PCR*, Eaton Publishing Company/BioTechniques Books (1995); the disclosure of which is incorporated herein by reference in its entirety.

PCR and hybridization methods may be used to identify and/or isolate allelic variants, homologous nucleic acid molecules and fragments of the nucleic acid molecules of the invention. PCR and hybridization methods may also be used to identify, amplify and/or isolate nucleic acid molecules that encode homologous proteins, analogs, fusion protein or muteins of the invention. The nucleic acid primers of the present invention can be used to prime amplification of nucleic acid molecules of the invention, using transcript-derived or genomic DNA as template.

The nucleic acid primers of the present invention can also be used, for example, to prime single base extension (SBE) for SNP detection (See, e.g., U.S. Pat. No. 6,004,744, the disclosure of which is incorporated herein by reference in its entirety).

Isothermal amplification approaches, such as rolling circle amplification, are also now well-described. See, e.g., Schweitzer et al, *Curr. Opin. Biotechnol.* 12(1): 21-7 (2001); U.S. Pat. Nos. 5,854,033 and 5,714,320; and international patent publications WO 97/19193 and WO 00/15779, the disclosures of which are incorporated herein by reference in their entireties. Rolling circle amplification can be combined with other techniques to facilitate SNP detection. See, e.g., Lizardi et al., *Nature Genet.* 19(3): 225-32 (1998).

Nucleic acid molecules of the present invention may be bound to a substrate either covalently or noncovalently. The substrate can be porous or solid, planar or non-planar, unitary or distributed. The bound nucleic acid molecules may be used as hybridization probes, and may be labeled or unlabeled. In a preferred embodiment, the bound nucleic acid molecules are unlabeled.

In one embodiment, the nucleic acid molecule of the present invention is bound to a porous substrate, e.g., a membrane, typically comprising nitrocellulose, nylon, or positively-charged derivatized nylon. The nucleic acid molecule of the present invention can be used to detect a hybridizing nucleic acid molecule that is present within a labeled nucleic acid sample, e.g., a sample of transcript-derived nucleic acids. In another embodiment, the nucleic acid molecule is bound to a solid substrate, including, without limitation, glass, amorphous silicon, crystalline silicon or plastics. Examples of plastics include, without limitation, polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof. The solid substrate may be any shape, including rectangular, disk-like and spherical. In a preferred embodiment, the solid substrate is a microscope slide or slide-shaped substrate.

The nucleic acid molecule of the present invention can be attached covalently to a surface of the support substrate or applied to a derivatized surface in a chaotropic agent that facilitates denaturation and adherence by presumed noncovalent interactions, or some combination thereof. The nucleic acid molecule of the present invention can be bound to a substrate to which a plurality of other nucleic acids are concurrently bound, hybridization to each of the plurality of bound nucleic acids being separately detectable. At low density, e.g. on a porous membrane, these substrate-bound collections are typically denominated macroarrays; at higher density, typically on a solid support, such as glass, these substrate bound collections of plural nucleic acids are colloquially termed microarrays. As used herein, the term microarray includes arrays of all densities. It is, therefore, another aspect of the invention to provide microarrays that include the nucleic acids of the present invention.

Expression Vectors, Host Cells and Recombinant Methods of Producing Polypeptides Another aspect of the present invention relates to vectors that comprise one or more of the isolated nucleic acid molecules of the present invention, and host cells in which such vectors have been introduced.

The vectors can be used, inter alia, for propagating the nucleic acids of the present invention in host cells (cloning vectors), for shuttling the nucleic acids of the present invention between host cells derived from disparate organisms (shuttle vectors), for inserting the nucleic acids of the present invention into host cell chromosomes (insertion vectors), for expressing sense or antisense RNA transcripts of the nucleic acids of the present invention in vitro or within a host cell, and for expressing polypeptides encoded by the nucleic acids of the present invention, alone or as fusions to heterologous polypeptides (expression vectors). Vectors of the present invention will often be suitable for several such uses.

Vectors are by now well-known in the art, and are described, inter alia, in Jones et al. (eds.), *Vectors: Cloning Applications: Essential Techniques* (Essential Techniques Series), John Wiley & Son Ltd. (1998); Jones et al (eds.), *Vectors: Expression Systems: Essential Techniques* (Essential Techniques Series), John Wiley & Son Ltd. (1998); Gacesa et al., *Vectors: Essential Data*, John Wiley & Sons Ltd. (1995); Cid-Arregui (eds.), *Viral Vectors: Basic Science and Gene Therapy*, Eaton Publishing Co. (2000); Sambrook (2001), supra; Ausubel (1999), supra; the disclosures of which are incorporated herein by reference in their entireties. Furthermore, an enormous variety of vectors are available commercially. Use of existing vectors and modifications thereof being well within the skill in the art, only basic features need be described here.

Nucleic acid sequences may be expressed by operatively linking them to an expression control sequence in an appropriate expression vector and employing that expression vector to transform an appropriate unicellular host. Expression control sequences are sequences which control the transcription, post-transcriptional events and translation of nucleic acid sequences. Such operative linking of a nucleic sequence of this invention to an expression control sequence, of course, includes, if not already part of the nucleic acid sequence, the provision of a translation initiation codon, ATG or GTG, in the correct reading frame upstream of the nucleic acid sequence.

A wide variety of host/expression vector combinations may be employed in expressing the nucleic acid sequences of this invention. Useful expression vectors, for example, may consist of segments of chromosomal, non-chromosomal and synthetic nucleic acid sequences.

In one embodiment, prokaryotic cells may be used with an appropriate vector. Prokaryotic host cells are often used for cloning and expression. In a preferred embodiment, prokaryotic host cells include *E. coli, Pseudomonas, Bacillus* and *Streptomyces*. In a preferred embodiment, bacterial host cells are used to express the nucleic acid molecules of the instant invention. Useful expression vectors for bacterial hosts include bacterial plasmids, such as those from *E. coli, Bacillus* or *Streptomyces*, including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g., NM989, λGT10 and λGT11, and other phages, e.g., M13 and filamentous single-stranded phage DNA. Where *E. coli* is used as host, selectable markers are, analogously, chosen for selectivity in gram negative bacteria: e.g., typical markers confer resistance to antibiotics, such as ampicillin, tetracycline, chloramphenicol, kanamycin, streptomycin and zeocin; auxotrophic markers can also be used.

In other embodiments, eukaryotic host cells, such as yeast, insect, mammalian or plant cells, may be used. Yeast cells, typically *S. cerevisiae*, are useful for eukaryotic genetic studies, due to the ease of targeting genetic changes by homologous recombination and the ability to easily complement genetic defects using recombinantly expressed proteins. Yeast cells are useful for identifying interacting protein components, e.g. through use of a two-hybrid system. In a preferred embodiment, yeast cells are useful for protein expression. Vectors of the present invention for use in yeast will typically, but not invariably, contain an origin of replication suitable for use in yeast and a selectable marker that is functional in yeast. Yeast vectors include Yeast Integrating plasmids (e.g., YIp5) and Yeast Replicating plasmids (the YRp and YEp series plasmids), Yeast Centromere plasmids (the YCp series plasmids), Yeast Artificial Chromosomes (YACs) which are based on yeast linear plasmids, denoted YLp, pGPD-2, 2 μ plasmids and derivatives thereof, and improved shuttle vectors such as those described in Gietz et al., *Gene,* 74: 527-34 (1988) (YIplac, YEplac and YCplac). Selectable markers in yeast vectors include a variety of auxotrophic markers, the most common of which are (in *Saccharomyces cerevisiae*) URA3, HIS3, LEU2, TRP1 and LYS2, which complement specific auxotrophic mutations, such as ura3-52, his3-D1, leu2-D1, trp1-D1 and lys2-201.

Insect cells are often chosen for high efficiency protein expression. Where the host cells are from *Spodoptera frugiperda*, e.g., Sf9 and Sf21 cell lines, and expresSF™ cells (Protein Sciences Corp., Meriden, Conn., USA)), the vector replicative strategy is typically based upon the baculovirus life cycle. Typically, baculovirus transfer vectors are used to replace the wild-type AcMNPV polyhedrin gene with a heterologous gene of interest. Sequences that flank the polyhedrin gene in the wild-type genome are positioned 5' and 3' of the expression cassette on the transfer vectors. Following co-transfection with AcMNPV DNA, a homologous recombination event occurs between these sequences resulting in a recombinant virus carrying the gene of interest and the polyhedrin or p10 promoter. Selection can be based upon visual screening for lacZ fusion activity.

In another embodiment, the host cells may be mammalian cells, which are particularly useful for expression of proteins intended as pharmaceutical agents, and for screening of potential agonists and antagonists of a protein or a physiological pathway. Mammalian vectors intended for autonomous extrachromosomal replication will typically include a viral origin, such as the SV40 origin (for replication in cell lines expressing the large T-antigen, such as COS1 and COS7 cells), the papillomavirus origin, or the EBV origin for long term episomal replication (for use, e.g., in 293-EBNA cells, which constitutively express the EBV EBNA-1 gene product and adenovirus E1A). Vectors intended for integration, and thus replication as part of the mammalian chromosome, can, but need not, include an origin of replication functional in mammalian cells, such as the SV40 origin. Vectors based upon viruses, such as adenovirus, adeno-associated virus, vaccinia virus, and various mammalian retroviruses, will typically replicate according to the viral replicative strategy. Selectable markers for use in mammalian cells include resistance to neomycin (G418), blasticidin, hygromycin and to zeocin, and selection based upon the purine salvage pathway using HAT medium.

Expression in mammalian cells can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL 941.

Plant cells can also be used for expression, with the vector replicon typically derived from a plant virus (e.g., cauliflower mosaic virus, CaMV; tobacco mosaic virus; TMV) and selectable markers chosen for suitability in plants.

It is known that codon usage of different host cells may be different. For example, a plant cell and a human cell may exhibit a difference in codon preference for encoding a particular amino acid. As a result, human mRNA may not be efficiently translated in a plant, bacteria or insect host cell. Therefore, another embodiment of this invention is directed to codon optimization. The codons of the nucleic acid molecules of the invention may be modified to resemble, as much-as possible, genes naturally contained within the host cell without altering the amino acid sequence encoded by the nucleic acid molecule.

Any of a wide variety of expression control sequences may be used in these vectors to express the DNA sequences of this invention. Such useful expression control sequences include the expression control sequences associated with structural genes of the foregoing expression vectors. Expression control sequences that control transcription include, e.g., promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation.

Examples of useful expression control sequences for a prokaryote, e.g., *E. coli*, will include a promoter, often a phage promoter, such as phage lambda pL promoter, the trc promoter, a hybrid derived from the trp and lac promoters, the bacteriophage T7 promoter (in *E. coli* cells engineered to express the T7 polymerase), the TAC or TRC system, the major operator and promoter regions of phage lambda, the control regions of fd coat protein, or the araBAD operon. Prokaryotic expression vectors may further include transcription terminators, such as the aspA terminator, and elements that facilitate translation, such as a consensus ribosome binding site and translation termination codon, Schomer et al., *Proc. Natl. Acad. Sci. USA* 83: 8506-8510 (1986).

Expression control sequences for yeast cells, typically *S. cerevisiae*, will include a yeast promoter, such as the CYC1 promoter, the GAL1 promoter, the GAL10 promoter, ADH1 promoter, the promoters of the yeast_-mating system, or the GPD promoter, and will typically have elements that facilitate transcription termination, such as the transcription termination signals from the CYC1 or ADH1 gene.

Expression vectors useful for expressing proteins in mammalian cells will include a promoter active in mammalian cells. These promoters include those derived from mammalian viruses, such as the enhancer-promoter sequences from the immediate early gene of the human cytomegalovirus (CMV), the enhancer-promoter sequences from the Rous sarcoma virus long terminal repeat (RSV LTR), the enhancer-promoter from SV40 or the early and late promoters of adenovirus. Other expression control sequences include the promoter for 3-phosphoglycerate kinase or other glycolytic enzymes, the promoters of acid phosphatase. Other expression control sequences include those from the gene comprising the CSNA of interest. Often, expression is enhanced by incorporation of polyadenylation sites, such as the late SV40 polyadenylation site and the polyadenylation signal and transcription termination sequences from the bovine growth hormone (BGH) gene, and ribosome binding sites. Furthermore, vectors can include introns, such as intron II of rabbit β-globin gene and the SV40 splice elements.

Preferred nucleic acid vectors also include a selectable or amplifiable marker gene and means for amplifying the copy number of the gene of interest. Such marker genes are well-known in the art. Nucleic acid vectors may also comprise stabilizing sequences (e.g., ori- or ARS-like sequences and telomere-like sequences), or may alternatively be designed to favor directed or non-directed integration into the host cell genome. In a preferred embodiment, nucleic acid sequences of this invention are inserted in frame into an expression vector that allows high level expression of an RNA which encodes a protein comprising the encoded nucleic acid sequence of interest. Nucleic acid cloning and sequencing methods are well-known to those of skill in the art and are described in an assortment of laboratory manuals, including Sambrook (1989), supra, Sambrook (2000), supra; and Ausubel (1992), supra, Ausubel (1999), supra. Product information from manufacturers of biological, chemical and immunological reagents also provide useful information.

Expression vectors may be either constitutive or inducible. Inducible vectors include either naturally inducible promoters, such as the trc promoter, which is regulated by the lac operon, and the pL promoter, which is regulated by tryptophan, the MMTV-LTR promoter, which is inducible by dexamethasone, or can contain synthetic promoters and/or additional elements that confer inducible control on adjacent promoters. Examples of inducible synthetic promoters are the hybrid Plac/ara-1 promoter and the PLtetO-1 promoter. The PltetO-1 promoter takes advantage of the high expression levels from the PL promoter of phage lambda, but replaces the lambda repressor sites with two copies of operator 2 of the Tn10 tetracycline resistance operon, causing this promoter to be tightly repressed by the Tet repressor protein and induced in response to tetracycline (Tc) and Tc derivatives such as anhydrotetracycline. Vectors may also be inducible because they contain hormone response elements, such as the glucocorticoid response element (GRE) and the estrogen response element (ERE), which can confer hormone inducibility where vectors are used for expression in cells having the respective hormone receptors. To reduce background levels of expression, elements responsive to ecdysone, an insect hormone, can be used instead, with coexpression of the ecdysone receptor.

In one aspect of the invention, expression vectors can be designed to fuse the expressed polypeptide to small protein tags that facilitate purification and/or visualization. Tags that facilitate purification include a polyhistidine tag that facilitates purification of the fusion protein by immobilized metal affinity chromatography, for example using NiNTA resin (Qiagen Inc., Valencia, Calif., USA) or TALON™ resin (cobalt immobilized affinity chromatography medium, Clontech Labs, Palo Alto, Calif., USA). The fusion protein can include a chitin-binding tag and self-excising intein, permitting chitin-based purification with self-removal of the fused tag (IMPACT™ system, New England Biolabs, Inc., Beverley, Mass., USA). Alternatively, the fusion protein can include a calmodulin-binding peptide tag, permitting purification by calmodulin affinity resin (Stratagene, La Jolla, Calif., USA), or a specifically excisable fragment of the biotin carboxylase carrier protein, permitting purification of in vivo biotinylated protein using an avidin resin and subsequent tag removal (Promega, Madison, Wis., USA). As another useful alternative, the proteins of the present invention can be expressed as a fusion protein with glutathione-S-transferase, the affinity and specificity of binding to glutathione permitting purification using glutathione affinity resins, such as Glutathione-Superflow Resin (Clontech Laboratories, Palo Alto, Calif., USA), with subsequent elution with free glutathione. Other tags include, for example, the Xpress epitope, detectable by anti-Xpress antibody (Invitrogen, Carlsbad, Calif., USA), a myc tag, detectable by anti-myc tag antibody, the V5 epitope, detectable by anti-V5 antibody (Invitrogen, Carlsbad, Calif., USA), FLAG® epitope, detectable by anti-FLAG® antibody (Stratagene, La Jolla, Calif., USA), and the HA epitope.

For secretion of expressed proteins, vectors can include appropriate sequences that encode secretion signals, such as leader peptides. For example, the pSecTag2 vectors (Invitrogen, Carlsbad, Calif., USA) are 5.2 kb mammalian expression vectors that carry the secretion signal from the V-J2-C region of the mouse Ig kappa-chain for efficient secretion of recombinant proteins from a variety of mammalian cell lines.

Expression vectors can also be designed to fuse proteins encoded by the heterologous nucleic acid insert to polypeptides that are larger than purification and/or identification tags. Useful fusion proteins include those that permit display of the encoded protein on the surface of a phage or cell, fusion to intrinsically fluorescent proteins, such as those that have a green fluorescent protein (GFP)-like chromophore, fusions to the IgG Fc region, and fusion proteins for use in two hybrid systems.

Vectors for phage display fuse the encoded polypeptide to, e.g., the gene III protein (pIII) or gene VIII protein (pVIII) for display on the surface of filamentous phage, such as M13. See Barbas et al., *Phage Display: A Laboratory Manual*, Cold Spring Harbor Laboratory Press (2001); Kay et al. (eds.), *Phage Display of Peptides and Proteins: A Laboratory Manual*, Academic Press, Inc., (1996); Abelson et al. (eds.), *Combinatorial Chemistry* (Methods in Enzymology, Vol. 267) Academic Press (1996). Vectors for yeast display, e.g. the pYD1 yeast display vector (Invitrogen, Carlsbad, Calif., USA), use the -agglutinin yeast adhesion receptor to display recombinant protein on the surface of *S. cerevisiae*. Vectors for mammalian display, e.g., the pDisplay™ vector (Invitrogen, Carlsbad, Calif., USA), target recombinant proteins using an N-terminal cell surface targeting signal and a C-terminal transmembrane anchoring domain of platelet derived growth factor receptor.

A wide variety of vectors now exist that fuse proteins encoded by heterologous nucleic acids to the chromophore of the substrate-independent, intrinsically fluorescent green fluorescent protein from *Aequorea victoria* ("GFP") and its variants. The GFP-like chromophore can be selected from GFP-like chromophores found in naturally occurring proteins, such as *A. victoria* GFP (GenBank accession number AAA27721), *Renilla reniformis* GFP, FP583 (GenBank accession no. AF168419) (DsRed), FP593 (AF272711), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are known in the art. See Li et al., *J. Biol. Chem.* 272: 28545-28549 (1997). Alternatively, the GFP-like chromophore can be selected from GFP-like chromophores modified from those found in nature. The methods for engineering such modified GFP-like chromophores and testing them for fluorescence activity, both alone and as part of protein fusions, are well-known in the art. See Heim et al., *Curr. Biol.* 6: 178-182 (1996) and Palm et al., *Methods Enzymol.* 302: 378-394 (1999), incorporated herein by reference in its entirety. A variety of such modified chromophores are now commercially available and can readily be used in the fusion proteins of the present invention. These include EGFP ("enhanced GFP"), EBFP ("enhanced blue fluorescent protein"), BFP2, EYFP ("enhanced yellow fluorescent protein"), ECFP ("enhanced cyan fluorescent protein") or Citrine. EGFP (see, e.g, Cormack et al., *Gene* 173: 33-38 (1996); U.S. Pat. Nos. 6,090,919 and 5,804,387) is found on a variety of vectors, both plasmid and viral, which are available commercially (Clontech Labs, Palo Alto, Calif., USA); EBFP is optimized for expression in mammalian cells whereas BFP2, which retains the original jellyfish codons, can be expressed in bacteria (see, e.g,. Heim et al., *Curr. Biol.* 6: 178-182 (1996) and Cormack et al., *Gene* 173: 33-38 (1996)). Vectors containing these blue-shifted variants are available from Clontech Labs (Palo Alto, Calif., USA). Vectors containing EYFP, ECFP (see, e.g., Heim et al., *Curr. Biol.* 6: 178-182 (1996); Miyawaki et al., *Nature* 388: 882-887 (1997)) and Citrine (see, e.g., Heikal et al., *Proc. Natl. Acad. Sci. USA* 97: 11996-12001 (2000)) are also available from Clontech Labs. The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties. See also Conn (ed.), *Green Fluorescent Protein* (Methods in Enzymology, Vol. 302), Academic Press, Inc. (1999). The GFP-like chromophore of each of these GFP variants can usefully be included in the fusion proteins of the present invention.

Fusions to the IgG Fc region increase serum half life of protein pharmaceutical products through interaction with the FcRn receptor (also denominated the FcRp receptor and the Brambell receptor, FcRb), further described in International Patent Application Nos. WO 97/43316, WO 97/34631, WO 96/32478, WO 96/18412.

For long-term, high-yield recombinant production of the proteins, protein fusions, and protein fragments of the present invention, stable expression is preferred. Stable expression is readily achieved by integration into the host cell genome of vectors having selectable markers, followed by selection of these integrants. Vectors such as pUB6/V5-His A, B, and C (Invitrogen, Carlsbad, Calif., USA) are designed for high-level stable expression of heterologous proteins in a wide range of mammalian tissue types and cell lines. pUB6/V5-His uses the promoter/enhancer sequence from the human ubiquitin C gene to drive expression of recombinant proteins: expression levels in 293, CHO, and NIH3T3 cells are comparable to levels from the CMV and human EF-1a promoters. The bsd gene permits rapid selection of stably transfected mammalian cells with the potent antibiotic blasticidin.

Replication incompetent retroviral vectors, typically derived from Moloney murine leukemia virus, also are useful for creating stable transfectants having integrated. provirus. The highly efficient transduction machinery of retroviruses, coupled with the availability of a variety of packaging cell lines such as RetroPack™ PT 67, Eco-Pack2™-293, AmphoPack-293, and GP2-293 cell lines (all available from Clontech Laboratories, Palo Alto, Calif., USA), allow a wide host range to be infected with high efficiency; varying the multiplicity of infection readily adjusts the copy number of the integrated provirus.

Of course, not all vectors and expression control sequences will function equally well to express the nucleic acid sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered. The present invention further includes host cells comprising the vectors of the present invention, either present episomally within the cell or integrated, in whole or in part, into the host cell chromosome. Among other considerations, some of which are described above, a host cell strain may be chosen for its ability to process the expressed protein in the desired fashion. Such post-translational modifications of the polypeptide include, but are not limited to, acetylation, carboxylation, glycosylation, phosphorylation, lipidation, and acylation, and it is an aspect of the present invention to provide CSPs with such post-translational modifications.

Polypeptides of the invention may be post-translationally modified. Post-translational modifications include phosphorylation of amino acid residues serine, threonine and/or tyrosine, N-linked and/or O-linked glycosylation, methylation, acetylation, prenylation, methylation, acetylation, arginylation, ubiquination and racemization. One may determine whether a polypeptide of the invention is likely to be post-translationally modified by analyzing the sequence of the polypeptide to determine if there are peptide motifs indicative of sites for post-translational modification. There are a number of computer programs that permit prediction of post-translational modifications. See, e.g., expasy with the extension .org of the world wide web, which includes PSORT, for prediction of protein sorting signals and localization sites, SignalP, for prediction of signal peptide cleavage sites, MITOPROT and Predotar, for prediction of mitochondrial targeting sequences, NetOGlyc, for prediction of type O-glycosylation sites in mammalian proteins, big-PT Predictor and DGPI, for prediction of prenylation-anchor and cleavage sites, and NetPhos, for prediction of Ser, Thr and Tyr phosphorylation sites in eukaryotic proteins. Other computer programs, such as those included in GCG, also may be used to determine post-translational modification peptide motifs.

General examples of types of post-translational modifications may be found in web sites such as the Delta Mass database abrf with the extension .org/ABRF/Research Committees/deltamass/deltamass.html of the world wide web; "GlycoSuiteDB: a new curated relational database of glycoprotein glycan structures and their biological sources" Cooper et al. Nucleic Acids Res. 29; 332-335 (2001) glycosuite with the extension .com of the world wide web; "O-GLYCBASE version 4.0: a revised database of O-glycosylated proteins" Gupta et al. Nucleic Acids Research, 27: 370-372 (1999) and cbs with the extension .dtu.dk/databases/OGLYCBASE/ of the world wide web; "PhosphoBase, a database of phosphorylation sites: release 2.0.", Kreegipuu et al. Nucleic Acids Res 27(1):237-239 (1999) and cbs with the extension .dtu.dk/databases/PhosphoBase/ of the world wide web; or pir with the extension .georgetown.edu/pirwww/search/textresid.html of the world wide web.

Tumorigenesis is often accompanied by alterations in the post-translational modifications of proteins. Thus, in another embodiment, the invention provides polypeptides from cancerous cells or tissues that have altered post-translational modifications compared to the post-translational modifications of polypeptides from normal cells or tissues. A number of altered post-translational modifications ate known. One common alteration is a change in phosphorylation state, wherein the polypeptide from the cancerous cell or tissue is hyperphosphorylated or hypophosphorylated compared to the polypeptide from a normal tissue, or wherein the polypeptide is phosphorylated on different residues than the polypeptide from a normal cell. Another common alteration is a change in glycosylation state, wherein the polypeptide from the cancerous cell or tissue has more or less glycosylation than the polypeptide from a normal tissue, and/or wherein the polypeptide from the cancerous cell or tissue has a different type of glycosylation than the polypeptide from a noncancerous cell or tissue. Changes in glycosylation may be critical because carbohydrate-protein and carbohydrate-carbohydrate interactions are important in cancer cell progression, dissemination and invasion. See, e.g., Barchi, *Curr. Pharm. Des.* 6: 485-501 (2000), Verma, *Cancer Biochem. Biophys.* 14: 151-162 (1994) and Dennis et al., *Bioessays* 5: 412-421 (1999).

Another post-translational modification that may be altered in cancer cells is prenylation. Prenylation is the covalent attachment of a hydrophobic prenyl group (either farnesyl or geranylgeranyl) to a polypeptide. Prenylation is required for localizing a protein to a cell membrane and is often required for polypeptide function. For instance, the Ras superfamily of GTPase signaling proteins must be prenylated for function in a cell. See, e.g., Prendergast et al., *Semin. Cancer Biol.* 10: 443-452 (2000) and Khwaja et al., *Lancet* 355: 741-744 (2000).

Other post-translation modifications that may be altered in cancer cells include, without limitation, polypeptide methylation, acetylation, arginylation or racemization of amino acid residues. In these cases, the polypeptide from the cancerous cell may exhibit either increased or decreased amounts of the post-translational modification compared to the corresponding polypeptides from noncancerous cells.

Other polypeptide alterations in cancer cells include abnormal polypeptide cleavage of proteins and aberrant protein-protein interactions. Abnormal polypeptide cleavage may be cleavage of a polypeptide in a cancerous cell that does not usually occur in a normal cell, or a lack of cleavage in a cancerous cell, wherein the polypeptide is cleaved in a normal cell. Aberrant protein-protein interactions may be either covalent cross-linking or non-covalent binding between proteins that do not normally bind to each other. Alternatively, in a cancerous cell, a protein may fail to bind to another protein to which it is bound in a noncancerous cell. Alterations in cleavage or in protein-protein interactions may be due to over- or underproduction of a polypeptide in a cancerous cell compared to that in a normal cell, or may be due to alterations in post-translational modifications (see above) of one or more proteins in the cancerous cell. See, e.g., Henschen-Edman, *Ann. N.Y. Acad. Sci.* 936: 580-593 (2001).

Alterations in polypeptide post-translational modifications, as well as changes in polypeptide cleavage and protein-protein interactions, may be determined by any method known in the art. For instance, alterations in phosphorylation may be determined by using anti-phosphoserine, anti-phosphothreonine or anti-phosphotyrosine antibodies or by amino acid analysis. Glycosylation alterations may be determined using antibodies specific for different sugar residues, by carbohydrate sequencing, or by alterations in the size of the glycoprotein, which can be determined by, e.g., SDS polyacrylamide gel electrophoresis (PAGE). Other alterations of post-translational modifications, such as prenylation, racemization, methylation, acetylation and arginylation, may-be determined by chemical analysis, protein sequencing, amino acid analysis, or by using antibodies specific for the particular post-translational modifications. Changes in protein-protein interactions and in polypeptide cleavage may be analyzed by any method known in the art including, without limitation, non-denaturing PAGE (for non-covalent protein-protein interactions), SDS PAGE (for covalent protein-protein interactions and protein cleavage), chemical cleavage, protein sequencing or immunoassays.

In another embodiment, the invention provides polypeptides that have been post-translationally modified. In one embodiment, polypeptides may be modified enzymatically or chemically, by addition or removal of a post-translational modification. For example, a polypeptide may be glycosylated or deglycosylated enzymatically. Similarly, polypeptides may be phosphorylated using a purified kinase, such as a MAP kinase (e.g, p38, ERK, or JNK) or a tyrosine kinase (e.g., Src or erbB2). A polypeptide may also be modified through synthetic chemistry. Alternatively, one may isolate the polypeptide of interest from a cell or tissue that expresses the polypeptide with the desired post-translational modification. In another embodiment, a nucleic acid molecule encoding the polypeptide of interest is introduced into a host cell that is capable of post-translationally modifying the encoded polypeptide in the desired fashion. If the polypeptide does not contain a motif for a desired post-translational modification, one may alter the post-translational modification by mutating the nucleic acid sequence of a nucleic acid molecule encoding the polypeptide so that it contains a site for the desired post-translational modification. Amino acid sequences that may be post-translationally modified are known in the art. See, e.g., the programs described above on the website expasy with the extension .org of the world wide web. The nucleic acid molecule is then be introduced into a host cell that is capable of post-translationally modifying the encoded polypeptide. Similarly, one may delete sites that are post-translationally modified by either mutating the nucleic acid sequence so that the encoded polypeptide does not contain the post-translational modification motif, or by introducing the native nucleic acid molecule into a host cell that is not capable of post-translationally modifying the encoded polypeptide.

In selecting an expression control sequence, a variety of factors should also be considered. These include, for example, the relative strength of the sequence, its controllability, and its compatibility with the nucleic acid sequence of this invention, particularly with regard to potential secondary structures. Unicellular hosts should be selected by consideration of their compatibility with the chosen vector, the toxicity of the product coded for by the nucleic acid sequences of this invention, their secretion characteristics, their ability to fold the polypeptide correctly, their fermentation or culture requirements, and the ease of purification from them of the products coded for by the nucleic acid sequences of this invention.

The recombinant nucleic acid molecules and more particularly, the expression vectors of this invention may be used to express the polypeptides of this invention as recombinant polypeptides in a heterologous host cell. The polypeptides of this invention may be full-length or less than full-length polypeptide fragments recombinantly expressed from the nucleic acid sequences according to this invention. Such polypeptides include analogs, derivatives and muteins that may or may not have biological activity.

Vectors of the present invention will also often include elements that permit in vitro transcription of RNA from the inserted heterologus nucleic acid. Such vectors typically include a phage promoter, such as that from T7, T3, or SP6, flanking the nucleic acid insert. Often two different such promoters flank the inserted nucleic acid, permitting separate in vitro production of both sense and antisense strands.

Transformation and other methods of introducing nucleic acids into a host cell (e.g., conjugation, protoplast transformation or fusion, transfection, electroporation, liposome delivery, membrane fusion techniques, high velocity DNA-coated pellets, viral infection and protoplast fusion) can be accomplished by a variety of methods which are well-known in the art (See, for instance, Ausubel, supra, and Sambrook et al., supra). Bacterial, yeast, plant or mammalian cells are transformed or transfected with an expression vector, such as a plasmid, a cosmid, or the like, wherein the expression vector comprises the nucleic acid of interest. Alternatively, the cells may be infected by a viral expression vector comprising the nucleic acid of interest. Depending upon the host cell, vector, and method of transformation used, transient or stable expression of the polypeptide will be constitutive or inducible. One having ordinary skill in the art will be able to decide whether to express a polypeptide transiently or stably, and whether to express the protein constitutively or inducibly.

A wide variety of unicellular host cells are useful in expressing the DNA sequences of this invention. These hosts may include well-known euikaryotic and prokaryotic hosts, such as strains of, fungi, yeast, insect cells such as *Spodoptera frugiperda* (*SF*9), animal cells such as CHO, as well as plant cells in tissue culture. Representative examples of appropriate host cells include, but are not limited to, bacterial cells, such as *E. coli, Caulobacter crescentus,*

*Streptomyces* species, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda*, e.g., *Sf*9 and *Sf*21 cell lines, and expresSF™ cells (Protein Sciences Corp., Meriden, Conn., USA), *Drosophila* S2 cells, and *Trichoplusia ni* High Five® Cells (Invitrogen, Carlsbad, Calif., USA); and mammalian cells. Typical mammalian cells include BHK cells, BSC 1 cells, BSC 40 cells, BMT 10 cells, VERO cells, COS1 cells, COS7 cells, Chinese hamster ovary (CHO) cells, 3T3 cells, NIH 3T3 cells, 293 cells, HEPG2 cells, HeLa cells, L cells, MDCK cells, HEK293 cells, WI38 cells, murine ES cell lines (e.g., from strains 129/SV, C57/BL6, DBA-1, 129/SVJ), K562 cells, Jurkat cells, and BW5147 cells. Other mammalian cell lines are well-known and readily available from the American Type Culture Collection (ATCC) (Manassas, Va., USA) and the National Institute of General Medical Sciences (NIGMS) Human Genetic Cell Repository at the Coriell Cell Repositories (Camden, N.J., USA). Cells or cell lines derived from colon are particularly preferred because they may provide a more native post-translational processing. Particularly preferred are human colon cells.

Particular details of the transfection, expression and purification of recombinant proteins are well documented and are understood by those of skill in the art. Further details on the various technical aspects of each of the steps used in recombinant production of foreign genes in bacterial cell expression systems can be found in a number of texts and laboratory manuals in the art. See, e.g., Ausubel (1992), supra, Ausubel (1999), supra, Sambrook (1989), supra, and Sambrook (2001), supra, herein incorporated by reference.

Methods for introducing the vectors and nucleic acids of the present invention into the host cells are well-known in the art; the choice of technique will depend primarily upon the specific vector to be introduced and the host cell chosen.

Nucleic acid molecules and vectors may be introduced into prokaryotes, such as *E. coli*, in a number of ways. For instance, phage lambda vectors will typically be packaged using a packaging extract (e.g., Gigapack® packaging extract, Stratagene, La Jolla, Calif., USA), and the packaged virus used to infect *E. coli.*

Plasmid vectors will typically be introduced into chemically competent or electrocompetent bacterial cells. *E. coil* cells can be rendered chemically competent by treatment, e.g., with $CaCl_2$, or a solution of $Mg^{2+}$, $Mn^{2+}$, $Ca^{2+}$, $Rb^+$ or $K^+$, dimethyl sulfoxide, dithiothreitol, and hexamine cobalt (III), Hanahan, *J. Mol. Biol.* 166(4):557-80 (1983), and vectors introduced by heat shock. A wide variety of chemically competent strains are also available commercially (e.g., Epicurian Coli® XL10-Gold® Ultracompetent Cells (Stratagene, La Jolla, Calif., USA); DH5 competent cells (Clontech Laboratories, Palo Alto, Calif., USA); and TOP10 Chemically Competent *E. coli* Kit (Invitrogen, Carlsbad, Calif., USA)). Bacterial cells can be rendered electrocompetent, that is, competent to take up exogenous DNA by electroporation, by various prepulse treatments; vectors are introduced by electroporation followed by subsequent outgrowth in selected media. An extensive series of protocols is provided online in Electroprotocols (BioRad, Richmond, Calif., USA) (biorad with the extension .com/LifeScience/pdf/New Gene Pulser.pdf of the world wide web).

Vectors can be introduced into yeast cells by spheroplasting, treatment with lithium salts, electroporation, or protoplast fusion. Spheroplasts are prepared by the action of hydrolytic enzymes such as snail-gut extract, usually denoted Glusulase, or Zymolyase, an enzyme from *Arthrobacter luteus*, to remove portions of the cell wall in the presence of osmotic stabilizers, typically 1 M sorbitol. DNA is added to the spheroplasts, and the mixture is co-precipitated with a solution of polyethylene glycol (PEG) and $Ca^{2+}$. Subsequently, the cells are resuspended in a solution of sorbitol, mixed with molten agar and then layered on the surface of a selective plate containing sorbitol.

For lithium-mediated transformation, yeast cells are treated with lithium acetate, which apparently permeabilizes the cell wall, DNA is added and the cells are co-precipitated with PEG. The cells are exposed to a brief heat shock, washed free of PEG and lithium acetate, and subsequently spread on plates containing ordinary selective medium. Increased frequencies of transformation are obtained by using specially-prepared single-stranded carrier DNA and certain organic solvents. Schiestl et al., *Curr. Genet.* 16(5-6): 339-46 (1989).

For electroporation, freshly-grown yeast cultures are typically washed, suspended in an osmotic protectant, such as sorbitol, mixed with DNA, and the cell suspension pulsed in an electroporation device. Subsequently, the cells are spread on the surface of plates containing selective media. Becker et al., *Methods Enzymol.* 194: 182-187 (1991). The efficiency of transformation by electroporation can be increased over 100-fold by using PEG, single-stranded carrier DNA and cells that are in late log-phase of growth. Larger constructs, such as YACs, can be introduced by protoplast fusion.

Mammalian and insect cells can be directly infected by packaged viral vectors, or transfected by chemical or electrical means. For chemical transfection, DNA can be coprecipitated with $CaPO_4$ or introduced using liposomal and nonliposomal lipid-based agents. Commercial kits are available for $CaPO_4$ transfection (CalPhos™ Mammalian Transfection Kit, Clontech Laboratories, Palo Alto, Calif., USA), and lipid-mediated transfection can be practiced using commercial reagents, such as LIPOFECTAMINE™ 2000, LIPOFECTAMINE™ Reagent, CELLFECTIN® Reagent, and LIPOFECTIN® Reagent (Invitrogen, Carlsbad, Calif., USA), DOTAP Liposomal Transfection Reagent, FuGENE 6, X-tremeGENE Q2, DOSPER, (Roche Molecular Biochemicals, Indianapolis, Ind. USA), Effectene™, PolyFect®, Superfect® (Qiagen, Inc., Valencia, Calif., USA). Protocols for electroporating mammalian cells can be found online in Electroprotocols (Bio-Rad, Richmond, Calif., USA) bio-rad with the extension .com/LifeScience/pdf/New Gene Pulser.pdf of the world wide web); Norton et al. (eds.), *Gene Transfer Methods: Introducing DNA into Living Cells and Organisms*, BioTechniques Books, Eaton Publishing Co. (2000); incorporated herein by reference in its entirety. Other transfection techniques include transfection by particle bombardment and microinjection. See, e.g., Cheng et al., *Proc. Natl. Acad. Sci. USA* 90(10): 4455-9 (1993); Yang et al., *Proc. Natl. Acad. Sci. USA* 87(24): 9568-72 (1990).

Production of the recombinantly produced proteins of the present invention can optionally be followed by purification.

Purification of recombinantly expressed proteins is now well by those skilled in the art. See, e.g., Thorner et al. (eds.), *Applications of Chimeric Genes and Hybrid Proteins, Part A: Gene Expression and Protein Purification* (Methods in Enzymology, Vol. 326), Academic Press (2000); Harbin (ed.), *Cloning, Gene Expression and Protein Purification: Experimental Procedures and Process Rationale*, Oxford Univ. Press (2001); Marshak et al., *Strategies for Protein Purification and Characterization: A Laboratory Course Manual*, Cold Spring Harbor Laboratory Press (1996); and Roe (ed.), *Protein Purification Applications*, Oxford University Press (2001); the disclosures of which are incorporated herein by reference in their entireties, and thus need not be detailed here.

Briefly, however, if purification tags have been fused through use of an expression vector that appends such tags, purification can be effected, at least in part, by means appropriate to the tag, such as use of immobilized metal affinity chromatography for polyhistidine tags. Other techniques common in the art include ammonium sulfate fractionation, immunoprecipitation, fast protein liquid chromatography (FPLC), high performance liquid chromatography (HPLC), and preparative gel electrophoresis.

Polypeptides

Another object of the invention is to provide polypeptides encoded by the nucleic acid molecules of the instant invention. In a preferred embodiment, the polypeptide is a colon specific polypeptide (CSP). In an even more preferred embodiment, the polypeptide is derived from a polypeptide comprising the amino acid sequence of SEQ ID NO: 148 through 250. A polypeptide as defined herein may be produced recombinantly, as discussed supra, may be isolated from a cell that naturally expresses the protein, or may be chemically synthesized following the teachings of the specification and using methods well-known to those having ordinary skill in the art.

In another aspect, the polypeptide may comprise a fragment of a polypeptide, wherein the fragment is as defined herein. In a preferred embodiment, the polypeptide fragment is a fragment of a CSP. In a more preferred embodiment, the fragment is derived from a polypeptide comprising the amino acid sequence of SEQ ID NO: 148 through 250. A polypeptide that comprises only a fragment of an entire CSP may or may not be a polypeptide that is also a CSP. For instance, a full-length polypeptide may be colon-specific, while a fragment thereof may be found in other tissues as well as in colon. A polypeptide that is not a CSP, whether it is a fragment, analog, mutein, homologous protein or derivative, is nevertheless useful, especially for immunizing animals to prepare anti-CSP antibodies. However, in a preferred embodiment, the part or fragment is a CSP. Methods of determining whether a polypeptide is a CSP are described infra.

Fragments of at least 6 contiguous amino acids are useful in mapping B cell and T cell epitopes of the reference protein. See, e.g., Geysen et al., *Proc. Natl. Acad. Sci. USA* 81: 3998-4002 (1984) and U.S. Pat. Nos. 4,708,871 and 5,595,915, the disclosures of which are incorporated herein by reference in their entireties. Because the fragment need not itself be immunogenic, part of an immunodominant epitope, nor even recognized by native antibody, to be useful in such epitope mapping, all fragments of at least 6 amino acids of the proteins of the present invention have utility in such a study.

Fragments of at least 8 contiguous amino acids, often at least 15 contiguous amino acids, are useful as immunogens for raising antibodies that recognize the proteins of the present invention. See, e.g., Lerner, Nature 299: 592-596 (1982); Shinnick et al., *Annu. Rev. Microbiol.* 37: 425-46 (1983); Sutcliffe et al., *Science* 219: 660-6 (1983), the disclosures of which are incorporated herein by reference in their entireties. As further described in the above-cited references, virtually all 8-mers, conjugated to a carrier, such as a protein, prove immunogenic, meaning that they are capable of eliciting antibody for the conjugated peptide; accordingly, all fragments of at least 8 amino acids of the proteins of the present invention have utility as inmmunogens.

Fragments of at least 8, 9, 10 or 12 contiguous amino acids are also useful as competitive inhibitors of binding of the entire protein, or a portion thereof, to antibodies (as in epitope mapping), and to natural binding partners, such as subunits in a multimeric complex or to receptors or ligands of the subject protein; this competitive inhibition permits identification and separation of molecules that bind specifically to the protein of interest, U.S. Pat. Nos. 5,539,084 and 5,783,674, incorporated herein by reference in their entireties.

The protein, or protein fragment, of the present invention is thus at least 6 amino acids in length, typically at least 8, 9, 10 or 12 amino acids in length, and often at least 15 amino acids in length. Often, the protein of the present invention, or fragment thereof, is at least 20 amino acids in length, even 25 amino acids, 30 amino acids, 35 amino acids, or 50 amino acids or more in length. Of course, larger fragments having at least 75 amino acids, 100 amino acids, or even 150 amino acids are also useful, and at times preferred.

One having ordinary skill in the art can produce fragments of a polypeptide by truncating the nucleic acid molecule, e.g., a CSNA, encoding the polypeptide and then expressing it recombinantly. Alternatively, one can produce a fragment by chemically synthesizing a portion of the full-length polypeptide. One may also produce a fragment by enzymatically cleaving either a recombinant polypeptide or an isolated naturally-occurring polypeptide. Methods of producing polypeptide fragments are well-known in the art. See, e.g., Sambrook (1989), supra; Sambrook (2001), supra; Ausubel (1992), supra; and Ausubel (1999), supra. In one embodiment, a polypeptide comprising only a fragment of polypeptide of the invention, preferably a CSP, may be produced by chemical or enzymatic cleavage of a polypeptide. In a preferred embodiment, a polypeptide fragment is produced by expressing a nucleic acid molecule encoding a fragment of the polypeptide, preferably a CSP, in a host cell.

By "polypeptides" as used herein it is also meant to be inclusive of mutants, fusion proteins, homologous proteins and allelic variants of the polypeptides specifically exemplified.

A mutant protein, or mutein, may have the same or different properties compared to a naturally-occurring polypeptide and comprises at least one amino acid insertion, duplication, deletion, rearrangement or substitution compared to the amino acid sequence of a native protein. Small deletions and insertions can often be found that do not alter the function of the protein. In one embodiment, the mutein may or may not be colon-specific. In a preferred embodiment, the mutein is colon-specific. In a preferred embodiment, the mutein is a polypeptide that comprises at least one amino acid insertion, duplication, deletion, rearrangement or substitution compared to the amino acid sequence of SEQ ID NO: 148 through 250. In a more preferred embodiment, the mutein is one that exhibits at least 50% sequence identity, more preferably at least 60% sequence identity, even more preferably at least 70%, yet more preferably at least 80% sequence identity to a CSP comprising an amino acid sequence of SEQ ID NO: 148 through 250. In yet a more preferred embodiment, the mutein exhibits at least 85%, more preferably 90%, even more preferably 95% or 96%, and yet more preferably at least 97%, 98%, 99% or 99.5% sequence identity to a CSP comprising an amino acid sequence of SEQ ID NO: 148 through 250.

A mutein may be produced by isolation from a naturally-occurring mutant cell, tissue or organism. A mutein may be produced by isolation from a cell, tissue or organism that has been experimentally mutagenized. Alternatively, a mutein may be produced by chemical manipulation of a polypeptide, such as by altering the amino acid residue to another amino acid residue using synthetic or semi-synthetic chemical techniques. In a preferred embodiment, a mutein may be produced from a host cell comprising an altered nucleic acid molecule compared to the naturally-occurring nucleic acid molecule. For instance, one may produce a mutein of a polypeptide by introducing one or more mutations into a nucleic acid sequence of the invention and then expressing it recombinantly. These mutations may be targeted, in which particular encoded amino acids are altered, or may be untargeted, in which random encoded amino acids within the polypeptide are altered. Muteins with random amino acid alterations can be screened for a particular biological activity or property, particularly whether the polypeptide is colon-specific, as described below. Multiple random mutations can be introduced into the gene by methods well-known to the art, e.g., by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis and site-specific mutagenesis. Methods of producing muteins with targeted or random amino acid alterations are well-known in the art. See, e.g., Sambrook (1989), supra; Sambrook (2001), supra; Ausubel (1992), supra; and Ausubel (1999), U.S. Pat. No. 5,223,408, and the references discussed supra, each herein incorporated by reference.

By "polypeptide" as used herein it is also meant to be inclusive of polypeptides homologous to those polypeptides exemplified herein. In a preferred embodiment, the polypeptide is homologous to a CSP. In an even more preferred embodiment, the polypeptide is homologous to a CSP selected from the group having an amino acid sequence of SEQ ID NO: 148 through 250. In a preferred embodiment, the homologous polypeptide is one that exhibits significant sequence identity to a CSP. In a more preferred embodiment, the polypeptide is one that exhibits significant sequence identity to an comprising an amino acid sequence of SEQ ID NO: 148 through 250. In an even more preferred embodiment, the homologous polypeptide is one that exhibits at least 50% sequence identity, more preferably at least 60% sequence identity, even more preferably at least 70%, yet more preferably at least 80% sequence identity to a CSP comprising an amino acid sequence of SEQ ID NO: 148 through 250. In a yet more preferred embodiment, the homologous polypeptide is one that exhibits at least 85%, more preferably 90%, even more preferably 95% or 96%, and yet more preferably at least 97% or 98% sequence identity to a CSP comprising an amino acid sequence of SEQ ID NO: 148 through 250. In another preferred embodiment, the homologous polypeptide is one that exhibits at least 99%, more preferably 99.5%, even more preferably 99.6%, 99.7%, 99.8% or 99.9% sequence identity to a CSP comprising an amino acid sequence of SEQ ID NO: 148 through 250. In a preferred embodiment, the amino acid substitutions are conservative amino acid substitutions as discussed above.

In another embodiment, the homologous polypeptide is one that is encoded by a nucleic acid molecule that selectively hybridizes to a CSNA. In a preferred embodiment, the homologous polypeptide is encoded by a nucleic acid molecule that hybridizes to a CSNA under low stringency, moderate stringency or high stringency conditions, as defined herein. In a more preferred embodiment, the CSNA is selected from the group consisting of SEQ ID NO: 1 through 147. In another preferred embodiment, the homologous polypeptide is encoded by a nucleic acid molecule that hybridizes to a nucleic acid molecule that encodes a CSP under low stringency, moderate stringency or high stringency conditions, as defined herein. In a more preferred embodiment, the CSP is selected from the group consisting of SEQ ID NO: 148 through 250.

The homologous polypeptide may be a naturally-occurring one that is derived from another species, especially one derived from another primate, such as chimpanzee, gorilla, rhesus macaque, baboon or gorilla, wherein the homologous polypeptide comprises an amino acid sequence that exhibits significant sequence identity to that of SEQ ID NO: 148 through 250. The homologous polypeptide may also be a naturally-occurring polypeptide from a human, when the CSP is a member of a family of polypeptides. The homologous polypeptide may also be a naturally-occurring polypeptide derived from a non-primate, mammalian species, including without limitation, domesticated species, e.g., dog, cat, mouse, rat, rabbit, guinea pig, hamster, cow, horse, goat or pig. The homologous polypeptide may also be a naturally-occurring polypeptide derived from a non-mammalian species, such as birds or reptiles. The naturally-occurring homologous protein may be isolated directly from humans or other species. Alternatively, the nucleic acid molecule encoding the naturally-occurring homologous polypeptide may be isolated and used to express the homologous polypeptide recombinantly. In another embodiment, the homologous polypeptide may be one that is experimentally produced by random mutation of a nucleic acid molecule and subsequent expression of the nucleic acid molecule. In another embodiment, the homologous polypeptide may be one that is experimentally produced by directed mutation of one or more codons to alter the encoded amino acid of a CSP. Further, the homologous protein may or may not encode polypeptide that is a CSP. However, in a preferred embodiment, the homologous polypeptide encodes a polypeptide that is a CSP.

Relatedness of proteins can also be characterized using a second functional test, the ability of a first protein competitively to inhibit the binding of a second protein to an antibody. It is, therefore, another aspect of the present invention to provide isolated proteins not only identical in sequence to those described with particularity herein, but also to provide isolated proteins ("cross-reactive proteins") that competitively inhibit the binding of antibodies to all or to a portion of various of the isolated polypeptides of the present invention. Such competitive inhibition can readily be determined using immunoassays well-known in the art.

As discussed above, single nucleotide polymorphisms (SNPs) occur frequently in eukaryotic genomes, and the sequence determined from one individual of a species may differ from other allelic forms present within the population. Thus, by "polypeptide" as used herein it is also meant to be inclusive of polypeptides encoded by an allelic variant of a nucleic acid molecule encoding a CSP. In a preferred embodiment, the polypeptide is encoded by an allelic variant of a gene that encodes a polypeptide having the amino acid sequence selected from the group consisting of SEQ ID NO: 148 through 250. In a yet more preferred embodiment, the polypeptide is encoded by an allelic variant of a gene that has the nucleic acid sequence selected from the group consisting of SEQ ID NO: 1 through 147.

In another embodiment, the invention provides polypeptides which comprise derivatives of a polypeptide encoded by a nucleic acid molecule according to the instant invention. In a preferred embodiment, the polypeptide is a CSP. In a preferred embodiment, the polypeptide has an amino acid sequence selected from the group consisting of SEQ ID NO: 148 through 250, or is a mutein, allelic variant, homologous protein or fragment thereof. In a preferred embodiment, the derivative has been acetylated, carboxylated, phosphorylated, glycosylated or ubiquitinated. In another preferred embodiment, the derivative has been labeled with, e.g., radioactive isotopes such as $^{1251}$I, $^{32}$P, $^{35}$S, and $^{3}$H. In another preferred embodiment, the derivative has been labeled with fluorophores, chemiluminescent agents, enzymes, and antiligands that can serve as specific binding pair members for a labeled ligand.

Polypeptide modifications are well-known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance Creighton, *Protein Structure and Molecular Properties,* 2nd ed., W. H. Freeman and Company (1993). Many detailed reviews are available on this subject, such as, for example, those provided by Wold, in Johnson (ed.), *Posttranslational Covalent Modification of Proteins*, pgs. 1-12, Academic Press (1983); Seifter et al., *Meth. Enzymol.* 182: 626-646 (1990) and Rattan et al., *Ann. N.Y. Acad. Sci.* 663: 48-62 (1992).

It will be appreciated, as is well-known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

Useful post-synthetic (and post-translational) modifications include conjugation to detectable labels, such as fluorophores. A wide variety of amine-reactive and thiol-reactive fluorophore derivatives have been synthesized that react under nondenaturing conditions with N-terminal amino groups and epsilon amino groups of lysine residues, on the one hand, and with free thiol groups of cysteine residues, on the other.

Kits are available commercially that permit conjugation of proteins to a variety of amine-reactive or thiol-reactive fluorophores: Molecular Probes, Inc. (Eugene, Oreg., USA), e.g., offers kits for conjugating proteins to Alexa Fluor 350, Alexa Fluor 430, Fluorescein-EX, Alexa Fluor 488, Oregon Green 488, Alexa Fluor 532, Alexa Fluor 546, Alexa Fluor 546, Alexa Fluor 568, Alexa Fluor 594, and Texas Red-X.

A wide variety of other amine-reactive and thiol-reactive fluorophores are available commercially (Molecular Probes, Inc., Eugene, Oreg., USA), including Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA).

The polypeptides of the present invention can also be conjugated to fluorophores, other proteins, and other macromolecules, using bifunctional linking reagents. Common homobifunctional reagents include, e.g., APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS (all available from Pierce, Rockford, Ill., USA); common heterobifuntional cross-linkers include ABH, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, M2C2H, MPBH, MSA, NHS-ASA, PDPH, PMPI, SADP, SAED, SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS, Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS (all available Pierce, Rockford, Ill., USA).

The polypeptides, fragments, and fusion proteins of the present invention can be conjugated, using such cross-linking reagents, to fluorophores that are not amine- or thiol-reactive. Other labels that usefully can be conjugated to the polypeptides, fragments, and fusion proteins of the present invention include radioactive labels, echosonographic contrast reagents, and MRI contrast agents.

The polypeptides, fragments, and fusion proteins of the present invention can also usefully be conjugated using cross-linking agents to carrier proteins, such as KLH, bovine thyroglobulin, and even bovine serum albumin (BSA), to increase immunogenicity for raising anti-CSP antibodies.

The polypeptides, fragments, and fusion proteins of the present invention can also usefully be conjugated to polyethylene glycol (PEG); PEGylation increases the serum half-life of proteins administered intravenously for replacement therapy. Delgado et al., *Crit. Rev. Ther. Drug Carrier Syst.* 9(3-4): 249-304 (1992); Scott et al., *Curr. Pharm. Des.* 4(6): 423-38 (1998); DeSantis et al., *Curr. Opin. Biotechnol.* 10(4): 324-30 (1999), incorporated herein by reference in their entireties. PEG monomers can be attached to the protein directly or through a linker, with PEGylation using PEG monomers activated with tresyl chloride (2,2,2-trifluoroethanesulphonyl chloride) permitting direct attachment under mild conditions.

In yet another embodiment, the invention provides analogs of a polypeptide encoded by a nucleic acid molecule according to the instant invention. In a preferred embodiment, the polypeptide is a CSP. In a more preferred embodiment, the analog is derived from a polypeptide having part or all of the amino acid sequence of SEQ ID NO: 148 through 250. In a preferred embodiment, the analog is one that comprises one or more substitutions of non-natural amino acids or non-native inter-residue bonds compared to the naturally-occurring polypeptide. In general, the non-peptide analog is structurally similar to a CSP, but one or more peptide linkages is replaced by a linkage selected from the group consisting of —$CH_2NH$—, —$CH_2S$—, —$CH_2$—$CH_2$—, —CH=CH— (cis and trans), —$COCH_2$—, —CH(OH)$CH_2$— and —$CH_2SO$—. In another embodiment, the non-peptide analog comprises substitution of one or more amino acids of a CSP with a D-amino acid of the same type or other non-natural amino acid in order to generate more stable peptides. D-amino acids can readily be incorporated during chemical peptide synthesis: peptides assembled from D-amino acids are more resistant to proteolytic attack; incorporation of D-amino acids can also be used to confer specific three-dimensional conformations on the peptide. Other amino acid analogues commonly added during chemical synthesis include ornithine, norleucine, phosphorylated amino acids (typically phosphoserine, phosphothreonine, phosphotyrosine), L-malonyltyrosine, a non-hydrolyzable analog of phosphotyrosine (see, e.g., Kole et al., *Biochem. Biophys. Res. Com.* 209: 817-821 (1995)), and various halogenated phenylalanine derivatives.

Non-natural amino acids can be incorporated during solid phase chemical synthesis or by recombinant techniques, although the former is typically more common. Solid phase chemical synthesis of peptides is well established in the art. Procedures are described, inter alia, in Chan et al. (eds.), *Fmoc Solid Phase Peptide Synthesis: A Practical Approach* (Practical Approach Series), Oxford Univ. Press (March 2000); Jones, *Amino Acid and Peptide Synthesis* (Oxford Chemistry Primers, No 7), Oxford Univ. Press (1992); and Bodanszky, *Principles of Peptide Synthesis* (Springer Laboratory), Springer Verlag (1993); the disclosures of which are incorporated herein by reference in their entireties.

Amino acid analogues having detectable labels are also usefully incorporated during synthesis to provide derivatives and analogs. Biotin, for example can be added using biotinoyl-(9-fluorenylmethoxycarbonyl)-L-lysine (FMOC biocytin) (Molecular Probes, Eugene, Oreg., USA). Biotin can also be added enzymatically by incorporation into a fusion protein of a *E. coli* BirA substrate peptide. The FMOC and tBOC derivatives of dabcyl-L-lysine (Molecular Probes, Inc., Eugene, Oreg., USA) can be used to incorporate the dabcyl chromophore at selected sites in the peptide sequence during synthesis. The aminonaphthalene derivative EDANS, the most common fluorophore for pairing with the dabcyl quencher in fluorescence resonance energy transfer (FRET) systems, can be introduced during automated synthesis of peptides by using EDANS-FMOC-L-glutamic acid or the corresponding tBOC derivative (both from Molecular Probes, Inc., Eugene, Oreg., USA). Tetramethylrhodamine fluorophores can be incorporated during automated FMOC synthesis of peptides using (FMOC)-TMR-L-lysine (Molecular Probes, Inc. Eugene, Oreg., USA).

Other useful amino acid analogues that can be incorporated during chemical synthesis include aspartic acid, glutamic acid, lysine, and tyrosine analogues having allyl side-chain protection (Applied Biosystems, Inc., Foster City, Calif., USA); the allyl side chain permits synthesis of cyclic, branched-chain, sulfonated, glycosylated, and phosphorylated peptides.

A large number of other FMOC-protected non-natural amino acid analogues capable of incorporation during chemical synthesis are available commercially, including, e.g., Fmoc-2-aminobicyclo[2.2.1]heptane-2-carboxylic acid, Fmoc-3-endo-aminobicyclo[2.2.1]heptane-2-endo-carboxylic acid, Fmoc-3-exo-aminobicyclo[2.2.1]heptane-2-exo-carboxylic acid, Fmoc-3-endo-amino-bicyclo[2.2.1]hept-5-ene-2-endo-carboxylic acid, Fmoc-3-exo-amino-bicyclo[2.2.1]hept-5-ene-2-exo-carboxylic acid, Fmoc-cis-2-amino-1-cyclohexanecarboxylic acid, Fmoc-trans-2-amino-1-cyclohexanecarboxylic acid, Fmoc-1-amino-1-cyclopentanecarboxylic acid, Fmoc-cis-2-amino-1-cyclopentanecarboxylic acid, Fmoc-1-amino-1-cyclopropanecarboxylic acid, Fmoc-D-2-amino-4-(ethylthio)butyric acid, Fmoc-L-2-amino-4-(ethylthio)butyric acid, Fmoc-L-buthionine, Fmoc-S-methyl-L-Cysteine, Fmoc-2-aminobenzoic acid (anthranillic acid), Fmoc-3-aminobenzoic acid, Fmoc-4-aminobenzoic acid, Fmoc-2-aminobenzophenone-2'-carboxylic acid, Fmoc-N-(4-aminobenzoyl)-β-alanine, Fmoc-2-amino-4,5-dimethoxybenzoic acid, Fmoc-4-aminohippuric acid, Fmoc-2-amino-3-hydroxybenzoic acid, Fmoc-2-amino-5-hydroxybenzoic acid, Fmoc-3-amino-4-hydroxybenzoic acid, Fmoc-4-amino-3-hydroxybenzoic acid, Fmoc-4-amino-2-hydroxybenzoic acid, Fmoc-5-amino-2-hydroxybenzoic acid, Fmoc-2-amino-3-methoxybenzoic acid, Fmoc-4-amino-3-methoxybenzoic acid, Fmoc-2-amino-3-methylbenzoic acid, Fmoc-2-amino-5-methylbenzoic acid, Fmoc-2-amino-6-methylbenzoic acid, Fmoc-3-amino-2-methylbenzoic acid, Fmoc-3-amino-4-methylbenzoic acid, Fmoc-4-amino-3-methylbenzoic acid, Fmoc-3-amino-2-naphtoic acid, Fmoc-D,L-3-amino-3-phenylpropionic acid, Fmoc-L-Methyldopa, Fmoc-2-amino-4,6-dimethyl-3-pyridinecarboxylic acid, Fmoc-D,L-amino-2-thiophenacetic acid, Fmoc-4-(carboxymethyl)piperazine, Fmoc-4-carboxypiperazine, Fmoc-4-(carboxymethyl)homopiperazine, Fmoc-4-phenyl-4-piperidinecarboxylic acid, Fmoc-L-1,2,3,4-tetrahydronorharman-3-carboxylic acid, Fmoc-L-thiazolidine-4-carboxylic acid, all available from The Peptide Laboratory (Richmond, Calif., USA).

Non-natural residues can also be added biosynthetically by engineering a suppressor tRNA, typically one that recognizes the UAG stop codon, by chemical aminoacylation with the desired unnatural amino acid. Conventional site-directed mutagenesis is used to introduce the chosen stop codon UAG at the site of interest in the protein gene. When the acylated suppressor tRNA and the mutant gene are combined in an in vitro transcription/translation system, the unnatural amino acid is incorporated in response to the UAG codon to give a protein containing that amino acid at the specified position. Liu et al., *Proc. Natl Acad. Sci. USA* 96(9): 4780-5 (1999); Wang et al., *Science* 292(5516): 498-500 (2001).

Fusion Proteins

The present invention further provides fusions of each of the polypeptides and fragments of the present invention to heterologous polypeptides. In a preferred embodiment, the polypeptide is a CSP. In a more preferred embodiment, the polypeptide that is fused to the heterologous polypeptide comprises part or all of the amino acid sequence of SEQ ID NO: 148 through 250, or is a mutein, homologous polypeptide, analog or derivative thereof. In an even more preferred embodiment, the nucleic acid molecule encoding the fusion protein comprises all or part of the nucleic acid sequence of SEQ ID NO: 1 through 147, or comprises all or part of a nucleic acid sequence that selectively hybridizes or is homologous to a nucleic acid molecule comprising a nucleic acid sequence of SEQ ID NO: 1 through 147.

The fusion proteins of the present invention will include at least one fragment of the protein of the present invention, which fragment is at least 6, typically at least 8, often at least 15, and usefully at least 16, 17, 18, 19, or 20 amino acids long. The fragment of the protein of the present to be included in the fusion can usefully be at least 25 amino acids long, at least 50 amino acids long, and can be at least 75, 100, or even 150 amino acids long. Fusions that include the entirety of the proteins of the present invention have particular utility.

The heterologous polypeptide included within the fusion protein of the present invention is at least 6 amino acids in length, often at least 8 amino acids in length, and usefully at least 15, 20, and 25 amino acids in length. Fusions that include larger polypeptides, such as the IgG Fc region, and even entire proteins (such as GFP chromophore-containing proteins) are particular useful.

As described above in the description of vectors and expression vectors of the present invention, which discussion is incorporated here by reference in its entirety, heterologous polypeptides to be included in the fusion proteins of the present invention can usefully include those designed to facilitate purification and/or visualization of recombinantly-expressed proteins. See, e.g., Ausubel, Chapter 16, (1992), supra. Although purification tags can also be incorporated into fusions that are chemically synthesized, chemical synthesis typically provides sufficient purity that further purification by HPLC suffices; however, visualization tags as above described retain their utility even when the protein is produced by chemical synthesis, and when so included render the fusion proteins of the present invention useful as directly detectable markers of the presence of a polypeptide of the invention.

As also discussed above, heterologous polypeptides to be included in the fusion proteins of the present invention can usefully include those that facilitate secretion of recombinantly expressed proteins—into the periplasmic space or extracellular milieu for prokaryotic hosts, into the culture medium for eukaryotic cells—through incorporation of secretion signals and/or leader sequences. For example, a $His_6$ tagged protein can be purified on a Ni affinity column and a GST fusion protein can be purified on a glutathione affinity column. Similarly, a fusion protein comprising the Fc domain of IgG can be purified on a Protein A or Protein G column and a fusion protein comprising an epitope tag such as myc can be purified using an immunoaffinity column containing an anti-c-myc antibody. It is preferable that the epitope tag be separated from the protein encoded by the essential gene by an enzymatic cleavage site that can be cleaved after purification. See also the discussion of nucleic acid molecules encoding fusion proteins that may be expressed on the surface of a cell.

Other useful protein fusions of the present invention include those that permit use of the protein of the present invention as bait in a yeast two-hybrid system. See Bartel et al. (eds.), *The Yeast Two-Hybrid System*, Oxford University Press (1997); Zhu et al., *Yeast Hybrid Technologies*, Eaton Publishing (2000); Fields et al., *Trends Genet.* 10(8): 286-92 (1994); Mendelsohn et al., *Curr. Opin. Biotechnol.* 5(5): 482-6 (1994); Luban et al., *Curr. Opin. Biotechnol.* 6(1): 59-64 (1995); Allen et al., *Trends Biochem. Sci.* 20(12): 511-6 (1995); Drees, *Curr. Opin. Chem. Biol.* 3(1): 64-70 (1999); Topcu et al., *Pharm. Res.* 17(9): 1049-55 (2000); Fashena et al., *Gene* 250(1-2): 1-14 (2000);; Colas et al., (1996) Genetic selection of peptide aptamers that recognize and inhibit cyclin-dependent kinase 2. *Nature* 380, 548-550; Norman, T. et al., (1999) Genetic selection of peptide inhibitors of biological pathways. *Science* 285, 591-595, Fabbrizio et al., (1999) Inhibition of mammalian cell proliferation by genetically selected peptide aptamers that functionally antagonize E2F activity. *Oncogene* 18, 4357-4363; Xu et al., (1997) Cells that register logical relationships among proteins. *Proc Natl Acad Sci USA*. 94, 12473-12478; Yang, et al., (1995) Protein-peptide interactions analyzed with the yeast two-hybrid system. *Nuc. Acids Res.* 23, 1152-1156; Kolonin et al., (1998) Targeting cyclin-dependent kinases in *Drosophila* with peptide aptamers. *Proc Natl Acad Sci USA* 95, 14266-14271; Cohen et al., (1998) An artificial cell-cycle inhibitor isolated from a combinatorial library. *Proc Natl Acad Sci USA* 95, 14272-14277; Uetz, P.; Giot, L.; al, e.; Fields, S.; Rothberg, J. M. (2000) A comprehensive analysis of protein-protein interactions in *Saccharomyces cerevisiae*. *Nature* 403, 623-627; Ito, et al., (2001) A comprehensive two-hybrid analysis to explore the yeast protein interactome. *Proc Natl Acad Sci USA* 98, 4569-4574, the disclosures of which are incorporated herein by reference in their entireties. Typically, such fusion is to either *E. coli* LexA or yeast GAL4 DNA binding domains. Related bait plasmids are available that express the bait fused to a nuclear localization signal.

Other useful fusion proteins include those that permit display of the encoded protein on the surface of a phage or cell, fusions to intrinsically fluorescent proteins, such as green fluorescent protein (GFP), and fusions to the IgG Fc region, as described above, which discussion is incorporated here by reference in its entirety.

The polypeptides and fragments of the present invention can also usefully be fused to protein toxins, such as *Pseudomonas* exotoxin A, *diphtheria* toxin, *shiga* toxin A, *anthrax* toxin lethal factor, ricin, in order to effect ablation of cells that bind or take up the proteins of the present invention.

Fusion partners include, inter alia, myc, hemagglutinin (HA), GST, inmmunoglobulins, β-galactosidase, biotin trpE, protein A, β-lactamase, -amylase, maltose binding protein, alcohol dehydrogenase, polyhistidine (for example, six histidine at the amino and/or carboxyl terminus of the polypeptide), lacZ, green fluorescent protein (GFP), yeast_mating factor, GAL4 transcription activation or DNA binding domain, luciferase, and serum proteins such as ovalbumin, albumin and the constant domain of IgG. See, e.g., Ausubel (1992), supra and Ausubel (1999), supra. Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques well-known in the art (e.g., a Merrifield synthesis), or produced by chemical cross-linking.

Another advantage of fusion proteins is that the epitope tag can be used to bind the fusion protein to a plate or column through an affinity linkage for screening binding proteins or other molecules that bind to the CSP.

As further described below, the isolated polypeptides, muteins, fusion proteins, homologous proteins or allelic variants of the present invention can readily be used as specific immunogens to raise antibodies that specifically recognize CSPs, their allelic variants and homologues. The antibodies, in turn, can be used, inter alia, specifically to assay for the polypeptides of the present invention, particularly CSPs, e.g. by ELISA for detection of protein fluid samples, such as serum, by immunohistochemistry or laser scanning cytometry, for detection of protein in tissue samples, or by flow cytometry, for detection of intracellular protein in cell suspensions, for specific antibody-mediated isolation and/or purification of CSPs, as for example by immunoprecipitation, and for use as specific agonists or antagonists of CSPs.

One may determine whether polypeptides including muteins, fusion proteins, homologous proteins or allelic variants are functional by methods known in the art. For instance, residues that are tolerant of change while retaining function can be identified by altering the protein at known residues using methods known in the art, such as alanine scanning mutagenesis, Cunningham et al., *Science* 244 (4908): 1081-5 (1989); transposon linker scanning mutagenesis, Chen et al., *Gene* 263(1-2): 39-48 (2001); combinations of homolog- and alanine-scarming mutagenesis, Jin et al., *J. Mol. Biol.* 226(3): 851-65 (1992); combinatorial alanine scanning, Weiss et al., *Proc. Natl. Acad. Sci USA* 97(16): 8950-4 (2000), followed by functional assay. Transposon linker scanning kits are available commercially (New England Biolabs, Beverly, Mass., USA, catalog. no. E7-102S; EZ::TN™ In-Frame Linker Insertion Kit, catalogue no. EZI04KN, Epicentre Technologies Corporation, Madison Wis., USA).

Purification of the polypeptides including fragments, homologous polypeptides, muteins, analogs, derivatives and fusion proteins is well-known and within the skill of one having ordinary skill in the art. See, e.g., Scopes, *Protein Purification,* 2d ed. (1987). Purification of recombinantly expressed polypeptides is described above. Purification of chemically-synthesized peptides can readily be effected, e.g., by HPLC.

Accordingly, it is an aspect of the present invention to provide the isolated proteins of the present invention in pure or substantially pure form in the presence of absence of a stabilizing agent. Stabilizing agents include both proteinaceous or non-proteinaceous material and are well-known in the art. Stabilizing agents, such as albumin and polyethylene glycol (PEG) are known and are commercially available.

Although high levels of purity are preferred when the isolated proteins of the present invention are used as therapeutic agents, such as in vaccines and as replacement therapy, the isolated proteins of the present invention are also useful at lower purity. For example, partially purified proteins of the present invention can be used as immunogens to raise antibodies in laboratory animals.

In preferred embodiments, the purified and substantially purified proteins of the present invention are in compositions that lack detectable am pholytes, acrylamide monomers, bis-acrylamide monomers, and polyacrylamide.

The polypeptides, fragments, analogs, derivatives and fusions of the present invention can usefully be attached to a substrate. The substrate can be porous or solid, planar or non-planar; the bond can be covalent or noncovalent.

For example, the polypeptides, fragments, analogs, derivatives and fusions of the present invention can usefully be bound to a porous substrate, commonly a membrane, typically comprising nitrocellulose, polyvinylidene fluoride (PVDF), or cationically derivatized, hydrophilic PVDF; so bound, the proteins, fragments, and fusions of the present invention can be used to detect and quantify antibodies, e.g. in serum, that bind specifically to the immobilized protein of the present invention.

As another example, the polypeptides, fragments, analogs, derivatives and fusions of the present invention can usefully be bound to a substantially nonporous substrate, such as plastic, to detect and quantify antibodies, e.g. in serum, that bind specifically to the immobilized protein of the present invention. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof; when the assay is performed in a standard microtiter dish, the plastic is typically polystyrene.

The polypeptides, fragments, analogs, derivatives and fusions of the present invention can also be attached to a substrate suitable for use as a surface enhanced laser desorption ionization source; so attached, the protein, fragment, or fusion of the present invention is useful for binding and then detecting secondary proteins that bind with sufficient affinity or avidity to the surface-bound protein to indicate biologic interaction there between. The proteins, fragments, and fusions of the present invention can also be attached to a substrate suitable for use in surface plasmon resonance detection; so attached, the protein, fragment, or fusion of the present invention is useful for binding and then detecting secondary proteins that bind with sufficient affinity or avidity to the surface-bound protein to indicate biological interaction there between.

Antibodies

In another aspect, the invention provides antibodies, including fragments and derivatives thereof, that bind specifically to polypeptides encoded by the nucleic acid molecules of the invention, as well as antibodies that bind to fragments, muteins, derivatives and analogs of the polypeptides. In a preferred embodiment, the antibodies are specific for a polypeptide that is a CSP, or a fragment, mutein, derivative, analog or fusion protein thereof. In a more preferred embodiment, the antibodies are specific for a polypeptide that comprises SEQ ID NO: 148 through 250, or a fragment, mutein, derivative, analog or fusion protein thereof.

The antibodies of the present invention can be specific for linear epitopes, discontinuous epitopes, or conformational epitopes of such proteins or protein fragments, either as present on the protein in its native conformation or, in some cases, as present on the proteins as denatured, as, e.g., by solubilization in SDS. New epitopes may be also due to a difference in post translational modifications (PTMs) in disease versus normal tissue. For example, a particular site on a CSP may be glycosylated in cancerous cells, but not glycosylated in normal cells or visa versa. In addition, alternative splice forms of a CSP may be indicative of cancer. Differential degradation of the C or N-terminus of a CSP may also be a marker or target for anticancer therapy. For example, a CSP may be N-terminal degraded in cancer cells exposing new epitopes to which antibodies may selectively bind for diagnostic or therapeutic uses.

As is well-known in the art, the degree to which an antibody can discriminate as among molecular species in a mixture will depend, in part, upon the conformational relatedness of the species in the mixture; typically, the antibodies of the present invention will discriminate over adventitious binding to non-CSP polypeptides by at least 2-fold, more typically by at least 5-fold, typically by more than 10-fold, 25-fold, 50-fold, 75-fold, and often by more than 100-fold, and on occasion by more than 500-fold or 1000-fold. When used to detect the proteins or protein fragments of the present invention, the antibody of the present invention is sufficiently specific when it can be used to determine the presence of the protein of the present invention in samples derived from human colon.

Typically, the affinity or avidity of an antibody (or antibody multimer, as in the case of an IgM pentamer) of the present invention for a protein or protein fragment of the present invention will be at least about $1\times10^{-6}$ molar (M), typically at least about $5\times10^{-7}$ M, $1\times10^{-7}$ M, with affinities and avidities of at least $1\times10^{-8}$ M, $5\times10^{-9}$ M, $1\times10^{-10}$ M and up to $1\times10^{-13}$ M proving especially useful.

The antibodies of the present invention can be naturally-occurring forms, such as IgG, IgM, IgD, IgE, IgY, and IgA, from any avian, reptilian, or mammalian species.

Human antibodies can, but will infrequently, be drawn directly from human donors or human cells. In this case, antibodies to the proteins of the present invention will typically have resulted from fortuitous immunization, such as autoimmune immunization, with the protein or protein fragments of the present invention. Such antibodies will typically, but will not invariably, be polyclonal. In addition, individual polyclonal antibodies may be isolated and cloned to generate monoclonals.

Human antibodies are more frequently obtained using transgenic animals that express human immunoglobulin genes, which transgenic animals can be affirmatively immunized with the protein immunogen of the present invention. Human Ig-transgenic mice capable of producing human antibodies and methods of producing human antibodies therefrom upon specific immunization are described,. inter alia, in U.S. Pat. Nos. 6,162,963; 6,150,584; 6,114,598; 6,075,181; 5,939,598; 5,877,397; 5,874,299; 5,814,318; 5,789,650; 5,770,429; 5,661,016; 5,633,425; 5,625,126; 5,569,825; 5,545,807; 5,545,806, and 5,591,669, the disclosures of which are incorporated herein by reference in their entireties. Such antibodies are typically monoclonal, and are typically produced using techniques developed for production of murine antibodies.

Human antibodies are particularly useful, and often preferred, when the antibodies of the present invention are to be administered to human beings as in vivo diagnostic or therapeutic agents, since recipient immune response to the administered antibody will often be substantially less than that occasioned by administration of an antibody derived from another species, such as mouse.

IgG, IgM, IgD, IgE, IgY, and IgA antibodies of the present invention can also be obtained from other species, including mammals such as rodents (typically mouse, but also rat, guinea pig, and hamster) lagomorphs, typically rabbits, and also larger mammals, such as sheep, goats, cows, and horses, and other egg laying birds or reptiles such as chickens or alligators. For example, avian antibodies may be generated using techniques described in WO 00/29444, published 25 May 2000, the contents of which are hereby incorporated in their entirety. In such cases, as with the transgenic human-antibody-producing non-human mammals, fortuitous immunization is not required, and the non-human mammal is typically affirmatively immunized, according to standard immunization protocols, with the protein or protein fragment of the present invention.

As discussed above, virtually all fragments of 8 or more contiguous amino acids of the proteins of the present invention can be used effectively as immunogens when conjugated to a carrier, typically a protein such as bovine thyroglobulin, keyhole limpet hemocyanin, or bovine serum albumin, conveniently using a bifunctional linker such as those described elsewhere above, which discussion is incorporated by reference here.

Immunogenicity can also be conferred by fusion of the polypeptide and fragments of the present invention to other moieties. For example, peptides of the present invention can be produced by solid phase synthesis on a branched polylysine core matrix; these multiple antigenic peptides (MAPs) provide high purity, increased avidity, accurate chemical definition and improved safety in vaccine development. Tam et al., *Proc. Natl. Acad. Sci. USA* 85: 5409-5413 (1988); Posnett et al., *J. Biol. Chem.* 263: 1719-1725 (1988).

Protocols for immunizing non-human mammals or avian species are well-established in the art. See Harlow et al. (eds.), *Using Antibodies: A Laboratory Manual*, Cold Spring Harbor Laboratory (1998); Coligan et al. (eds.), *Current Protocols in Immunology*, John Wiley & Sons, Inc. (2001); Zola, *Monoclonal Antibodies: Preparation and Use of Monoclonal Antibodies and Engineered Antibody Derivatives* (*Basics: From Background to Bench*), Springer Verlag (2000); Gross M, Speck *J.Dtsch. Tierarztl. Wochenschr.* 103: 417-422 (1996), the disclosures of which are incorporated herein by reference. Immunization protocols often include multiple immunizations, either with or without adjuvants such as Freund's complete adjuvant and Freund's incomplete adjuvant, and may include naked DNA immunization (Moss, *Semin. Immunol.* 2: 317-327 (1990).

Antibodies from non-human mammals and avian species can be polyclonal or monoclonal, with polyclonal antibodies having certain advantages in immunohistochemical detection of the proteins of the present invention and monoclonal antibodies having advantages in identifying and distinguishing particular epitopes of the proteins of the present invention. Antibodies from avian species may have particular advantage in detection of the proteins of the present invention, in human serum or tissues (Vikinge et al., *Biosens. Bioelectron.* 13: 1257-1262 (1998).

Following immunization, the antibodies of the present invention can be produced using any art-accepted technique. Such techniques are well-known in the art, Coligan, supra; Zola, supra; Howard et al. (eds.), *Basic Methods in Antibody Production and Characterization*, CRC Press (2000); Harlow, supra, Davis (ed.), *Monoclonal Antibody Protocols*, Vol. 45, Humana Press (1995); Delves (ed.), *Antibody Production: Essential Techniques*, John Wiley & Son Ltd (1997); Kenney, *Antibody Solution: An Antibody Methods Manual*, Chapman & Hall (1997), incorporated herein by reference in their entireties, and thus need not be detailed here.

Briefly, however, such techniques include, inter alia, production of monoclonal antibodies by hybridomas and expression of antibodies or fragments or derivatives thereof from host cells engineered to express immunoglobulin genes or fragments thereof. These two methods of production are not mutually exclusive: genes encoding antibodies specific for the proteins or protein fragments of the present invention can be cloned from hybridomas and thereafter expressed in other host cells. Nor need the two necessarily be performed together: e.g., genes encoding antibodies specific for the proteins and protein fragments of the present invention can be cloned directly from B cells known to be specific for the desired protein, as further described in U.S. Pat. No. 5,627,052, the disclosure of which is incorporated herein by reference in its entirety, or from antibody-displaying phage.

Recombinant expression in host cells is particularly useful when fragments or derivatives of the antibodies of the present invention are desired.

Host cells for recombinant production of either whole antibodies, antibody fragments, or antibody derivatives can be prokaryotic or eukaryotic.

Prokaryotic hosts are particularly useful for producing phage displayed antibodies of the present invention.

The technology of phage-displayed antibodies, in which antibody variable region fragments are fused, for example, to the gene III protein (pIII) or gene VIII protein (pVIII) for display on the surface of filamentous phage, such as M13, is by now well-established. See, e.g., Sidhu, *Curr. Opin. Bio-*

*technol.* 11(6): 610-6 (2000); Griffiths et al., *Curr. Opin. Biotechnol.* 9(1): 102-8 (1998); Hoogenboom et al., *Immunotechnology,* 4(1): 1-20 (1998); Rader et al., *Current Opinion in Biotechnology* 8: 503-508 (1997); Aujame et al., *Human Antibodies* 8: 155-168 (1997); Hoogenboom, *Trends in Biotechnol.* 15: 62-70 (1997); de Kruif et al., 17: 453-455 (1996); Barbas et al., *Trends in Biotechnol.* 14: 230-234 (1996); Winter et al., *Ann. Rev. Immunol.* 433-455 (1994). Techniques and protocols required to generate, propagate, screen (pan), and use the antibody fragments from such libraries have recently been compiled. See, e.g., Barbas (2001), supra; Kay, supra; Abelson, supra, the disclosures of which are incorporated herein by reference in their entireties.

Typically, phage-displayed antibody fragments are scFv fragments or Fab fragments; when desired, full length antibodies can be produced by cloning the variable regions from the displaying phage into a complete antibody and expressing the full length antibody in a further prokaryotic or a eukaryotic host cell.

Eukaryotic cells are also useful for expression of the antibodies, antibody fragments, and antibody derivatives of the present invention.

For example, antibody fragments of the present invention can be produced in *Pichia pastoris* and in *Saccharomyces cerevisiae*. See, e.g., Takahashi et al., *Biosci. Biotechnol. Biochem.* 64(10): 2138-44 (2000); Freyre et al., J. Biotechnol. 76(2-3):1 57-63 (2000); Fischer et al., *Biotechnol. Appl. Biochem.* 30 (Pt 2): 117-20 (1999); Pennell et al., *Res. Immunol.* 149(6): 599-603 (1998); Eldin et al., *J. Immunol. Methods.* 201(1): 67-75 (1997);, Frenken et al., *Res. Immunol.* 149(6): 589-99 (1998); Shusta et al., *Nature Biotechnol.* 16(8): 773-7 (1998), the disclosures of which are incorporated herein by reference in their entireties.

Antibodies, including antibody fragments and derivatives, of the present invention can also be produced in insect cells. See, e.g., Li et al., *Protein Expr. Purif.* 21(1): 121-8 (2001); Ailor et al., *Biotechnol. Bioeng.* 58(2-3): 196-203 (1998); Hsu et al., *Biotechnol. Prog.* 13(1): 96-104 (1997); Edelman et al, *Immunology* 91(1): 13-9 (1997); and Nesbit et al., *J. Immunol. Methods* 151(1-2): 201-8 (1992), the disclosures of which are incorporated herein by reference in their entireties.

Antibodies and fragments and derivatives thereof of the present invention can also be produced in plant cells, particularly maize or tobacco, Giddings et al., *Nature Biotechnol.* 18(11): 1151-5 (2000); Gavilondo et al., *Biotechniques* 29(1): 128-38 (2000); Fischer et al., *J. Biol. Regul. Homeost. Agents* 14(2): 83-92 (2000); Fischer et al., *Biotechnol. Appl. Biochem.* 30 (Pt 2): 113-6 (1999); Fischer et al., *Biol. Chem.* 380(7-8): 825-39 (1999); Russell, *Curr. Top. Microbiol. Immunol.* 240: 119-38 (1999); and Ma et al., *Plant Physiol.* 109(2): 341-6 (1995), the disclosures of which are incorporated herein by reference in their entireties.

Antibodies, including antibody fragments and derivatives, of the present invention can also be produced in transgenic, non-human, mammalian milk. See, e.g. Pollock et al., *J. Immunol. Methods.* 231: 147-57 (1999); Young et al., *Res. Immunol.* 149: 609-10 (1998); Limonta et al., *Immunotechnology* 1: 107-13 (1995), the disclosures of which are incorporated herein by reference in their entireties.

Mammalian cells useful for recombinant expression of antibodies, antibody fragments, and antibody derivatives of the present invention include CHO cells, COS cells, 293 cells, and myeloma cells.

Verma et al., *J. Immunol. Methods* 216(1-2):165-81 (1998), herein incorporated by reference, review and compare bacterial, yeast, insect and mammalian expression systems for expression of antibodies.

Antibodies of the present invention can also be prepared by cell free translation, as further described in Merk et al., *J. Biochem.* (Tokyo) 125(2): 328-33 (1999) and Ryabova et al., *Nature Biotechnol.* 15(1): 79-84 (1997), and in the milk of transgenic animals, as further described in Pollock et al., *J. Immunol. Methods* 231(1-2): 147-57 (1999), the disclosures of which are incorporated herein by reference in their entireties.

The invention further provides antibody fragments that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful fragments are Fab, Fab', Fv, $F(ab)'_2$, and single chain Fv (scFv) fragments. Other useful fragments are described in Hudson, *Curr. Opin. Biotechnol.* 9(4): 395-402 (1998).

It is also an aspect of the present invention to provide antibody derivatives that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful derivatives are chimeric, primatized, and humanized antibodies; such derivatives are less immunogenic in human beings, and thus more suitable for in vivo administration, than are unmodified antibodies from non-human mammalian species. Another useful derivative is PEGylation to increase the serum half life of the antibodies.

Chimeric antibodies typically include heavy and/or light chain variable regions (including both CDR and framework residues) of immunoglobulins of one species, typically mouse, fused to constant regions of another species, typically human. See, e.g., U.S. Pat. No. 5,807,715; Morrison et al., *Proc. Natl. Acad. Sci USA.*81(21): 6851-5 (1984); Sharon et al., *Nature* 309(5966): 364-7 (1984); Takeda et al., *Nature* 314(6010): 452-4 (1985), the disclosures of which are incorporated herein by reference in their entireties. Primatized and humanized antibodies typically include heavy and/or light chain CDRs from a murine antibody grafted into a non-human primate or human antibody V region framework, usually further comprising a human constant region, Riechmann et al., *Nature* 332(6162): 323-7 (1988); Co et al., *Nature* 351(6326): 501-2 (1991); U.S. Pat. Nos. 6,054,297; 5,821,337; 5,770,196; 5,766,886; 5,821,123; 5,869,619; 6,180,377; 6,013,256; 5,693,761; and 6,180,370, the disclosures of which are incorporated herein by reference in their entireties.

Other useful antibody derivatives of the invention include heteromeric antibody complexes and antibody fusions, such as diabodies (bispecific antibodies), single-chain diabodies, and intrabodies.

It is contemplated that the nucleic acids encoding the antibodies of the present invention can be operably joined to other nucleic acids forming a recombinant vector for cloning or for expression of the antibodies of the invention. The present invention includes any recombinant vector containing the coding sequences, or part thereof, whether for eukaryotic transduction, transfection or gene therapy. Such vectors may be prepared using conventional molecular biology techniques, known to those with skill in the art, and would comprise DNA encoding sequences for the immunoglobulin V-regions including framework and CDRs or parts thereof, and a suitable promoter either with or without a signal sequence for intracellular transport. Such vectors may be transduced or transfected into eukaryotic cells or used for gene therapy (Marasco et al., *Proc. Natl. Acad. Sci.* (*USA*) 90: 7889-7893 (1993); Duan et al., *Proc. Natl. Acad. Sci.* (*USA*) 91: 5075-5079 (1994), by conventional techniques, known to those with skill in the art.

The antibodies of the present invention, including fragments and derivatives thereof, can usefully be labeled. It is, therefore, another aspect of the present invention to provide labeled antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

The choice of label depends, in part, upon the desired use.

For example, when the antibodies of the present invention are used for immunohistochemical staining of tissue samples, the label is preferably an enzyme that catalyzes production and local deposition of a detectable product.

Enzymes typically conjugated to antibodies to permit their immunohistochemical visualization are well-known, and include alkaline phosphatase, β-galactosidase, glucose oxidase, horseradish peroxidase (HRP), and urease. Typical substrates for production and deposition of visually detectable products include o-nitrophenyl-beta-D-galactopyranoside (ONPG); o-phenylenediamine dihydrochloride (OPD); p-nitrophenyl phosphate (PNPP); p-nitrophenyl-beta-D-galactopryanoside (PNPG); 3',3'-diaminobenzidine (DAB); 3-amino-9-ethylcarbazole (AEC); 4-chloro-1-naphthol (CN); 5-bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Other substrates can be used to produce products for local deposition that are luminescent. For example, in the presence of hydrogen peroxide ($H_2O_2$), horseradish peroxidase (HRP) can catalyze the oxidation of cyclic diacylhydrazides, such as luminol. Immediately following the oxidation, the luminol is in an excited state (intermediate reaction product), which decays to the ground state by emitting light. Strong enhancement of the light emission is produced by enhancers, such as phenolic compounds. Advantages include high sensitivity, high resolution, and rapid detection without radioactivity and requiring only small amounts of antibody. See, e.g., Thorpe et al., *Methods Enzymol.* 133: 331-53 (1986); Kricka et al., *J. Immunoassay* 17(1): 67-83 (1996); and Lundqvist et al., *J. Biolumin. Chemilumin.* 10(6): 353-9 (1995), the disclosures of which are incorporated herein by reference in their entireties. Kits for such enhanced chemiluminescent detection (ECL) are available commercially.

The antibodies can also be labeled using colloidal gold.

As another example, when the antibodies of the present invention are used, e.g., for flow cytometric detection, for scanning laser cytometric detection, or for fluorescent immunoassay, they can usefully be labeled with fluorophores.

There are a wide variety of fluorophore labels that can usefully be attached to the antibodies of the present invention.

For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCP-Cy5.5, PE-CyS, PE-Cy5.5, PE-Cy7, PE-Texas Red, and APC-Cy7.

Other fluorophores include, inter alia, Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention.

For secondary detection using labeled avidin, streptavidin, captavidin or neutravidin, the antibodies of the present invention can usefully be labeled with biotin.

When the antibodies of the present invention are used, e.g. for Western blotting applications, they can usefully be labeled with radioisotopes, such as $^{33}P$, $^{32}P$, $^{35}S$, $^{3}H$, and $^{125}I$.

As another example, when the antibodies of the present invention are used for radioimmunotherapy, the label can usefully be $^{228}Th$, $^{227}Ac$, $^{225}Ac$, $^{223}Ra$, $^{213}Bi$, $^{212}Pb$, $^{212}Bi$, $^{211}At$, $^{203}Pb$, $^{194}Os$, $^{188}Re$, $^{186}Re$, $^{153}Sm$, $^{149}Tb$, $^{131}I$, $^{125}I$, $^{111}In$, $^{105}Rh$, $^{99m}Tc$, $^{97}Ru$, $^{90}Y$, $^{90}Sr$, $^{88}Y$, $^{72}Se$, $^{67}Cu$, or $^{47}Sc$.

As another example, when the antibodies of the present invention are to be used for in vivo diagnostic use, they can be rendered detectable by conjugation to MRI contrast agents, such as gadolinium diethylenetriaminepentaacetic acid (DTPA), Lauffer et al., *Radiology* 207(2): 529-38 (1998), or by radioisotopic labeling.

As would be understood, use of the labels described above is not restricted to the application for which they are mentioned.

The antibodies of the present invention, including fragments and derivatives thereof, can also be conjugated to toxins, in order to target the toxin's ablative action to cells that display and/or express the proteins of the present invention. Commonly, the antibody in such immunotoxins is conjugated to *Pseudomonas* exotoxin A, *diphtheria* toxin, *shiga* toxin A, *anthrax* toxin lethal factor, or ricin. See Hall (ed.), *Immunotoxin Methods and Protocols* (Methods in Molecular Biology, vol. 166), Humana Press (2000); and Frankel et al. (eds.), *Clinical Applications of Immunotoxins*, Springer-Verlag (1998), the disclosures of which are incorporated herein by reference in their entireties.

The antibodies of the present invention can usefully be attached to a substrate, and it is, therefore, another aspect of the invention to provide antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention, attached to a substrate.

Substrates can be porous or nonporous, planar or nonplanar.

For example, the antibodies of the present invention can usefully be conjugated to filtration media, such as NHS-activated Sepharose or CNBr-activated Sepharose for purposes of immunoaffinity chromatography.

For example, the antibodies of the present invention can usefully be attached to paramagnetic microspheres, typically by biotin-streptavidin interaction, which microspheres can then be used for isolation of cells that express or display the proteins of the present invention. As another example, the antibodies of the present invention can usefully be attached to the surface of a microtiter plate for ELISA.

As noted above, the antibodies of the present invention can be produced in prokaryotic and eukaryotic cells. It is, therefore, another aspect of the present invention to provide cells that express the antibodies of the present invention, including hybridoma cells, B cells, plasma cells, and host cells recombinantly modified to express the antibodies of the present invention.

In yet a further aspect, the present invention provides aptamers evolved to bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Transgenic Animals and Cells

In another aspect, the invention provides transgenic cells and non-human organisms comprising nucleic acid molecules of the invention. In a preferred embodiment, the transgenic cells and non-human organisms comprise a nucleic acid molecule encoding a CSP. In a preferred embodiment, the CSP comprises an amino acid sequence selected from SEQ ID NO: 148 through 250, or a fragment, mutein, homologous protein or allelic variant thereof. In another preferred embodiment, the transgenic cells and non-human organism comprise a CSNA of the invention, preferably a CSNA comprising a nucleotide sequence selected from the group consisting of SEQ ID NO: 1 through 147, or a part, substantially similar nucleic acid molecule, allelic variant or hybridizing nucleic acid molecule thereof.

In another embodiment, the transgenic cells and non-human organisms have a targeted disruption or replacement of the endogenous orthologue of the human CSG. The transgenic cells can be embryonic stem cells or somatic cells. The transgenic non-human organisms can be chimeric, nonchimeric heterozygotes, and nonchimeric homozygotes. Methods of producing transgenic animals are well-known in the art. See, e.g., Hogan et al., *Manipulating the Mouse Embryo: A Laboratory Manual,* 2d ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999).

Any technique known in the art may be used to introduce a nucleic acid molecule of the invention into an animal to produce the founder lines of transgenic animals. Such techniques include, but are not limited to, pronuclear microinjection. (see, e.g., Paterson et al., *Appl. Microbiol. Biotechnol.* 40: 691-698 (1994); Carver et al., *Biotechnology* 11: 1263-1270 (1993); Wright et al., *Biotechnology* 9: 830-834 (1991); and U.S. Pat. No. 4,873,191 (1989 retrovirus-mediated gene transfer into germ lines, blastocysts or embryos (see, e.g., Van der Putten et al., *Proc. Natl. Acad. Sci., USA* 82: 6148-6152 (1985)); gene targeting in embryonic stem cells (see, e.g., Thompson et al., *Cell* 56: 313-321 (1989)); electroporation of cells or embryos (see, e.g., Lo, 1983*, Mol. Cell. Biol.* 3: 1803-1814 (1983)); introduction using a gene gun (see, e.g., Ulmer et al., *Science* 259: 1745-49 (1993); introducing nucleic acid constructs into embryonic pleuripotent stem cells and transferring the stem cells back into the blastocyst; and sperm-mediated gene transfer (see, e.g., Lavitrano et al., *Cell* 57: 717-723 (1989)).

Other techniques include, for example, nuclear transfer into enucleated oocytes of nuclei from cultured embryonic, fetal, or adult cells induced to quiescence (see, e.g., Campell et al., *Nature* 380: 64-66 (1996); Wilmut et al., *Nature* 385: 810-813 (1997)). The present invention provides for transgenic animals that carry the transgene (i.e., a nucleic acid molecule of the invention) in all their cells, as well as animals which carry the transgene in some, but not all their cells, i. e., mosaic animals or chimeric animals.

The transgene may be integrated as a single transgene or as multiple copies, such as in concatamers, e. g., head-to-head tandems or head-to-tail tandems. The transgene may also be selectively introduced into and activated in a particular cell type by following, e.g., the teaching of Lasko et al. et al., *Proc. Natl. Acad. Sci. USA* 89: 6232-6236 (1992). The regulatory sequences required for such a cell-type specific activation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Methods for creating a transgenic animal with a disruption of a targeted gene are also well-known in the art. In general, a vector is designed to comprise some nucleotide sequences homologous to the endogenous targeted gene. The vector is introduced into a cell so that it may integrate, via homologous recombination with chromosomal sequences, into the endogenous gene, thereby disrupting the function of the endogenous gene. The transgene may also be selectively introduced into a particular cell type, thus inactivating the endogenous gene in only that cell type. See, e.g., Gu et al., *Science* 265: 103-106 (1994). The regulatory sequences required for such a cell-type specific inactivation will depend upon the particular cell type of interest, and will be apparent to those of skill in the art. See, e.g., Smithies et al., *Nature* 317: 230-234 (1985); Thomas et al., *Cell* 51: 503-512 (1987); Thompson et al., *Cell* 5: 313-321 (1989).

In one embodiment, a mutant, non-functional nucleic acid molecule of the invention (or a completely unrelated DNA sequence) flanked by DNA homologous to the endogenous nucleic acid sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene. See, e.g., Thomas, supra and Thompson, supra. However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from an animal or patient or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc.

The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. See, e.g., U.S. Pat. Nos. 5,399,349 and 5,460,959, each of which is incorporated by reference herein in its entirety.

When the cells to be administered are non-autologous or non-MHC compatible cells, they can be administered using well-known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Computer Readable Means

A further aspect of the invention relates to a computer readable means for storing the nucleic acid and amino acid sequences of the instant invention. In a preferred embodiment, the invention provides a computer readable means for storing SEQ ID NO: 1 through 147 and SEQ ID NO: 148 through 250 as described herein, as the complete set of sequences or in any combination. The records of the computer readable means can be accessed for reading and display and for interface with a computer system for the application of programs allowing for the location of data upon a query for data meeting certain criteria, the comparison of sequences, the alignment or ordering of sequences meeting a set of criteria, and the like.

The nucleic acid and amino acid sequences of the invention are particularly useful as components in databases useful for search analyses as well as in sequence analysis algorithms. As used herein, the terms "nucleic acid sequences of the invention" and "amino acid sequences of the invention" mean any detectable chemical or physical characteristic of a polynucleotide or polypeptide of the invention that is or may be reduced to or stored in a computer readable form. These include, without limitation, chromatographic scan data or peak data, photographic data or scan data therefrom, and mass spectrographic data.

This invention provides computer readable media having stored thereon sequences of the invention. A computer readable medium may comprise one or more of the following: a nucleic acid sequence comprising a sequence of a nucleic acid sequence of the invention; an amino acid sequence comprising an amino acid sequence of the invention; a set of nucleic acid sequences wherein at least one of said sequences comprises the sequence of a nucleic acid sequence of the invention; a set of amino acid sequences wherein at least one of said sequences comprises the sequence of an amino acid sequence of the invention; a data set representing a nucleic acid sequence comprising the sequence of one or more nucleic acid sequences of the invention; a data set representing a nucleic acid sequence encoding an amino acid sequence comprising the sequence of an amino acid sequence of the invention; a set of nucleic acid sequences wherein at least one of said sequences comprises the sequence of a nucleic acid sequence of the invention; a set of amino acid sequences wherein at least one of said sequences comprises the sequence of an amino acid sequence of the invention; a data set representing a nucleic acid sequence comprising the sequence of a nucleic acid sequence of the invention; a data set representing a nucleic acid sequence encoding an amino acid sequence comprising the sequence of an amino acid sequence of the invention. The computer readable medium can be any composition of matter used to store information or data, including, for example, commercially available floppy disks, tapes, hard drives, compact disks, and video disks.

Also provided by the invention are methods for the analysis of character sequences, particularly genetic sequences. Preferred methods of sequence analysis include, for example, methods of sequence homology analysis, such as identity and similarity analysis, RNA structure analysis, sequence assembly, cladistic analysis, sequence motif analysis, open reading frame determination, nucleic acid base calling, and sequencing chromatogram peak analysis.

A computer-based method is provided for performing nucleic acid sequence identity or similarity identification. This method comprises the steps of providing a nucleic acid sequence comprising the sequence of a nucleic acid of the invention in a computer readable medium; and comparing said nucleic acid sequence to at least one nucleic acid or amino acid sequence to identify sequence identity or similarity.

A computer-based method is also provided for performing amino acid homology identification, said method comprising the steps of: providing an amino acid sequence comprising the sequence of an amino acid of the invention in a computer readable medium; and comparing said an amino acid sequence to at least one nucleic acid or an amino acid sequence to identify homology.

A computer-based method is still further provided for assembly of overlapping nucleic acid sequences into a single nucleic acid sequence, said method comprising the steps of: providing a first nucleic acid sequence comprising the sequence of a nucleic acid of the invention in a computer readable medium; and screening for at least one overlapping region between said first nucleic acid sequence and a second nucleic acid sequence.

Diagnostic Methods for Colon Cancer

The present invention also relates to quantitative and qualitative diagnostic assays and methods for detecting, diagnosing, monitoring, staging and predicting cancers by comparing expression of a CSNA or a CSP in a human patient that has or may have colon cancer, or who is at risk of developing colon cancer, with the expression of a CSNA or a CSP in a normal human control. For purposes of the present invention, "expression of a CSNA" or "CSNA expression" means the quantity of CSG mRNA that can be measured by any method known in the art or the level of transcription that can be measured by any method known in the art in a cell, tissue, organ or whole patient. Similarly, the term "expression of a CSP" or "CSP expression" means the amount of CSP that can be measured by any method known in the art or the level of translation of a CSG CSNA that can be measured by any method known in the art.

The present invention provides methods for diagnosing colon cancer in a patient, in particular squamous cell carcinoma, by analyzing for changes in levels of CSNA or CSP in cells, tissues, organs or bodily fluids compared with levels of CSNA or CSP in cells, tissues, organs or bodily fluids of preferably the same type from a normal human control, wherein an increase, or decrease in certain cases, in levels of a CSNA or CSP in the patient versus the normal human control is associated with the presence of colon cancer or with a predilection to the disease. In another preferred embodiment, the present invention provides methods for diagnosing colon cancer in a patient by analyzing changes in the structure of the mRNA of a CSG compared to the mRNA from a normal control. These changes include, without limitation, aberrant splicing, alterations in polyadenylation and/or alterations in 5' nucleotide capping. In yet another preferred embodiment, the present invention provides methods for diagnosing colon cancer in a patient by analyzing changes in a CSP compared to a CSP from a normal control. These changes include, e.g., alterations in glycosylation and/or phosphorylation of the CSP or subcellular CSP localization.

In a preferred embodiment, the expression of a CSNA is measured by determining the amount of an mRNA that encodes an amino acid sequence selected from SEQ ID NO: 148 through 250, a homolog, an allelic variant, or a fragment thereof. In a more preferred embodiment, the CSNA expression that is measured is the level of expression of a CSNA mRNA selected from SEQ ID NO: 1 through 147, or a hybridizing nucleic acid, homologous nucleic acid or allelic variant thereof, or a part of any of these nucleic acids. CSNA expression may be measured by any method known in the art, such as those described supra, including measuring mRNA expression by Northern blot, quantitative or qualitative reverse transcriptase PCR (RT-PCR), microarray, dot or slot blots or in situ hybridization. See, e.g., Ausubel (1992), supra; Ausubel (1999), supra; Sambrook (1989), supra; and Sambrook (2001), supra. CSNA transcription may be measured by any method known in the art including using a reporter gene hooked up to the promoter of a CSG of interest or doing nuclear run-off assays. Alterations in mRNA structure, e.g., aberrant splicing variants, may be determined by any method known in the art, including, RT-PCR followed by sequencing or restriction analysis. As necessary, CSNA expression may be compared to a known control, such as normal colon nucleic acid, to detect a change in expression.

In another preferred embodiment, the expression of a CSP is measured by determining the level of a CSP having an amino acid sequence selected from the group consisting of SEQ ID NO: 148 through 250, a homolog, an allelic variant, or a fragment thereof. Such levels are preferably determined in at least one of cells, tissues, organs and/or bodily fluids, including determination of normal and abnormal levels. Thus, for instance, a diagnostic assay in accordance with the invention for diagnosing over- or underexpression of CSNA or CSP compared to normal control bodily fluids, cells, or tissue samples may be used to diagnose the presence of colon cancer. The expression level of a CSP may be determined by any method known in the art, such as those described supra. In a preferred embodiment, the CSP expression level may be determined by radioimmunoassays, competitive-binding assays, ELISA, Western blot, FACS, immunohistochemistry, immunoprecipitation, proteomic approaches: two-dimensional gel electrophoresis (2D electrophoresis) and non-gel-based approaches such as mass spectrometry or protein interaction profiling. See, e.g, Harlow (1999), supra; Ausubel (1992), supra; and Ausubel (1999), supra. Alterations in the CSP structure may be determined by any method known in the art, including, e.g., using antibodies that specifically recognize phosphoserine, phosphothreonine or phosphotyrosine residues, two-dimensional polyacrylamide gel electrophoresis (2D PAGE) and/or chemical analysis of amino acid residues of the protein. Id.

In a preferred embodiment, a radioimmunoassay (RIA) or an ELISA is used. An antibody specific to a CSP is prepared if one is not already available. In a preferred embodiment, the antibody is a monoclonal antibody. The anti-CSP antibody is bound to a solid support and any free protein binding sites on the solid support are blocked with a protein such as bovine serum albumin. A sample of interest is incubated with the antibody on the solid support under conditions in which the CSP will bind to the anti-CSP antibody. The sample is removed, the solid support is washed to remove unbound material, and an anti-CSP antibody that is linked to a detectable reagent (a radioactive substance for RIA and an enzyme for ELISA) is added to the solid support and incubated under conditions in which binding of the CSP to the labeled antibody will occur. After binding, the unbound labeled antibody is removed by washing. For an ELISA, one or more substrates are added to produce a colored reaction product that is based upon the amount of a CSP in the sample. For an RIA, the solid support is counted for radioactive decay signals by any method known in the art. Quantitative results for both RIA and ELISA typically are obtained by reference to a standard curve.

Other methods to measure CSP levels are known in the art. For instance, a competition assay may be employed wherein an anti-CSP antibody is attached to a solid support and an allocated amount of a labeled CSP and a sample of interest are incubated with the solid support. The amount of labeled CSP detected which is attached to the solid support can be correlated to the quantity of a CSP in the sample.

Of the proteomic approaches, 2D PAGE is a well-known technique. Isolation of individual proteins from a sample such as serum is accomplished using sequential separation of proteins by isoelectric point and molecular weight. Typically, polypeptides are first separated by isoelectric point (the first dimension) and then separated by size using an electric current (the second dimension). In general, the second dimension is perpendicular to the first dimension. Because no two proteins with different sequences are identical on the basis of both size and charge, the result of 2D PAGE is a roughly square gel in which each protein occupies a unique spot. Analysis of the spots with chemical or antibody probes, or subsequent protein microsequencing can reveal the relative abundance of a given protein and the identity of the proteins in the sample.

Expression levels of a CSNA can be determined by any method known in the art, including PCR and other nucleic acid methods, such as ligase chain reaction (LCR) and nucleic acid sequence based amplification (NASBA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction.

Hybridization to specific DNA molecules (e.g., oligonucleotides) arrayed on a solid support can be used to both detect the expression of and quantitate the level of expression of one or more CSNAs of interest. In this approach, all or a portion of one or more CSNAs is fixed to a substrate. A sample of interest, which may comprise RNA, e.g., total RNA or polyA-selected mRNA, or a complementary DNA (cDNA) copy of the RNA is incubated with the solid support under conditions in which hybridization will occur between the DNA on the solid support and the nucleic acid molecules in the sample of interest. Hybridization between the substrate-bound DNA and the nucleic acid molecules in the sample can be detected and quantitated by several means, including, without limitation, radioactive labeling or fluorescent labeling of the nucleic acid molecule or a secondary molecule designed to detect the hybrid.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood. In a preferred embodiment, the specimen tested for expression of CSNA or CSP includes, without limitation, colon tissue, fluid obtained by bronchial alveolar lavage (BAL), sputum, colon cells grown in cell culture, blood, serum, lymph node tissue and lymphatic fluid. In another preferred embodiment, especially when metastasis of a primary colon cancer is known or suspected, specimens include, without limitation, tissues from brain, bone, bone marrow, liver, adrenal glands and colon. In general, the tissues may be sampled by biopsy, including, without limitation, needle biopsy, e.g., transthoracic needle aspiration, cervical mediatinoscopy, endoscopic lymph node biopsy, video-assisted thoracoscopy, exploratory thoracotomy, bone marrow biopsy and bone marrow aspiration. See Scott, supra and Franklin, pp. 529-570, in Kane, supra. For early and inexpensive detection, assaying for changes in CSNAs or CSPs in cells in sputum samples may be particularly useful. Methods of obtaining and analyzing sputum samples is disclosed in Franklin, supra.

All the methods of the present invention may optionally include determining the expression levels of one or more other cancer markers in addition to determining the expression level of a CSNA or CSP. In many cases, the use of another cancer marker will decrease the likelihood of false positives or false negatives. In one embodiment, the one or more other cancer markers include other CSNA or CSPs as disclosed herein. Other cancer markers useful in the present invention will depend on the cancer being tested and are known to those of skill in the art. In a preferred embodiment, at least one other cancer marker in addition to a particular CSNA or CSP is measured. In a more preferred embodiment, at least two other additional cancer markers are used. In an even more preferred embodiment, at least three, more preferably at least five, even more preferably at least ten additional cancer markers are used.

Diagnosing

In one aspect, the invention provides a method for determining the expression levels and/or structural alterations of one or more CSNAs and/or CSPs in a sample from a patient suspected of having colon cancer. In general, the method comprises the steps of obtaining the sample from the patient, determining the expression level or structural alterations of a CSNA and/or CSP and then ascertaining whether the patient has colon cancer from the expression level of the CSNA or CSP. In general, if high expression relative to a control of a CSNA or CSP is indicative of colon cancer, a diagnostic assay is considered positive if the level of expression of the CSNA or CSP is at least two times higher, and more preferably are at least five times higher, even more preferably at least ten times higher, than in preferably the same cells, tissues or bodily fluid of a normal human control. In contrast, if low expression relative to a control of a CSNA or CSP is indicative of colon cancer, a diagnostic assay is considered positive if the level of expression of the CSNA or CSP is at least two times lower, more preferably are at least five times lower, even more preferably at least ten times lower than in preferably the same cells, tissues or bodily fluid of a normal human control. The normal human control may be from a different patient or from uninvolved tissue of the same patient.

The present invention also provides a method of determining whether colon cancer has metastasized in a patient. One may identify whether the colon cancer has metastasized by measuring the expression levels and/or structural alterations of one or more CSNAs and/or CSPs in a variety of tissues. The presence of a CSNA or CSP in a certain tissue at levels higher than that of corresponding noncancerous tissue (e.g., the same tissue from another individual) is indicative of metastasis if high level expression of a CSNA or CSP is associated with colon cancer. Similarly, the presence of a CSNA or CSP in a tissue at levels lower than that of corresponding noncancerous tissue is indicative of metastasis if low level expression of a CSNA or CSP is associated with colon cancer. Further, the presence of a structurally altered CSNA or CSP that is associated with colon cancer is also indicative of metastasis.

In general, if high expression relative to a control of a CSNA or CSP is indicative of metastasis, an assay for metastasis is considered positive if the level of expression of the CSNA or CSP is at least two times higher, and more preferably are at least five times higher, even more preferably at least ten times higher, than in preferably the same cells, tissues or bodily fluid of a normal human control. In contrast, if low expression relative to a control of a CSNA or CSP is indicative of metastasis, an assay for metastasis is considered positive if the level of expression of the CSNA or CSP is at least two times lower, more preferably are at least five times lower, even more preferably at least ten times lower than in preferably the same cells, tissues or bodily fluid of a normal human control.

The CSNA or CSP of this invention may be used as element in an array or a multi-analyte test to recognize expression patterns associated with colon cancers or other colon related disorders. In addition, the sequences of either the nucleic acids or proteins may be used as elements in a computer program for pattern recognition of colon disorders.

Staging

The invention also provides a method of staging colon cancer in a human patient. The method comprises identifying a human patient having colon cancer and analyzing cells, tissues or bodily fluids from such human patient for expression levels and/or structural alterations of one or more CSNAs or CSPs. First, one or more tumors from a variety of patients are staged according to procedures well-known in the art, and the expression level of one or more CSNAs or CSPs is determined for each stage to obtain a standard expression level for each CSNA and CSP. Then, the CSNA or CSP expression levels are determined in a biological sample from a patient whose stage of cancer is not known. The CSNA or CSP expression levels from the patient are then compared to the standard expression level. By comparing the expression level of the CSNAs and CSPs from the patient to the standard expression levels, one may determine the stage of the tumor. The same procedure may be followed using structural alterations of a CSNA or CSP to determine the stage of a colon cancer.

Monitoring

Further provided is a method of monitoring colon cancer in a human patient. One may monitor a human patient to determine whether there has been metastasis and, if there has been, when metastasis began to occur. One may also monitor a human patient to determine whether a preneoplastic lesion has become cancerous. One may also monitor a human patient to determine whether a therapy, e.g., chemotherapy, radiotherapy or surgery, has decreased or eliminated the colon cancer. The method comprises identifying a human patient that one wants to monitor for colon cancer, periodically analyzing cells, tissues or bodily fluids from such human patient for expression levels of one or more CSNAs or CSPs, and comparing the CSNA or CSP levels over time to those CSNA or CSP expression levels obtained previously. Patients may also be monitored by measuring one or more structural alterations in a CSNA or CSP that are associated with colon cancer.

If increased expression of a CSNA or CSP is associated with metastasis, treatment failure, or conversion of a preneoplastic lesion to a cancerous lesion, then detecting an increase in the expression level of a CSNA or CSP indicates that the tumor is metastasizing, that treatment has failed or that the lesion is cancerous, respectively. One having ordinary skill in the art would recognize that if this were the case, then a decreased expression level would be indicative of no metastasis, effective therapy or failure to progress to a neoplastic lesion. If decreased expression of a CSNA or CSP is associated with metastasis, treatment failure, or conversion of a preneoplastic lesion to a cancerous lesion, then detecting an decrease in the expression level of a CSNA or CSP indicates that the tumor is metastasizing, that treatment has failed or that the lesion is cancerous, respectively. In a preferred embodiment, the levels of CSNAs or CSPs are determined from the same cell type, tissue or bodily fluid as prior patient samples. Monitoring a patient for onset of colon cancer metastasis is periodic and preferably is done on a quarterly basis, but may be done more or less frequently.

The methods described herein can further be utilized as prognostic assays to identify subjects having or at risk of developing a disease or disorder associated with increased or decreased expression levels of a CSNA and/or CSP. The present invention provides a method in which a test sample is obtained from a human patient and one or more CSNAs and/or CSPs are detected. The presence of higher (or lower) CSNA or CSP levels as compared to normal human controls is diagnostic for the human patient being at risk for developing cancer, particularly colon cancer. The effectiveness of therapeutic agents to decrease (or increase) expression or activity of one or more CSNAs and/or CSPs of the invention can also be monitored by analyzing levels of expression of the CSNAs and/or CSPs in a human patient in clinical trials or in in vitro screening assays such as in human cells. In this way, the gene expression pattern can serve as a marker, indicative of the physiological response of the human patient or cells, as the case may be, to the agent being tested.

Detection of Genetic Lesions or Mutations

The methods of the present invention can also be used to detect genetic lesions or mutations in a CSG, thereby determining if a human with the genetic lesion is susceptible to developing colon cancer or to determine what genetic lesions are responsible, or are partly responsible, for a person's existing colon cancer. Genetic lesions can be detected, for example, by ascertaining the existence of a deletion, insertion and/or substitution of one or more nucleotides from the CSGs of this invention, a chromosomal rearrangement of CSG, an aberrant modification of CSG (such as of the methylation pattern of the genomic DNA), or allelic loss of a CSG. Methods to detect such lesions in the CSG of this invention are known to those having ordinary skill in the art following the teachings of the specification.

Methods of Detecting Noncancerous Colon Diseases

The invention also provides a method for determining the expression levels and/or structural alterations of one or more CSNAs and/or CSPs in a sample from a patient suspected of having or known to have a noncancerous colon disease. In general, the method comprises the steps of obtaining a sample from the patient, determining the expression level or structural alterations of a CSNA and/or CSP, comparing the expression level or structural alteration of the CSNA or CSP to a normal colon control, and then ascertaining whether the patient has a noncancerous colon disease. In general, if high expression relative to a control of a CSNA or CSP is indicative of a particular noncancerous colon disease, a diagnostic assay is considered positive if the level of expression of the CSNA or CSP is at least two times higher, and more preferably are at least five times higher, even more preferably at least ten times higher, than in preferably the same cells, tissues or bodily fluid of a normal human control. In contrast, if low expression relative to a control of a CSNA or CSP is indicative of a noncancerous colon disease, a diagnostic assay is considered positive if the level of expression of the CSNA or CSP is at least two times lower, more preferably are at least five times lower, even more preferably at least ten times lower than in preferably the same cells, tissues or bodily fluid of a normal human control. The normal human control may be from a different patient or from uninvolved tissue of the same patient.

One having ordinary skill in the art may determine whether a CSNA and/or CSP is associated with a particular noncancerous colon disease by obtaining colon tissue from a patient having a noncancerous colon disease of interest and determining which CSNAs and/or CSPs are expressed in the tissue at either a higher or a lower level than in normal colon tissue. In another embodiment, one may determine whether a CSNA or CSP exhibits structural alterations in a particular noncancerous colon disease state by obtaining colon tissue from a patient having a noncancerous colon disease of interest and determining the structural alterations in one or more CSNAs and/or CSPs relative to normal colon tissue.

Methods for Identifying Colon Tissue

In another aspect, the invention provides methods for identifying colon tissue. These methods are particularly useful in, e.g., forensic science, colon cell differentiation and development, and in tissue engineering.

In one embodiment, the invention provides a method for determining whether a sample is colon tissue or has colon tissue-like characteristics. The method comprises the steps of providing a sample suspected of comprising colon tissue or having colon tissue-like characteristics, determining whether the sample expresses one or more CSNAs and/or CSPs, and, if the sample expresses one or more CSNAs and/or CSPs, concluding that the sample comprises colon tissue. In a preferred embodiment, the CSNA encodes a polypeptide having an amino acid sequence selected from SEQ ID NO: 148 through 250, or a homolog, allelic variant or fragment thereof. In a more preferred embodiment, the CSNA has a nucleotide sequence selected from SEQ ID NO: 1 through 147, or a hybridizing nucleic acid, an allelic variant or a part thereof. Determining whether a sample expresses a CSNA can be accomplished by any method known in the art. Preferred methods include hybridization to microarrays, Northern blot hybridization, and quantitative or qualitative RT-PCR. In another preferred embodiment, the method can be practiced by determining whether a CSP is expressed. Determining whether a sample expresses a CSP can be accomplished by any method known in the art. Preferred methods include Western blot, ELISA, RIA and 2D PAGE. In one embodiment, the CSP has an amino acid sequence selected from SEQ ID NO: 148 through 250, or a homolog, allelic variant or fragment thereof. In another preferred embodiment, the expression of at least two CSNAs and/or CSPs is determined. In a more preferred embodiment, the expression of at least three, more preferably four and even more preferably five CSNAs and/or CSPs are determined.

In one embodiment, the method can be used to determine whether an unknown tissue is colon tissue. This is particularly useful in forensic science, in which small, damaged pieces of tissues that are not identifiable by microscopic or other means are recovered from a crime or accident scene. In another embodiment, the method can be used to determine whether a tissue is differentiating or developing into colon tissue. This is important in monitoring the effects of the addition of various agents to cell or tissue culture, e.g., in producing new colon tissue by tissue engineering. These agents include, e.g., growth and differentiation factors, extracellular matrix proteins and culture medium. Other factors that may be measured for effects on tissue development and differentiation include gene transfer into the cells or tissues, alterations in pH, aqueous:air interface and various other culture conditions.

Methods for Producing and Modifying Colon Tissue

In another aspect, the invention provides methods for producing engineered colon tissue or cells. In one embodiment, the method comprises the steps of providing cells, introducing a CSNA or a CSG into the cells, and growing the cells under conditions in which they exhibit one or more properties of colon tissue cells. In a preferred embodiment, the cells are pluripotent. As is well-known in the art, normal colon tissue comprises a large number of different cell types. Thus, in one embodiment, the engineered colon tissue or cells comprises one of these cell types. In another embodiment, the engineered colon tissue or cells comprises more than one colon cell type. Further, the culture conditions of the cells or tissue may require manipulation in order to achieve full differentiation and development of the colon cell tissue. Methods for manipulating culture conditions are well-known in the art.

Nucleic acid molecules encoding one or more CSPs are introduced into cells, preferably pluripotent cells. In a preferred embodiment, the nucleic acid molecules encode CSPs having amino acid sequences selected from SEQ ID NO: 148 through 250, or homologous proteins, analogs, allelic variants or fragments thereof. In a more preferred embodiment, the nucleic acid molecules have a nucleotide sequence selected from SEQ ID NO: 1 through 147, or hybridizing nucleic acids, allelic variants or parts thereof. In another highly preferred embodiment, a CSG is introduced into the cells. Expression vectors and methods of introducing nucleic acid molecules into cells are well-known in the art and are described in detail, supra.

Artificial colon tissue may be used to treat patients who have lost some or all of their colon function.

Pharmaceutical Compositions

In another aspect, the invention provides pharmaceutical compositions comprising the nucleic acid molecules, polypeptides, antibodies, antibody derivatives, antibody fragments, agonists, antagonists, and inhibitors of the present invention. In a preferred embodiment, the pharmaceutical composition comprises a CSNA or part thereof. In a more preferred embodiment, the CSNA has a nucleotide sequence selected from the group consisting of SEQ ID NO: 1 through 147, a nucleic acid that hybridizes thereto, an allelic variant thereof, or a nucleic acid that has substantial sequence identity thereto. In another preferred embodiment, the pharmaceutical composition comprises a CSP or fragment thereof. In a more preferred embodiment, the CSP having an amino acid sequence that is selected from the group consisting of SEQ ID NO: 148 through 250, a polypeptide that is homologous thereto, a fusion protein comprising all or a portion of the polypeptide, or an analog or derivative thereof. In another preferred embodiment, the pharmaceutical composition comprises an anti-CSP antibody, preferably an antibody that specifically binds to a CSP having an amino acid that is selected from the group consisting of SEQ ID NO: 148 through 250, or an antibody that binds to a polypeptide that is homologous thereto, a fusion protein comprising all or a portion of the polypeptide, or an analog or derivative thereof.

Such a composition typically contains from about 0.1 to 90% by weight of a therapeutic agent of the invention formulated in and/or with a pharmaceutically acceptable carrier or excipient.

Pharmaceutical formulation is a well-established art, and is further described in Gennaro (ed.), *Remington: The Science and Practice of Pharmacy,* $20^{th}$ ed., Lippincott, Williams & Wilkins (2000); Ansel et al., *Pharmaceutical Dosage Forms and Drug Delivery Systems,* $7^{th}$ ed., Lippincott Williams & Wilkins (1999); and Kibbe (ed.), *Handbook of Pharmaceutical Excipients* American Pharmaceutical Association, $3^{rd}$ ed. (2000), the disclosures of which are incorporated herein by reference in their entireties, and thus need not be described in detail herein.

Briefly, formulation of the pharmaceutical compositions of the present invention will depend upon the route chosen for administration. The pharmaceutical compositions utilized in this invention can be administered by various routes including both enteral and parenteral routes, including oral, intravenous, intramuscular, subcutaneous, inhalation, topical, sublingual, rectal, intra-arterial, intramedullary, intrathecal, intraventricular, transmucosal, transdermal, intranasal, intraperitoneal, intrapulmonary, and intrauterine.

Oral dosage forms can be formulated as tablets, pills, dragees, capsules, liquids, gels, syrups, slurries, suspensions, and the like, for ingestion by the patient.

Solid formulations of the compositions for oral administration can contain suitable carriers or excipients, such as carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; and other agents such as acacia and alginic acid.

Agents that facilitate disintegration and/or solubilization can be added, such as the cross-linked polyvinyl pyrrolidone, agar, alginic acid, or a salt thereof, such as sodium alginate, microcrystalline cellulose, corn starch, sodium starch glycolate, and alginic acid.

Tablet binders that can be used include acacia, methylcellulose, sodium carboxymethylcellulose, polyvinylpyrrolidone (Povidone™), hydroxypropyl methylcellulose, sucrose, starch and ethylcellulose.

Lubricants that can be used include magnesium stearates, stearic acid, silicone fluid, talc, waxes, oils, and colloidal silica.

Fillers, agents that facilitate disintegration and/or solubilization, tablet binders and lubricants, including the aforementioned, can be used singly or in combination.

Solid oral dosage forms need not be uniform throughout. For example, dragee cores can be used in conjunction with suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures.

Oral dosage forms of the present invention include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Additionally, dyestuffs or pigments can be added to the tablets or dragee coatings for product identification or to characterize the quantity of active compound, i.e., dosage.

Liquid formulations of the pharmaceutical compositions for oral (enteral) administration are prepared in water or other aqueous vehicles and can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents.

The pharmaceutical compositions of the present invention can also be formulated for parenteral administration. Formulations for parenteral administration can be in the form of aqueous or non-aqueous isotonic sterile injection solutions or suspensions.

For intravenous injection, water soluble versions of the compounds of the present invention are formulated in, or if provided as a lyophilate, mixed with, a physiologically acceptable fluid vehicle, such as 5% dextrose ("D5"), physiologically buffered saline, 0.9% saline, Hanks' solution, or Ringer's solution. Intravenous formulations may include carriers, excipients or stabilizers including, without limitation, calcium, human serum albumin, citrate, acetate, calcium chloride, carbonate, and other salts.

Intramuscular preparations, e.g. a sterile formulation of a suitable soluble salt form of the compounds of the present invention, can be dissolved and administered in a pharmaceutical excipient such as Water-for-Injection, 0.9% saline, or 5% glucose solution. Alternatively, a suitable insoluble form of the compound can be prepared and administered as a suspension in an aqueous base or a pharmaceutically acceptable oil base, such as an ester of a long chain fatty acid (e.g., ethyl oleate), fatty oils such as sesame oil, triglycerides, or liposomes.

Parenteral formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like).

Aqueous injection suspensions can also contain substances that increase the viscosity of the suspension, such as sodium carboxymethyl cellulose, sorbitol, or dextran. Non-lipid polycationic amino polymers can also be used for delivery. Optionally, the suspension can also contain suitable stabilizers or agents that increase the solubility of the compounds to allow for the preparation of highly concentrated solutions.

Pharmaceutical compositions of the present invention can also be formulated to permit injectable, long-term, deposition. Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in microemulsions that are compatible with body tissues.

The pharmaceutical compositions of the present invention can be administered topically.

For topical use the compounds of the present invention can also be prepared in suitable forms to be applied to the skin, or mucus membranes of the nose and throat, and can take the form of lotions, creams, ointments, liquid sprays or inhalants, drops, tinctures, lozenges, or throat paints. Such topical formulations further can include chemical compounds such as dimethylsulfoxide (DMSO) to facilitate surface penetration of the active ingredient. In other transdermal formulations, typically in patch-delivered formulations, the pharmaceutically active compound is formulated with one or more skin penetrants, such as 2-N-methyl-pyrrolidone (NMP) or Azone. A topical semi-solid ointment formulation typically contains a concentration of the active ingredient from about 1 to 20%, e.g., 5 to 10%, in a carrier such as a pharmaceutical cream base.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Inhalation formulations can also readily be formulated. For inhalation, various powder and liquid formulations can be prepared. For aerosol preparations, a sterile formulation of the compound or salt form of the compound may be used in inhalers, such as metered dose inhalers, and nebulizers. Aerosolized forms may be especially useful for treating respiratory disorders.

Alternatively, the compounds of the present invention can be in powder form for reconstitution in the appropriate pharmaceutically acceptable carrier at the time of delivery.

The pharmaceutically active compound in the pharmaceutical compositions of the present invention can be provided as the salt of a variety of acids, including but not limited to hydrochloric, sulfuric, acetic, lactic, tartaric, malic, and succinic acid. Salts tend to be more soluble in aqueous or other protonic solvents than are the corresponding free base forms.

After pharmaceutical compositions have been prepared, they are packaged in an appropriate container and labeled for treatment of an indicated condition.

The active compound will be present in an amount effective to achieve the intended purpose. The determination of an effective dose is well within the capability of those skilled in the art.

A "therapeutically effective dose" refers to that amount of active ingredient, for example CSP polypeptide, fusion protein, or fragments thereof, antibodies specific for CSP, agonists, antagonists or inhibitors of CSP, which ameliorates the signs or symptoms of the disease or prevents progression thereof; as would be understood in the medical arts, cure, although desired, is not required.

The therapeutically effective dose of the pharmaceutical agents of the present invention can be estimated initially by in vitro tests, such as cell culture assays, followed by assay in model animals, usually mice, rats, rabbits, dogs, or pigs. The animal model can also be used to determine an initial preferred concentration range and route of administration.

For example, the ED50 (the dose therapeutically effective in 50% of the population) and LD50 (the dose lethal to 50% of the population) can be determined in one or more cell culture of animal model systems. The dose ratio of toxic to therapeutic effects is the therapeutic index, which can be expressed as LD50/ED50. Pharmaceutical compositions that exhibit large therapeutic indices are preferred.

The data obtained from cell culture assays and animal studies are used in formulating an initial dosage range for human use, and preferably provide a range of circulating concentrations that includes the ED50 with little or no toxicity. After administration, or between successive administrations, the circulating concentration of active agent varies within this range depending upon pharmacokinetic factors well-known in the art, such as the dosage form employed, sensitivity of the patient, and the route of administration.

The exact dosage will be determined by the practitioner, in light of factors specific to the subject requiring treatment. Factors that can be taken into account by the practitioner include the severity of the disease state, general health of the subject, age, weight, gender of the subject, diet, time and frequency of administration, drug combination(s), reaction sensitivities, and tolerance/response to therapy. Long-acting pharmaceutical compositions can be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Where the therapeutic agent is a protein or antibody of the present invention, the therapeutic protein or antibody agent typically is administered at a daily dosage of 0.01 mg to 30 mg/kg of body weight of the patient (e.g., 1 mg/kg to 5 mg/kg). The pharmaceutical formulation can be administered in multiple doses per day, if desired, to achieve the total desired daily dose.

Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions.

Therapeutic Methods

The present invention further provides methods of treating subjects having defects in a gene of the invention, e.g., in expression, activity, distribution, localization, and/or solubility, which can manifest as a disorder of colon function. As used herein, "treating" includes all medically-acceptable types of therapeutic intervention, including palliation and prophylaxis (prevention) of disease. The term "treating" encompasses any improvement of a disease, including minor improvements. These methods are discussed below.

Gene Therapy and Vaccines

The isolated nucleic acids of the present invention can also be used to drive in vivo expression of the polypeptides of the present invention. In vivo expression can be driven from a vector, typically a viral vector, often a vector based upon a replication incompetent retrovirus, an adenovirus, or an adeno-associated virus (AAV), for purpose of gene therapy. In vivo expression can also be driven from signals endogenous to the nucleic acid or from a vector, often a plasmid vector, such as pVAX1 (Invitrogen, Carlsbad, Calif., USA), for purpose of "naked" nucleic acid vaccination, as further described in U.S. Pat. Nos. 5,589,466; 5,679,647; 5,804,566; 5,830,877; 5,843,913; 5,880,104; 5,958,891; 5,985,847; 6,017,897; 6,110,898; and 6,204,250, the disclosures of which are incorporated herein by reference in their entireties. For cancer therapy, it is preferred that the vector also be tumor-selective. See, e.g., Doronin et al., *J. Virol.* 75: 3314-24 (2001).

In another embodiment of the therapeutic methods of the present invention, a therapeutically effective amount of a pharmaceutical composition comprising a nucleic acid of the present invention is administered. The nucleic acid can be delivered in a vector that drives expression of a CSP, fusion protein, or fragment thereof, or without such vector. Nucleic acid compositions that can drive expression of a CSP are administered, for example, to complement a deficiency in the native CSP, or as DNA vaccines. Expression vectors derived from Virus, replication deficient retroviruses, adenovirus, adeno-associated (AAV) virus, herpes virus, or vaccinia virus can be used as can plasmids. See, e.g., Cid-Arregui, supra. In a preferred embodiment, the nucleic acid molecule encodes a CSP having the amino acid sequence of SEQ ID NO: 148 through 250, or a fragment, fusion protein, allelic variant or homolog thereof.

In still other therapeutic methods of the present invention, pharmaceutical compositions comprising host cells that express a CSP, fusions, or fragments thereof can be administered. In such cases, the cells are typically autologous, so as to circumvent xenogeneic or allotypic rejection, and are administered to complement defects in CSP production or activity. In a preferred embodiment, the nucleic acid molecules in the cells encode a CSP having the amino acid sequence of SEQ ID NO: 148 through 250, or a fragment, fusion protein, allelic variant or homolog thereof.

Antisense Administration

Antisense nucleic acid compositions, or vectors that drive expression of a CSG antisense nucleic acid, are administered to downregulate transcription and/or translation of a CSG in circumstances in which excessive production, or production of aberrant protein, is the pathophysiologic basis of disease.

Antisense compositions useful in therapy can have a sequence that is complementary to coding or to noncoding regions of a CSG. For example, oligonucleotides derived from the transcription initiation site, e.g., between positions −10 and +10 from the start site, are preferred.

Catalytic antisense compositions, such as ribozymes, that are capable of sequence-specific hybridization to CSG transcripts, are also useful in therapy. See, e.g., Phylactou, *Adv. Drug Deliv. Rev.* 44(2-3): 97-108 (2000); Phylactou et al., *Hum. Mol. Genet.* 7(10): 1649-53 (1998); Rossi, *Ciba Found. Symp.* 209: 195-204 (1997); and Sigurdsson et al., *Trends Biotechnol.* 13(8): 286-9 (1995), the disclosures of which are incorporated herein by reference in their entireties.

Other nucleic acids useful in the therapeutic methods of the present invention are those that are capable of triplex helix formation in or near the CSG genomic locus. Such triplexing oligonucleotides are able to inhibit transcription. See, e.g., Intody et al., *Nucleic Acids Res.* 28(21): 4283-90 (2000); McGuffie et al., *Cancer Res.* 60(14): 3790-9 (2000), the disclosures of which are incorporated herein by reference. Pharmaceutical compositions comprising such triplex forming oligos (TFOs) are administered in circumstances in which excessive production, or production of aberrant protein, is a pathophysiologic basis of disease.

In a preferred embodiment, the antisense molecule is derived from a nucleic acid molecule encoding a CSP, preferably a CSP comprising an amino acid sequence of SEQ ID NO: 148 through 250, or a fragment, allelic variant or homolog thereof. In a more preferred embodiment, the antisense molecule is derived from a nucleic acid molecule having a nucleotide sequence of SEQ ID NO: 1 through 147, or a part, allelic variant, substantially similar or hybridizing nucleic acid thereof.

Polypeptide Administration

In one embodiment of the therapeutic methods of the present invention, a therapeutically effective amount of a pharmaceutical composition comprising a CSP, a fusion protein, fragment, analog or derivative thereof is administered to a subject with a clinically-significant CSP defect.

Protein compositions are administered, for example, to complement a deficiency in native CSP. In other embodiments, protein compositions are administered as a vaccine to elicit a humoral and/or cellular immune response to CSP. The immune response can be used to modulate activity of CSP or, depending on the immunogen, to immunize against aberrant or aberrantly expressed forms, such as mutant or inappropriately expressed isoforms. In yet other embodiments, protein fusions having a toxic moiety are administered to ablate cells that aberrantly accumulate CSP.

In a preferred embodiment, the polypeptide is a CSP comprising an amino acid sequence of SEQ ID NO: 148 through 250, or a fusion protein, allelic variant, homolog, analog or derivative thereof. In a more preferred embodiment, the polypeptide is encoded by a nucleic acid molecule having a nucleotide sequence of SEQ ID NO: 1 through 147, or a part, allelic variant, substantially similar or hybridizing nucleic acid thereof.

Antibody, Agonist and Antagonist Administration

In another embodiment of the therapeutic methods of the present invention, a therapeutically effective amount of a pharmaceutical composition comprising an antibody (including fragment or derivative thereof) of the present invention is administered. As is well-known, antibody compositions are administered, for example, to antagonize activity of CSP, or to target therapeutic agents to sites of CSP presence and/or accumulation. In a preferred embodiment, the antibody specifically binds to a CSP comprising an amino acid sequence of SEQ ID NO: 148 through 250, or a fusion protein, allelic variant, homolog, analog or derivative thereof. In a more preferred embodiment, the antibody specifically binds to a CSP encoded by a nucleic acid molecule having a nucleotide sequence of SEQ ID NO: 1 through 147, or a part, allelic variant, substantially similar or hybridizing nucleic acid thereof.

The present invention also provides methods for identifying modulators which bind to a CSP or have a modulatory effect on the expression or activity of a CSP. Modulators which decrease the expression or activity of CSP (antagonists) are believed to be useful in treating colon cancer. Such screening assays are known to those of skill in the art and include, without limitation, cell-based assays and cell-free assays. Small molecules predicted via computer imaging to specifically bind to regions of a CSP can also be designed, synthesized and tested for use in the imaging and treatment of colon cancer. Further, libraries of molecules can be screened for potential anticancer agents by assessing the ability of the molecule to bind to the CSPs identified herein. Molecules identified in the library as being capable of binding to a CSP are key candidates for further evaluation for use in the treatment of colon cancer. In a preferred embodiment, these molecules will downregulate expression and/or activity of a CSP in cells.

In another embodiment of the therapeutic methods of the present invention, a pharmaceutical composition comprising a non-antibody antagonist of CSP is administered. Antagonists of CSP can be produced using methods generally known in the art. In particular, purified CSP can be used to screen libraries of pharmaceutical agents, often combinatorial libraries of small molecules, to identify those that specifically bind and antagonize at least one activity of a CSP.

In other embodiments a pharmaceutical composition comprising an agonist of a CSP is administered. Agonists can be identified using methods analogous to those used to identify antagonists.

In a preferred embodiment, the antagonist or agonist specifically binds to and antagonizes or agonizes, respectively, a CSP comprising an amino acid sequence of SEQ ID NO: 148 through 250, or a fusion protein, allelic variant, homolog, analog or derivative thereof. In a more preferred embodiment, the antagonist or agonist specifically binds to and antagonizes or agonizes, respectively, a CSP encoded by a nucleic acid molecule having a nucleotide sequence of SEQ ID NO: 1 through 147, or a part, allelic variant, substantially similar or hybridizing nucleic acid thereof.

Targeting Colon Tissue

The invention also provides a method in which a polypeptide of the invention, or an antibody thereto, is linked to a therapeutic agent such that it can be delivered to the colon or to specific cells in the colon. In a preferred embodiment, an anti-CSP antibody is linked to a therapeutic agent and is administered to a patient in need of such therapeutic agent. The therapeutic agent may be a toxin, if colon tissue needs to be selectively destroyed. This would be useful for targeting and killing colon cancer cells. In another embodiment, the therapeutic agent may be a growth or differentiation factor, which would be useful for promoting colon cell function.

In another embodiment, an anti-CSP antibody may be linked to an imaging agent that can be detected using, e.g., magnetic resonance imaging, CT or PET. This would be useful for determining and monitoring colon function, identifying colon cancer tumors, and identifying noncancerous colon diseases.

EXAMPLES

Example 1

Gene Expression Analysis

CSGs were identified by a systematic analysis of gene expression data in the LIFESEQ® Gold database available from Incyte Genomics Inc (Palo Alto, Calif.) using the data mining software package CLASP™ (Candidate Lead Automatic Search Program). CLASP™ is a set of algorithms that interrogate Incyte's database to identify genes that are both specific to particular tissue types as well as differentially expressed in tissues from patients with cancer. LifeSeq® Gold contains information about which genes are expressed in various tissues in the body and about the dynamics of expression in both normal and diseased states. CLASP™ first sorts the LifeSeq® Gold database into defined tissue types, such as breast, ovary and prostate. CLASP™ categorizes each tissue sample by disease state. Disease states include "healthy," "cancer," "associated with cancer," "other disease" and "other." Categorizing the disease states improves our ability to identify tissue and cancer-specific molecular targets. CLASP™ then performs a simultaneous parallel search for genes that are expressed both (1) selectively in the defined tissue type compared to other tissue types and (2) differentially in the "cancer" disease state compared to the other disease states affecting the same, or different, tissues. This sorting is accomplished by using mathematical and statistical filters that specify the minimum change in expression levels and the minimum frequency that the differential expression pattern must be observed across the tissue samples for the gene to be considered statistically significant. The CLASP™ algorithm quantifies the relative abundance of a particular gene in each tissue type and in each disease state.

To find the CSGs of this invention, the following specific CLASP™ profiles were utilized: tissue-specific expression (CLASP 1), detectable expression only in cancer tissue (CLASP 2), highest differential expression for a given cancer (CLASP 4); differential expression in cancer tissue (CLASP 5), and. cDNA libraries were divided into 60 unique tissue types (early versions of LifeSeq® had 48 tissue types). Genes or ESTs were grouped into "gene bins," where each bin is a cluster of sequences grouped together where they share a common contig. The expression level for each gene bin was calculated for each tissue type. Differential expression significance was calculated with rigorous statistical significant testing taking into account variations in sample size and relative gene abundance in different libraries and within each library (for the equations used to determine statistically significant expression see Audic and Claverie "The significance of digital gene expression profiles," Genome Res 7(10): 986-995 (1997), including Equation 1 on page 987 and Equation 2 on page 988, the contents of which are incorporated by reference). Differentially expressed tissue-specific genes were selected based on the percentage abundance level in the targeted tissue versus all the other tissues (tissue-specificity). The expression levels for each gene in libraries of normal tissues or non-tumor tissues from cancer patients were compared with the expression levels in tissue libraries associated with tumor or disease (cancer-specificity). The results were analyzed for statistical significance.

The selection of the target genes meeting the rigorous CLASP™ profile criteria were as follows:

(a) CLASP 1: tissue-specific expression: To qualify as a CLASP 1 candidate, a gene must exhibit statistically significant expression in the tissue of interest compared to all other tissues. Only if the gene exhibits such differential expression with a 90% of confidence level is it selected as a CLASP 1 candidate.

(b) CLASP 2: detectable expression only in cancer tissue: To qualify as a CLASP 2 candidate, a gene must exhibit detectable expression in tumor tissues and undetectable expression in libraries from normal individuals and libraries from normal tissue obtained from diseased patients. In addition, such a gene must also exhibit further specificity for the tumor tissues of interest.

(c) CLASP 5: differential expression in cancer tissue: To qualify as a CLASP 5 candidate, a gene must be differentially expressed in tumor libraries in the tissue of interest compared to normal libraries for all tissues. Only if the gene exhibits such differential expression with a 90% of confidence level is it selected as a CLASP 5 candidate.

The CLASP™ scores for SEQ ID NO: 1-147 are listed below:

| | | |
|---|---|---|
| SEQ ID NO: 1 | DEX0253_1 | CLASP2 |
| SEQ ID NO: 2 | DEX0253_2 | CLASP2 |
| SEQ ID NO: 3 | DEX0253_3 | CLASP2 |
| SEQ ID NO: 4 | DEX0253_4 | CLASP2 CLASP1 |
| SEQ ID NO: 5 | DEX0253_5 | CLASP2 CLASP1 |
| SEQ ID NO: 6 | DEX0253_6 | CLASP5 CLASP1 |
| SEQ ID NO: 7 | DEX0253_7 | CLASP5 CLASP1 |
| SEQ ID NO: 8 | DEX0253_8 | CLASP2 |
| SEQ ID NO: 9 | DEX0253_9 | CLASP2 |
| SEQ ID NO: 10 | DEX0253_10 | CLASP2 |
| SEQ ID NO: 11 | DEX0253_11 | CLASP2 CLASP1 |
| SEQ ID NO: 12 | DEX0253_12 | CLASP2 |
| SEQ ID NO: 13 | DEX0253_13 | CLASP2 |
| SEQ ID NO: 14 | DEX0253_14 | CLASP5 CLASP1 |
| SEQ ID NO: 15 | DEX0253_15 | CLASP2 |
| SEQ ID NO: 16 | DEX0253_16 | CLASP2 |
| SEQ ID NO: 17 | DEX0253_17 | CLASP2 |
| SEQ ID NO: 18 | DEX0253_18 | CLASP2 |
| SEQ ID NO: 19 | DEX0253_19 | CLASP2 |
| SEQ ID NO: 20 | DEX0253_20 | CLASP2 |
| SEQ ID NO: 21 | DEX0253_21 | CLASP2 |
| SEQ ID NO: 22 | DEX0253_22 | CLASP2 |
| SEQ ID NO: 23 | DEX0253_23 | CLASP2 |
| SEQ ID NO: 24 | DEX0253_24 | CLASP2 CLASP1 |
| SEQ ID NO: 25 | DEX0253_25 | CLASP2 CLASP1 |
| SEQ ID NO: 26 | DEX0253_26 | CLASP2 CLASP1 |
| SEQ ID NO: 27 | DEX0253_27 | CLASP2 CLASP1 |
| SEQ ID NO: 28 | DEX0253_28 | CLASP2 |
| SEQ ID NO: 29 | DEX0253_29 | CLASP2 |
| SEQ ID NO: 30 | DEX0253_30 | CLASP2 |
| SEQ ID NO: 31 | DEX0253_31 | CLASP2 |
| SEQ ID NO: 32 | DEX0253_32 | CLASP2 |
| SEQ ID NO: 33 | DEX0253_33 | CLASP2 |
| SEQ ID NO: 34 | DEX0253_34 | CLASP2 |
| SEQ ID NO: 35 | DEX0253_35 | CLASP2 |
| SEQ ID NO: 36 | DEX0253_36 | CLASP2 |
| SEQ ID NO: 37 | DEX0253_37 | CLASP2 |

-continued

| | | |
|---|---|---|
| SEQ ID NO: 38 | DEX0253_38 | CLASP2 |
| SEQ ID NO: 39 | DEX0253_39 | CLASP2 |
| SEQ ID NO: 40 | DEX0253_40 | CLASP2 |
| SEQ ID NO: 41 | DEX0253_41 | CLASP2 |
| SEQ ID NO: 42 | DEX0253_42 | CLASP2 |
| SEQ ID NO: 43 | DEX0253_43 | CLASP2 |
| SEQ ID NO: 44 | DEX0253_44 | CLASP2 |
| SEQ ID NO: 45 | DEX0253_45 | CLASP2 |
| SEQ ID NO: 46 | DEX0253_46 | CLASP2 |
| SEQ ID NO: 47 | DEX0253_47 | CLASP2 |
| SEQ ID NO: 48 | DEX0253_48 | CLASP2 CLASP1 |
| SEQ ID NO: 50 | DEX0253_50 | CLASP2 CLASP1 |
| SEQ ID NO: 51 | DEX0253_51 | CLASP2 CLASP1 |
| SEQ ID NO: 52 | DEX0253_52 | CLASP2 CLASP1 |
| SEQ ID NO: 53 | DEX0253_53 | CLASP2 |
| SEQ ID NO: 54 | DEX0253_54 | CLASP2 CLASP1 |
| SEQ ID NO: 55 | DEX0253_55 | CLASP2 CLASP1 |
| SEQ ID NO: 56 | DEX0253_56 | CLASP2 |
| SEQ ID NO: 57 | DEX0253_57 | CLASP2 |
| SEQ ID NO: 58 | DEX0253_58 | CLASP2 |
| SEQ ID NO: 59 | DEX0253_59 | CLASP2 |
| SEQ ID NO: 60 | DEX0253_60 | CLASP2 |
| SEQ ID NO: 61 | DEX0253_61 | CLASP2 |
| SEQ ID NO: 62 | DEX0253_62 | CLASP5 CLASP1 |
| SEQ ID NO: 63 | DEX0253_63 | CLASP5 CLASP1 |
| SEQ ID NO: 64 | DEX0253_64 | CLASP5 CLASP1 |
| SEQ ID NO: 65 | DEX0253_65 | CLASP5 CLASP1 |
| SEQ ID NO: 66 | DEX0253_66 | CLASP2 |
| SEQ ID NO: 68 | DEX0253_68 | CLASP2 |
| SEQ ID NO: 69 | DEX0253_69 | CLASP2 CLASP1 |
| SEQ ID NO: 70 | DEX0253_70 | CLASP5 CLASP1 |
| SEQ ID NO: 71 | DEX0253_71 | CLASP5 CLASP1 |
| SEQ ID NO: 72 | DEX0253_72 | CLASP2 |
| SEQ ID NO: 73 | DEX0253_73 | CLASP2 |
| SEQ ID NO: 74 | DEX0253_74 | CLASP2 |
| SEQ ID NO: 75 | DEX0253_75 | CLASP2 |
| SEQ ID NO: 76 | DEX0253_76 | CLASP2 CLASP1 CLASP4 |
| SEQ ID NO: 77 | DEX0253_77 | CLASP2 |
| SEQ ID NO: 78 | DEX0253_78 | CLASP5 CLASP1 |
| SEQ ID NO: 79 | DEX0253_79 | CLASP5 CLASP1 |
| SEQ ID NO: 80 | DEX0253_80 | CLASP5 CLASP1 |
| SEQ ID NO: 81 | DEX0253_81 | CLASP5 CLASP1 |
| SEQ ID NO: 82 | DEX0253_82 | CLASP2 |
| SEQ ID NO: 83 | DEX0253_83 | CLASP2 |
| SEQ ID NO: 84 | DEX0253_84 | CLASP1 |
| SEQ ID NO: 85 | DEX0253_85 | CLASP1 |
| SEQ ID NO: 86 | DEX0253_86 | CLASP2 |
| SEQ ID NO: 87 | DEX0253_87 | CLASP2 |
| SEQ ID NO: 88 | DEX0253_88 | CLASP2 |
| SEQ ID NO: 89 | DEX0253_89 | CLASP2 |
| SEQ ID NO: 90 | DEX0253_90 | CLASP2 |
| SEQ ID NO: 91 | DEX0253_91 | CLASP2 |
| SEQ ID NO: 92 | DEX0253_92 | CLASP2 |
| SEQ ID NO: 93 | DEX0253_93 | CLASP2 |
| SEQ ID NO: 94 | DEX0253_94 | CLASP2 |
| SEQ ID NO: 95 | DEX0253_95 | CLASP2 CLASP1 |
| SEQ ID NO: 96 | DEX0253_96 | CLASP2 CLASP1 |
| SEQ ID NO: 97 | DEX0253_97 | CLASP2 |
| SEQ ID NO: 98 | DEX0253_98 | CLASP2 |
| SEQ ID NO: 99 | DEX0253_99 | CLASP2 |
| SEQ ID NO: 100 | DEX0253_100 | CLASP2 |
| SEQ ID NO: 101 | DEX0253_101 | CLASP2 |
| SEQ ID NO: 102 | DEX0253_102 | CLASP2 |
| SEQ ID NO: 103 | DEX0253_103 | CLASP2 |
| SEQ ID NO: 104 | DEX0253_104 | CLASP5 CLASP1 |
| SEQ ID NO: 105 | DEX0253_105 | CLASP2 |
| SEQ ID NO: 106 | DEX0253_106 | CLASP2 |
| SEQ ID NO: 107 | DEX0253_107 | CLASP2 |
| SEQ ID NO: 108 | DEX0253_108 | CLASP2 |
| SEQ ID NO: 109 | DEX0253_109 | CLASP2 CLASP1 |
| SEQ ID NO: 110 | DEX0253_110 | CLASP2 |
| SEQ ID NO: 111 | DEX0253_111 | CLASP2 |
| SEQ ID NO: 112 | DEX0253_112 | CLASP2 |
| SEQ ID NO: 113 | DEX0253_113 | CLASP2 |
| SEQ ID NO: 114 | DEX0253_114 | CLASP2 |
| SEQ ID NO: 115 | DEX0253_115 | CLASP5 CLASP1 |
| SEQ ID NO: 116 | DEX0253_116 | CLASP2 |
| SEQ ID NO: 117 | DEX0253_117 | CLASP2 |
| SEQ ID NO: 118 | DEX0253_118 | CLASP2 |

-continued

| | | |
|---|---|---|
| SEQ ID NO: 119 | DEX0253_119 | CLASP2 |
| SEQ ID NO: 120 | DEX0253_120 | CLASP2 |
| SEQ ID NO: 121 | DEX0253_121 | CLASP2 |
| SEQ ID NO: 123 | DEX0253_123 | CLASP2 |
| SEQ ID NO: 124 | DEX0253_124 | CLASP2 |
| SEQ ID NO: 125 | DEX0253_125 | CLASP5 CLASP1 |
| SEQ ID NO: 126 | DEX0253_126 | CLASP5 CLASP1 |
| SEQ ID NO: 127 | DEX0253_127 | CLASP2 |
| SEQ ID NO: 128 | DEX0253_128 | CLASP2 |
| SEQ ID NO: 129 | DEX0253_129 | CLASP2 |
| SEQ ID NO: 130 | DEX0253_130 | CLASP2 |
| SEQ ID NO: 131 | DEX0253_131 | CLASP2 |
| SEQ ID NO: 132 | DEX0253_132 | CLASP2 |
| SEQ ID NO: 133 | DEX0253_133 | CLASP5 CLASP1 |
| SEQ ID NO: 134 | DEX0253_134 | CLASP2 |
| SEQ ID NO: 135 | DEX0253_135 | CLASP2 |
| SEQ ID NO: 136 | DEX0253_136 | CLASP2 |
| SEQ ID NO: 139 | DEX0253_139 | CLASP2 |
| SEQ ID NO: 140 | DEX0253_140 | CLASP5 |
| SEQ ID NO: 141 | DEX0253_141 | CLASP2 |
| SEQ ID NO: 142 | DEX0253_142 | CLASP2 |
| SEQ ID NO: 143 | DEX0253_143 | CLASP2 |
| SEQ ID NO: 144 | DEX0253_144 | CLASP2 |
| SEQ ID NO: 145 | DEX0253_145 | CLASP2 |
| SEQ ID NO: 146 | DEX0253_146 | CLASP2 |
| SEQ ID NO: 147 | DEX0253_147 | CLASP2 |

Example 2

Relative Quantitation of Gene Expression

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA). Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH), ATPase, or 18S ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene are evaluated for every sample in normal and cancer tissues. Total RNA is extracted from normal tissues, cancer tissues, and from cancers and the corresponding matched adjacent tissues. Subsequently, first strand cDNA is prepared with reverse transcriptase and the polymerase chain reaction is done using primers and Taqman probes specific to each target gene. The results are analyzed using the ABI PRISM 7700 Sequence Detector. The absolute numbers are relative levels of expression of the target gene in a particular tissue compared to the calibrator tissue.

One of ordinary skill can design appropriate primers. The relative levels of expression of the CSNA versus normal tissues and other cancer tissues can then be determined. All the values are compared to normal thymus (calibrator). These RNA samples are commercially available pools, originated by pooling samples of a particular tissue from different individuals.

The relative levels of expression of the CSNA in pairs of matching samples and 1 cancer and 1 normal/normal adjacent of tissue may also be determined. All the values are compared to normal thymus (calibrator). A matching pair is formed by mRNA from the cancer sample for a particular tissue and mRNA from the normal adjacent sample for that same tissue from the same individual.

In the analysis of matching samples, the CSNAs that show a high degree of tissue specificity for the tissue of interest. These results confirm the tissue specificity results obtained with normal pooled samples.

Further, the level of mRNA expression in cancer samples and the isogenic normal adjacent tissue from the same individual are compared. This comparison provides an indication of specificity for the cancer stage (e.g. higher levels of mRNA expression in the cancer sample compared to the normal adjacent).

Altogether, the high level of tissue specificity, plus the mRNA overexpression in matching samples tested are indicative of SEQ ID NO: 1 through 147 being a diagnostic marker for cancer.

| | |
|---|---|
| DEX0095_71 | |
| cln150 -sqcln033 | |
| Sequence | Sequence ID # |
| Dex0095_71 (cln150-sqcln033) | DEX0253_104(SEQ ID No.: 104) |

Semi quantitative PCR was done using the following primers:

| Primer | DexSeqID | From | To | Primer Length |
|---|---|---|---|---|
| Sqcln033F | DEX0253_104 | 36 | 56 | 21 |
| Sqcln033R | DEX0253_104 | 256 | 236 | 21 |

The relative levels of expression of sqcln0033 in 12 normal samples from 12 different tissues were determined. These RNA samples are individual samples or are commercially available pools, originated by pooling samples of a particular tissue from different individuals. Using Polymerase Chain Reaction (PCR) technology expression levels were analyzed from four 10× serial cDNA dilutions in duplicate. Relative expression levels of 0, 1, 10, 100 and 1000 are used to evaluate gene expression. A positive reaction in the most dilute sample indicates the highest relative expression value.

| Tissue | Normal |
|---|---|
| Breast | 0 |
| Colon | 1000 |
| Endometrium | 0 |
| Kidney | 0 |
| Liver | 0 |
| Lung | 0 |
| Ovary | 0 |
| Prostate | 0 |
| Small Intestine | 1000 |
| Stomach | 0 |
| Testis | 10 |
| Uterus | 0 |

Relative levels of expression in the table above show that none of the normal tissues examined here except colon and small intestine exhibit appreciable levels of sqcln033 gene expression.

The relative levels of expression of sqcln033 in 12 cancer samples from 12 different tissues were determined. Using Polymerase Chain Reaction (PCR) technology expression levels were analyzed from four 10× serial cDNA dilutions in duplicate. Relative expression levels of 0, 1, 10, 100 and 1000 are used to evaluate gene expression. A positive reaction in the most dilute sample indicates the highest relative expression value.

| Tissue | Cancer |
|---|---|
| Bladder | 1 |
| Breast | 0 |
| Colon | 1000 |
| Kidney | 1 |
| Liver | 0 |
| Lung | 0 |
| Ovary | 0 |
| pancreas | 0 |
| prostate | 1 |
| Stomach | 0 |
| Testes | 1 |
| Uterus | 0 |

Relative levels of expression in Table 2 show that sqcln033 is expressed in very low levels in bladder, kidney, prostate and testicular cancer. High levels of expression were observed for colon cancer.

The relative levels of expression of sqcln033 in 6 matching pair colon samples were determined. Each matching pair is formed by mRNA from the cancer sample for a particular tissue and mRNA from the normal adjacent sample for that same tissue from the same individual.

Using Polymerase Chain Reaction (PCR) technology expression levels were analyzed from four 10× serial cDNA dilutions in duplicate. Relative expression levels of 0, 1, 10, 100 and 1000 are used to evaluate gene expression. A positive reaction in the most dilute sample indicates the highest relative expression value.

| Sample ID | Tissue | Cancer | NAT |
|---|---|---|---|
| 9609B019 | Colon | 10 | 100 |
| 9709C074RA | Colon | 1 | 10 |
| 9705F002D | Colon | 10 | 100 |
| 9608B012 | Colon | 0 | 100 |
| 4004709A1 | Colon | 10 | 10 |
| 9707C004GB | Colon | 100 | 10 |

Relative levels of expression in the table above show that sqcln033 is expressed in low levels in four and in moderate levels in one of the six colon cancer samples. Moderate levels of expression was observed in matching normal adjacent tissue (NAT).

From the semi-quantitative PCR experiments exhibited above especially from the results in the tables above high degree of specificity of sqCln033 for colon tissue is observed.

Experiments are underway to design and test primers and probe for quantitative PCR experiments.

Example 3

Protein Expression

The CSNA is amplified by polymerase chain reaction (PCR) and the amplified DNA fragment encoding the CSNA is subcloned in pET-21d for expression in *E. coli*. In addition to the CSNA coding sequence, codons for two amino acids, Met-Ala, flanking the $NH_2$-terminus of the coding sequence of CSNA, and six histidines, flanking the COOH-terminus of the coding sequence of CSNA, are incorporated to serve as initiating Met/restriction site and purification tag, respectively.

An over-expressed protein band of the appropriate molecular weight may be observed on a Coomassie blue stained polyacrylamide gel. This protein band is confirmed by Western blot analysis using monoclonal antibody against 6× Histidine tag.

Large-scale purification of CSP was achieved using cell paste generated from 6-liter bacterial cultures, and purified using immobilized metal affinity chromatography (IMAC). Soluble fractions that had been separated from total cell lysate were incubated with a nickle chelating resin. The column was packed and washed with five column volumes of wash buffer. CSP was eluted stepwise with various concentration imidazole buffers.

Example 4

Protein Fusions

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 2, is ligated into this BamHI site. Note that the polynucleotide is cloned without a stop codon, otherwise a fusion protein will not be produced. If the naturally occurring signal sequence is used to produce the secreted protein, pC4 does not need a second signal peptide. Alternatively, if the naturally occurring signal sequence is not used, the vector can be modified to include a heterologous signal sequence. See, e. g., WO 96/34891.

Example 5

Production of an Antibody from a Polypeptide

In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Eagle's modified Eagle's medium supplemented with 10% fetal bovine serum (inactivated at about 56° C.), and supplemented with about 10 g/l of nonessential amino acids, about 1,000 U/ml of penicillin, and about 100, μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al., *Gastroenterology* 80: 225-232 (1981).

The hybridoma cells obtained through such a selection are then assayed to identify clones which secrete antibodies capable of binding the polypeptide. Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein specific antibody and can be used to immunize an animal to induce formation of further protein-specific antibodies. Using the Jameson-Wolf methods the following epitopes were predicted. (Jameson and Wolf, CABIOS, 4(1), 181-186, 1988, the contents of which are incorporated by reference).

| | Antigenicity Index(Jameson-Wolf) | |
|---|---|---|
| positions | AI | avg length |
| DEX0253_151 | | |
| 68-108 | 1.02 | 41 |
| DEX0253_154 | | |
| 13-31 | 1.00 | 19 |
| DEX0253_155 | | |
| 8-22 | 1.25 | 15 |
| 67-98 | 1.06 | 32 |
| DEX0253_156 | | |
| 14-33 | 1.13 | 20 |
| DEX0253_161 | | |
| 32-46 | 0.98 | 15 |
| DEX0253_170 | | |
| 6-48 | 1.02 | 43 |
| DEX0253_172 | | |
| 19-28 | 1.00 | 10 |
| DEX0253_174 | | |
| 13-29 | 1.01 | 17 |
| DEX0253_178 | | |
| 2-17 | 0.99 | 16 |
| DEX0253_179 | | |
| 7-20 | 0.96 | 14 |
| DEX0253_184 | | |
| 18-33 | 1.00 | 16 |
| DEX0253_187 | | |
| 42-54 | 1.09 | 13 |
| DEX0253_188 | | |
| 14-41 | 1.03 | 28 |
| 81-97 | 0.96 | 17 |
| DEX0253_192 | | |
| 25-75 | 0.97 | 51 |
| DEX0253_197 | | |
| 31-58 | 1.06 | 28 |
| DEX0253_198 | | |
| 73-82 | 1.22 | 10 |
| 154-165 | 1.21 | 12 |
| 213-224 | 1.06 | 12 |
| 38-58 | 1.05 | 21 |
| 314-323 | 1.03 | 10 |
| 250-267 | 0.99 | 18 |
| 275-295 | 0.98 | 21 |
| 137-149 | 0.96 | 13 |
| DEX0253_203 | | |
| 3-28 | 0.99 | 26 |
| DEX0253_204 | | |
| 29-39 | 1.10 | 11 |
| 52-65 | 0.97 | 14 |
| DEX0253_208 | | |
| 3-14 | 1.04 | 12 |
| DEX0253_211 | | |
| 33-54 | 1.22 | 22 |
| 59-76 | 1.08 | 18 |
| DEX0253_212 | | |
| 22-31 | 1.00 | 10 |
| DEX0253_214 | | |
| 7-22 | 1.24 | 16 |
| DEX0253_217 | | |
| 34-46 | 1.06 | 13 |
| DEX0253_218 | | |
| 23-32 | 1.16 | 10 |
| DEX0253_219 | | |
| 19-30 | 1.24 | 12 |
| DEX0253_221 | | |
| 58-69 | 1.08 | 12 |
| 42-51 | 1.04 | 10 |
| DEX0253_222 | | |
| 58-69 | 1.08 | 12 |
| 42-51 | 1.04 | 10 |
| DEX0253_226 | | |
| 8-18 | 1.01 | 11 |
| DEX0253_229 | | |
| 8-36 | 1.02 | 29 |
| DEX0253_237 | | |
| 14-31 | 0.91 | 18 |
| DEX0253_245 | | |
| 3-27 | 1.12 | 25 |
| DEX0253_246 | | |
| 23-32 | 0.93 | 10 |

Examples of post-translational modifications (PTMs) of the BSPs of this invention are listed below. In addition, antibodies that specifically bind such post-translational modifications may be useful as a diagnostic or as therapeutic. Using the ProSite database (Bairoch et al., Nucleic Acids Res. 25(1):217-221 (1997), the contents of which are incorporated by reference), the following PTMs were predicted for the LSPs of the invention npsa-pbil with the extension .ibcp.fr/cgi-bin/npsa automat.pl?page=npsa prosite.html of the world wide web most recently accessed Oct. 23, 2001). For full definitions of the PTMs see expasy with the extension .org/cgi-bin/prosite-list.pl of the world wide web.

| | |
|---|---|
| DEX0253_148 | Tyr_Phospho_Site 3-9; |
| DEX0253_150 | Ck2_Phospho_Site 19-22; 23-26; |
| DEX0253_151 | Ck2_Phospho_Site 83-86; 128-131; Myristyl 28-33; 49-54; Pkc_Phospho_Site 77-79; 83-85; 105-107; 139-141; |
| DEX0253_152 | Leucine_Zipper 6-27; Pkc_Phospho_Site 16-18; |
| DEX0253_153 | Pkc_Phospho_Site 16-18; 24-26; |
| DEX0253_154 | Ck2_Phospho_Site 2-5; 23-26; |
| DEX0253_155 | Amidation 12-15; Myristyl 12-17; 31-36; 34-39; Pkc_Phospho_Site 75-77; |
| DEX0253_156 | Ck2_Phospho_Site 8-11; Pkc_Phospho_Site 16-18; |
| DEX0253_158 | Pkc_Phospho_Site 2-4; |
| DEX0253_159 | Myristyl 26-31; Pkc_Phospho_Site 9-11; 14-16; |
| DEX0253_160 | Myristyl 13-18; Pkc_Phospho_Site 31-33; |
| DEX0253_161 | Pkc_Phospho_Site 8-10; 17-19; |
| DEX0253_162 | Ck2_Phospho_Site 28-31; Myristyl 48-53; Pkc_Phospho_Site 28-30; |
| DEX0253_164 | Asn_Glycosylation 21-24; Myristyl 17-22; |
| DEX0253_165 | Pkc_Phospho_Site 44-46; |
| DEX0253_166 | Asn_Glycosylation 7-10; Camp_Phospho_Site 3-6; Ck2_Phospho_Site 19-22; Myristyl 32-37; Pkc_Phospho_Site 6-8; 45-47; Tyr_Phospho_Site 28-34; |
| DEX0253_167 | Asn_Glycosylation 14-17; Myristyl 23-28; Pkc_Phospho_Site 9-11; |
| DEX0253_168 | Asn_Glycosylation 38-41; Ck2_Phospho_Site 40-43; Myristyl 49-54; Pkc_Phospho_Site 16-18; 35-37; |
| DEX0253_170 | Camp_Phospho_Site 43-46; Myristyl 36-41; |
| DEX0253_171 | Asn_Glycosylation 37-40; Ck2_Phospho_Site 79-82; 86-89; Myristyl 22-27; 34-39; 47-52; Pkc_Phospho_Site 7-9; 15-17; |
| DEX0253_172 | Asn_Glycosylation 7-10; 11-14; 21-24; Pkc_Phospho_Site 52-54; 55-57; |
| DEX0253_173 | Ck2_Phospho_Site 27-30; |
| DEX0253_174 | Myristyl 56-61; |
| DEX0253_175 | Myristyl 24-29; |
| DEX0253_176 | Pkc_Phospho_Site 8-10; |
| DEX0253_177 | Pkc_Phospho_Site 9-11; |
| DEX0253_178 | Ck2_Phospho_Site 52-55; Myristyl 24-29; Pkc_Phospho_Site 45-47; |
| DEX0253_179 | Asn_Glycosylation 63-66; Ck2_Phospho_Site 25-28; Pkc_Phospho_Site 27-29; |
| DEX0253_180 | Ck2_Phospho_Site 26-29; |
| DEX0253_181 | Amidation 51-54; Pkc_Phospho_Site 6-8; 51-53; |
| DEX0253_183 | Ck2_Phospho_Site 17-20; Pkc_Phospho_Site 36-38; 39-41; |
| DEX0253_184 | Pkc_Phospho_Site 31-33; |
| DEX0253_186 | Pkc_Phospho_Site 18-20; |
| DEX0253_187 | Ck2_Phospho_Site 42-45; 77-80; |
| DEX0253_188 | Ck2_Phospho_Site 21-24; 86-89; Myristyl 25-30; Pkc_Phospho_Site 73-75; |
| DEX0253_189 | Amidation 25-28; Camp_Phospho_Site 10-13; Ck2_Phospho_Site 37-40; |
| DEX0253_191 | Ck2_Phospho_Site 11-14; Myristyl 16-21; |
| DEX0253_192 | Ck2_Phospho_Site 48-51; 61-64; Myristyl 57-62; Pkc_Phospho_Site 22-24; 58-60; |
| DEX0253_193 | Ck2_Phospho_Site 43-46; Pkc_Phospho_Site 18-20; 34-36; |
| DEX0253_196 | Asn_Glycosylation 3-6; Ck2_Phospho_Site 8-11; |
| DEX0253_197 | Myristyl 4-9; |
| DEX0253_198 | Asn_Glycosylation 46-49; 54-57; 99-102; 123-126; 135-138; 182-185; 195-198; 223-226; 229-232; 272-275; 305-308; Camp_Phospho_Site 259-262; Ck2_Phospho_Site 75-78; 82-85; 114-117; 197-200; 208-211; 247-250; 308-311; 382-385; 395-398; Myristyl 173-178; 316-321; 320-325; 334-339; 339-344; Pkc_Phospho_Site 63-65; 82-84; |

-continued

| | |
|---|---|
| | 101-103; 114-116; 157-159; 187-189; 197-199; 212-214; 225-227; 293-295; 395-397; Receptor_Cytokines_1 126-138; Receptor_Cytokines_2 304-310; |
| DEX0253_199 | Camp_Phospho_Site 6-9; |
| DEX0253_202 | Amidation 38-41; Asn_Glycosylation 2-5; 45-48; |
| DEX0253_203 | Camp_Phospho_Site 24-27; Pkc_Phospho_Site 20-22; |
| DEX0253_204 | Asn_Glycosylation 65-68; Pkc_Phospho_Site 54-56; |
| DEX0253_205 | Ck2_Phospho_Site 6-9; Myristyl 46-51; 47-52; 59-64; 63-68; 78-83; Pkc_Phospho_Site 6-8; 19-21; |
| DEX0253_207 | Ck2_Phospho_Site 57-60; 61-64; Myristyl 69-74; Pkc_Phospho Site 34-36; |
| DEX0253_208 | Camp_Phospho_Site 5-8; Ck2_Phospho_Site 37-40; Myristyl 26-31; |
| DEX0253_209 | Pkc_Phospho_Site 52-54; |
| DEX0253_210 | Camp_Phospho_Site 34-37; Ck2_Phospho_Site 9-12; Pkc_Phospho_Site 9-11; 33-35; |
| DEX0253_211 | Amidation 67-70; Camp_Phospho_Site 69-72; Ck2_Phospho_Site 5-8; 10-13; 23-26; Myristyl 35-40; 54-59; Pkc_Phospho_Site 67-69; |
| DEX0253_212 | Prokar_Lipoprotein 6-16; |
| DEX0253_213 | Asn_Glycosylation 44-47; Camp_Phospho_Site 37-40; Ck2_Phospho_Site 2-5; Pkc_Phospho_Site 8-10; |
| DEX0253_215 | Asn_Glycosylation 3-6; Ck2_Phospho_Site 28-31; |
| DEX0253_216 | Ck2_Phospho Site 9-12; Pkc_Phospho_Site 32-34; |
| DEX0253_217 | Camp_Phospho Site 28-31; Myristyl 12-17; Rieske_2 35-40; |
| DEX0253_218 | Ck2_Phospho_Site 21-24; Myristyl 29-34; |
| DEX0253_221 | Camp_Phospho_Site 51-54; Ck2_Phospho_Site 29-32; 98-101; Myristyl 21-26; 70-75; 75-80; Pkc_Phospho_Site 50-52; 57-59; 104-106; Prokar_Lipoprotein 66-76; 68-78; |
| DEX0253_222 | Camp_Phospho_Site 51-54; Ck2_Phospho_Site 29-32; 98-101; Myristyl 21-26; 70-75; 75-80; Pkc_Phospho_Site 50-52; 57-59; 104-106; Prokar_Lipoprotein 66-76; 68-78; |
| DEX0253_223 | Ck2_Phospho_Site 75-78; |
| DEX0253_224 | Ck2_Phospho_Site 96-99; Myristyl 72-77; 76-81; 105-110; Pkc_Phospho_Site 63-65; 87-89; |
| DEX0253_225 | Asn_Glycosylation 3-6; 8-11; 9-12; Pkc_Phospho_Site 12-14; |
| DEX0253_226 | Camp_Phospho_Site 14-17; |
| DEX0253_228 | Ck2_Phospho_Site 14-17; |
| DEX0253_229 | Asn_Glycosylation 41-44; Ck2_Phospho_Site 20-23; 39-42; Myristyl 25-30; 30-35; 37-42; 45-50; Pkc_Phospho_Site 9-11; 20-22; |
| DEX0253_230 | Ck2_Phospho_Site 15-18; |
| DEX0253_231 | Camp_Phospho_Site 25-28; |
| DEX0253_232 | Ck2_Phospho_Site 7-10; Rgd 8-10; |
| DEX0253_235 | Ck2_Phospho_Site 21-24; Myristyl 4-9; Pkc_Phospho_Site 21-23; |
| DEX0253_236 | Ck2_Phospho_Site 12-15; 26-29; Myristyl 10-15; 24-29; 30-35; |
| DEX0253_237 | Ck2_Phospho_Site 41-44; |
| DEX0253_238 | Ck2_Phospho_Site 2-5; Pkc_Phospho_Site 46-48; |
| DEX0253_239 | Pkc_Phospho Site 9-11; 17-19; |
| DEX0253_240 | Camp_Phospho_Site 2-5; Ck2_Phospho_Site 5-8; |
| DEX0253_241 | Pkc_Phospho_Site 20-22; |
| DEX0253_242 | Ck2_Phospho_Site 30-33; Myristyl 4-9; 27-32; 36-41; |
| DEX0253_243 | Asn_Glycosylation 40-43; Pkc_Phospho_Site 12-14; 48-50; |
| DEX0253_245 | Asn_Glycosylation 7-10; Glycosaminoglycan 9-12; Myristyl 10-15; 19-24; Pkc_Phospho_Site 23-25; |
| DEX0253_246 | Ck2_Phospho_Site 3-6; 35-38; |
| DEX0253_247 | Ck2_Phospho_Site 12-15; 27-30; |

-continued

| | |
|---|---|
| DEX0253_248 | Glycosaminoglycan 30-33; Myristyl 18-23; Pkc_Phospho_Site 22-24; |
| DEX0253_250 | Asn_Glycosylation 21-24; Ck2_Phospho_Site 14-17; 28-31; Myristyl 26-31; |

Example 6

Method of Determining Alterations in a Gene Corresponding to a Polynucleotide

RNA is isolated from individual patients or from a family of individuals that have a phenotype of interest. cDNA is then generated from these RNA samples using protocols known in the art. See, Sambrook (2001), supra. The cDNA is then used as a template for PCR, employing primers surrounding regions of interest in SEQ ID NO: 1 through 147. Suggested PCR conditions consist of 35 cycles at 95° C. for 30 seconds; 60-120 seconds at 52-58° C.; and 60-120 seconds at 70° C., using buffer solutions described in Sidransky et al., *Science* 252(5006): 706-9 (1991). See also Sidransky et al., *Science* 278(5340): 1054-9 (1997).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations are then cloned and sequenced to validate the results of the direct sequencing. PCR products is cloned into T-tailed vectors as described in Holton et al., *Nucleic Acids Res.,* 19: 1156 (1991) and sequenced with T7 polymerase (United States Biochemical). Affected individuals are identified by mutations not present in unaffected individuals.

Genomic rearrangements may also be determined. Genomic clones are nick-translated with digoxigenin deoxyuridine 5' triphosphate (Boehringer Manheim), and FISH is performed as described in Johnson et al., *Methods Cell Biol.* 35: 73-99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C-and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. Id. Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 7

Method of Detecting Abnormal Levels of a Polypeptide in a Biological Sample

Antibody-sandwich ELISAs are used to detect polypeptides in a sample, preferably a biological sample. Wells of a microtiter plate are coated with specific antibodies, at a final concentration of 0.2 to 10 μg/ml. The antibodies are either monoclonal or polyclonal and are produced by the method described above. The wells are blocked so that non-specific binding of the polypeptide to the well is reduced. The coated wells are then incubated for >2 hours at RT with a sample containing the polypeptide. Preferably, serial dilutions of the sample should be used to validate results. The plates are then washed three times with deionized or distilled water to remove unbound polypeptide. Next, 50 μl of specific antibody-alkaline phosphatase conjugate, at a concentration of 25-400 ng, is added and incubated for 2 hours at room temperature. The plates are again washed three times with deionized or distilled water to remove unbound conjugate. 75 μl of 4-methylumbelliferyl phosphate (MUP) or p-nitrophenyl phosphate (NPP) substrate solution are added to each well and incubated 1 hour at room temperature.

The reaction is measured by a microtiter plate reader. A standard curve is prepared, using serial dilutions of a control sample, and polypeptide concentrations are plotted on the, X-axis (log scale) and fluorescence or absorbance on the Y-axis (linear scale). The concentration of the polypeptide in the sample is calculated using the standard curve.

Example 8

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1, μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 μg/kg/hour to about 50 mg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semipermeable polymer matrices in the form of shaped articles, e. g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22: 547-556 (1983)), poly (2-hydroxyethyl methacrylate) (R. Langer et al., J. Biomed. Mater. Res. 15: 167-277 (1981), and R. Langer, Chem. Tech. 12: 98-105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: D E Epstein et al., Proc. Natl. Acad. Sci. USA 82: 3688-3692 (1985); Hwang et al., Proc. Natl. Acad. Sci. USA 77: 4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, I. e., one that is non-toxic to recipients at the dosages and concentrations employed and is compatible with other ingredients of the formulation.

For example, the formulation preferably does not include oxidizing agents and other compounds that are known to be deleterious to polypeptides. Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e. g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e. g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container (s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 9

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1-100 μ/kg of the polypeptide for six consecutive days. Preferably, the polypeptide is in the secreted form. The exact details of the dosing scheme, based on administration and formulation, are provided above.

Example 10

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided above.

Example 11

Method of Treatment Using Gene Therapy

One method of gene therapy transplants fibroblasts, which are capable of expressing a polypeptide, onto a patient.

Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e. g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7: 219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media.

If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 12

Method of Treatment Using Gene Therapy-In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide.

The polynucleotide of the present invention may be operatively linked to a promoter or any other genetic elements necessary for the expression of the polypeptide by the target tissue. Such gene therapy and delivery techniques and methods are known in the art, see, for example, WO 90/11092, WO 98/11779; U.S. Pat. Nos. 5,693,622; 5,705,151; 5,580,859; Tabata H. et al. (1997) Cardiovasc. Res. 35 (3): 470-479, Chao J et al. (1997) Pharmacol. Res. 35 (6): 517-522, Wolff J. A. (1997) Neuromuscul. Disord. 7 (5): 314-318, Schwartz B. et al. (1996) Gene Ther. 3 (5): 405-411, Tsurumi Y. et al. (1996) Circulation 94 (12): 3281-3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772: 126-139 and Abdallah B. et al. (1995) Biol. Cell 85 (1): 1-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts.

In vivo muscle cells are particularly competent in their ability to take up and express polynucleotides.

For the naked polynucleotide injection, an effective dosage amount of DNA or RNA will be in the range of from about 0.05 μg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e. g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice.

The results of the above experimentation in mice can be use to extrapolate proper dosages and other treatment parameters in humans and other animals using naked DNA.

Example 13

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e. g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i. e., polynucleotides of the invention) into animals to produce the founder lines of transgenic animals. Such techniques include, but are not limited to, pronuclear microinjection (Paterson et al., Appl. Microbiol. Biotechnol. 40: 691-698 (1994); Carver et al., Biotechnology (NY) 11: 1263-1270 (1993); Wright et al., Biotechnology (NY) 9: 830-834 (1991); and Hoppe et al., U.S. Pat. No. 4,873,191 (1989)); retrovirus mediated gene transfer into germ lines (Van der Putten et al., Proc. Natl. Acad. Sci., USA 82: 6148-6152 (1985)), blastocysts or embryos; gene targeting in embryonic stem cells (Thompson et al., Cell 56: 313-321 (1989)); electroporation of cells or embryos (Lo, 1983, Mol Cell. Biol. 3: 1803-1814 (1983)); introduction of the polynucleotides of the invention using a gene gun (see, e. g., Ulmer et al., Science 259: 1745 (1993); introducing nucleic acid constructs into embryonic pleuripotent stem cells and transferring the stem cells back into the blastocyst; and sperm mediated gene transfer (Lavitrano et al., Cell 57: 717-723 (1989); etc. For a review of such techniques, see Gordon, "Transgenic Animals," Intl. Rev. Cytol. 115: 171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380: 64-66 (1996); Wilmut et al., Nature 385: 810813 (1997)).

The present invention provides for transgenic animals that carry the transgene in all their cells, as well as animals which carry the transgene in some, but not all their cells, I. e., mosaic animals or chimeric. The transgene may be integrated as a single transgene or as multiple copies such as in concatamers, e. g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89: 6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265: 103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 14

Knock-Out Animals

Endogenous gene expression can also be reduced by inactivating or "knocking out" the gene and/or its promoter using targeted homologous recombination. (E. g., see Smithies et al., Nature 317: 230-234 (1985); Thomas & Capecchi, Cell 51: 503512 (1987); Thompson et al., Cell 5: 313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e. g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e. g., knockouts) are administered to a patient in vivo. Such cells may be obtained from the patient (I. e., animal, including human) or an MHC compatible donor and can include, but are not limited to fibroblasts, bone marrow cells, blood cells (e. g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e. g., by transduction (using viral vectors, and preferably vectors that integrate the transgene into the cell genome) or transfection procedures, including, but not limited to, the use of plasmids, cosmids, YACs, naked DNA, electroporation, liposomes, etc.

The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e. g., in the circulation, or intraperitoneally.

Alternatively, the cells can be incorporated into a matrix and implanted in the body, e. g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

We claim:

1. An isolated antibody or fragment thereof that binds to a polypeptide selected from the group comprising:

(a) a polypeptide comprising an amino acid sequence of SEQ ID NO:151; and (b) a polypeptide encoded by a nucleic acid molecule comprising a nucleic acid sequence of SEQ ID NO:5.

2. A method for determining the presence of a polypeptide comprising an amino acid sequence of SEQ ID NO:151 or a polypeptide encoded by a nucleic acid molecule comprising a nucleic acid sequence of SEQ ID NO:5 in a sample, comprising the steps of:

(a) contacting the sample with the antibody according to claim 1 under conditions in which the antibody binds to said polypeptide; and (b) detecting binding of the antibody to said polypeptide in the sample, wherein the detection of binding indicates the presence of said polypeptide in the sample.

3. A method of treating a patient with colon cancer, comprising the step of administering a composition according to claim 1 to a patient in need thereof.

4. A method for diagnosing and monitoring the presence and metastases of colon cancer in a patient, comprising the steps of:

(a) determining an amount of a polypeptide comprising an amino acid sequence of SEQ ID NO:151 or a polypeptide encoded by a nucleic acid molecule comprising a nucleic acid sequence of SEQ ID NO:5 in a sample from a patient; and (b) comparing the amount of the determined polypeptide in the sample from the patient to a normal control; wherein a difference in the amount of the polypeptide in the sample compared to the normal control is associated with the presence of colon cancer.

5. A kit for detecting a risk of cancer or presence of cancer in a patient, said kit comprising an antibody or fragment thereof for determining the presence a polypeptide selected from the group comprising:

(a) a polypeptide comprising an amino acid sequence of SEQ ID NO:151; and (b) a polypeptide encoded by a nucleic acid molecule comprising a nucleic acid sequence of SEQ ID NO:5.

* * * * *